· US008143049B2

(12) United States Patent
Hill et al.

(10) Patent No.: US 8,143,049 B2
(45) Date of Patent: Mar. 27, 2012

(54) MODIFIED BETA-GLUCOSIDASES WITH IMPROVED STABILITY

(75) Inventors: Christopher Hill, Ottawa (CA); James Lavigne, Nepean (CA); Martine Whissel, Ottawa (CA); John J. Tomashek, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 66 days.

(21) Appl. No.: 12/550,615

(22) Filed: Aug. 31, 2009

(65) Prior Publication Data

US 2010/0093040 A1   Apr. 15, 2010

Related U.S. Application Data

(60) Provisional application No. 61/093,010, filed on Aug. 29, 2008.

(51) Int. Cl.
*C12N 9/42* (2006.01)
*C12N 1/00* (2006.01)
*C12P 19/00* (2006.01)
*C12P 21/06* (2006.01)
*C12P 21/04* (2006.01)
*C12P 19/34* (2006.01)
*C07H 21/04* (2006.01)
*C07K 1/00* (2006.01)

(52) U.S. Cl. ............ 435/209; 435/72; 435/254.11; 435/254.2; 435/254.21; 435/254.6; 435/69.1; 435/69.7; 435/91.1; 536/23.1; 536/23.2; 536/23.7; 536/23.74; 530/350

(58) Field of Classification Search .......... 435/209, 435/72, 254.11, 254.2, 254.21, 254.6, 69.1, 435/69.9, 91.1; 536/23.1, 23.2, 23.7, 23.74; 530/350

See application file for complete search history.

(56) References Cited

U.S. PATENT DOCUMENTS

| 5,792,641 | A | 8/1998 | Schülein et al. |
|---|---|---|---|
| 5,866,408 | A | 2/1999 | Sung et al. |
| 5,958,739 | A | 9/1999 | Mitchinson et al. |
| 6,015,703 | A | 1/2000 | White et al. |
| 6,022,725 | A | 2/2000 | Fowler et al. |
| 6,087,131 | A | 7/2000 | Gunata et al. |
| 2004/0253702 | A1 | 12/2004 | Fidantsef et al. |
| 2005/0287656 | A1 | 12/2005 | Hakamada et al. |
| 2010/0304438 | A1* | 12/2010 | Scott et al. ............... 435/72 |

FOREIGN PATENT DOCUMENTS

| EP | 0 870 037 | 7/2002 |
|---|---|---|
| KR | 2003-046570 | 6/2003 |
| WO | 97/21822 | 6/1997 |
| WO | 2004/099228 | 11/2004 |

OTHER PUBLICATIONS

Broun et al., Catalytic plasticity of fatty acid modification enzymes underlying chemical diversity of plant lipids. Science, 1998, vol. 282: 1315-1317.*

Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Chica et al., Semi-rational approaches to engineering enzyme activity: combining the benefits of directed evolution and rational design. Curr. Opi. Biotechnol., 2005, vol. 16: 378-384.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Sen et al., Developments in directed evolution for improving enzyme functions. Appl. Biochem. Biotechnol., 2007, vol. 143: 212-223.*
Bhatia et al., "Microbial β-Glucosidases: Cloning, Properties and Applications", Crit. Rev. Biotech, vol. 22, No. 4 (2002) 375-407.
Cummings et al., "Secretion of *Trichoderma reesei*β-glucosidase by *Saccharmyces cerevisiae*", Curr. Genet, vol. 29 (1996) 227-33.
Ducret et al., "Screening of Various Glycosidases for the Synthesis of Octyl Glucoside", Biotech. and Bioeng, vol. 77, No. 7 (2002) 752-7.
Elias et al., "Role of Hydrodynamic Shear on Activity and Structure of Proteins", Adv. Biochem. Eng., vol. 59 (1998) 47-71.
Fersht, "Structure and Mechanism in Protein Science", W.H. Freeman and Co., U.S.A. (1998) 516-7.
Gunjikar et al., "Shear Deactivation of Cellulase, Exoglucanase, Endoglucanase, and β-Glucosidase in a Mechanically Agitated Reactor", Biotech. Prog., vol. 17 (2001) 1166-8.
Huang et al., "*Tricoderma* sp. SSL" NCBI Entrez Protein GenBank Acc. No. ACH92574.1 (2008).
Jones et al., "Kinetic Analysis of Bioconversion of Cellulose in Attrition Bioreactor", Biotech and Bioeng., vol. 31 (1988) 35-40.
Reese, "Inactivation of Cellulase by Shaking and its Prevention by Surfactants", Journ. of Applied Biochem., vol. 2 (1980) 36-9.
Sachse, et al. "Production of Cellulase in a Rotating Disc Fermenter Using Immobilized *Trichoderma reesei* Cells", Acta. Biotech., vol. 10, No. 6 (1990) 523-9.

(Continued)

*Primary Examiner* — Ganapathirama Raghu
(74) *Attorney, Agent, or Firm* — Fitzpatrick, Cella, Harper & Scinto

(57) ABSTRACT

Provided are modified beta-glucosidase enzymes, derived from the *Trichoderma reesei* Cel3A beta-glucosidase, that exhibit improved stability at low pH, low pH and high aeration, low pH and high agitation, or low pH and elevated temperature. Also provided are genetic constructs comprising nucleotide sequences encoding for modified beta-glucosidase enzymes, methods for the production of modified beta-glucosidase enzymes from host strains and the use of the modified beta-glucosidase enzymes in the hydrolysis of cellulose.

21 Claims, 36 Drawing Sheets

OTHER PUBLICATIONS

Sinnot, "Catalytic Mechanisms of Enzymic Glycosyl Transfer", Chem. Rev., vol. 90 (1990) 1171-1202.

Varghese, et al. "Three-dimensional structure of a barley β-D-glucan exohydrolase, a family 3 glycosyl hydrolase", Structure, vol. 7, No. 2 (1999) 179-90.

Weijers et al. "Enzyme Stability in Downstream Processing Part 2: Quantification of Inactivation", Biotech. Adv., vol. 10 (1992) 251-73.

Woodward et al., "The Inhibition of β-Glucosidase Activity in *Trichoderma reesei* C30 Cellulase by Derivatives and Isomers of Glucose", Biotech Bioeng., vol. 23 (1981) 1553-62.

Bommarius, et al, "Deactivation of Formate Dehydrogenase (FDH) in Solution and at Gas-Liquid Interfaces", Biotechnol. Prog., vol. 21 (2005) 1663-72.

Butler, et al., "Preparing Libraries in *Saccharomyces cerevisiae*", Methods in Molecular Biology, vol. 231 (2003) 17-22.

Eijsink, et al., "Directed evolution of enzyme stability", Biomolecular Engineering, vol. 22, No. 1-3 (2005) 21-30.

Gietz, et al., "Transformation of Yeast by Lithium Acetate/Single-Stranded Carrier DNA/Polyethylene Glycol Method", Methods in Enzymology, vol. 350 (2002) 87-96.

Harlow, et al., "Antibody Capture Assays—Detecting and Quantitating Antibodies Using Antigen Excess Assays", Antibodies, A Laboratory Manual, Cold Spring Harbor Press (1988) 564-65.

Henrissat, et al., "New Families in the classification of glycosyl hydrolases based on amino acid sequence similarities", Biochem. J., vol. 293 (1993) 781-88.

Henrissat, et al., "Updating the sequence-based classification of glycosyl hydrolases", Biochemical Journal, vol. 316 (1996) 695-96.

Montenecourt, et al., "Selective Screening Methods for the Isolation of High Yielding Cellulase Mutants of *Trichoderma reesei*", Adv. Chem., vol. 181 (1979) 289-301.

Motulsky, et al., "Fitting Models to Biological Data using Linear and Nonlinear Regression. A practical guide to curve fitting", GraphPad Prism, 1-351, 2003.

Trinder, "Determination of Glucose in Blood using Glucose Oxidase with an alternative oxygen acceptor", Ann. clin. Biochem., vol. 6 (1969) 24-7.

\* cited by examiner

```
SEQ ID NO: 1    1  --------VVPPAGTPWGTAYDKAKAALAKLNLQDKV--- 29
CONSENSUS       1  --------W--G-QGEWAEAYARAKDLVSQMTLAEKV--- 26
SEQ ID NO: 56   1  -------PWANG-QGEWAEAYQRAVAIVSQMTLDEKV--- 29
SEQ ID NO: 57   1  --------------GSWAAAYAKAKKFVAQLTPEEKV--- 23
SEQ ID NO: 58   1  -------PWADG-QGEWADAHRRAVEIVSQMTLAEKV--- 29
SEQ ID NO: 59   1  -------PWANG-QGDWAQAYQRAVDIVSQMTLAEKV--- 29
SEQ ID NO: 60   1  --------ALPIYKNASYCVDERVRDLLSRMTLEEKAGQL 32
SEQ ID NO: 61   1  ------------------------AQIESVLSKLTLEEKI--- 16
SEQ ID NO: 62   1  -------PWANG-QGDWAQAYQRAVDIVSQMTLDEKV--- 29
SEQ ID NO: 63   1  -------PWANG-QGDWAEAYQRAVDIVSQMTLAEKV--- 29
SEQ ID NO: 64   1  -------PWADG-QGEWAEVYKRAVDIVSQMTLTEKV--- 29
SEQ ID NO: 65   1  -------PWADG-QGEWAEVYKRAVDIVSQMTLTEKV--- 29
SEQ ID NO: 66   1  --------PNGGWISEWASAYEKAHRVVSNMTLAEKV--- 29
SEQ ID NO: 67   1  --------PETKGLGDWEEAFTKARSLVAQMTDKEKN--- 29
SEQ ID NO: 68   1  --------RASTSFQNWTHAHHLALTFVNQLNITEKS--- 29
SEQ ID NO: 69   1  -------PWASG-QGEWSEAYNKAREFVSQLTLTEKV--- 29
SEQ ID NO: 70   1  ------------------EAYSKAHTVVSKMTLAGKV--- 19
SEQ ID NO: 71   1  SQIYPKKQLNQENINFMSARDTFVDNLMSKMSITEKIGQM 40
SEQ ID NO: 72   1  --------DYLKYKDPKQPLGVRIKDLLGRMTLAEKIGQM 32
SEQ ID NO: 73   1  ---------------------VEAILKKLTLAEKV--- 14
SEQ ID NO: 74   1  --------------GPWAHAYRRAEKLVRQMTLEEKA--- 23
SEQ ID NO: 75   1  ---------------------------------------- 1
SEQ ID NO: 76   1  --------WMDPSAPGWEQAYAQAKEFVSGLTLLEKV--- 29
SEQ ID NO: 77   1  --------KNNLVCDSSAGYVERAQALISLFTLEELILN- 31
SEQ ID NO: 78   1  ----------------------VEQLLSELNQDEKI--- 14
SEQ ID NO: 79   1  --------PEISGLGDWFAYQRAREIVALMTNEEKT--- 29
SEQ ID NO: 80   1  --------EYVKYKDPKPVGARIKDLMKRMTLEEKIGQM 32
SEQ ID NO: 81   1  -------PWMDPSAAGWAEAYTKAQAFVRQLTLLEKV--- 30
SEQ ID NO: 82   1  -------PWIEG-LGDWEAAYQKAQAFVSQLTLLEKV--- 29
SEQ ID NO: 83   1  --------TVANVSPEWAAAYVKAQAAVAKLSVTDMV--- 29
SEQ ID NO: 84   1  --------TVANVSPEWAAAYVKAQAAVAKLSVTDMV--- 29
SEQ ID NO: 85   1  --------------GKWQAAFYRARELVDQMSIAEKV--- 23
SEQ ID NO: 86   1  --------VSQVFATSWSEADEKAKSFMSDLSESEKI--- 29
SEQ ID NO: 87   1  --------QGGRLQGVWQDAYTKAKALVSQMTIVEKV--- 29
SEQ ID NO: 88   1  --------QGGRLQDVWQEAYARAKAIVGQMTIVEKV--- 29
SEQ ID NO: 89   1  ------------------MMEHDVEDLINQLDISEKA--- 19
SEQ ID NO: 90   1  ----------------WKAAFEKAADAVSRLNLTQKV--- 21
SEQ ID NO: 91   1  -------PWANG-QGDWAEAYQKAVQFVSQLTLAEKV--- 29
SEQ ID NO: 92   1  ------------WVSDWAPAYAKAYEVVSNMTLAEKV--- 25
SEQ ID NO: 93   1  -------PWMDG-NGEWAEAYRRAVDFVSQLTLAEKV--- 29
SEQ ID NO: 94   1  -------PWMNG-NGEWAEAYRRAVDFVSQLTLAEKV--- 29
SEQ ID NO: 95   1  --------PPGGWVSDWAPAYAKAYEVVSNMTLAEKV--- 29
SEQ ID NO: 96   1  --------VVLPAGTPWGTAYDKAKAALAKLNLQDKV--- 29
SEQ ID NO: 97   1  --------EYMRYKDPKKPLNVRIKDLMSRMTLAEKIGQM 32
SEQ ID NO: 98   1  --------PVQSGLSPWSESIVRARAFVAQLTIEEKV--- 29
SEQ ID NO: 99   1  ------------MPPSDFAKANIDEIVEQLTLDEAI--- 24
```

Figure 11A-1

```
SEQ ID NO: 1    29 ---------------------------------GIVSG 34
CONSENSUS       26 ---------------------------------NLTTG 31
SEQ ID NO: 56   29 ---------------------------------NLTTG 34
SEQ ID NO: 57   23 ---------------------------------NLTAG 28
SEQ ID NO: 58   29 ---------------------------------NLTTG 34
SEQ ID NO: 59   29 ---------------------------------NLTTG 34
SEQ ID NO: 60   33 FHKQLSEGPLDDDSSGNSTETMIGKKHMTHFNLASDITNA 72
SEQ ID NO: 61   16 ---------------------------------SLLAG 21
SEQ ID NO: 62   29 ---------------------------------NLTTG 34
SEQ ID NO: 63   29 ---------------------------------NLTTG 34
SEQ ID NO: 64   29 ---------------------------------NLTTG 34
SEQ ID NO: 65   29 ---------------------------------NLTTG 34
SEQ ID NO: 66   29 ---------------------------------NLSG 34
SEQ ID NO: 67   29 ---------------------------------NITYG 34
SEQ ID NO: 68   29 ---------------------------------NIVTG 34
SEQ ID NO: 69   29 ---------------------------------NLTTG 34
SEQ ID NO: 70   19 ---------------------------------NLTTG 24
SEQ ID NO: 71   41 TQLDITTLTSPNTITINETTLAYYAKTYYIGSYLNSPVSG 80
SEQ ID NO: 72   33 TQIERENATAEAMSKY---------------FIGSVLSG 56
SEQ ID NO: 73   14 ---------------------------------DLLAG 19
SEQ ID NO: 74   23 ---------------------------------NITRG 28
SEQ ID NO: 75    1 ---------------------------------------  1
SEQ ID NO: 76   29 ---------------------------------NLTTG 34
SEQ ID NO: 77   31 ---------------------------------TQNSG 36
SEQ ID NO: 78   14 ---------------------------------SLLSA 19
SEQ ID NO: 79   29 ---------------------------------NLTFG 34
SEQ ID NO: 80   33 TQIERKVATADVMKQN---------------FIGSVLSG 56
SEQ ID NO: 81   30 ---------------------------------NLTTG 35
SEQ ID NO: 82   29 ---------------------------------NLTTG 34
SEQ ID NO: 83   29 ---------------------------------NLATG 34
SEQ ID NO: 84   29 ---------------------------------NLATG 34
SEQ ID NO: 85   23 ---------------------------------NLTTG 28
SEQ ID NO: 86   29 ---------------------------------DIVTG 34
SEQ ID NO: 87   29 ---------------------------------NLTTG 34
SEQ ID NO: 88   29 ---------------------------------NLTTG 34
SEQ ID NO: 89   19 ---------------------------------MLLSG 24
SEQ ID NO: 90   21 ---------------------------------ALTTG 26
SEQ ID NO: 91   29 ---------------------------------NLTTG 34
SEQ ID NO: 92   25 ---------------------------------NMTTG 30
SEQ ID NO: 93   29 ---------------------------------NLTTG 34
SEQ ID NO: 94   29 ---------------------------------NLTTG 34
SEQ ID NO: 95   29 ---------------------------------NMTTG 34
SEQ ID NO: 96   29 ---------------------------------GIVSG 34
SEQ ID NO: 97   33 TQIERKEATPDVISKY---------------FIGSVLSG 56
SEQ ID NO: 98   29 ---------------------------------NLTTG 34
SEQ ID NO: 99   24 ---------------------------------SLTAG 29
```

Figure 11A-2

```
SEQ ID NO: 1    35  VGWNGGP------CVGNTSPASKIS-YP---SLCLQDGPL  64
CONSENSUS       32  TGWELGP------CVGNTGSVPRLGIP----GLCLQDGPL  61
SEQ ID NO: 56   35  TGWELEK------CVGQTGGVPRLNIG----GMCLQDSPL  64
SEQ ID NO: 57   28  -TDANN-------GCSGNIAAIPRLNFP----GLCVSDAGN  57
SEQ ID NO: 58   35  TGWEMDR------CVGQTGSVPRLGINW---GLCGQDSPL  65
SEQ ID NO: 59   35  TGWELEL------CVGQTGGVPRLGVP----GMCLQDSPL  64
SEQ ID NO: 60   73  TQTAEFIN-----LIQKRALQTRLGIP-----ITISTDPR  102
SEQ ID NO: 61   22  KNFWETQ-----------DYPEKGVP----PVKTSDGPN  45
SEQ ID NO: 62   35  TGWELEL------CVGQTGGVPRLGVP----GMCLQDSPL  64
SEQ ID NO: 63   35  TGWELEL------CVGQTGGVPRLGIP----GMCAQDSPL  64
SEQ ID NO: 64   35  TGWQLER------CVGQTGSVPRLNIP----SLCLQDSPL  64
SEQ ID NO: 65   35  TGWQLER------CVGQTGSVPRLNIP----SLCLQDSPL  64
SEQ ID NO: 66   35  TGIYMGP------CAGQTGSVPRFGIPN---LCLHDSPL  64
SEQ ID NO: 67   35  YSSTAN-------GCGGTSGGVPRLGFP----GICLQDAGN  64
SEQ ID NO: 68   35  TYHTSTLDGKPMNCIGNIGPIPRLNFT----GICLNDPA  70
SEQ ID NO: 69   35  VGWMQEA------CVGNVGSIPRLGFR----SLCMQDGPL  64
SEQ ID NO: 70   25  TGFLMA-------LVGQTGSALRFGIPR----LCLQDGPL  53
SEQ ID NO: 71   81  GLAGDIHHINSSVWLDMINTIQTIVIEGSPNKIPMIYGLD  120
SEQ ID NO: 72   57  GGSVPSPQASAAAWQSMVNEMQKGALSTRL-GIPMIYGID  95
SEQ ID NO: 73   20  IDFWHTK-----------ALPKHGVP----SLRFTDGPN  43
SEQ ID NO: 74   28  -FTGDN-------VCAGNTGSVPRLGWP----GMCVHDAGN  57
SEQ ID NO: 75    1  ----------------------------------------  1
SEQ ID NO: 76   35  VGWMGEK------CVGNVGTVPRLGMR----SLCMQDGPL  64
SEQ ID NO: 77   37  PGVPRLG------------LPNYQVWN-EALHGLDRANF  62
SEQ ID NO: 78   20  VDFWHTK-----------KIERLGIP----AVRVSDGPN  43
SEQ ID NO: 79   34  -SSGDT-------GCSGMISDVPDVDFP----GLCLQDAGN  63
SEQ ID NO: 80   57  GGSVPAPKASAQVWTNMVDEIQKGSLSTRL-GIPMIYGID  95
SEQ ID NO: 81   36  VGWEGEA------CVGNTGSIPRLGFP----GFCTQDSPL  65
SEQ ID NO: 82   35  TGWQSDH------CVGNTGGVPRLNFT----GICNQDAPL  64
SEQ ID NO: 83   35  VQWEKGP------CVGNTPAISSIPGFT---GLCLQDSPV  65
SEQ ID NO: 84   35  VQWQKGP------CVGNTPAISSIPGFT---GLCLQDSPV  65
SEQ ID NO: 85   29  VGSASGP------CSGNTGSVPRLNIS----SICVQDGPL  58
SEQ ID NO: 86   35  YMNMQGT------CVGNIKPLDRKNFK----GLCLQDGPA  64
SEQ ID NO: 87   35  TGWQLGP------CVGNTGSVPRFGIP----NLCLQDGPL  64
SEQ ID NO: 88   35  TGWQLDP------CVGNTGSVPRFGIP----NLCLQDGPL  64
SEQ ID NO: 89   25  TDLWHTA-----------AIPRLNIP----SIRLSDGPN  48
SEQ ID NO: 90   27  TTAG--------LSCNGNIAPIPEINFS----GLCLADGPV  55
SEQ ID NO: 91   35  TGWEQDR------CVGQVGSIPRLGFP----GLCMQDSPL  64
SEQ ID NO: 92   31  TGIFMGP------CVGQTGSALRFGIPN---LCLMDSPL  60
SEQ ID NO: 93   35  VGWMQEK------CVGETGSIPRLGFR----GLCLQDSPL  64
SEQ ID NO: 94   35  VGWMQEK------CVGETGSIPRLGFR----GLCLQDSPL  64
SEQ ID NO: 95   35  TGIFMGP------CVGQTGSALRFGIPN---LCLMDSPL  64
SEQ ID NO: 96   35  VGWNGGP------CVGNTSPASKFS-YP---SLCLQDGPL  64
SEQ ID NO: 97   57  GGSVPAPKASPEAWVDLVNGMQKAALSTRL-GIPMIYGID  95
SEQ ID NO: 98   35  AG-TQGR------CVGETGTVPRLGFNQ---PICLQDGPV  64
SEQ ID NO: 99   30  VGFWHTH-----------AIERLGVP----AVKVSDGPN  53
```

Figure 11A-3

```
SEQ ID NO: 1    65   GVRYST--------GSTAFTPGVQAASTWDVNLIRERG--  94
CONSENSUS       62   GVRGTD--------YNSAFPAGVNVAATWDKNLAYLRG--  91
SEQ ID NO: 56   65   GIRDSD--------YNSAFPAGVNVAATWDKNLAYLRG--  94
SEQ ID NO: 57   58   GLRGTD--------YVSSWPSGLHVGASWNKALARQRA--  87
SEQ ID NO: 58   66   GIRFSD--------LNSAFPAGTNVAATWDKTLAYLRG--  95
SEQ ID NO: 59   65   GVRDSD--------YNSAFPSGMNVAATWDKNLAYLRG--  94
SEQ ID NO: 60  103   HSFTENVGTGFQAGVFSQWPESLGLAALRDPQLVREFA-- 140
SEQ ID NO: 61   46   GARGATFKG---GVTAACFPASSLLAATWDLDAAKHIG--  80
SEQ ID NO: 62   65   GVRDSD--------YNSAFPAGMNVAATWDKNLAYLRG--  94
SEQ ID NO: 63   65   GVRDSD--------YNSAFPAGVNVAATWDKNLAYLRG--  94
SEQ ID NO: 64   65   GIRFSD--------YNSAFPAGVNVAATWDKTLAYLRG--  94
SEQ ID NO: 65   65   GIRFSD--------YNSAFPAGVNVAATWDKTLAYLRG--  94
SEQ ID NO: 66   65   GVRNSD--------HNTAFPAGITVGATFDKDLMYERG--  94
SEQ ID NO: 67   65   GVRGTD--------MVNSYASGVHVGASWNRDLTYSRA--  94
SEQ ID NO: 68   71   LLLVRD--------LISVFPSGVTLAATWDRELVYQSY-- 100
SEQ ID NO: 69   65   GIRFAD--------HVSAFPAGINVGATWSKSLAYLRG--  94
SEQ ID NO: 70   54   GLRNTD--------HNTAFPAGISVGATFDKKLMYERG--  83
SEQ ID NO: 71  121   SVHGAN--Y---VHKATLFPHNTGLAATFNIEHATTAA-- 153
SEQ ID NO: 72   96   AVHGHNN-----VYKATIFPHNVGLGATRDPMLVKRIG-- 128
SEQ ID NO: 73   44   GVRTKFFN---GVPAACFPCGTSLGSTFNQTLLEEAG--  78
SEQ ID NO: 74   58   GVRATD--------LVNSYPSGIHVGASWDRNLTYERG--  87
SEQ ID NO: 75    1   ----------------------------------------  1
SEQ ID NO: 76   65   GLRFNT--------YNSAFSVGLTAAASWSRHLWVDRG--  94
SEQ ID NO: 77   63   ATKGGQ------FEWATSFPMPILTTAALNRTLIHQIADI  96
SEQ ID NO: 78   44   GIRGTKFFD---GVPSGCFPNGTGLASTFDRDLLETAG--  78
SEQ ID NO: 79   64   GVRGTD--------MVNAYASGLHVGASWNRQLAYDRA--  93
SEQ ID NO: 80   96   AVHGHNN-----VYGATIFPHNVGLGVTRDPDLVKRIG-- 128
SEQ ID NO: 81   66   GVRFAD--------YVSAFTAGGTIAASWDRSEFYRRG--  95
SEQ ID NO: 82   65   GVRFAD--------YVSAFPSGGTIAAAWDRGEWYLRG--  94
SEQ ID NO: 83   66   GVRYAD--------GTSVFPPEINVAATWNRTLMRQRG--  95
SEQ ID NO: 84   66   GVRYAD--------GTSVFPPEINVAATWNRTLMRQRG--  95
SEQ ID NO: 85   59   SVRAAD--------LTDVFPCGMAASSSFNKQLIYDRA--  88
SEQ ID NO: 86   65   GVRFNGG-------TSTTWQAGINNAATFNKDLLYKIG--  95
SEQ ID NO: 87   65   GVRLTD--------FSTGYPSGMATGATFNKDLFLQRG--  94
SEQ ID NO: 88   65   GVRFAD--------FVTGYPSGLATGATFNKDLFLQRG--  94
SEQ ID NO: 89   49   GIRGTSFFN---SSPSACFPCGTALGATFDKKLLFEVG--  83
SEQ ID NO: 90   56   SVRIAD--------LATVFPAGLTAAATWDRQLIYERA--  85
SEQ ID NO: 91   65   GVRDTD--------YNSAFPAGVNVAATWDRNLAYRRG--  94
SEQ ID NO: 92   61   GIRNTD--------HNTAFPAGITVGATFDKELMYARG--  90
SEQ ID NO: 93   65   GVRFAD--------YVSAFPAGVNVAATWDKNLAYLRG--  94
SEQ ID NO: 94   65   GVRFAD--------YISAFPAGVNVAATWDKNLAYLRG--  94
SEQ ID NO: 95   65   GIRNTD--------HNTAFPAGITVGATFDKELMYARG--  94
SEQ ID NO: 96   65   GVRYST--------GSTAFTPGVQAASTWDVNLIRERG--  94
SEQ ID NO: 97   96   AVHGHNN-----VYNATIFPHNVGLGVTRDPALIKRIG-- 128
SEQ ID NO: 98   65   GIRYTD--------FNSVFPAAINVAATFDKQLMFKRA--  94
SEQ ID NO: 99   54   GIRGNHFFM---GTPAKCLPSSTALGATWDPEVVEEVGL-  89
```

Figure 11A-4

```
SEQ ID NO: 1    94  -QFIGEEVKASGIH--VILGPVAGPLGKTPQGGRNWEGFG 131
CONSENSUS       91  -QAMGEEFRGKGVD--VQLGPVAGPLGRSPDGGRNWEGFS 128
SEQ ID NO: 56   94  -QAMGQEFSDKGID--VQLGPAAGPLGRSPDGGRNWEGFS 131
SEQ ID NO: 57   87  -VQMATEFRKKGVN--VLLGPVVGPLGRVAEAGRNWEGFS 124
SEQ ID NO: 58   95  -KAMGEEFNDKGVD--ILLGPAAGPLGKYPDGGRIWEGFS 132
SEQ ID NO: 59   94  -KAMGQEFSDKGAD--IQLGPAAGPLGRSPDGGRNWEGFS 131
SEQ ID NO: 60   140 -EVAREEYLAVGIR--AALHPQVD-LSTEPRWARISGTWG 176
SEQ ID NO: 61   80  -EALADETRSKGAR--VLLAPTVC-IHRHPLGGRNFESFS 116
SEQ ID NO: 62   94  -KAMGQEFSDKGAD--IQLGPAAGPLGRSPDGGRNWEGFS 131
SEQ ID NO: 63   94  -QAMGQEFSDKGAD--IQLGPAAGPLGRSPDGGRNWEGFS 131
SEQ ID NO: 64   94  -QAMGEEFSDKGID--VQLGPAAGPLGAHPDGGRNWEGFS 131
SEQ ID NO: 65   94  -QAMGEEFSDKGID--VQLGPAAGPLGAHPDGGRNWEGFS 131
SEQ ID NO: 66   94  -VGLGEEARGKGIN--VLLGPSVGPIGRKPRGGRNWEGFG 131
SEQ ID NO: 67   94  -QYMGAEFKRKGVN--VALGPVAGPIGRIARGGRNWEGFS 131
SEQ ID NO: 68   100 -KALGEEFRGKGTH--VALGPVAGPLGRHPLGGRNWEGFS 137
SEQ ID NO: 69   94  -KAMGEEHRDKGVD--VQLGPAVGPLGRSPDGGRNWEGFS 131
SEQ ID NO: 70   83  -CAMGEEFRGKGAN--VHLGPSVGPLGRKPRGGRNWEGFG 120
SEQ ID NO: 71   153 -QITSKDTVAVGIP--WVFAPVLG-IGVQPLWSRIYETFG 189
SEQ ID NO: 72   128 -EATALEVRATGIP--YAFAPCIA-VCRDPRWGRCYESYS 164
SEQ ID NO: 73   78  -KMMGKEAIAKSAH--VILGPTIN-MQRSPLGGRGFESIG 114
SEQ ID NO: 74   87  -LHMGGEFKAKGVN--VPLGPNAGPLGRTPLGGRNWEGFS 124
SEQ ID NO: 75   1   ---------------------------------------- 1
SEQ ID NO: 76   94  -TALGSEAKGKGVD--VLLGPVAGPLGRNPNGGRNVEGFG 131
SEQ ID NO: 77   97  ISTQARAFSNSGRYGLDVYAPNVN-GFRSPLWRGRGQETPG 135
SEQ ID NO: 78   78  -KLMAKESIAKNAA--VILGPTTN-MQRGPLGGRGFESFS 114
SEQ ID NO: 79   93  -VYMGAEFRHKGVN--VLLGPVVGPIGRVATGGRNWEGFT 130
SEQ ID NO: 80   128 -AATALEVRATGIP--YAFAPCIA-VCRNPRWGRCYESYS 164
SEQ ID NO: 81   95  -YQMGVEHRGKGVD--VQLGPVVGPIGRHPKGGRNWEGFS 132
SEQ ID NO: 82   94  -YQMGSEHRSKGVD--VQLGPVVGPLGRNPKGGRNWEGFS 131
SEQ ID NO: 83   95  -AAMGAEFKGKGVH--VALGPMMN-LMRVPAAGRNWEGGG 131
SEQ ID NO: 84   95  -AAMGAEFKGKGVH--VALGPMMN-LMRVPAAGRNWEGGG 131
SEQ ID NO: 85   88  -VAIGSEFKGKGAD--AILGPVYGPMGVKAAGGRGWEGHG 125
SEQ ID NO: 86   95  -KDQGAEFYAKGIN--IALAPSMN-ILRAPASGRVWENFG 131
SEQ ID NO: 87   94  -QALGHEFNSKGVH--IALGPAVGPLGVKARGGRNFEAFG 131
SEQ ID NO: 88   94  -QALGHEFNSKGVH--IALGPAVGPLGVKARGGRNFEAFG 131
SEQ ID NO: 89   83  -EYLAEEAKAKGVS--VVLGPTVN-IHRGPLNGRGFESFS 119
SEQ ID NO: 90   85  -RALGSEFRGKGSQ--VHLGPASGALGRHPLGGRNWESFS 122
SEQ ID NO: 91   94  -VAMGEEHRGKGVD--VQLGPVAGPLGRSPDAGRNWEGFA 131
SEQ ID NO: 92   90  -VALGEEARGKGVN--VLMGPMVGPIGRKPRGGRNWEGFG 127
SEQ ID NO: 93   94  -KAMGEEHRGKGVD--VQLGPVAGPLGRHPDGGRNWEGFS 131
SEQ ID NO: 94   94  -KAMGEEHRGKGVD--VQLGPVAGPLGRHPDGGRNWEGFS 131
SEQ ID NO: 95   94  -VALGEEARGKGVN--VLMGPMVGPIGRKPRGGRNWEGFG 131
SEQ ID NO: 96   94  -QFIGEEVKASGIH--VILGPVAGPLGKTPQGGRNWEGFG 131
SEQ ID NO: 97   128 -EATALECRATGIP--YAFAPCIA-VCRDPRWGRCYESYS 164
SEQ ID NO: 98   94  -QAMAEEFRGKGAN--VVLAPMTN-LMRTPQAGRAWEGYG 130
SEQ ID NO: 99   89  -KLLAPEAKLRAAS--LVLAPTSN-IQRNPLGGRSFESFS 125
```

Figure 11A-5

```
SEQ ID NO: 1    132 VD----------PYLTGIAMGQTINGIQSVG-------- 152
CONSENSUS       129 PD----------PYLSGVLAAETIKGIQSAG-------- 149
SEQ ID NO: 56   132 PD----------PALTGVLFAETIKGIQDAG-------- 152
SEQ ID NO: 57   125 ND----------PYLSGALVYETVDGAQSVG-------- 145
SEQ ID NO: 58   133 PD----------PALTGVLFAETIKGIQDAG-------- 153
SEQ ID NO: 59   132 PD----------PALSGVLFAETIKGIQDAG-------- 152
SEQ ID NO: 60   177 EN----------STLTSELIVEYIKGFQGEGKLGP---- 201
SEQ ID NO: 61   117 ED----------PFLAGKLAAQYIKGLQGNG-------- 137
SEQ ID NO: 62   132 PD----------PALSGVLFAETIKGIQDAG-------- 152
SEQ ID NO: 63   132 PD----------PALSGVLFAETIKGIQDAG-------- 152
SEQ ID NO: 64   132 PD----------PALTGVLFAETIKGIQDAG-------- 152
SEQ ID NO: 65   132 PD----------PALTGVLFAETIKGIQDAG-------- 152
SEQ ID NO: 66   132 AD----------PSLQAFGGSLTIKGMQSTG-------- 152
SEQ ID NO: 67   132 ND----------PYLSGALTGDTVRGLQES--------- 151
SEQ ID NO: 68   138 PD----------PYLTGHLMTASITGMQSVG-------- 158
SEQ ID NO: 69   132 PD----------PVLSGYLVAETIKGIQDAG-------- 152
SEQ ID NO: 70   121 SD----------PSLQAIAAVETIKGVQSKG-------- 141
SEQ ID NO: 71   190 ED----------PYVASMMGAAAVRGFQGGNNSFDGPIN 218
SEQ ID NO: 72   165 EDPKVVQSMTTLISGLQGDVPAGSE-GRPYVGGSKK---- 199
SEQ ID NO: 73   115 ED----------PFLAGLGAAALIRGIQSTG-------- 135
SEQ ID NO: 74   125 ID----------PYLSGQLNAETITGMQDAG-------- 145
SEQ ID NO: 75   1   ----------------------MILGCESTG-------- 9
SEQ ID NO: 76   132 SD----------PYLAGLALADTVTGIQNAG-------- 152
SEQ ID NO: 77   136 ED---------AFFLSSAYTYEYITGIQGGVDP-----E 160
SEQ ID NO: 78   115 ED----------PYLAGMATSSVVKGMQGEG-------- 135
SEQ ID NO: 79   131 ND----------PYLAGALVYETTKGIQEN--------- 150
SEQ ID NO: 80   165 EDHRIVRSMTEIIPGLQGDLPAKSKNGVPYVGGKTK---- 200
SEQ ID NO: 81   133 PD----------PVLSGIAVAETVKGIQDAG-------- 153
SEQ ID NO: 82   132 PD----------PYLSGIASAESVRGIQDAG-------- 152
SEQ ID NO: 83   132 GD----------PFLSGELAFETITGIQSSG-------- 152
SEQ ID NO: 84   132 GD----------PFLSGEVAFETITGIQSSG-------- 152
SEQ ID NO: 85   126 PD----------PYLEGVIAYLQTIGIQSQG-------- 146
SEQ ID NO: 86   132 ED----------PYLSGVCGAQITKGYQDSG-------- 152
SEQ ID NO: 87   132 SD----------PYLQGIAAAATIKGLQENN-------- 152
SEQ ID NO: 88   132 SD----------PYLQGTAAAATIKGLQENN-------- 152
SEQ ID NO: 89   120 ED----------STLSGLAASYVILGLQSKN-------- 140
SEQ ID NO: 90   123 PD----------PYLSGVAMDFSIRGIQEMG-------- 143
SEQ ID NO: 91   132 PD----------PVLTGNMMASTIQGIQDAG-------- 152
SEQ ID NO: 92   128 AD----------PTLQAIGGAQTIKGMQSTG-------- 148
SEQ ID NO: 93   132 PD----------PVLTGVLMAETIKGIQDAG-------- 152
SEQ ID NO: 94   132 PD----------PVLTGVLMAETIKGIQDAG-------- 152
SEQ ID NO: 95   132 AD----------PTLQAIGGAQTIKGMQSTG-------- 152
SEQ ID NO: 96   132 VD----------PYLTGIAMGQTINGIQSVG-------- 152
SEQ ID NO: 97   165 EDHTIVQAMTEIIPGLQGDVPPDVKKGVPFVGGKTK---- 200
SEQ ID NO: 98   131 SD----------PYLSGVATVQSVLGIQSTR-------- 151
SEQ ID NO: 99   126 ED----------PYLSGIISASYVNGVQKGG-------- 146
```

Figure 11A-6

```
SEQ ID NO:  1    152  ---VQATAKHYILNEQELNR----------------E  170
CONSENSUS        149  ---VIAYAKHFIGNEQEHFRQAS---------------E  170
SEQ ID NO: 56    152  ---VVATAKHYILNEQEHFRQVAE------AAGYGFNISD 183
SEQ ID NO: 57    145  ---VATCTKHYILNEQETNRNP-G--------MEDGVEVA 173
SEQ ID NO: 58    153  ---VIATAKHYILNEQEHFRQVGE------AQGYGYNITE 184
SEQ ID NO: 59    152  ---VVATAKHYIAYEQEHFRQAPE------AQGYGFNISE 183
SEQ ID NO: 60    201  -KSVKTVTKHFPGGGPMENGEDSH-------------FY 226
SEQ ID NO: 61    137  ---VAATIKHYAANEQETCRFTVN--------------- 158
SEQ ID NO: 62    152  ---VVATAKHYIAYEQEHFRQAPE------AQGFGFNISE 183
SEQ ID NO: 63    152  ---VVATAKHYIAYEQEHFRQAPE------AQGYGFNITE 183
SEQ ID NO: 64    152  ---VIATAKHYIMNEQEHFRQQPE------AAGYGFNVSD 183
SEQ ID NO: 65    152  ---VIATAKHYIMNEQEHFRQQPE------AAGYGFNVSD 183
SEQ ID NO: 66    152  ---AIASLKHLIGNEQEQHRMSS-----------VITQ 176
SEQ ID NO: 67    151  ---VIACVKHLIGNEQETHRSTPS--------MLANSRNQ 180
SEQ ID NO: 68    158  ---VQTSSKHFIGNEQETQRSNSP--------LPDGTNID 187
SEQ ID NO: 69    152  ---VIACVKHFIVNEQERFRQAPE------AQGYGFNISE 183
SEQ ID NO: 70    141  ---VIATIKHLVGNEQEMYRMTN------------IVQR 165
SEQ ID NO: 71    219  APSAVCTAKHYFGYSNPTSGKDRT--------------- 242
SEQ ID NO: 72    199  ---VAACAKHYVGDGGTFMGINEN--------------- 220
SEQ ID NO: 73    135  ---VQATIKHFLCNDQEDRRMVQ--------------- 156
SEQ ID NO: 74    145  ---VIANIKHFIANEQETLRRP----------YFGVE 169
SEQ ID NO: 75    9    ---VISAVKHFVANDQEHERRAVD--------------- 30
SEQ ID NO: 76    152  ---TIACAKHFLLNEQEHFRQVGE------ANGYGYPITE 183
SEQ ID NO: 77    161  HLKVAATVKHFAGYDLENWNNQSR--------------L 185
SEQ ID NO: 78    135  ---IAATVKHFVCNDLEDQRFSSN--------------- 156
SEQ ID NO: 79    150  ---VIACTKHFIGNEQETNRNP----------SGTYNQ 175
SEQ ID NO: 80    200  ---VAACAKHFVGDGGTLHGVDES--------------- 221
SEQ ID NO: 81    153  ---VIACTKHFILNEQEHFRQPGN------VGDFGF--VD 182
SEQ ID NO: 82    152  ---VIACTKHYIMNEQEHFRQPGN------FEDQGF--VD 181
SEQ ID NO: 83    152  ---AQACAKHFINNEQEHFR----------------D 170
SEQ ID NO: 84    152  ---AQACAKHFINNEQEHFR----------------D 170
SEQ ID NO: 85    146  ---VVSTAKHLIGNEQEHFRFAKKDKHAGKIDPGMFNTSS 183
SEQ ID NO: 86    152  ---VIVAAKHYVANDIEHNR----------------E 170
SEQ ID NO: 87    152  ---VMACVKHFIGNEDIYRQPSNSKVDPEYDP---ATKE 186
SEQ ID NO: 88    152  ---VMACVKHFIGNEQEKYRQPDD--INPATNQ---TTKE 184
SEQ ID NO: 89    140  ---VQACIKHFVCNDMEDERNSVS--------------- 161
SEQ ID NO: 90    143  ---VQANRKHFIGNEQETQRSNTF--------TDDGTEIQ 172
SEQ ID NO: 91    152  ---VIACAKHFILYEQEHFRQG---------AQDGYDISD 180
SEQ ID NO: 92    148  ---VIATLKHFIGNEQEMYRMTS-----------VIQR 172
SEQ ID NO: 93    152  ---VIACAKHFIGNEMEHFRQASE------AVGYGFDITE 183
SEQ ID NO: 94    152  ---VIACAKHFIGNEMEHFRQASE------AVGYGFDITE 183
SEQ ID NO: 95    152  ---VIATLKHFIGNEQEMYRMTS-----------VIQR 176
SEQ ID NO: 96    152  ---VQATAKHYILNEQELNR----------------E 170
SEQ ID NO: 97    200  ---VAACAKHFVGDGGTTKGIDEN--------------- 221
SEQ ID NO: 98    151  ---ASACVKHYIGNEQEHYRGGS----------GAT- 174
SEQ ID NO: 99    146  ---IGATIKHFVGNDKEDDRQGYD--------------- 167
```

Figure 11A-7

```
SEQ ID NO:  1   171  TISSNPDDRTLHELYTWPFADAVQAN-VASVMCSYNKVNT  209
CONSENSUS       171  S-SSNIDDRTLHELYLWPFADAVRAG-VGSVMCSYNQVNN  208
SEQ ID NO: 56   184  TISSNVDDKTIHEMYLWPFADAVRAG-VGAIMCSYNQINN  222
SEQ ID NO: 57   174  AVSSNIDDKTMHELYLWPFQDAVLAG-SASIMCSYNRVNN  212
SEQ ID NO: 58   185  TISSNVDDKTMHELYLWPFADAVRAG-VGAVMCSYNQINN  223
SEQ ID NO: 59   184  SGSANLDDKTMHELYLWPFADAIRAG-AGAVMCSYNQINN  222
SEQ ID NO: 60   227  YGKNQTYPGNNIDEHLIPFKAALAAG-ATEIMPYYSRPIG  265
SEQ ID NO: 61   158  ---EHITERALREIYLKPFEIAIKESNPLAVMTAYNIVNG  195
SEQ ID NO: 62   184  SGSANLDDKTMHELYLWPFADAIRAG-AGAVMCSYNQINN  222
SEQ ID NO: 63   184  SGSANLDDKTMHELYLWPFADAIRAG-AGAVMCSYNQINN  222
SEQ ID NO: 64   184  SLSSNVDDKTMHELYLWPFADAVRAG-VGAVMCSYNQINN  222
SEQ ID NO: 65   184  SLSSNVDDKTMHELYLWPFADAVRAG-VGAVMCSYNQINN  222
SEQ ID NO: 66   177  GYSSNIDDRTLHELYLWPFAESVRAG-AGSVMIAYNDVNR  215
SEQ ID NO: 67   181  SSSSNLDDKTMHELYLWPFQDAVKAG-AGSVMCSYNRINN  219
SEQ ID NO: 68   188  AISSNIDDRTLHELYLWPFADAVRAG-TTSILCSYNRINE  226
SEQ ID NO: 69   184  SSSSNVDDVTMHELYLWPFADAVRAG-VGSVMCSYNQINN  222
SEQ ID NO: 70   166  AYSANIDDRTMHELYLWPFAESVRAG-VGAVMMAYNDVNG  204
SEQ ID NO: 71   242  --AAWIPERMLRRYFLPSFAEAITGAGAGTIMINSGEVNG  280
SEQ ID NO: 72   220  --DTIIDAHGLMTIHMPAYYNSIIRG-VSTVMTSYSSWNG  257
SEQ ID NO: 73   156  ---SIVTERALREIYALPFQIAVRDSQPGAFMTAYNGING  193
SEQ ID NO: 74   170  AVSANIDDRTLHEYYLWPFMDSVHAG-VGSVMCSYNRINN  208
SEQ ID NO: 75    30  ---CLITQRALREVYLRPFIVARDARPGALMTSYNKVNG   67
SEQ ID NO: 76   184  ALSSNVDDKTIHEVYGWPFQDAVKAG-VGSFMCSYNQVNN  222
SEQ ID NO: 77   186  GFDAIITQQDLSEYYTPQFLAAARYAKSRSLMCAYNSVNG  225
SEQ ID NO: 78   156  ---SIVSERALREIYLEPFRLAVKHANPVCIMTAYNKVNG  193
SEQ ID NO: 79   176  SVSANIDDKTMHELYLWPFQDSVRAG-LGSIMGSYNRVNN  214
SEQ ID NO: 80   221  --NTVISSNSLFSIHMPAYYDSLRKG-VATVMVSYSSWNG  258
SEQ ID NO: 81   183  AVSANLADKTLHELYLWPFADAVRAG-TGSIMCSYNKANN  221
SEQ ID NO: 82   182  ALSSNLDDKTLHELYLWPFADAVRAG-TGSIMCSYNKVNN  220
SEQ ID NO: 83   171  SSSSNVDDRTEHELYGHPFLRSVQAN-VASVMCSYNQING  209
SEQ ID NO: 84   171  SSSSNVDDRTEHELYGHPFLRSVQAN-VASVMCSYNQING  209
SEQ ID NO: 85   184  SLSSEIDDRAMHEIYLWPFAEVRGG-VSSIMCSYNKLNG   222
SEQ ID NO: 86   171  ASSSNMDDQTLMEIHVEPFYRTIKDGDAGSVMASYNAVNN  210
SEQ ID NO: 87   187  SISANIPDRAMHELYLWPFADSIRAG-VGSVMCSYNRVNN  225
SEQ ID NO: 88   185  AISANIPDRAMHALYLWPFADSVRAG-VGSVMCSYNRVNN  223
SEQ ID NO: 89   161  ---IDVSQRALREVYLMPFQLACKYSNFKSLMTSYNKVNG  198
SEQ ID NO: 90   173  AISSNIDDRTMHELYLWPFANAVRSG-VASVMCSYNRLNQ  211
SEQ ID NO: 91   181  SISANADDKTMHELYLWPFADAVRAG-VGSVMCSYNQVNN  219
SEQ ID NO: 92   173  GYSSNIDDRTLHELYLWPFAEGVRAG-VGSVMMAYNDVNG  211
SEQ ID NO: 93   184  SVSSNIDDKTLHELYLWPFADAVRAG-VGSFMCSYNQVNN  222
SEQ ID NO: 94   184  SVSSNIDDKTLHELYLWPFADAVRAG-VGSFMCSYNQVNN  222
SEQ ID NO: 95   177  GYSSNIDDRTLHELYLWPFAEGVRAG-VGSVMMAYNDVNG  215
SEQ ID NO: 96   171  TISSNPDDRTLHELYTWPFADAVQAN-VASVMCSYNKVNT  209
SEQ ID NO: 97   221  --NTVIDSRGLFSIHMPAYHDSIKKG-VATVMVSYSSWNG  258
SEQ ID NO: 98   175  ASSSNIDDRTLRELYEWPFAEAIHAG-VDYIMCSYNRVNQ  213
SEQ ID NO: 99   167  ---SIISERALREIYLLPFMLTQKYAAPWAIMTAYNRVNG  204
```

Figure 11A-8

```
SEQ ID NO: 1    210  T-----WACEDQYTLQTVLKDQLGF--PGYVMTDWNAQHT  242
CONSENSUS       209  S-----YACQNSKLLNGLLKGELGF--QGFVMSDWGAQHS  241
SEQ ID NO: 56   223  S-----YGCQNSYTLNKLLKAELGF--QGFVMSDWGAHHS  255
SEQ ID NO: 57   213  S-----YGCQNSKTLNGLLKTELGF--QGYVMTDWGAQHA  245
SEQ ID NO: 58   224  S-----YGCQNSQTLNKLLKAELGF--QGFVMSDWSAHHS  256
SEQ ID NO: 59   223  S-----YGCQNSYTLNKLLKAELGF--QGFVMSDWAAHHA  255
SEQ ID NO: 60   266  TNWEAVGFSFNKEIVTDLLRGELGF--DGIVLTDWGLITD  303
SEQ ID NO: 61   196  T-----HADSNNFLLRDVLRGEWGW--KGLVMSDWGGTNS  228
SEQ ID NO: 62   223  S-----YGCQNSYTLNKLLKAELGF--QGFVMSDWAAHHA  255
SEQ ID NO: 63   223  S-----YGCQNSYTLNKLLKAELGF--QGFVMSDWAAHHA  255
SEQ ID NO: 64   223  S-----YGCENSETLNKLLKAELGF--QGFVMSDWTAHHS  255
SEQ ID NO: 65   223  S-----YGCENSETLNKLLKAELGF--QGFVMSDWTAHHS  255
SEQ ID NO: 66   216  S-----ACSQNSKLINGILKDELGF--QGFVVTDWLAHIG  248
SEQ ID NO: 67   220  S-----YGCQNSKAMNGLLKGELGF--QGFVVSDWGAQHT  252
SEQ ID NO: 68   227  T-----YACENPHLLNNILKGELGF--QGYVVSDWFATHS  259
SEQ ID NO: 69   223  S-----YGCSNSYTQNKLLKGELGF--QGFIMSDWQAHHS  255
SEQ ID NO: 70   205  S-----ASCQNSKLINGILKDELGF--QGFVMTDWYAQIG  237
SEQ ID NO: 71   281  V-----PMHTSYKYLTEVLRGELQF--EGVAVTDWQDIEK  313
SEQ ID NO: 72   258  K-----KMHANHFLVTDFLKNLKF--RGFVISDWQGIDR   290
SEQ ID NO: 73   194  V-----SCSENPKYLDGMLRKEWGW--DGLIMSDWYGTYS  226
SEQ ID NO: 74   209  T-----YGCMNDKLMNGILKAELGF--QGFVMLDWNAQHD  241
SEQ ID NO: 75   68   K-----HVADSAEFLQGILRTEWNW--DPLIVSDWYGTYT  100
SEQ ID NO: 76   223  S-----YACQNSKLINGLLKEEYGF--QGFVMSDWQAQHT  255
SEQ ID NO: 77   226  V-----PSCANSFFLQTLLRESWGFPEWGYVSSDCDAVYN  260
SEQ ID NO: 78   194  D-----HCSQSKKLLIDILRDEWKW--DGMLMSDWFGTYT  226
SEQ ID NO: 79   215  S-----YACKNSKVLNGLLKSELGF--QGFVVSDWGGQHT  247
SEQ ID NO: 80   259  R-----KMHANRDLVTGFLKDKLKF--RGFVISDWQGIDR  291
SEQ ID NO: 81   222  S-----QVCQNSYLQNYILKGELGF--QGFTMSDWDAQHS  254
SEQ ID NO: 82   221  S-----QACQNSYLQNYILKGELGF--QGFIMSDWDAQHS  253
SEQ ID NO: 83   210  T-----FSCENEKTLSGLLKGEYGF--QGYVMSDWWATHS  242
SEQ ID NO: 84   210  T-----FSCENEKTLSGLLKGEYGF--QGYVMSDWWATHS  242
SEQ ID NO: 85   223  S-----HACQNSYLLNYLLKEELGF--QGFVMTDWGALYS  255
SEQ ID NO: 86   211  I-----YVVQNKKVLTEILKEGIGF--QGFVMSDWWAIHD  243
SEQ ID NO: 87   226  T-----YSCENSYMINHLLKEELGF--QGFVVSDWAAQMS  258
SEQ ID NO: 88   224  T-----YACENSYMMNHLLKEELGF--QGFVVSDWGAQLS  256
SEQ ID NO: 89   199  E-----HVSQSRILLDNILRKEWEW--KGTIISDWFGTYS  231
SEQ ID NO: 90   212  T-----YACENSKLMNGILKGELGF--QGYVVSDWYATHS  244
SEQ ID NO: 91   220  S-----YACSNSYTMNKLLKSELGF--QGFVMTDWGGHHS  252
SEQ ID NO: 92   212  S-----ACSQNSKLINGILKDELGF--QGFVMTDWLTQIG  244
SEQ ID NO: 93   223  S-----YSCSNSYLLNKLLKSELDF--QGFVMSDWGAHHS  255
SEQ ID NO: 94   223  S-----YSCSNSYLLNKLLKSELDF--QGFVMSDWGAHHS  255
SEQ ID NO: 95   216  S-----ACSQNSKLINGILKDELGF--QGFVMTDWLTQIG  248
SEQ ID NO: 96   210  T-----WACEDQYTLQTVLKDQLGF--PGYVMTDWNAQHA  242
SEQ ID NO: 97   259  L-----RMHANRDLVTGYLKNKLKF--RGFVISDWEGIDR  291
SEQ ID NO: 98   214  T-----YACENSKLINGIAKGEHKF--QGVMVTDWAAAES  246
SEQ ID NO: 99   205  V-----HVAEDPFLLKQVLRNEWKY--KGLIMSDWFGMYS  237
```

Figure 11A-9

```
SEQ ID NO: 1    243 TVQSANSGLDMSMP----------G-TDFNG----NNRLW 267
CONSENSUS       242 GVGSALAGLDMSMP----------GD--F------GTSYW 263
SEQ ID NO: 56   256 GVGSALAGLDMSMP----------GDITFDS----ATSFW 281
SEQ ID NO: 57   246 GIAGANAGLDMVMP------------------STETWG 265
SEQ ID NO: 58   257 GVGAALAGLDMSMP----------GDISFDD----GLSFW 282
SEQ ID NO: 59   256 GVSGALAGLDMSMP----------GDVDYDS----GTSYW 281
SEQ ID NO: 60   304 TYIGNQYMPARAWGVEYLSELQRAARILDAGCDQFGGEER 343
SEQ ID NO: 61   229 TADALNAGLDLEMPG--------------------PTRWR 248
SEQ ID NO: 62   256 GVSGALAGLDMSMP----------GDVDYDS----GTSYW 281
SEQ ID NO: 63   256 GVSGALAGLDMSMP----------GDVDYDS----GTSYW 281
SEQ ID NO: 64   256 GVGAALAGLDMSMP----------GDVTFDS----GTSFW 281
SEQ ID NO: 65   256 GVGAALAGLDMSMP----------GDVTFDS----GTSFW 281
SEQ ID NO: 66   249 GVSSALAGLDMSMP----------GDGAIP---LLGTSYW 275
SEQ ID NO: 67   253 GIASAAAGLDMAMP------------------SSSYWE 272
SEQ ID NO: 68   260 GYPAANAGLDMDMPG---------YIS--QSAINTGETYF 288
SEQ ID NO: 69   256 GVGDDLAGLDMSMP----------GDTLFLT----GKSYW 281
SEQ ID NO: 70   238 GVSSALAGLDMSMP----------GDGSVP---LSGTSFW 264
SEQ ID NO: 71   314 LVYFHHTAGSAEEAIL--------QALDAGIICLCHDLLS 345
SEQ ID NO: 72   291 ITSPPGVNYSYSVEAG-------VGAGIDMIMVPFAYTEF 323
SEQ ID NO: 73   227 TTEAVVAGLDLEMPG--------------------PPRFR 246
SEQ ID NO: 74   241 -LQSANAGLDMVMP--------------------LGGSWG 260
SEQ ID NO: 75   101 TIDAIKAGLDLEMPG--------------------VSRYR 120
SEQ ID NO: 76   256 GVASVAGLDMTMP----------GDTAFNT----GASYF 281
SEQ ID NO: 77   261 VFNPHDYASNQSSAAAS---------SLRAGTDIDCGQTY 291
SEQ ID NO: 78   227 TAAAIKNGLDIEFPG--------------------PTRWR 246
SEQ ID NO: 79   248 GIASANAGLDMAMP------------------SSTYWE 267
SEQ ID NO: 80   292 ITDPPHANYSYSVQAG-------IMAGIDMIMVPENYREF 324
SEQ ID NO: 81   255 GVASTLAGLDMNMP----------GDTDFDS----GFSFW 280
SEQ ID NO: 82   254 GVASTFAGLDMTMP----------GDTDFNS----GKTFW 279
SEQ ID NO: 83   243 GAPAVNAGLDMTMP----------GDETTNS----GTTYF 268
SEQ ID NO: 84   243 GAPAVNAGLDMTMP----------GDETLSS----GTTYF 268
SEQ ID NO: 85   256 GIDAANAGLDMDMP----------CEAQ----------YF 275
SEQ ID NO: 86   244 LEGSFNAGMDMNMP----------GGKAWGP-DYVNNSFW 272
SEQ ID NO: 87   259 GAYSAISGLDMSMP----------GELLGGW--NTGKSYW 286
SEQ ID NO: 88   257 GVYSAISGLDMSMP----------GEVYGGW--NTGTSFW 284
SEQ ID NO: 89   232 LKKAIDAGLDLEMPG--------------------KPRFR 251
SEQ ID NO: 90   245 GVESVNAGLDMTMPG--------PLDSPSTALRPPPSYL 275
SEQ ID NO: 91   253 GVGSALAGLDMSMP----------GDIAFDS----GTSFW 278
SEQ ID NO: 92   245 GVSSALAGLDMAMP----------GDGPIP---LFGDSYW 271
SEQ ID NO: 93   256 GVGAALAGLDMSMP----------GDTAFGT----GKSFW 281
SEQ ID NO: 94   256 GVGAALAGLDMSMP----------GDTAFGT----GKSFW 281
SEQ ID NO: 95   249 GVSSALAGLDMAMP----------GDGPIP---LFGDSYW 275
SEQ ID NO: 96   243 TVQSANSGLDVSMP----------G-TDFNG----NNRLW 267
SEQ ID NO: 97   292 ITDPPGRNYSYSVEAG-------VGAGIDMIMVPEDFTKF 324
SEQ ID NO: 98   247 GVRTALAGTDMNMPGFMA-----YGQPSEPNPSTANGSYW 281
SEQ ID NO: 99   238 VDHGIKAGLDLEMPG--------------------INKWR 257
```

Figure 11A-10

```
SEQ ID NO:  1   268 GPALTNAVNSNQVPTSR--VDDMVTRILAAWYLTGQDQ-- 303
CONSENSUS       264 GTNLTNAVLNGTVPQWR--LDDMATRILAAYYKVGQD--D 299
SEQ ID NO: 56   282 GTNLTIAVLNGTVPQWR--VDDMAVRIMAAYYKVGRDR-L 318
SEQ ID NO: 57   266 AN-LTTAISNGTMDASR--LDDMATRIIASWYQMNQD-SD 301
SEQ ID NO: 58   283 GTNLTVSVLNGTVPAWR--VDDMAVRIMTAYYKVGRDR-L 319
SEQ ID NO: 59   282 GTNLTVSVLNGTVPQWR--VDDMAVRIMAAYYKVGRDR-L 318
SEQ ID NO: 60   344 PELIVQLVREGTISEDR--IDVSVARLLKEKFLLGLFDNP 381
SEQ ID NO: 61   249 KVDEVLAVVKSGAVLEE-TIDERARNVLELLAKLN----- 282
SEQ ID NO: 62   282 GTNLTISVLNGTVPQWR--VDDMAVRIMAAYYKVGRDR-L 318
SEQ ID NO: 63   282 GTNLTISVLNGTVPQWR--VDDMAVRIMAAYYKVGRDR-L 318
SEQ ID NO: 64   282 GANLTVGVLNGTIPQWR--VDDMAVRIMAAYYKVGRDT-K 318
SEQ ID NO: 65   282 GANLTVGVLNGTIPQWR--VDDMAVRIMAAYYKVGRDT-K 318
SEQ ID NO: 66   276 SWELSRSVLNGSVPVER--LNDMVTRIVATWYKMGQDK-D 312
SEQ ID NO: 67   273 NGTLALAVKNESLPSTR--LDDMATRIVATWYKY----AE 306
SEQ ID NO: 68   289 GPHLISAIQAGNMTEDR--LDDMVTRIMTSYFLLNQS-SN 325
SEQ ID NO: 69   282 GPNLTIAVTNGTIPQWR--LDDMAVRIMAAYYKVRRDQ-T 318
SEQ ID NO: 70   265 ASELSRSILNGTVALDR--LNDMVTRIVATWFKFGQDK-D 301
SEQ ID NO: 71   346 QLFSLEILAAGTVPESR--LDLSVRRILNLKYALGLFSNP 383
SEQ ID NO: 72   324 IDDLTYQVKNNIIPMSR--INDAVYRILRVKFTMGLFESP 361
SEQ ID NO: 73   247 GETLKFNVSNGKPFIH--VIDQRAREVLQFVKKCAA---- 280
SEQ ID NO: 74   261 KN-LTDAVANGTVSESR--ITDMATRIIAAWYLVGQDGNN 297
SEQ ID NO: 75   120 -GKYIESALQARLLKQS-TIDERARRVLRFAQKASH--LK 156
SEQ ID NO: 76   282 GSNLTLAVLNGTVPEWR--IDDMVMRIMAPFFKVGKTVDS 319
SEQ ID NO: 77   292 PWHLNESFVAGEVSRGE--IERSVTRLYANLVRLGYFDKK 329
SEQ ID NO: 78   247 TRALVSHSLNSREQITTEDVDDRVRQVLKMIKFVVDNLEK 286
SEQ ID NO: 79   268 EG-LIEAVKNGTVDQSR--LDDMATRIIAAWYKY----AR 300
SEQ ID NO: 80   325 IDTLTSQVKANIIPMSR--IDDAVKRILRVKFVMGLFENP 362
SEQ ID NO: 81   281 GPNMTLSIINGTVPEWR--LDDAATRIMAAYYLVGRDR-H 317
SEQ ID NO: 82   280 GTNFTTSILNGTVPQWR--LDDAVTRIMAAFYYVGRDK-A 316
SEQ ID NO: 83   269 GQNLVNAVNSGQVSQAR--IKDMATRILAAWYLLGQDNF 306
SEQ ID NO: 84   269 GQNLVNAVNSGQVSQAR--VKDMATRILAAWYLLGQDNF 306
SEQ ID NO: 85   276 GGNLTTAVLNGTLPQDR--LDDMATRILSALIYSGVHNPD 313
SEQ ID NO: 86   273 GSNISNAIRSGQVSSSR--LDDAVRRIIRTLYRFDQMS-G 309
SEQ ID NO: 87   287 GQNLTKAVYNETVPIER--LDDMATRILAALYATNSFPTK 324
SEQ ID NO: 88   285 GQNLTKAIYNETVPIER--LDDMATRILAALYATNSFPTE 322
SEQ ID NO: 89   252 NVNTIQHLVGSKELSES-ILDERAKNVLKLVKHS----WQ 286
SEQ ID NO: 90   276 GGNLTEAVLNGTIPEAR--VDDMARRILMPYFFLGQD-TD 312
SEQ ID NO: 91   279 GTNLTVAVLNGSIPEWR--VDDMAVRIMSAYYKVGRDR-Y 315
SEQ ID NO: 92   272 GSELSRAVLNGTVPVDR--LNDMVTRIVATWYKFGQDK-D 308
SEQ ID NO: 93   282 GTNLTIAVLNGTVPEWR--VDDMAVRIMAAFYKVGRDR-Y 318
SEQ ID NO: 94   282 GTNLTIAVLNGTVPEWR--VDDMAVRIMAAFYKVGRDR-Y 318
SEQ ID NO: 95   276 GSELSRAVLNGTVPVDR--LNDMVTRIVATWYKFGQDK-D 312
SEQ ID NO: 96   268 GPALTNAVNSNQVPTSR--VDDMVTRILAAWYLTGQDQ-- 303
SEQ ID NO: 97   325 LNELTSQVKKNIIPMSR--IDDAVKRILRVKFVMGLFESP 362
SEQ ID NO: 98   282 GLRMIEAVKNGTVPMER--LDDMVTRVISTYYKQGQDKSD 319
SEQ ID NO: 99   258 TLDLVNRTIQARKLTPR-DIKDRARVVLELVKKCAQG--A 294
```

Figure 11A-11

```
SEQ ID NO: 1    303  ---AGYPSFNISR------------------------NVQ         316
CONSENSUS       300  YPPPNFSSWTRDEYGYEY--------------VNQ-VDVQ         324
SEQ ID NO: 56   319  YQPPNFSSWTRDEYGFKYFYPQEGP----YEKVNHFVNVQ         354
SEQ ID NO: 57   302  FPSPGAGMPSDMYAPHQR---------------VIGRDAS         326
SEQ ID NO: 58   320  RIPPNFSSWTRDEYGWEHSAVSEGA----WTKVNDFVNVQ         355
SEQ ID NO: 59   319  WTPPNFSSWTRDEYGYKYYVSEGP----YEKVNHYVNVQ          354
SEQ ID NO: 60   382  FVNASAANNIVGNEHFVN----------------------         399
SEQ ID NO: 61   283  CFENPTIPEEKAINRPEHQKLIRSVGSQGLVLLKNEGDVL         322
SEQ ID NO: 62   319  WTPPNFSSWTRDEYGYKYYVSEGP----YEKVNQYVNVQ          354
SEQ ID NO: 63   319  WTPPNFSSWTRDEYGFKYYVSEGP----YEKVNQFVNVQ          354
SEQ ID NO: 64   319  YTPPNFSSWTRDEYGFAHNHVSEGA----YERVNEFVDVQ         354
SEQ ID NO: 65   319  YTPPNFSSWTRDEYGFAHNHVSEGA----YERVNEFVDVQ         354
SEQ ID NO: 66   313  YPLPNFSSNTEDETGPLYPGALFSP----SGIVNQYVNVQ         348
SEQ ID NO: 67   307  IENPGHGLPYSLLAPHNL---------------TDARDPK         331
SEQ ID NO: 68   326  YPTPDPSQTYVMANMYGY---------DYGAQIPARDVR          355
SEQ ID NO: 69   319  QVPINFNSWTRDEFGYLHAGGQEG-----YGRVNQMVNVR         353
SEQ ID NO: 70   302  FPLPNFSSYTQNAKGLLYPGALFSP----LGVVNQFVNVQ         337
SEQ ID NO: 71   384  YPNPNAAIVDTIGQVQD----------------------          400
SEQ ID NO: 72   362  YADPSLVGELGKQEHR-----------------------          377
SEQ ID NO: 73   281  SGVTENGPETTVNNTPETAALLRKVGNEGIVLLKNENNVL         320
SEQ ID NO: 74   298  FPVPGIGLK-QLTKPHEQ--------------VDARDPA          321
SEQ ID NO: 75   157  VSEVEQGRD-FPED----RVLNRQICGSSIVLLKNENSIL         191
SEQ ID NO: 76   320  LIDTNFDSWTNGEYGYVQAAVNEN-----WEKVNYGVDVR         354
SEQ ID NO: 77   330  NQYRSLGWKDVVKTDAWN---------------------          347
SEQ ID NO: 78   287  TGIVENGPESTSNNTKETSDLLREIAADSIVLLKNKNNYL         326
SEQ ID NO: 79   301  LDDPGFGMPVSLAEDHEL--------------VDARDPA          325
SEQ ID NO: 80   363  MSDPSLANQLGSQEHR-----------------------          378
SEQ ID NO: 81   318  AVPVNFNSWSKDTYGYQHAYAKVG-----YGLINQHVDVR         352
SEQ ID NO: 82   317  RIPVNFDSWSRDTYGFDHYYGKAG-----YSQINSHVDVR         351
SEQ ID NO: 83   307  PA-VNFNSWNSGQG------------------QHVNVS           325
SEQ ID NO: 84   307  PA-VNFNSWNSGQG------------------QHVNVS           325
SEQ ID NO: 85   314  G--PNYNAQTFLTEGHEYFKQQEGD----IVVLNKHVDVR         347
SEQ ID NO: 86   310  YPNVNLKAPSMHADTN-----------------------          325
SEQ ID NO: 87   325  DRLPNFSSFTTKEYGNEFFVDKTSP----VVKVNHFVDPS         360
SEQ ID NO: 88   323  DHLPNFSSWTTKEYGNKYYADNTTE----IVKVNYNVDPS         358
SEQ ID NO: 89   287  NTEAENHCE-LNNDSSCLREALKKFASQSIVLLKNKKKLL         325
SEQ ID NO: 90   313  FPTVDPSTGFVFARTYNYPDEYLTLGGLDYNPPPARDVR          352
SEQ ID NO: 91   316  SVPINFDSWTLDTYGPEHYAVGQG-----QTKINEHVDVR         350
SEQ ID NO: 92   309  FPLPNFSSNTDAATGLLYPGAVFSP----IGVVNQFVDVQ         344
SEQ ID NO: 93   319  QVPVNFDSWTKDEYGYEHALVGQN-----YVKVNDKVDVR         353
SEQ ID NO: 94   319  QVPVNFDSWTKDEHGYEHALVGQD-----YVKVNDKVDVR         353
SEQ ID NO: 95   313  FPLPNFSSNTDAATGLLYPGAVFSP----IGVVNQFVDVQ         348
SEQ ID NO: 96   303  ---AGYPSFNISR------------------------NVQ         316
SEQ ID NO: 97   363  LADYSLANQLGSQEHR-----------------------          378
SEQ ID NO: 98   320  YPKLNFMSMGQGTP---------AE----QAVSNHHVNVQ         346
SEQ ID NO: 99   295  PEILDGDEERTVELESDKLLMRRIASESIVLLKNDN-VL          333
```

Figure 11A-12

```
SEQ ID NO: 1    317 GNH--------------KTNVRAIARDGIVLLKN-DANIL 341
CONSENSUS       325 GNH--------------ADLIRRIAAASTVLLKN-DNALP 349
SEQ ID NO: 56   355 RNH--------------SEVIRKLGADSTVLLKN-NNALP 379
SEQ ID NO: 57   327 S----------------KQTLLRGAIEGHVLVKNNHSALP 350
SEQ ID NO: 58   356 RSH--------------SQIIREIGAASTVLLKN-TGALP 380
SEQ ID NO: 59   355 RNH--------------SELIRRIGADSTVLLKN-DGALP 379
SEQ ID NO: 60   399 -----------------LGRDAQRRSYTLLTNNQTILP 420
SEQ ID NO: 61   323 PLRKEILTNKKVALLG-FAREALIHGGGSASVNAHYRVTP 361
SEQ ID NO: 62   355 RNH--------------SELIRRIGADSTVLLKN-DGALP 379
SEQ ID NO: 63   355 RNH--------------SELIRRIGADSTVLLKN-DGALP 379
SEQ ID NO: 64   355 RDH--------------ADLIRRIGAQSTVLLKN-KGALP 379
SEQ ID NO: 65   355 RDH--------------ADLIRRIGAQSTVLLKN-KGALP 379
SEQ ID NO: 66   349 GNH--------------NVTARAIARDAITLLKNNENVLP 374
SEQ ID NO: 67   332 S----------------KSTILQGAVEGHVLVKNTNNALP 355
SEQ ID NO: 68   356 ANH--------------SSLIRQIGSAGTVLLKNTNNILP 381
SEQ ID NO: 69   354 GRH--------------AVIARKVASASTVLLKN-RGVLP 378
SEQ ID NO: 70   338 ADH--------------HKLARVIARESITLLKNEDNLLP 363
SEQ ID NO: 71   400 -----------------REAAAATAEESITLLLFKNNILP 423
SEQ ID NO: 72   377 -----------------DLAREAVRKSLVLLKNGKSAST 399
SEQ ID NO: 73   321 PLSK----KKKTLIVGPNAKQATYHGGGSAALRAYYAVTP 356
SEQ ID NO: 74   322 S----------------KPVLLEGAIAGHVLVKNENNALP 345
SEQ ID NO: 75   192 PLPKS---VKKVALVGSHVRLPAISGGGSASLVPYYAISL 228
SEQ ID NO: 76   355 ANH--------------ANHIREVGAKGTVIFKN-NGILP 379
SEQ ID NO: 77   347 -----------------ISYEAAVEGIVLLKN-DGTLP 367
SEQ ID NO: 78   327 TSKE----RRQYHVIGPNAKAKTSSGGGSASMNSYYVVSP 362
SEQ ID NO: 79   326 A----------------ASTIFQGAVEGHVLVKNEN-ALP 348
SEQ ID NO: 80   378 -----------------ELAREAVRKSLVLLKNGKTPSQ 400
SEQ ID NO: 81   353 ADH--------------FKSIRTAAAKSTVLLKN-NGVLP 377
SEQ ID NO: 82   352 ADH--------------FRSIRRTAAMSTVLLKN-EGALP 376
SEQ ID NO: 83   326 GNH--------------ASLIRTIGAASQILLKN-VNGAL 350
SEQ ID NO: 84   326 GNH--------------ASLIRTIGAASQILLKN-VNSAL 350
SEQ ID NO: 85   348 SDIN-------------RAVALRSAVEGVVLLKNEHETLP 374
SEQ ID NO: 86   325 --------------------RQAAIESSVLLKNADDILP 344
SEQ ID NO: 87   361 NDFT-------------EDTALKVAEESIVLLKNEKNTLP 387
SEQ ID NO: 88   359 NDFT-------------EDTALKVAEESIVLLKNENNTLP 385
SEQ ID NO: 89   326 PLSR----KGTFAVIGPNAKVCNYSGGGSANLKPYYTVSM 361
SEQ ID NO: 90   353 GNH--------------SDIVRKVAAAGTVLLKNVNNVLP 378
SEQ ID NO: 91   351 GNH--------------AEIIHEIGAASAVLLKN-KGGLP 375
SEQ ID NO: 92   345 GDH--------------KVVARAIARDAITLLKNEDNALP 370
SEQ ID NO: 93   354 ADH--------------ADIIRQIGSASVVLLKN-DGGLP 378
SEQ ID NO: 94   354 ADH--------------ADIIRQIGSASVVLLKN-DGGLP 378
SEQ ID NO: 95   349 GDH--------------KVVARAIARDAITLLKNEDNALP 374
SEQ ID NO: 96   317 GNH--------------KTNVRAIARDGIVLLKN-DANIL 341
SEQ ID NO: 97   378 -----------------DLAREAVRKSLVLLKNGESADK 400
SEQ ID NO: 98   347 KDH--------------YLIIRQIATASTILLKNVNHTLP 372
SEQ ID NO: 99   334 PLKPEGGAIKKIAVVGGNAKQVLSGGGSAALKASYFISP 373
```

Figure 11A-13

| | | | |
|---|---|---|---|
| SEQ ID NO: 1 | 342 | PLKKPASIAVVGSAAIIGNHARNS---------------- | 365 |
| CONSENSUS | 350 | LKGKEKKIAVFGED--AGSNPYGA---------------- | 371 |
| SEQ ID NO: 56 | 380 | LTGKERKVAILGED--AGSNSYGA---------------- | 401 |
| SEQ ID NO: 57 | 351 | LKSPQ-LLSVFGYDAKGPNALKQN---------------- | 373 |
| SEQ ID NO: 58 | 381 | LTGKEVKVGVLGED--AGSNPWGA---------------- | 402 |
| SEQ ID NO: 59 | 380 | LTGKERLVALIGED--AGSNPYGA---------------- | 401 |
| SEQ ID NO: 60 | 421 | LAKPGEGTRFYIEGFDSAFMSARN---------------- | 444 |
| SEQ ID NO: 61 | 362 | EEGLRAALGDT-VEFEYAKGAHTFRQLPLMSDNVVNLEGQ | 400 |
| SEQ ID NO: 62 | 380 | LTGKERLVALIGED--AGSNPYGA---------------- | 401 |
| SEQ ID NO: 63 | 380 | LTGKERLVALIGED--AGSNPYGA---------------- | 401 |
| SEQ ID NO: 64 | 380 | LSRKEKLVALLGED--AGSNSWGA---------------- | 401 |
| SEQ ID NO: 65 | 380 | LSRKEKLVALLGED--AGSNSWGA---------------- | 401 |
| SEQ ID NO: 66 | 375 | LKRND---TLKIFGTDAGTNSDGI---------------- | 395 |
| SEQ ID NO: 67 | 356 | LKKPQ-FLSLFGYDAVAAARNTMDDLDWNMWSMGYDNSLT | 394 |
| SEQ ID NO: 68 | 382 | LSKPL-NIGVFGNSAPDPTDG------------------- | 401 |
| SEQ ID NO: 69 | 379 | LKGKEKLTAVIGED--AGPNLWGP---------------- | 400 |
| SEQ ID NO: 70 | 364 | LDPNR---AIKYSEQMPGTNPRGI---------------- | 384 |
| SEQ ID NO: 71 | 424 | LNTNTIKNVLLTGPSADSIRNLNG---------------- | 447 |
| SEQ ID NO: 72 | 400 | PLLPLPKKAGKILVAGSHADDLGN---------------- | 423 |
| SEQ ID NO: 73 | 357 | FDGLSKQLET---PPSYTVGAYTTVPP-ILGEQCLTPDGA | 392 |
| SEQ ID NO: 74 | 346 | FNKKLTMISVFGYDATIPRTKNTDILFQLGYTSSPE---- | 381 |
| SEQ ID NO: 75 | 229 | YDAVSEVLAGA--TITHEVGAYAHQMLPVIDAMISN---- | 262 |
| SEQ ID NO: 76 | 380 | LK-KPKFLTVIGED--AGGNPAGP---------------- | 400 |
| SEQ ID NO: 77 | 368 | LSKKVRSIALIGPWANATTQMQGN---------------- | 391 |
| SEQ ID NO: 78 | 363 | YEGIVNKLGK---EVDYTVGAYSHKSIGGLAESSLIDAAK | 399 |
| SEQ ID NO: 79 | 349 | LKKPK-YISLFGYDGVSTDVNTVG---------------- | 371 |
| SEQ ID NO: 80 | 401 | PLLPLPKKAPKILVAGTHADNLGY---------------- | 424 |
| SEQ ID NO: 81 | 378 | LKGTEKYTAVFGND--AGEAQYGP---------------- | 399 |
| SEQ ID NO: 82 | 377 | LTGSEKWTAVFGDD--AGEGQLGP---------------- | 398 |
| SEQ ID NO: 83 | 351 | PLKKPKTIGIIGNG--AGSNPSGP---------------- | 372 |
| SEQ ID NO: 84 | 351 | PLKKPKTIGIIGNG--AGSNPNGP---------------- | 372 |
| SEQ ID NO: 85 | 375 | LG-REKVKRISILGQAAGDDSKG----------------- | 396 |
| SEQ ID NO: 86 | 345 | LTKKYRKIAIIGKDADKAQS-------------------- | 364 |
| SEQ ID NO: 87 | 388 | IS-PNKVRKLLLSGIAAGPDPKG----------------- | 409 |
| SEQ ID NO: 88 | 386 | IS-PEKAKRLLLSGIAAGPDPIG----------------- | 407 |
| SEQ ID NO: 89 | 362 | YDGIAAKIDG---VPEYALGCHNYLNLPNIANLLVNPRTG | 398 |
| SEQ ID NO: 90 | 379 | LKEPK-SVGIFGNGAADVTEG------------------- | 398 |
| SEQ ID NO: 91 | 376 | LTGTERFVGVFGKD--AGSNPWGV---------------- | 397 |
| SEQ ID NO: 92 | 371 | LKRND---SLKIFGTDAGTNPDGI---------------- | 391 |
| SEQ ID NO: 93 | 379 | LTGYEKFTGVFGED--AGSNRWGA---------------- | 400 |
| SEQ ID NO: 94 | 379 | LTGYEKFTGVFGED--AGSNRWGA---------------- | 400 |
| SEQ ID NO: 95 | 375 | LKRND---SLKIFGTDAGTNPDGI---------------- | 395 |
| SEQ ID NO: 96 | 342 | PLKKPASIAVVGSAAIIGNHARNS---------------- | 365 |
| SEQ ID NO: 97 | 401 | PFVPLPKNAKKILVAGSHADNLGR---------------- | 424 |
| SEQ ID NO: 98 | 373 | LKSPDKMRSVVVVGSDAGDNPQGP---------------- | 396 |
| SEQ ID NO: 99 | 374 | YDGIKAALEPHGVEVTFSEGARAYKTLPTLEWDLETETGE | 413 |

Figure 11A-14

```
SEQ ID NO: 1      365 ------------------------------------------ 365
CONSENSUS         371 ------------------------------------------ 371
SEQ ID NO: 56     401 ------------------------------------------ 401
SEQ ID NO: 57     373 ------------------------------------------ 373
SEQ ID NO: 58     402 ------------------------------------------ 402
SEQ ID NO: 59     401 ------------------------------------------ 401
SEQ ID NO: 60     444 ------------------------------------------ 444
SEQ ID NO: 61     401 P------GWTLDFFADEEP---NGEPGSSISSEQPSYIPL    431
SEQ ID NO: 62     401 ------------------------------------------ 401
SEQ ID NO: 63     401 ------------------------------------------ 401
SEQ ID NO: 64     401 ------------------------------------------ 401
SEQ ID NO: 65     401 ------------------------------------------ 401
SEQ ID NO: 66     395 ------------------------------------------ 395
SEQ ID NO: 67     395 Y----------------------------------------- 395
SEQ ID NO: 68     401 ------------------------------------------ 401
SEQ ID NO: 69     400 ------------------------------------------ 400
SEQ ID NO: 70     384 ------------------------------------------ 384
SEQ ID NO: 71     447 ------------------------------------------ 447
SEQ ID NO: 72     423 ------------------------------------------ 423
SEQ ID NO: 73     393 P------GMRWRVFNEPP----GTPNRQHIDELFFTKTDM   422
SEQ ID NO: 74     381 ------------------------------------------ 381
SEQ ID NO: 75     262 --------AVIHFYNDPI----DVKDRKLLGSENVSSTSF   290
SEQ ID NO: 76     400 ------------------------------------------ 400
SEQ ID NO: 77     391 ------------------------------------------ 391
SEQ ID NO: 78     400 PADAENAGLIAKFYSNPVEE--RSEDEEPFHVTKVNRSNV   437
SEQ ID NO: 79     371 ------------------------------------------ 371
SEQ ID NO: 80     424 ------------------------------------------ 424
SEQ ID NO: 81     399 ------------------------------------------ 399
SEQ ID NO: 82     398 ------------------------------------------ 398
SEQ ID NO: 83     372 ------------------------------------------ 372
SEQ ID NO: 84     372 ------------------------------------------ 372
SEQ ID NO: 85     396 ------------------------------------------ 396
SEQ ID NO: 86     364 ------------------------------------------ 364
SEQ ID NO: 87     409 ------------------------------------------ 409
SEQ ID NO: 88     407 ------------------------------------------ 407
SEQ ID NO: 89     399 K-----HGYVAKFYLEPA----TSENRTLIDDYDLEDGVV   429
SEQ ID NO: 90     398 ------------------------------------------ 398
SEQ ID NO: 91     397 ------------------------------------------ 397
SEQ ID NO: 92     391 ------------------------------------------ 391
SEQ ID NO: 93     400 ------------------------------------------ 400
SEQ ID NO: 94     400 ------------------------------------------ 400
SEQ ID NO: 95     395 ------------------------------------------ 395
SEQ ID NO: 96     365 ------------------------------------------ 365
SEQ ID NO: 97     424 ------------------------------------------ 424
SEQ ID NO: 98     396 ------------------------------------------ 396
SEQ ID NO: 99     414 R------GWIGTWHTHESDDSMTALDQPFIAPRLVDETRI   447
```

Figure 11A-15

```
SEQ ID NO: 1    365 ---------------------------------------- 365
CONSENSUS       371 ---------------------------------------- 371
SEQ ID NO: 56   401 ---------------------------------------- 401
SEQ ID NO: 57   373 -------------------------------FNWLS---- 378
SEQ ID NO: 58   402 ---------------------------------------- 402
SEQ ID NO: 59   401 ---------------------------------------- 401
SEQ ID NO: 60   444 ---------------------------------------- 444
SEQ ID NO: 61   432 FVKESWG---------SVRASAHFTPTQ-SGKHYFGMSG 460
SEQ ID NO: 62   401 ---------------------------------------- 401
SEQ ID NO: 63   401 ---------------------------------------- 401
SEQ ID NO: 64   401 ---------------------------------------- 401
SEQ ID NO: 65   401 ---------------------------------------- 401
SEQ ID NO: 66   395 ---------------------------------------- 395
SEQ ID NO: 67   395 --------------P------NGSAVDAMMLKYIFLSSANP 416
SEQ ID NO: 68   401 -------------------------------LTWPQSD-- 408
SEQ ID NO: 69   400 ---------------------------------------- 400
SEQ ID NO: 70   384 ---------------------------------------- 384
SEQ ID NO: 71   447 ---------------------------------------- 447
SEQ ID NO: 72   423 ---------------------------------------- 423
SEQ ID NO: 73   423 HLVDYYHPKAADT---WYADMEGTYTADE-DCTYELGLVV 458
SEQ ID NO: 74   381 -----------------------MAQAVLGN--- 389
SEQ ID NO: 75   291 QLMDYNNIPTLNKA-MFWGTLVGEFIPTA-TGIWEFGLSV 328
SEQ ID NO: 76   400 ---------------------------------------- 400
SEQ ID NO: 77   391 ---------------------------------------- 391
SEQ ID NO: 78   438 HLFDFKHEKVDPKNPYFFVTLTGQYVPQE-DGDYIFSLQV 476
SEQ ID NO: 79   371 --------------------GG---------FSFFS---- 378
SEQ ID NO: 80   424 ---------------------------------------- 424
SEQ ID NO: 81   399 ---------------------------------------- 399
SEQ ID NO: 82   398 ---------------------------------------- 398
SEQ ID NO: 83   372 ---------------------------------------- 372
SEQ ID NO: 84   372 ---------------------------------------- 372
SEQ ID NO: 85   396 ---------------------------------------- 396
SEQ ID NO: 86   364 ---------------------------------------- 364
SEQ ID NO: 87   409 ---------------------------------------- 409
SEQ ID NO: 88   407 ---------------------------------------- 407
SEQ ID NO: 89   430 RFYDYCN-DKMKDG-YFYIDIEGYLIPDE-DAVYEFGISV 466
SEQ ID NO: 90   398 --------------------------------LTFTGDDS- 406
SEQ ID NO: 91   397 ---------------------------------------- 397
SEQ ID NO: 92   391 ---------------------------------------- 391
SEQ ID NO: 93   400 ---------------------------------------- 400
SEQ ID NO: 94   400 ---------------------------------------- 400
SEQ ID NO: 95   395 ---------------------------------------- 395
SEQ ID NO: 96   365 ---------------------------------------- 365
SEQ ID NO: 97   424 ---------------------------------------- 424
SEQ ID NO: 98   396 ---------------------------------------- 396
SEQ ID NO: 99   448 FISTSYPKGITKR---WTMRLKGYLKPREKDTNFEFGLIA 484
```

Figure 11A-16

```
SEQ ID NO: 1    366  PSCNDKGCDDGALGMGWGSGAVNYP-YFVAPYDAINT-RA  403
CONSENSUS       372  NGCSDRGCDNGTLAMGWGSGTANFP-YLVTPEEAIQN--V  408
SEQ ID NO: 56   402  NGCSDRGCDNGTLAMAWGSGTAEFP-YLVTPEQAIQA-EV  439
SEQ ID NO: 57   378  --YSPAIQENHTLWVGGGSGANNAA-YIDAPIDAIQR--Q  413
SEQ ID NO: 58   403  NGCPDRGCDNGTLAMAWGSGTANFP-YLVTPEQAIQR-EV  440
SEQ ID NO: 59   402  NGCSDRGCDNGTLAMGWGSGTANFP-YLVTPEQAISN-EV  439
SEQ ID NO: 60   444  -----------YTVVNTTEEADFALLRYNAPYEPRN---  469
SEQ ID NO: 61   461  LGRSKLLIDGEVIYEQKLNCPDSMGFLLGGVEEPEIQYSF  500
SEQ ID NO: 62   402  NGCSDRGCDNGTLAMGWGSGTANFP-YLVTPEQAISN-EV  439
SEQ ID NO: 63   402  NGCSDRGCDNGTLAMGWGSGTANFP-YLVTPEQAISN-EV  439
SEQ ID NO: 64   402  NGCDDRGCDNGTLAMAWGSGTANFP-YLVTPEQAIQN-EV  439
SEQ ID NO: 65   402  NGCDDRGCDNGTLAMAWGSGTANFP-YLVTPEQAIQN-EV  439
SEQ ID NO: 66   396  NSCTDKGCNKGVLTMGWGSGTSRLP-YLITPQEAIAN--I  432
SEQ ID NO: 67   417  SAFGPGVALNATTITGGGSGASTAS-YIDAPFNAFQR--Q  453
SEQ ID NO: 68   408  ---LQTGFDIGTLDIGGGSGSARHT-TLISPLTALRT--R  442
SEQ ID NO: 69   401  NGCPDRGCANGTLAMGWGSGTADFP-YLVTPAQAIEN-EV  438
SEQ ID NO: 70   385  NACPDKGCNKGVLTMGWGSGTSNLP-YLVTPEDAIRN--I  421
SEQ ID NO: 71   447  -----------GWSVHWQGAYEDSEFPFGTSILTGLREIT  476
SEQ ID NO: 72   423  --------QCGGWTITWQGQTGNDKTAGTTILSAIKS---  452
SEQ ID NO: 73   459  CGTAKAYVDDQLVVDNATKQVPGDAFFGSATREETGRINL  498
SEQ ID NO: 74   390  EAHFDQAAKGGTIMTGGRAGANAPS-YIDDPLAAIQR--R  426
SEQ ID NO: 75   329  FGTADLYIDNELVIENTTHQTRGTAFFGKGTTEKVATRRM  368
SEQ ID NO: 76   401  NGCGDRGCDDGTLAMEWGSGTTNFP-YLVTPDAALQS-QA  438
SEQ ID NO: 77   391  ------------------YYGPAPYLISPLEAAKKAGY  411
SEQ ID NO: 78   477  YGSGLFYLNDELIIDQKHNQERGSFCFGAGTKERTKKLTL  516
SEQ ID NO: 79   378  --FDVKAIENKTLISGGGSGTNTPS-YVDAPFNAFVA--K  413
SEQ ID NO: 80   424  --------QCGGWTIEWQGVAGNDLTGTTILTAIKK---  453
SEQ ID NO: 81   400  NGCADHGCDNGTLAMGWGSGTADYP-YLVTPLEAIKR-TV  437
SEQ ID NO: 82   399  NGFPDHGGNNGTLAMGWGSGTSDYP-YLVTPLESIKA-TV  436
SEQ ID NO: 83   373  NAFSDRAGDVGVLALGWGSGTANFP-YLVAPVDAITA-RA  410
SEQ ID NO: 84   373  NAFSDRAGDVGVLALGWGSGTANFP-YLVAPVDAITA-RA  410
SEQ ID NO: 85   397  TSCSLRGCGSGAIGTGYGSG-AGTFSYFVTPADGIGA-R  433
SEQ ID NO: 86   364  --CTDTACSGGNIIQGWGSGTTDFT-GISDPITAIKN-RA  400
SEQ ID NO: 87   410  YECSDQSCVDGALFEGWGSGSVGYPKYQVTPFEEISA--N  447
SEQ ID NO: 88   408  YQCEDQSCTNGALFQGWGSGSVGSPKYQVTPFEEISY--L  445
SEQ ID NO: 89   467  FGTALLFIDDVLLIDNKTKQTPTNHTFEFGTIEERNSIYL  506
SEQ ID NO: 90   406  ---GPWGADIGALSVGGGSGAGRHT-HLVSPLAAIRK--R  440
SEQ ID NO: 91   398  NGCSDRGCDNGTLAMGWGSGTANFP-YLVTPEQAIQR-EV  435
SEQ ID NO: 92   392  NSCADKGCDKGVLTMGWGSGTSKLP-YLNTPQEAIAN--A  428
SEQ ID NO: 93   401  DGCSDRGCDNGTLAMGWGSGTADFP-YLVTPEQAIQN-EI  438
SEQ ID NO: 94   401  DGCSDRGCDNGTLAMGWGSGTADFP-YLVTPEQAIQN-EI  438
SEQ ID NO: 95   396  NSCADKGCDKGVLTMGWGSGTSKLP-YLNTPQEAIAN--A  432
SEQ ID NO: 96   366  PSCNDKGCDDGALGMGWGSGAVNYP-YFVAPYDAINT-RA  403
SEQ ID NO: 97   424  --------QCGGWTIEWQGVNGNDLTTGTTILNAIKK---  453
SEQ ID NO: 98   397  NSCVDRGCNRGILAIGWGSGTANFA-HLTAPATSIQNYLL  435
SEQ ID NO: 99   485  AGRAKLWVDGQLVIDNWTRQRRGEAFFGSGSQEETGVYLL  524
```

Figure 11A-17

```
SEQ ID NO: 1    404  SSQGTQVTLSNTDN-------------------TSSGAS-  423
CONSENSUS       409  LSN-KGNVSSVTDN--------------------AL-QIE  426
SEQ ID NO: 56   440  LKH-KGSVYAITDN-------------------WALSQVE  459
SEQ ID NO: 57   414  AYEDGTSVLYDIS-----------------------SED  429
SEQ ID NO: 58   441  ISN-GGNVFAVTDN-------------------GALSQMA  460
SEQ ID NO: 59   440  LKN-KNGVFTATDN-------------------WAIDQIE  459
SEQ ID NO: 60   469  ---GTFEANFHAGS-------------------------  480
SEQ ID NO: 61   501  EAGKTYAVEVVSVKP----TSKGGLALLDGFIGFRLGFMT 536
SEQ ID NO: 62   440  LKH-KNGVFTATDN-------------------WAIDQIE  459
SEQ ID NO: 63   440  LKN-KNGVFTATDN-------------------WAIDQIE  459
SEQ ID NO: 64   440  LQG-RGNVFAVTDS-------------------WALDKIA  459
SEQ ID NO: 65   440  LQG-RGNVFAVTDS-------------------WALDKIA  459
SEQ ID NO: 66   433  SSNAEFHITDTFPL-------------------GVT----  449
SEQ ID NO: 67   454  AYDDDTFLAWDFA---------------------SQN    469
SEQ ID NO: 68   443  AATY-ARVQYLTNNA---------------LLSSSSSSSF 466
SEQ ID NO: 69   439  ITKGVGEAMSVFDN-------------------YATSQIE 459
SEQ ID NO: 70   422  SKNTEFHITDKFPN-------------------NVQ---- 438
SEQ ID NO: 71   477  NDTADFNIQYTIG----------------------HEI   492
SEQ ID NO: 72   453  TVDPSTEVVFSENP--------------------DSA    469
SEQ ID NO: 73   499  VKGNTYKFKIEFGSA-PTYTLKGD-TIVPGHGSLRVGGCK 536
SEQ ID NO: 74   427  ARKDDTWVNWDLD---------------------SFN    442
SEQ ID NO: 75   369  VAGSTYKLRLEFGSA-NTTKMETTGVVNFGGGAVHLGACL 407
SEQ ID NO: 76   439  LQD-GTRYESILSN-------------------YAISQTQ 458
SEQ ID NO: 77   412  HVNFELGTEIAGNS----------------------TT   427
SEQ ID NO: 78   517  KKGQVYNVRVEYGSG-PTSGLVG----EFGAGGFQAGVIK 551
SEQ ID NO: 79   414  AREDNTFLSWDFT--------------------SAE     429
SEQ ID NO: 80   454  TVDPSTQVVYQQNP-------------------DAN     470
SEQ ID NO: 81   438  GDH-GGVIASVTDN-------------------YAFSQIM 457
SEQ ID NO: 82   437  AQN-GGIVTSVTDN-------------------WAYTQIQ 456
SEQ ID NO: 83   411  SQDGTTVSSSLSDT-------------------DLTGAAN 431
SEQ ID NO: 84   411  SQDGTTVSSSLSDT-------------------DLTGAAN 431
SEQ ID NO: 85   434  AQQEKISYEFIGDS-------------------WNQAAAM 454
SEQ ID NO: 86   401  SKEGISIVSSISDS--------------------ANEG   418
SEQ ID NO: 87   448  ARKNKMQFDYIRES-------------------FDLTQVS 468
SEQ ID NO: 88   446  ARKNKMQFDYIRES-------------------YDLAQVT 466
SEQ ID NO: 89   507  KKGRKYNVRVEYGSA-ATYTLSTN-LSPSTGGRYSIGCVK 544
SEQ ID NO: 90   441  TESVGGRVQYLLSNS---------------RIVN---DDF 462
SEQ ID NO: 91   436  LSR-NGTFTGITDN-------------------GALAEMA 455
SEQ ID NO: 92   429  SSNAEFFVTDSFPS-------------------NVN---- 445
SEQ ID NO: 93   439  LSKGKGLVSAVTDN-------------------GALDQME 459
SEQ ID NO: 94   439  LSKGKGLVSAVTDN-------------------GALDQME 459
SEQ ID NO: 95   433  SSNAEFFVTDSFPS-------------------NVN---- 449
SEQ ID NO: 96   404  SSQGTQVTLSNTDN-------------------TSSGAS- 423
SEQ ID NO: 97   454  TVDPTTQVIYNENP-------------------DSN     470
SEQ ID NO: 98   436  QSNPTITYRSIFDD-------------------YAYDEIA 456
SEQ ID NO: 99   525  KAGKKHEIYVEYCNVRAPADGDEDEAIMDSNPGVRLGGAE 564
```

Figure 11A-18

```
SEQ ID NO: 1      424 AARGKD--VAIVFITADSGEGYITVEGNAGDR--------  453
CONSENSUS         427 AVASQA-DVAIVFVNADSGEGYITVDGNEGDR--------  457
SEQ ID NO: 56     460 TLAKQA-SVSLVFVNSDAGEGYISVDGNEGDR--------  490
SEQ ID NO: 57     430 PEVDPTTDACLVFINSYATEG-------WDR--------  453
SEQ ID NO: 58     461 DVASQS-SVSLVFVNADSGEGFISVDGNEGDR--------  491
SEQ ID NO: 59     460 ALAKTA-SVSLVFVNADSGEGYINVDGNLGDR--------  490
SEQ ID NO: 60     480 ----------------------------------------  480
SEQ ID NO: 61     537 EEEHNRDLLSEAVDVAKRSDIAIVFTGHTPDWETEGQDQI  576
SEQ ID NO: 62     460 ALAKTA-SVSLVFVNADSGEGYINVDGNLGDR--------  490
SEQ ID NO: 63     460 ALAKTA-SVSLVFVNADSGEGYINVDGNLGDR--------  490
SEQ ID NO: 64     460 AAARQA-SVSLVFVNSDSGESYLSVDGNEGDR--------  490
SEQ ID NO: 65     460 AAARQA-SVSLVFVNSDSGEYLSVDGNEGDR--------  490
SEQ ID NO: 66     449 --AGPD-DIAIVFINSDSGENYITVDGNPGDRTL------  480
SEQ ID NO: 67     470 PLVNPASDACIVFINEQSSEG-------WDR--------  493
SEQ ID NO: 68     467 AGIYPIPEICLVFLKTFSSEG-------VDR--------  490
SEQ ID NO: 69     460 SVVSQA-TVSLVFVNAGAGEGFISVDGNEGDR--------  490
SEQ ID NO: 70     438 --PGPD-DVAIVFVNADSGENYIIVESNPGDRTV------  469
SEQ ID NO: 71     493 GVPTNQTSIDEAVELAQSSDVVVVVIGELPEAETPG---D  529
SEQ ID NO: 72     470 AVDSGKYDYAIVVVGEPPYAETFGDN-------------  495
SEQ ID NO: 73     537 VIDDQ-AEIEKSVALAKEHDQVIICAGLNADWETEGADRA  575
SEQ ID NO: 74     443 PEVNAASDACLVFINAIATEG-------WDR--------  466
SEQ ID NO: 75     408 KVDPQ-EMIARAVKAAADADYTIICTGLSGEWESEGFDRP  446
SEQ ID NO: 76     459 ALVSQPDAIAIVFANSDSGEGYINVDGNEGDR--------  490
SEQ ID NO: 77     428 GFAKAIAAAKKSDAIIYLGGIDNTIEQEGADR--------  459
SEQ ID NO: 78     552 AIDDD-EEIRNAAELAAKHDKAVLIIGLNGEWETEGYDRE  590
SEQ ID NO: 79     430 PVANPASDACIDFINAAASEG-------YDR--------  453
SEQ ID NO: 80     471 FVKSNKFSYAIVVVGEVPYAEMFGDS-------------  496
SEQ ID NO: 81     458 ALAKQA-THAIVFVNADSGEGYITVDGNEGDR--------  488
SEQ ID NO: 82     457 TLAKQA-SVAIVFVNADSGEGYITVDGNAGDR--------  487
SEQ ID NO: 83     432 TATGKD--VAMVFITADSGEGYLTVEGNAGDR--------  461
SEQ ID NO: 84     432 TATGKD--VAMVFITADSGEGYLTVEGNAGDR--------  461
SEQ ID NO: 85     455 DSALYA-DAAIEVANSVAGEEIGDVDGNYGDL--------  485
SEQ ID NO: 86     419 ANVAKDADVAVVFVRATSGEEYIVVDNNKGDR--------  450
SEQ ID NO: 87     469 TVASDA-HMSIVVVSAVSGEGYLIIDGNRGDK--------  499
SEQ ID NO: 88     467 KVASDA-HLSIVVVSAASGEGYITVDGNQGDR--------  497
SEQ ID NO: 89     545 VIDPE-TEIDYAVRVAKSVDCVILCVGLTAEWETEGEDRK  583
SEQ ID NO: 90     463 TSIYPTPEVCLVFLKTWAREG-------TDR--------  486
SEQ ID NO: 91     456 AAASQA-DTCLVFANADSGEGYITVDGNEGDR--------  486
SEQ ID NO: 92     445 --ANPE-DIAIVFINADSGENYITVEGNYGDRSA------  476
SEQ ID NO: 93     460 QVASQA-SVSIVFVNADSGEGYINVDGNEGDR--------  490
SEQ ID NO: 94     460 QVASQA-SVSIVFVNADSGEGYINVDGNEGDR--------  490
SEQ ID NO: 95     449 --ANPE-DIAIVFINADSGENYITVEGNYGDRSA------  480
SEQ ID NO: 96     424 AARGKD--VAIVFITADSGEGYITVEGNAGDR--------  453
SEQ ID NO: 97     471 YVKTNSFDYAIVVVGEPPYAEMQGDS-------------  496
SEQ ID NO: 98     457 KAASTA-DVSIVHVSSDSGEGYLTVEGNQGDR--------  487
SEQ ID NO: 99     565 VANAD-DLLSEAVKLASEADAVIAVVGLNADWETEGNDRR  603
```

Figure 11A-19

| | | | |
|---|---|---|---|
| SEQ ID NO: 1 | 453 | -NNLDPWHNGNALVQAVAGANS-NVIVVVHSVGAIILEQI | 491 |
| CONSENSUS | 457 | -NNLTLWHNGDNLIKAVASNCN-NTVVVIHSVGPVLVEEW | 495 |
| SEQ ID NO: 56 | 490 | -NNLTLWKNGDNLIKAAANNCN-NTIVVIHSVGPVLVDEW | 528 |
| SEQ ID NO: 57 | 453 | -PGLADNSSDTLVKN-VARKCA-NTIVTIHNAGIRVVGEW | 490 |
| SEQ ID NO: 58 | 491 | -KNLTLWKNGEAVIDTVVSHCN-NTIVVIHSVGPVLIDRW | 529 |
| SEQ ID NO: 59 | 490 | -KNLTLWRNGDNVIKAAASNCN-NTIVIIHSVGPVLVNEW | 528 |
| SEQ ID NO: 60 | 480 | ---LAFNATEKARQAKIYSSLP--TIVDIILDRPAVIPEV | 515 |
| SEQ ID NO: 61 | 577 | SFHLPSNGSQDRLVAAVGAANP-NTVVVNCTGVAVAMP-- | 613 |
| SEQ ID NO: 62 | 490 | -RNLTLWRNGDNVIKAAASNCN-NTIVVIHSVGPVLVNEW | 528 |
| SEQ ID NO: 63 | 490 | -RNLTLWRNGDNVIKAAASNCN-NTIVIIHSVGPVLVNEW | 528 |
| SEQ ID NO: 64 | 490 | -NNITLWKNGDNVVKTAANNCN-NTVVIIHSVGPVLIDEW | 528 |
| SEQ ID NO: 65 | 490 | -NNITLWKNGDNVVKTAANNCN-NTVVIIHSVGPVLIDEW | 528 |
| SEQ ID NO: 66 | 480 | -AGLHAWHNGDNLVKAAAEKFS-NVVVVVHTVGPILMEEW | 518 |
| SEQ ID NO: 67 | 493 | -PYLADPYSDTLVQN-VASQCS-NTMVVIHNAGVRLVDRW | 530 |
| SEQ ID NO: 68 | 490 | -TSYPLDWNSTLVVNNVASFCQGNTIVITHSSGINTLP-F | 528 |
| SEQ ID NO: 69 | 490 | -KNLTLWKNGDELIKTVASMCN-NTVVVMHTAGPVLVNKW | 528 |
| SEQ ID NO: 70 | 469 | -AQMKLWHNGDELIESAAKKFSNVVVVVVHTVGPIIMEKW | 508 |
| SEQ ID NO: 71 | 530 | IYDLSMDPNEVLLLQQLVDTGK-PVVLILVEARPRILPP- | 567 |
| SEQ ID NO: 72 | 495 | -LNLTIPAPGPSVIQNVCKSVR--CVVVLISGRPLVVEP- | 531 |
| SEQ ID NO: 73 | 576 | SMKLP--GVLDQLIADVAAANP-NTVVVMQTGPEEMP-- | 610 |
| SEQ ID NO: 74 | 466 | -DGLHDDFSDGLVLN-VAANCS-NTIVVVHAAGTRLVDQW | 503 |
| SEQ ID NO: 75 | 447 | HMDLP--PGVDTMISQVLDAAP-NAVVVNQSGTPVTMS-- | 481 |
| SEQ ID NO: 76 | 490 | -KNLTLWKNGDDLIKTVAANP-KTIVVIHSTGPVILKDY | 528 |
| SEQ ID NO: 77 | 459 | -TDIAWPGNQLDLIKQLSEVGK-PLVVLQMGGGQVDSSSL | 497 |
| SEQ ID NO: 78 | 591 | NMDLP--KRTNELVRAVLKANP-NTVIVNQSGTPVEFP-- | 625 |
| SEQ ID NO: 79 | 453 | -PNLADKYSDKLVEA-VASQCS-NTIVVIHNAGIRLVDNW | 490 |
| SEQ ID NO: 80 | 496 | -SNLTIAEPGPSTISNICGSVK--CVVVVVSGRPVVLEP- | 532 |
| SEQ ID NO: 81 | 488 | -NNLTLWQNGEELVRNVSGYCN-NTIVVIHSVGPVLDSF | 526 |
| SEQ ID NO: 82 | 487 | -NNLTLWQDGDTLIKNVSSLCN-NTIVVIHSVGPVLVNSF | 525 |
| SEQ ID NO: 83 | 461 | -NDLQAWHGGDALVQQVASHNK-NTIVVINSVGPINMEAW | 499 |
| SEQ ID NO: 84 | 461 | -NDLQAWHGGDALVQQVASHNK-NTIVVINSVGPINMEAW | 499 |
| SEQ ID NO: 85 | 485 | -NNLTLWHNAVPLIKNISSINN-NTIVIVTSGQQIDLEPF | 523 |
| SEQ ID NO: 86 | 450 | -NNLDWHGGNDLVKSVAAVNK-NTVVVIHAPATVNLP-F | 487 |
| SEQ ID NO: 87 | 499 | -NNVTLWHNSDNLIKAVAENCA-NTVVVITSTGQVDVESF | 537 |
| SEQ ID NO: 88 | 497 | -KNLTLWNNGDKLIETVAENCA-NTVVVVTSTGQINFEGF | 535 |
| SEQ ID NO: 89 | 584 | TMTLP--SLSDKLVYSILQSNP-NTVVVTQSGTPIEMP-- | 618 |
| SEQ ID NO: 90 | 486 | -LSYENDWNSTAVVNNVARRCP-NTIVVTHSGGINTMP-W | 523 |
| SEQ ID NO: 91 | 486 | -KNLTLWQGADQVIHNVSANCN-NTVVVLHTVGPVLIDDW | 524 |
| SEQ ID NO: 92 | 476 | -AGLYAWHNGDDLVKAAAKFS-KVVVVVHTVGPIILENW | 514 |
| SEQ ID NO: 93 | 490 | -KNLTLWKGGEEVIKTVAANCN-NTIVMHTVGPVLIDEW | 528 |
| SEQ ID NO: 94 | 490 | -KNLTLWKGGEEVIKTVAANCN-NTIVMHTVGPVLIDEW | 528 |
| SEQ ID NO: 95 | 480 | -AGLYAWHNGDDLVKAAAAKFS-KVVVVVHTVGPIILENW | 518 |
| SEQ ID NO: 96 | 453 | -NNLDPWHNGNALVQAVAGANS-NVIVVVHSVGAIILEQI | 491 |
| SEQ ID NO: 97 | 496 | -FNLTIPEPGPTTISSVCGAVK--CVVVVISGRPVVLQP- | 532 |
| SEQ ID NO: 98 | 487 | -SNTSLWNKGDELILKAAEACN-NVVVVIHSVGPVDMEAW | 525 |
| SEQ ID NO: 99 | 604 | TLALP--GRTDELVEKVAKVNS-KTVVVTQAGSAITLP-- | 638 |

Figure 11A-20

```
SEQ ID NO: 1    492  LALPQVKAVVWAGLPSQESGNALVDVLWGDVSPSGKLVYT  531
CONSENSUS       496  YDHPNVTAIVWAGLPGQESGNALADVLYGRVNPSGKLPFT  535
SEQ ID NO: 56   529  YDHPNVTAILWAGLPGQESGNSLADVLYGRVNPGAKSPFT  568
SEQ ID NO: 57   491  IDHENVTAVIFAHLPGQDSGRALVELLYGRANPSGKLPYT  530
SEQ ID NO: 58   530  YDNPNVTAIIWAGLPGQESGNSLVDVLYGRVNPSAKTPFT  569
SEQ ID NO: 59   529  YDNPNVTAILWGGLPGQESGNSLADVLYGRVNPGAKSPFT  568
SEQ ID NO: 60   516  VEQAQAVLASYGSD-----SEAFLDVVFGVSKPEGKLPFD  550
SEQ ID NO: 61   613  -WLDKVKAVVQAWFPGQEAGNAIADVLTGAVNPSGRLPVS  652
SEQ ID NO: 62   529  YDNPNVTAILWGGLPGQESGNSLADVLYGRVNPGAKSPFT  568
SEQ ID NO: 63   529  YDNPNVTAILWGGLPGQESGNSLADVLYGRVNPGAKSPFT  568
SEQ ID NO: 64   529  YDHPNVTGILWAGLPGQESGNSIADVLYGRVNPGAKSPFT  568
SEQ ID NO: 65   529  YDHPNVTGILWAGLPGQESGNSIADVLYGRVNPGAKSPFT  568
SEQ ID NO: 66   519  IDLDSVKAVLVAHLPGQEAGWSLTDILFGDYSPSGHLPYT  558
SEQ ID NO: 67   531  IENDNITAVIYAHLPGQDSGRALVEVMYGKQSPSGRLPYT  570
SEQ ID NO: 68   529  AQNPNVSAILLAHYPGQESGNSIVDVLFGVVNPSGKLPYT  568
SEQ ID NO: 69   529  YDHPNVTAILWAGLPGQESGNALGDVIYGRVNPGAKSPFT  568
SEQ ID NO: 70   509  IDLLRSR---VSCLPDFQDKKLEILLLISCSETSVRVAAS  545
SEQ ID NO: 71   568  DLVYSCAAVLMAYLPGSEGGKPIANILMGNVNPSGRLPLT  607
SEQ ID NO: 72   531  -YISAMDAFVAAWLPGSE-GQGVADVLFGDYGFSGKLART  569
SEQ ID NO: 73   610  -WLDATPAVIQAWYGGNETGNSIADVVFGDYNPSGKLSLS  649
SEQ ID NO: 74   504  IEHPNVTAAVIAHLPGQDSGRALVKLLYGEANFSGKLPYT  543
SEQ ID NO: 75   481  -WAHKAKAIVQAWYGGNETGHGISDVLFGNVNPSGKLSLS  520
SEQ ID NO: 76   529  ANHPNISAILWAGAPGQESGNSLVDILYGKQSPG-RTPFT  567
SEQ ID NO: 77   498  KSNKKVNSLVWGGYPGQSGGVALFDILSGKRAPAGRLVTT  537
SEQ ID NO: 78   625  -WLEEANALVQAWYGGNELGNAIADVLYGDVVPNGKLSLS  664
SEQ ID NO: 79   491  IEHENVTGVILAHLPGQDTGTSLIEVLYGNQSPSGRLPYT  530
SEQ ID NO: 80   532  -YVSKMDALVAAWLPGTE-GQGVADALFGDYGFTGKLART  570
SEQ ID NO: 81   527  NNSPNVSAILWAGLPGQESGNAITDVLYGRVNPGGKLPFT  566
SEQ ID NO: 82   526  YDSENVTAILWAGLPGQESGNAIADILYGRHNPGGKLPFT  565
SEQ ID NO: 83   500  VNHPNVTAIVWSGLPGQEAGNAVTDVLFGAVNPGGKLPFT  539
SEQ ID NO: 84   500  VNHPNVTAIVWSGLPGQEAGNAVTDVLFGAVNPGGKLPFT  539
SEQ ID NO: 85   524  IDNENVTAVIYSSYLGQDFGTVLAKVLFGDENPSGKLPFT  563
SEQ ID NO: 86   488  LNN--VKAIIHAGMPGAESGNAIASILFGDSNPSGHLPFT  525
SEQ ID NO: 87   538  ADHPNVTAIVWAGPLGDRSGTAIANILFGNANPSGHLPFT  577
SEQ ID NO: 88   536  ADHPNVTAIVWAGPLGDRSGTAIANILFGKANPSGHLPFT  575
SEQ ID NO: 89   618  -WISEAHTLLHIWYNGNELGNALANIIFGEQNPCGKLPIT  657
SEQ ID NO: 90   524  ADNANVTAILAAHYPGQENGNSIMDILYGDVNPSGRLPYT  563
SEQ ID NO: 91   525  YDHPNVTAILWAGLPGQESGNSLVDVLYGRVNPG-KTPFT  563
SEQ ID NO: 92   515  IDLPSVKSVVFAHLPGQEAGDSLVDVLFGDYSPSGHLPYT  554
SEQ ID NO: 93   529  YDNPNVTAIVWAGLPGQESGNSLVDVLYGRVSPGGKTPFT  568
SEQ ID NO: 94   529  YDNPNVTAIVWAGLPGQESGNSLVDVLYGRVSPGGKTPFT  568
SEQ ID NO: 95   519  IDLPSVKSVVFAHLPGQEAGDSLVDVLFGDYSPSGHLPYT  558
SEQ ID NO: 96   492  LALPQVKAVVWTGLPSQESGNALVDVLWGDVSPSGKLVYT  531
SEQ ID NO: 97   532  -YVSYMDALVAAWLPGTE-GQGVTDVLFGDYGFTGKLART  570
SEQ ID NO: 98   526  INHPNVTAVLLAGLPGQEAGSAEVDVLWGSTNPSGRLPYT  565
SEQ ID NO: 99   638  -WLDSVAAVVHAWYLGNATGDAIADVLFGKQNPSGKLSLT  677
```

Figure 11A-21

```
SEQ ID NO: 1     532 IAKSPND-YNTRIVS---------GGS----DSFSEGLFI 557
CONSENSUS        536 WGKTRED-YGPSLVT-P-------NG-G-PQDDFTEGVFI 564
SEQ ID NO: 56    569 WGKTREA-YGDYLVRELN------NGNGAPQDDFSEGVFI 601
SEQ ID NO: 57    531 VAKKVEDYGSLLHPSLPE----TPYGL-FPQSDFDEGVYI 565
SEQ ID NO: 58    570 WGKTRES-YGAPLLTEPN------NGNGAPQDDFNEGVFI 602
SEQ ID NO: 59    569 WGKTREA-YQDYLVTEPN------NGNGAPQEDFVEGVFI 601
SEQ ID NO: 60    551 LPRSMDA---------------------------VEAQA 562
SEQ ID NO: 61    653 FPRAIED--APAHGNFPGDYTDGKDNRRHLEVTYKEGVFV 690
SEQ ID NO: 62    569 WGKTREA-YQDYLVTEPN------NGNGAPQEDFVEGVFI 601
SEQ ID NO: 63    569 WGKTREA-YQDYLYTEPN------NGNGAPQEDFVEGVFI 601
SEQ ID NO: 64    569 WGKTRES-YGSPLVKDAN------NGNGAPQSDFTQGVFI 601
SEQ ID NO: 65    569 WGKTRES-YGSPLVKDAN------NGNGAPQSDFTQGVFI 601
SEQ ID NO: 66    559 IPHSES--DYPESVGLIA------QPFGQIQDDYTEGLYI 590
SEQ ID NO: 67    571 VAKNESDYGSLLNPVIQS----GTDDIYYPQDNFTEGVYI 606
SEQ ID NO: 68    569 IPVHESDMHIPVVNLSTSEVLAHHQSQNAWQSNFTEKLAI 608
SEQ ID NO: 69    569 WAATSED-YGVSILKEPN------AATKAPQIDFEEGIFI 601
SEQ ID NO: 70    546 IYDTESRIGLSDSVSLIN------QRFGQIQDTFTEGLFI 579
SEQ ID NO: 71    608 YPGTTGD-------------------------------IGV 617
SEQ ID NO: 72    570 WFKSADQ-------------------------------LPMNV 581
SEQ ID NO: 73    650 FPKRLQD--NPAFLNFR--TEAGR-------TLYGEDVYV 678
SEQ ID NO: 74    544 IAKNESDY-SVYTPCQRR----SPEDT-DPQCDFTEGVYL 577
SEQ ID NO: 75    521 WPVDVKH--NPAYLNYA--SVGGR-------VLYGEDVYV 549
SEQ ID NO: 76    568 WGPSLES-YGVSVMTTPN------NGNGAPQDNFNEGAFI 600
SEQ ID NO: 77    538 QYPAEYVHQFPQNDMNLR---------------PDGKSN 561
SEQ ID NO: 78    665 WPFKLQD--NPAFLNFK--TEFGR-------VVYGEDIFV 693
SEQ ID NO: 79    531 VAKKASDYGGLLWPTEPE----GDLDLYFPQSNFTEGVYI 566
SEQ ID NO: 80    571 WFKRVDQ-------------------------------LPMNF 582
SEQ ID NO: 81    567 IGKSAEE-YGPDIIYEPT------AGHGSPQANFEEGVFI 599
SEQ ID NO: 82    566 IGSDAAE-YGPDLIYEPT------NNSSSPQDNFEEGVFI 598
SEQ ID NO: 83    540 IGKSISD-YSAQIIT---------TGSGIVPIPYNEGLFI 569
SEQ ID NO: 84    540 IGKSISD-YSAQIIT---------TGSGIVPIPYNEGLFI 569
SEQ ID NO: 85    564 IAKDVND-YIPVIEK---------VDVPDVDKFTESIYV 593
SEQ ID NO: 86    526 WAAREDYCCDVSYPAELP-----HGGNSKTAYDYKEGLFV 560
SEQ ID NO: 87    578 VAKSNDD-YIPIVTYNPP------NGEPEDNTLAEHDLLV 610
SEQ ID NO: 88    576 IAKTDDD-YIPIETYSPS------SGEPEDNHLVENDLLV 608
SEQ ID NO: 89    658 FPKKLKD--NPAYLSFR--SSRGH-------CVYGEDVFV 686
SEQ ID NO: 90    564 IPKLATDYDFPVVNITN-----EAQDPYVWQADFTEGLLI 598
SEQ ID NO: 91    564 WGRARDD-YGAPLIVKPN------NGKGAPQQDFTEGIFI 596
SEQ ID NO: 92    555 IPRSED--QYPSSVSLIN------QPFGQIQDTFTEGLYI 586
SEQ ID NO: 93    569 WGKTRES-YGAPLLTKPN------NGKGAPQDDFTEGVFI 601
SEQ ID NO: 94    569 WGKTRES-YGAPLLTKPN------NGKGAPQDDFTEGVFI 601
SEQ ID NO: 95    559 IPRSED--QYPSSVSLIN------QPFGQIQDTFIEGLYI 590
SEQ ID NO: 96    532 IAKSPND-YNTRIVS---------GGS----DSFSEGLFI 557
SEQ ID NO: 97    571 WFKTVDQ-------------------------------LPMNV 582
SEQ ID NO: 98    566 IAKKPS--DYPAEL-LYE------SNMTVPQINYSERLNI 596
SEQ ID NO: 99    678 FPKRLED--VPSHGHFG--SENGK-------VRYAEDLFV 706
```

Figure 11A-22

| | | | | | % Ident. with TrCel3A |
|---|---|---|---|---|---|
| SEQ ID NO: 1 | 558 | DYKHFDDAN--------ITPRYEFGYGLSYTKF--- | 582 | | |
| CONSENSUS | 565 | DYRHFDKAN--------ITPRYEFGYGLSYTTF--- | 589 | | 52.1 |
| SEQ ID NO: 56 | 602 | DYRGFDKRN--------ETPIYEFGHGLSYTTF--- | 626 | | 44.1 |
| SEQ ID NO: 57 | 566 | DYRAFDRAN--------ITAQFEFGFGLSYTSF--- | 590 | | 35.2 |
| SEQ ID NO: 58 | 603 | DYRHFDKRN--------ETPIYEFGHGLSYTTF--- | 627 | | 43.1 |
| SEQ ID NO: 59 | 602 | DYRGFDKRN--------ETPIYEFGYGLSYTTF--- | 626 | | 42.6 |
| SEQ ID NO: 60 | 563 | EDLPFDTEN----------PVFRYGHGLEYEDN--- | 585 | | 13.2 |
| SEQ ID NO: 61 | 691 | GYRHYDLSEANR-----AKVLFPFGYGLSYTTF--- | 718 | | 19.4 |
| SEQ ID NO: 62 | 602 | DYRGFDKRN--------ETPIYEFGYGLSYTTF--- | 626 | | 42.8 |
| SEQ ID NO: 63 | 602 | DYRGFDKRN--------ETPIYEFGYGLSYTTF--- | 626 | | 42.6 |
| SEQ ID NO: 64 | 602 | DYRHFDKFN--------ETPIYEFGYGLSYTTF--- | 626 | | 42.2 |
| SEQ ID NO: 65 | 602 | DYRHFDKFN--------ETPIYEFGYGLSYTTF--- | 626 | | 42.3 |
| SEQ ID NO: 66 | 591 | DYRHFLKAN--------ITPRYPFGHGLSYTTF--- | 615 | | 43.4 |
| SEQ ID NO: 67 | 607 | DYKAFVAAN--------ITPRYEFGYGLTYSTF--- | 631 | | 31.6 |
| SEQ ID NO: 68 | 609 | DYRGFEMKN--------VTPLYEFGHGLSYTTF--- | 633 | | 35.9 |
| SEQ ID NO: 69 | 602 | DYRAFDKSN--------TKPIYEFGFGLSYTTF--- | 626 | | 41.4 |
| SEQ ID NO: 70 | 580 | DYRHFQKEN--------ITPRYHFGYGLSYTTF--- | 604 | | 40.4 |
| SEQ ID NO: 71 | 618 | PYYHKYSENG------VTTPLFQFGDGLSYTTF--- | 644 | | 16.6 |
| SEQ ID NO: 72 | 582 | GDKHY------------DPLFPFGFGLTTEA---- | 600 | | 19.5 |
| SEQ ID NO: 73 | 679 | GYRYYEFADK-------DVNFPFGHGLSYTTF--- | 703 | | 19.4 |
| SEQ ID NO: 74 | 578 | DYRAFDANN--------MTPRFEFGYGLSYTSF--- | 602 | | 36.5 |
| SEQ ID NO: 75 | 550 | GYKFYDKTER-------EVLFPFGHGLSYATF--- | 574 | | 12.8 |
| SEQ ID NO: 76 | 601 | DYRYFDKVAPGKPRSSDKAPTYEFGFGLSWSTF--- | 633 | | 41.5 |
| SEQ ID NO: 77 | 562 | PGQTYIWYTG-------KPVYEFGSGLFYTTF--- | 586 | | 19.2 |
| SEQ ID NO: 78 | 694 | GYRYYEKLQR-------KVAFPFGYGLSYTTF--- | 718 | | 18.0 |
| SEQ ID NO: 79 | 567 | DYKYFIQKN--------ITPRYEFGYGLTYTTF--- | 591 | | 33.0 |
| SEQ ID NO: 80 | 583 | DDAHV------------DPLFPFGFGITTKPVKGY | 605 | | 20.0 |
| SEQ ID NO: 81 | 600 | DY------------------------------- | 601 | | 41.9 |
| SEQ ID NO: 82 | 599 | DYRAFDKQN--------VTPIYEFGFGLSYTKF--- | 623 | | 42.7 |
| SEQ ID NO: 83 | 570 | DYRHFDQAG--------IAPRFEFGFGLSYTTF--- | 594 | | 52.6 |
| SEQ ID NO: 84 | 570 | DYRHFDQAG--------IAPRFEFGFGLSYTTF--- | 594 | | 52.6 |
| SEQ ID NO: 85 | 594 | DYRYFDKYN--------KPVRYEFGYGLSYSNF--- | 618 | | 36.4 |
| SEQ ID NO: 86 | 561 | GYRWFDKKN--------KTPIFPFGHGLSYTTF--- | 585 | | 38.3 |
| SEQ ID NO: 87 | 611 | DYRYFEEKN--------IEPRYAFGYGLSYNEY--- | 635 | | 38.2 |
| SEQ ID NO: 88 | 609 | DYRYFEEKN--------IEPRYAFGYGLSYNEY--- | 633 | | 38.3 |
| SEQ ID NO: 89 | 687 | GYKYYEAVER-------EVLFPFGYGLSYTTF--- | 711 | | 17.4 |
| SEQ ID NO: 90 | 599 | DYRHFDARN--------ITPLYEFGYGLSYTTF--- | 623 | | 37.2 |
| SEQ ID NO: 91 | 597 | DYRRFDKYN--------ITPIYEFGFGLSYTTF--- | 621 | | 43.2 |
| SEQ ID NO: 92 | 587 | DYRHFLHAN--------LTPRYPFGHGLSYTTF--- | 611 | | 45.0 |
| SEQ ID NO: 93 | 602 | DYRRFDKYN--------ETPIYEFGFGLSYTTF--- | 626 | | 44.3 |
| SEQ ID NO: 94 | 602 | DYRRFDKYN--------ETPIYEFGFGLSYTTF--- | 626 | | 44.3 |
| SEQ ID NO: 95 | 591 | DYRHFLHAN--------LTPRYPFGHGLSYTTF--- | 615 | | 45.0 |
| SEQ ID NO: 96 | 558 | DYKHFDDAN--------ITPRYEFGYGL-------- | 577 | | 98.3 |
| SEQ ID NO: 97 | 583 | GDKHY------------DPLFPFGFGLTTKPS--- | 602 | | 20.3 |
| SEQ ID NO: 98 | 597 | DYRHFDTYN--------IEPRFEFGFGLSYTTF--- | 621 | | 39.8 |
| SEQ ID NO: 99 | 707 | GYKHYHHRNI-------EPLFPFGFGLSYTTF--- | 731 | | 18.8 |

SEQUENCE LISTING

```
<160> NUMBER OF SEQ ID NOS: 116

<210> SEQ ID NO 1
<211> LENGTH: 582
<212> TYPE: PRT
<213> ORGANISM: Trichoderma reesei

<400> SEQUENCE: 1

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205
```

```
Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Asn Asp Lys Gly Cys Asp Asp Gly Ala Leu Gly Met Gly Trp Gly Ser
    370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
    450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
    530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
            580

<210> SEQ ID NO 2
<211> LENGTH: 582
<212> TYPE: PRT
<213> ORGANISM: Trichoderma reesei

<400> SEQUENCE: 2
```

-continued

```
Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Ile Arg Tyr Ser Thr Gly Ser Thr Ala Phe Thr Pro Gly Val Gln
65              70                  75                  80

Ala Ala Ser Thr Trp Asp Val Asn Leu Ile Arg Glu Arg Gly Gln Phe
            85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
            165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
            210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
            290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
            355                 360                 365

Asn Asp Lys Gly Cys Asp Asp Gly Ala Leu Gly Met Gly Trp Gly Ser
            370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
            405                 410                 415

Asn Thr Ser Ser Gly Ala Ser Ala Ala Arg Gly Lys Asp Val Ala Ile
            420                 425                 430
```

-continued

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val
465                 470                 475                 480

His Ser Val Gly Ala Ile Ile Leu Glu Gln Ile Leu Ala Leu Pro Gln
            485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
            530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                    565                 570                 575

Leu Ser Tyr Thr Lys Phe
            580

<210> SEQ ID NO 3
<211> LENGTH: 582
<212> TYPE: PRT
<213> ORGANISM: Trichoderma reesei

<400> SEQUENCE: 3

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
210                 215                 220

```
Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
            245                 250                 255

Gly Thr Asp Phe Asn Gly Asn Asn Arg Leu Trp Gly Pro Ala Leu Thr
        260                 265                 270

Asn Ala Val Asn Ser Asn Gln Val Pro Thr Ser Arg Val Asp Asp Met
    275                 280                 285

Val Thr Arg Ile Leu Ala Ala Trp Tyr Leu Thr Gly Gln Asp Gln Ala
290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Asn Asp Lys Gly Cys Asp Asp Gly Ala Leu Gly Met Gly Trp Gly Ser
370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
            580

<210> SEQ ID NO 4
<211> LENGTH: 582
<212> TYPE: PRT
<213> ORGANISM: Trichoderma reesei

<400> SEQUENCE: 4

Val Val Pro Pro Ala Gly Thr Pro Trp Gly Thr Ala Tyr Asp Lys Ala
1               5                   10                  15
```

```
Lys Ala Ala Leu Ala Lys Leu Asn Leu Gln Asp Lys Val Gly Ile Val
             20                  25                  30
Ser Gly Val Gly Trp Asn Gly Gly Pro Cys Val Gly Asn Thr Ser Pro
         35                  40                  45
Ala Ser Lys Ile Ser Tyr Pro Ser Leu Cys Leu Gln Asp Gly Pro Leu
     50                  55                  60
Gly Val Arg Tyr Ser Thr Gly Glu Thr Ala Phe Thr Pro Gly Val Gln
 65                  70                  75                  80
Ala Ala Ser Thr Trp Asp Val Asn Leu Ile Arg Glu Arg Gly Gln Leu
                 85                  90                  95
Ile Gly Glu Glu Met Lys Ala Ser Gly Ile His Val Ile Leu Gly Pro
                100                 105                 110
Val Ala Gly Pro Leu Gly Lys Thr Pro Gln Gly Gly Arg Asn Trp Glu
             115                 120                 125
Gly Phe Gly Val Asp Pro Tyr Leu Thr Gly Ile Ala Met Gly Gln Thr
         130                 135                 140
Ile Asn Gly Ile Gln Ser Val Gly Val Gln Ala Thr Ala Lys His Tyr
145                 150                 155                 160
Ile Leu Asn Glu Gln Glu Leu Asn Arg Glu Thr Ile Ser Ser Asn Pro
                165                 170                 175
Asp Asp Arg Thr Leu His Glu Leu Tyr Thr Trp Pro Phe Ala Asp Ala
             180                 185                 190
Val Gln Ala Asn Val Ala Ser Val Met Cys Ser Tyr Asn Lys Val Asn
         195                 200                 205
Thr Thr Trp Ala Cys Glu Asp Gln Tyr Thr Leu Gln Thr Val Leu Lys
210                 215                 220
Asp Gln Leu Gly Phe Pro Gly Tyr Val Met Thr Asp Trp Asn Ala Gln
225                 230                 235                 240
His Thr Thr Val Gln Ser Ala Asn Ser Gly Leu Asp Met Ser Met Pro
                245                 250                 255
Gly Thr Asp Phe Asn Gly Asn Asn Arg Leu Trp Gly Pro Ala Leu Thr
             260                 265                 270
Asn Ala Val Asn Ser Asn Gln Val Pro Thr Ser Arg Val Asp Asp Met
         275                 280                 285
Val Thr Arg Ile Leu Ala Ala Trp Tyr Leu Thr Gly Gln Asp Gln Ala
290                 295                 300
Gly Tyr Pro Ser Phe Asn Ile Ser Arg Asn Val Gln Gly Asn His Lys
305                 310                 315                 320
Thr Asn Val Arg Ala Ile Ala Arg Asp Gly Ile Val Leu Leu Lys Asn
                325                 330                 335
Asp Ala Asn Ile Leu Pro Leu Lys Lys Pro Ala Ser Ile Ala Val Val
             340                 345                 350
Gly Ser Ala Ala Ile Ile Gly Asn His Ala Arg Asn Ser Pro Ser Cys
         355                 360                 365
Lys Asp Lys Gly Cys Asp Asp Gly Ala Leu Gly Met Gly Trp Gly Ser
     370                 375                 380
Gly Thr Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
Asn Thr Ser Ser Gly Ala Ser Ala Ala Arg Gly Lys Asp Val Ala Ile
             420                 425                 430
Val Phe Ile Thr Ala Asp Ser Gly Glu Gly Tyr Ile Thr Val Glu Gly
```

```
                435                 440                 445
Asn Ala Gly Asp Arg Asn Asn Leu Asp Pro Trp His Asn Gly Asn Ala
            450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
    530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
            580

<210> SEQ ID NO 5
<211> LENGTH: 582
<212> TYPE: PRT
<213> ORGANISM: Trichoderma reesei

<400> SEQUENCE: 5

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Met Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
```

```
                  225                 230                 235                 240
His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Asn Asp Lys Gly Cys Asp Asp Gly Ala Leu Gly Met Gly Trp Gly Ser
    370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
    450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
    530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
            580

<210> SEQ ID NO 6
<211> LENGTH: 582
<212> TYPE: PRT
<213> ORGANISM: Trichoderma reesei

<400> SEQUENCE: 6

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
```

```
                 20                  25                  30
Ser Gly Val Gly Trp Asn Gly Gly Pro Cys Val Gly Asn Thr Ser Pro
             35                  40                  45

Ala Ser Lys Ile Ser Tyr Pro Ser Leu Cys Leu Gln Asp Gly Pro Leu
 50                  55                  60

Gly Val Arg Tyr Ser Thr Gly Ser Thr Ala Phe Thr Pro Gly Val Gln
 65                  70                  75                  80

Ala Ala Ser Thr Trp Asp Val Asn Leu Ile Arg Glu Arg Gly Gln Phe
                 85                  90                  95

Ile Gly Glu Glu Val Lys Ala Ser Gly Ile His Val Ile Leu Gly Pro
             100                 105                 110

Val Ala Gly Pro Leu Gly Lys Thr Pro Gln Gly Gly Arg Asn Trp Glu
             115                 120                 125

Gly Phe Gly Val Asp Pro Tyr Leu Thr Gly Ile Ala Met Gly Gln Thr
             130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                 165                 170                 175

Asp Asp Arg Thr Leu His Glu Leu Tyr Thr Trp Pro Phe Ala Asp Ala
             180                 185                 190

Val Gln Ala Asn Val Ala Ser Val Met Cys Ser Tyr Asn Lys Val Asn
             195                 200                 205

Thr Thr Trp Ala Cys Glu Asp Gln Tyr Thr Leu Gln Thr Val Leu Lys
             210                 215                 220

Asp Gln Leu Gly Phe Pro Gly Tyr Val Met Ser Asp Trp Asn Ala Gln
225                 230                 235                 240

His Thr Thr Val Gln Ser Ala Asn Ser Gly Leu Asp Met Ser Met Pro
                 245                 250                 255

Gly Thr Asp Phe Asn Gly Asn Asn Arg Leu Trp Gly Pro Ala Leu Thr
             260                 265                 270

Asn Ala Val Asn Ser Asn Gln Val Pro Thr Ser Arg Val Asp Asp Met
             275                 280                 285

Val Thr Arg Ile Leu Ala Ala Trp Tyr Leu Thr Gly Gln Asp Gln Ala
             290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                 325                 330                 335

Asp Ala Asn Ile Leu Pro Leu Lys Lys Pro Ala Ser Ile Ala Val Val
             340                 345                 350

Gly Ser Ala Ala Ile Ile Gly Asn His Ala Arg Asn Ser Pro Ser Cys
             355                 360                 365

Asn Asp Lys Gly Cys Asp Asp Gly Ala Leu Gly Met Gly Trp Gly Ser
             370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                 405                 410                 415

Asn Thr Ser Ser Gly Ala Ser Ala Ala Arg Gly Lys Asp Val Ala Ile
             420                 425                 430

Val Phe Ile Thr Ala Asp Ser Gly Glu Gly Tyr Ile Thr Val Glu Gly
             435                 440                 445
```

```
Asn Ala Gly Asp Arg Asn Asn Leu Asp Pro Trp His Asn Gly Asn Ala
            450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
            485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
            530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
            565                 570                 575

Leu Ser Tyr Thr Lys Phe
            580

<210> SEQ ID NO 7
<211> LENGTH: 582
<212> TYPE: PRT
<213> ORGANISM: Trichoderma reesei

<400> SEQUENCE: 7

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
                20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
        50                  55                  60

Gly Val Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240
```

```
His Thr Thr Val Gln Ser Ala Lys Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Asn Asp Lys Gly Cys Asp Asp Gly Ala Leu Gly Met Gly Trp Gly Ser
    370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
    450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
    530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
            580

<210> SEQ ID NO 8
<211> LENGTH: 582
<212> TYPE: PRT
<213> ORGANISM: Trichoderma reesei

<400> SEQUENCE: 8

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30
```

```
Ser Gly Val Gly Trp Asn Gly Pro Cys Val Gly Asn Thr Ser Pro
         35                  40                  45

Ala Ser Lys Ile Ser Tyr Pro Ser Leu Cys Leu Gln Asp Gly Pro Leu
 50                  55                  60

Gly Val Arg Tyr Ser Thr Gly Ser Thr Ala Phe Thr Pro Gly Val Gln
 65                  70                  75                  80

Ala Ala Ser Thr Trp Asp Val Asn Leu Ile Arg Glu Arg Gly Gln Phe
                 85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
        130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
        210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
        290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Lys Asp Lys Gly Cys Asp Asp Gly Ala Leu Gly Met Gly Trp Gly Ser
370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
450                 455                 460
```

```
Leu Val Gln Ala Val Ala Gly Ala Asn Ser Asn Val Ile Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
    530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
            580
```

<210> SEQ ID NO 9
<211> LENGTH: 582
<212> TYPE: PRT
<213> ORGANISM: Trichoderma reesei

<400> SEQUENCE: 9

```
Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255
```

```
Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
            290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
            325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
            355                 360                 365

Asn Asp Lys Gly Cys Asp Asp Gly Ala Leu Gly Met Gly Trp Gly Ser
            370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
            405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
            485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
            530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
            565                 570                 575

Leu Ser Tyr Thr Lys Phe
            580

<210> SEQ ID NO 10
<211> LENGTH: 582
<212> TYPE: PRT
<213> ORGANISM: Trichoderma reesei

<400> SEQUENCE: 10

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
            35                  40                  45
```

```
Ala Ser Lys Ile Ser Tyr Pro Ser Leu Cys Leu Gln Asp Gly Pro Leu
     50                  55                  60

Gly Ile Arg Tyr Ser Thr Gly Asn Thr Ala Phe Thr Pro Gly Val Gln
 65                  70                  75                  80

Ala Ala Ser Thr Trp Asp Val Asn Leu Ile Arg Glu Arg Gly Gln Phe
                 85                  90                  95

Ile Gly Glu Glu Val Lys Ala Ser Gly Ile His Val Ile Leu Gly Pro
                100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
            130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
            355                 360                 365

Asn Asp Lys Gly Cys Asp Asp Gly Ala Leu Gly Met Gly Trp Gly Ser
370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val Val
```

```
            465                 470                 475                 480
His Ser Val Gly Ala Ile Ile Leu Glu Gln Ile Leu Ala Leu Pro Gln
                    485                 490                 495

Val Lys Ala Val Val Trp Ala Gly Leu Pro Ser Gln Glu Ser Gly Asn
                500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
                580

<210> SEQ ID NO 11
<211> LENGTH: 582
<212> TYPE: PRT
<213> ORGANISM: Trichoderma reesei

<400> SEQUENCE: 11

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
                20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
        50                  55                  60

Gly Val Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Leu
                85                  90                  95

Ile Gly Glu Glu Met Lys Ala Ser Gly Ile His Val Ile Leu Gly Pro
                100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
        130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
                180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
        210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
```

```
                    260                 265                 270
Asn Ala Val Asn Ser Asn Gln Val Pro Thr Ser Arg Val Asp Asp Met
                275                 280                 285
Val Thr Arg Ile Leu Ala Ala Trp Tyr Leu Thr Gly Gln Asp Gln Ala
            290                 295                 300
Gly Tyr Pro Ser Phe Asn Ile Ser Arg Asn Val Gln Gly Asn His Lys
305                 310                 315                 320
Thr Asn Val Arg Ala Ile Ala Arg Asp Gly Ile Val Leu Leu Lys Asn
                325                 330                 335
Asp Ala Asn Ile Leu Pro Leu Lys Lys Pro Ala Ser Ile Ala Val Val
                340                 345                 350
Gly Ser Ala Ala Ile Ile Gly Asn His Ala Arg Asn Ser Pro Ser Cys
            355                 360                 365
Asn Asp Lys Gly Cys Asp Asp Gly Ala Leu Gly Met Gly Trp Gly Ser
370                 375                 380
Gly Ala Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
Asn Thr Ser Ser Gly Ala Ser Ala Ala Arg Gly Lys Asp Val Ala Ile
                420                 425                 430
Val Phe Ile Thr Ala Asp Ser Gly Glu Gly Tyr Ile Thr Val Glu Gly
            435                 440                 445
Asn Ala Gly Asp Arg Asn Asn Leu Asp Pro Trp His Asn Gly Asn Ala
450                 455                 460
Leu Val Gln Ala Val Ala Gly Ala Asn Ser Asn Val Ile Val Val Val
465                 470                 475                 480
His Ser Val Gly Ala Ile Ile Leu Glu Gln Ile Leu Ala Leu Pro Gln
                485                 490                 495
Val Lys Ala Val Val Trp Ala Gly Leu Pro Ser Gln Glu Ser Gly Asn
                500                 505                 510
Ala Leu Val Asp Val Leu Trp Gly Asp Val Ser Pro Ser Gly Lys Leu
            515                 520                 525
Val Tyr Thr Ile Ala Lys Ser Pro Asn Asp Tyr Asn Thr Arg Ile Val
            530                 535                 540
Ser Gly Gly Ser Asp Ser Phe Ser Glu Gly Leu Phe Ile Asp Tyr Lys
545                 550                 555                 560
His Phe Asp Asp Ala Asn Ile Thr Pro Arg Tyr Glu Phe Gly Tyr Gly
                565                 570                 575
Leu Ser Tyr Thr Lys Phe
            580

<210> SEQ ID NO 12
<211> LENGTH: 582
<212> TYPE: PRT
<213> ORGANISM: Trichoderma reesei

<400> SEQUENCE: 12

Val Val Pro Pro Ala Gly Thr Pro Trp Gly Thr Ala Tyr Asp Lys Ala
1               5                   10                  15
Lys Ala Ala Leu Ala Lys Leu Asn Leu Gln Asp Lys Val Gly Ile Val
                20                  25                  30
Ser Gly Val Gly Trp Asn Gly Gly Pro Cys Val Gly Asn Thr Ser Pro
            35                  40                  45
Ala Ser Lys Ile Ser Tyr Pro Ser Leu Cys Leu Gln Asp Gly Pro Leu
```

```
                50                  55                  60
Gly Val Arg Tyr Ser Thr Gly Asn Thr Ala Phe Thr Pro Gly Val Gln
 65                  70                  75                  80

Ala Ala Ser Thr Trp Asp Val Asn Leu Ile Arg Glu Arg Gly Gln Leu
                 85                  90                  95

Ile Gly Glu Glu Met Lys Ala Ser Gly Ile His Val Ile Leu Gly Pro
                100                 105                 110

Val Ala Gly Pro Leu Gly Lys Thr Pro Gln Gly Gly Arg Asn Trp Glu
                115                 120                 125

Gly Phe Gly Val Asp Pro Tyr Leu Thr Gly Ile Ala Met Gly Gln Thr
                130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
                180                 185                 190

Val Gln Ala Asn Val Ala Ser Val Met Cys Ser Tyr Asn Lys Val Asn
                195                 200                 205

Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
                260                 265                 270

Asn Ala Val Asn Ser Asn Gln Val Pro Thr Ser Arg Val Asp Asp Met
                275                 280                 285

Val Thr Arg Ile Leu Ala Ala Trp Tyr Leu Thr Gly Gln Asp Gln Ala
                290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
                340                 345                 350

Gly Ser Ala Ala Ile Ile Gly Asn His Ala Arg Asn Ser Pro Ser Cys
                355                 360                 365

Lys Asp Lys Gly Cys Asp Asp Gly Ala Leu Gly Met Gly Trp Gly Ser
370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
                420                 425                 430

Val Phe Ile Thr Ala Asp Ser Gly Glu Gly Tyr Ile Thr Val Glu Gly
                435                 440                 445

Asn Ala Gly Asp Arg Asn Asn Leu Asp Pro Trp His Asn Gly Asn Ala
                450                 455                 460

Leu Val Gln Ala Val Ala Gly Ala Asn Ser Asn Val Ile Val Val Val
465                 470                 475                 480
```

```
His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
            530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
                580

<210> SEQ ID NO 13
<211> LENGTH: 582
<212> TYPE: PRT
<213> ORGANISM: Trichoderma reesei

<400> SEQUENCE: 13

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Met Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270
```

```
Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
        290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Lys Asp Lys Gly Cys Asp Asp Gly Ala Leu Gly Met Gly Trp Gly Ser
370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
            580

<210> SEQ ID NO 14
<211> LENGTH: 582
<212> TYPE: PRT
<213> ORGANISM: Trichoderma reesei

<400> SEQUENCE: 14

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60
```

-continued

```
Gly Ile Arg Tyr Ser Thr Gly Asn Thr Ala Phe Thr Pro Gly Val Gln
 65                  70                  75                  80

Ala Ala Ser Thr Trp Asp Val Asn Leu Ile Arg Glu Arg Gly Gln Phe
                 85                  90                  95

Ile Gly Glu Glu Met Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Lys Asp Lys Gly Cys Asp Asp Gly Ala Leu Gly Met Gly Trp Gly Ser
    370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
    450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495
```

```
Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
            530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
            565                 570                 575

Leu Ser Tyr Thr Lys Phe
            580

<210> SEQ ID NO 15
<211> LENGTH: 582
<212> TYPE: PRT
<213> ORGANISM: Trichoderma reesei

<400> SEQUENCE: 15

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
        50                  55                  60

Gly Val Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Leu
            85                  90                  95

Ile Gly Glu Glu Met Lys Ala Ser Gly Ile His Val Ile Leu Gly Pro
            100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
        130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
            165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
        210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
            245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285
```

```
Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
                340                 345                 350

Gly Ser Ala Ala Ile Ile Gly Asn His Ala Arg Asn Ser Pro Ser Cys
            355                 360                 365

Lys Asp Lys Gly Cys Asp Asp Gly Ala Leu Gly Met Gly Trp Gly Ser
    370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
                420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
    450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
    515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
            580

<210> SEQ ID NO 16
<211> LENGTH: 582
<212> TYPE: PRT
<213> ORGANISM: Trichoderma reesei

<400> SEQUENCE: 16

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
                20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
    50                  55                  60

Gly Ile Arg Tyr Ser Thr Gly Asn Thr Ala Phe Thr Pro Gly Val Gln
65                  70                  75                  80
```

```
Ala Ala Ser Thr Trp Asp Val Asn Leu Ile Arg Glu Arg Gly Gln Leu
                85                  90                  95
Ile Gly Glu Glu Met Lys Ala Ser Gly Ile His Val Ile Leu Gly Pro
            100                 105                 110
Val Ala Gly Pro Leu Gly Lys Thr Pro Gln Gly Gly Arg Asn Trp Glu
            115                 120                 125
Gly Phe Gly Val Asp Pro Tyr Leu Thr Gly Ile Ala Met Gly Gln Thr
130                 135                 140
Ile Asn Gly Ile Gln Ser Val Gly Val Gln Ala Thr Ala Lys His Tyr
145                 150                 155                 160
Ile Leu Asn Glu Gln Glu Leu Asn Arg Glu Thr Ile Ser Ser Asn Pro
                165                 170                 175
Asp Asp Arg Thr Leu His Glu Leu Tyr Thr Trp Pro Phe Ala Asp Ala
            180                 185                 190
Val Gln Ala Asn Val Ala Ser Val Met Cys Ser Tyr Asn Lys Val Asn
            195                 200                 205
Thr Thr Trp Ala Cys Glu Asp Gln Tyr Thr Leu Gln Thr Val Leu Lys
210                 215                 220
Asp Gln Leu Gly Phe Pro Gly Tyr Val Met Thr Asp Trp Asn Ala Gln
225                 230                 235                 240
His Thr Thr Val Gln Ser Ala Asn Ser Gly Leu Asp Met Ser Met Pro
                245                 250                 255
Gly Thr Asp Phe Asn Gly Asn Asn Arg Leu Trp Gly Pro Ala Leu Thr
            260                 265                 270
Asn Ala Val Asn Ser Asn Gln Val Pro Thr Ser Arg Val Asp Asp Met
            275                 280                 285
Val Thr Arg Ile Leu Ala Ala Trp Tyr Leu Thr Gly Gln Asp Gln Ala
            290                 295                 300
Gly Tyr Pro Ser Phe Asn Ile Ser Arg Asn Val Gln Gly Asn His Lys
305                 310                 315                 320
Thr Asn Val Arg Ala Ile Ala Arg Asp Gly Ile Val Leu Leu Lys Asn
                325                 330                 335
Asp Ala Asn Ile Leu Pro Leu Lys Lys Pro Ala Ser Ile Ala Val Val
            340                 345                 350
Gly Ser Ala Ala Ile Ile Gly Asn His Ala Arg Asn Ser Pro Ser Cys
            355                 360                 365
Lys Asp Lys Gly Cys Asp Asp Gly Ala Leu Gly Met Gly Trp Gly Ser
    370                 375                 380
Gly Thr Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
Asn Thr Ser Ser Gly Ala Ser Ala Ala Arg Gly Lys Asp Val Ala Ile
            420                 425                 430
Val Phe Ile Thr Ala Asp Ser Gly Glu Gly Tyr Ile Thr Val Glu Gly
            435                 440                 445
Asn Ala Gly Asp Arg Asn Asn Leu Asp Pro Trp His Asn Gly Asn Ala
450                 455                 460
Leu Val Gln Ala Val Ala Gly Ala Asn Ser Asn Val Ile Val Val Val
465                 470                 475                 480
His Ser Val Gly Ala Ile Ile Leu Glu Gln Ile Leu Ala Leu Pro Gln
                485                 490                 495
Val Lys Ala Val Val Trp Ala Gly Leu Pro Ser Gln Glu Ser Gly Asn
```

```
                   500             505             510
Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
        530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
        580

<210> SEQ ID NO 17
<211> LENGTH: 26
<212> TYPE: DNA
<213> ORGANISM: Artificial
<220> FEATURE:
<223> OTHER INFORMATION: Primer sequence

<400> SEQUENCE: 17
cgccaggcta gcgttgtacc tcctgc                                    26

<210> SEQ ID NO 18
<211> LENGTH: 25
<212> TYPE: DNA
<213> ORGANISM: Artificial
<220> FEATURE:
<223> OTHER INFORMATION: Primer sequence

<400> SEQUENCE: 18
ctgagggtac cgctacgcta ccgac                                     25

<210> SEQ ID NO 19
<211> LENGTH: 26
<212> TYPE: DNA
<213> ORGANISM: Artificial
<220> FEATURE:
<223> OTHER INFORMATION: Primer sequence

<400> SEQUENCE: 19
cccgctagta ttgccgtcgt tggatc                                    26

<210> SEQ ID NO 20
<211> LENGTH: 27
<212> TYPE: DNA
<213> ORGANISM: Artificial
<220> FEATURE:
<223> OTHER INFORMATION: Primer sequence

<400> SEQUENCE: 20
ccaacgacgg caatactagc gggcttc                                   27

<210> SEQ ID NO 21
<211> LENGTH: 37
<212> TYPE: DNA
<213> ORGANISM: Artificial
<220> FEATURE:
<223> OTHER INFORMATION: Primer sequence

<400> SEQUENCE: 21
gttcggctat ggactgtctt acaccaagtt caactac                        37

<210> SEQ ID NO 22
<211> LENGTH: 36
```

```
<212> TYPE: DNA
<213> ORGANISM: Artificial
<220> FEATURE:
<223> OTHER INFORMATION: Primer sequence

<400> SEQUENCE: 22
gttgaacttg gtgtaagaca gtccatagcc gaactc                                  36

<210> SEQ ID NO 23
<211> LENGTH: 22
<212> TYPE: DNA
<213> ORGANISM: Artificial
<220> FEATURE:
<223> OTHER INFORMATION: Primer sequence

<400> SEQUENCE: 23
ctagctgatc actgaggtac cg                                                 22

<210> SEQ ID NO 24
<211> LENGTH: 22
<212> TYPE: DNA
<213> ORGANISM: Artificial
<220> FEATURE:
<223> OTHER INFORMATION: Primer sequence

<400> SEQUENCE: 24
aattcggtac ctcagtgatc ag                                                 22

<210> SEQ ID NO 25
<211> LENGTH: 46
<212> TYPE: DNA
<213> ORGANISM: Artificial
<220> FEATURE:
<223> OTHER INFORMATION: Primer sequence

<400> SEQUENCE: 25
ctagtcatca ccatcaccat cacgctagct gatcactgag gtaccg                       46

<210> SEQ ID NO 26
<211> LENGTH: 46
<212> TYPE: DNA
<213> ORGANISM: Artificial
<220> FEATURE:
<223> OTHER INFORMATION: Primer sequence

<400> SEQUENCE: 26
aattcggtac ctcagtgatc agctagcgtg atggtgatgg tgatga                       46

<210> SEQ ID NO 27
<211> LENGTH: 21
<212> TYPE: DNA
<213> ORGANISM: Artificial
<220> FEATURE:
<223> OTHER INFORMATION: Primer sequence

<400> SEQUENCE: 27
agcacaaata acgggttatt g                                                  21

<210> SEQ ID NO 28
<211> LENGTH: 23
<212> TYPE: DNA
<213> ORGANISM: Artificial
<220> FEATURE:
<223> OTHER INFORMATION: Primer sequence

<400> SEQUENCE: 28
gcaacacctg gcaattcctt acc                                                23
```

<210> SEQ ID NO 29
<211> LENGTH: 29
<212> TYPE: DNA
<213> ORGANISM: Artificial
<220> FEATURE:
<223> OTHER INFORMATION: 5' phosphorylated primer
<220> FEATURE:
<221> NAME/KEY: misc_feature
<222> LOCATION: (15)..(16)
<223> OTHER INFORMATION: n is a, c, g, or t

<400> SEQUENCE: 29
gatactcgac aggcnnsaca gcctttacg                     29

<210> SEQ ID NO 30
<211> LENGTH: 22
<212> TYPE: DNA
<213> ORGANISM: Artificial
<220> FEATURE:
<223> OTHER INFORMATION: 5' phosphorylated primer

<400> SEQUENCE: 30
gaacaccgag gggtccgtct tg                            22

<210> SEQ ID NO 31
<211> LENGTH: 23
<212> TYPE: DNA
<213> ORGANISM: Artificial
<220> FEATURE:
<223> OTHER INFORMATION: 5' phosphorylated primer
<220> FEATURE:
<221> NAME/KEY: misc_feature
<222> LOCATION: (11)..(12)
<223> OTHER INFORMATION: n is a, c, g, or t

<400> SEQUENCE: 31
cggtgaggag nnsaaggcct cgg                           23

<210> SEQ ID NO 32
<211> LENGTH: 21
<212> TYPE: DNA
<213> ORGANISM: Artificial
<220> FEATURE:
<223> OTHER INFORMATION: 5' phosphorylated primer

<400> SEQUENCE: 32
atgaactgtc cacgttcgcg g                             21

<210> SEQ ID NO 33
<211> LENGTH: 24
<212> TYPE: DNA
<213> ORGANISM: Artificial
<220> FEATURE:
<223> OTHER INFORMATION: 5' phosphorylated primer
<220> FEATURE:
<221> NAME/KEY: misc_feature
<222> LOCATION: (11)..(12)
<223> OTHER INFORMATION: n is a, c, g, or t

<400> SEQUENCE: 33
gccctcgtgc nnsgacaaag gctg                          24

<210> SEQ ID NO 34
<211> LENGTH: 20
<212> TYPE: DNA
<213> ORGANISM: Artificial
<220> FEATURE:
<223> OTHER INFORMATION: 5' phosphorylated primer

```
<400> SEQUENCE: 34
gagtttctgg cgtggttacc                                          20

<210> SEQ ID NO 35
<211> LENGTH: 24
<212> TYPE: DNA
<213> ORGANISM: Artificial
<220> FEATURE:
<223> OTHER INFORMATION: 5' phosphorylated primer
<220> FEATURE:
<221> NAME/KEY: misc_feature
<222> LOCATION: (11)..(12)
<223> OTHER INFORMATION: n is a, c, g, or t

<400> SEQUENCE: 35
gggttccggc nnsgtcaact atcc                                     24

<210> SEQ ID NO 36
<211> LENGTH: 18
<212> TYPE: DNA
<213> ORGANISM: Artificial
<220> FEATURE:
<223> OTHER INFORMATION: 5' phosphorylated primer

<400> SEQUENCE: 36
caacccatgc ccaaggcc                                            18

<210> SEQ ID NO 37
<211> LENGTH: 41
<212> TYPE: DNA
<213> ORGANISM: Artificial
<220> FEATURE:
<223> OTHER INFORMATION: Primer sequence

<400> SEQUENCE: 37
cgcgaacgtg gacagctgat cggtgaggag atgaaggcct c                  41

<210> SEQ ID NO 38
<211> LENGTH: 41
<212> TYPE: DNA
<213> ORGANISM: Artificial
<220> FEATURE:
<223> OTHER INFORMATION: Primer sequence

<400> SEQUENCE: 38
gaggccttca tctcctcacc gatcagctgt ccacgttcgc g                  41

<210> SEQ ID NO 39
<211> LENGTH: 45
<212> TYPE: DNA
<213> ORGANISM: Artificial
<220> FEATURE:
<223> OTHER INFORMATION: Primer sequence

<400> SEQUENCE: 39
cgacggggcc ttgggcatgg gttggggttc cggcaccgtc aacta              45

<210> SEQ ID NO 40
<211> LENGTH: 45
<212> TYPE: DNA
<213> ORGANISM: Artificial
<220> FEATURE:
<223> OTHER INFORMATION: Primer sequence

<400> SEQUENCE: 40
ccatgcccaa ggccccgtcg tcgcagcctt tgtccttgca cgagg              45
```

<210> SEQ ID NO 41
<211> LENGTH: 33
<212> TYPE: DNA
<213> ORGANISM: Artificial
<220> FEATURE:
<223> OTHER INFORMATION: Primer sequence

<400> SEQUENCE: 41
gacggacccc tcggtatccg atactcgaca ggc                           33

<210> SEQ ID NO 42
<211> LENGTH: 33
<212> TYPE: DNA
<213> ORGANISM: Artificial
<220> FEATURE:
<223> OTHER INFORMATION: Primer sequence

<400> SEQUENCE: 42
gcctgtcgag tatcggatac cgaggggtcc gtc                           33

<210> SEQ ID NO 43
<211> LENGTH: 33
<212> TYPE: DNA
<213> ORGANISM: Artificial
<220> FEATURE:
<223> OTHER INFORMATION: Primer sequence

<400> SEQUENCE: 43
cgcgaacgtg gacagttcat cggtgaggag atg                           33

<210> SEQ ID NO 44
<211> LENGTH: 33
<212> TYPE: DNA
<213> ORGANISM: Artificial
<220> FEATURE:
<223> OTHER INFORMATION: Primer sequence

<400> SEQUENCE: 44
catctcctca ccgatgaact gtccacgttc gcg                           33

<210> SEQ ID NO 45
<211> LENGTH: 23
<212> TYPE: DNA
<213> ORGANISM: Artificial
<220> FEATURE:
<223> OTHER INFORMATION: Primer sequence

<400> SEQUENCE: 45
gggttccggc gccgtcaact atc                                      23

<210> SEQ ID NO 46
<211> LENGTH: 23
<212> TYPE: DNA
<213> ORGANISM: Artificial
<220> FEATURE:
<223> OTHER INFORMATION: Primer sequence

<400> SEQUENCE: 46
gatagttgac ggcgccggaa ccc                                      23

<210> SEQ ID NO 47
<211> LENGTH: 37
<212> TYPE: DNA
<213> ORGANISM: Artificial
<220> FEATURE:
<223> OTHER INFORMATION: Primer sequence

```
<400> SEQUENCE: 47
gcagagctcg cggccgcgaa ccgacgactc gtccgtc                              37

<210> SEQ ID NO 48
<211> LENGTH: 42
<212> TYPE: DNA
<213> ORGANISM: Artificial
<220> FEATURE:
<223> OTHER INFORMATION: Primer sequence

<400> SEQUENCE: 48
ctgggatccg atatcacgcg tgtgacatcg gcttcaaatg gc                        42

<210> SEQ ID NO 49
<211> LENGTH: 32
<212> TYPE: DNA
<213> ORGANISM: Artificial
<220> FEATURE:
<223> OTHER INFORMATION: Primer sequence

<400> SEQUENCE: 49
tttacgcgtg attatggcgt actagagagc gg                                   32

<210> SEQ ID NO 50
<211> LENGTH: 39
<212> TYPE: DNA
<213> ORGANISM: Artificial
<220> FEATURE:
<223> OTHER INFORMATION: Primer sequence

<400> SEQUENCE: 50
ctgcaggagg tacaacctgg cgcttctcca cagccacgg                            39

<210> SEQ ID NO 51
<211> LENGTH: 41
<212> TYPE: DNA
<213> ORGANISM: Artificial
<220> FEATURE:
<223> OTHER INFORMATION: Primer sequence

<400> SEQUENCE: 51
gtggagaagc gccaggttgt acctcctgca gggactccat g                         41

<210> SEQ ID NO 52
<211> LENGTH: 32
<212> TYPE: DNA
<213> ORGANISM: Artificial
<220> FEATURE:
<223> OTHER INFORMATION: Primer sequence

<400> SEQUENCE: 52
tttggtaccc tacgctaccg acagagtgct cg                                   32

<210> SEQ ID NO 53
<211> LENGTH: 30
<212> TYPE: DNA
<213> ORGANISM: Artificial
<220> FEATURE:
<223> OTHER INFORMATION: Primer sequence

<400> SEQUENCE: 53
tttgcggccg ccatcattcg tcgctttcgg                                      30

<210> SEQ ID NO 54
<211> LENGTH: 27
```

```
<212> TYPE: DNA
<213> ORGANISM: Artificial
<220> FEATURE:
<223> OTHER INFORMATION: Primer sequence

<400> SEQUENCE: 54
ttcgatcgac tataccacca cccaccg                                        27

<210> SEQ ID NO 55
<211> LENGTH: 582
<212> TYPE: PRT
<213> ORGANISM: Trichoderma reesei

<400> SEQUENCE: 55
```

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Leu
                85                  90                  95

Ile Gly Glu Glu Met Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

-continued

```
Asp Ala Asn Ile Leu Pro Leu Lys Lys Pro Ala Ser Ile Ala Val Val
        340                 345                 350

Gly Ser Ala Ala Ile Ile Gly Asn His Ala Arg Asn Ser Pro Ser Cys
            355                 360                 365

Pro Asp Lys Gly Cys Asp Gly Ala Leu Gly Met Gly Trp Gly Ser
        370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Arg Gly Lys Asp Val Ala Ile
                420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
        450                 455                 460

Leu Val Gln Ala Val Ala Gly Ala Asn Ser Asn Val Ile Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
        500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe
            580
```

<210> SEQ ID NO 56
<211> LENGTH: 626
<212> TYPE: PRT
<213> ORGANISM: Aspergillus aculeatus

<400> SEQUENCE: 56

```
Pro Trp Ala Asn Gly Gln Gly Glu Trp Ala Glu Ala Tyr Gln Arg Ala
1               5                   10                  15

Val Ala Ile Val Ser Gln Met Thr Leu Asp Glu Lys Val Asn Leu Thr
            20                  25                  30

Thr Gly Thr Gly Trp Glu Leu Glu Lys Cys Val Gly Gln Thr Gly Gly
        35                  40                  45

Val Pro Arg Leu Asn Ile Gly Gly Met Cys Leu Gln Asp Ser Pro Leu
    50                  55                  60

Gly Ile Arg Asp Ser Asp Tyr Asn Ser Ala Phe Pro Ala Gly Val Asn
65                  70                  75                  80

Val Ala Ala Thr Trp Asp Lys Asn Leu Ala Tyr Leu Arg Gly Gln Ala
                85                  90                  95

Met Gly Gln Glu Phe Ser Asp Lys Gly Ile Asp Val Gln Leu Gly Pro
            100                 105                 110

Ala Ala Gly Pro Leu Gly Arg Ser Pro Asp Gly Gly Arg Asn Trp Glu
        115                 120                 125
```

```
Gly Phe Ser Pro Asp Pro Ala Leu Thr Gly Val Leu Phe Ala Glu Thr
130                 135                 140

Ile Lys Gly Ile Gln Asp Ala Gly Val Val Ala Thr Ala Lys His Tyr
145                 150                 155                 160

Ile Leu Asn Glu Gln Glu His Phe Arg Gln Val Ala Glu Ala Ala Gly
                165                 170                 175

Tyr Gly Phe Asn Ile Ser Asp Thr Ile Ser Ser Asn Val Asp Asp Lys
                180                 185                 190

Thr Ile His Glu Met Tyr Leu Trp Pro Phe Ala Asp Ala Val Arg Ala
            195                 200                 205

Gly Val Gly Ala Ile Met Cys Ser Tyr Asn Gln Ile Asn Asn Ser Tyr
210                 215                 220

Gly Cys Gln Asn Ser Tyr Thr Leu Asn Lys Leu Leu Lys Ala Glu Leu
225                 230                 235                 240

Gly Phe Gln Gly Phe Val Met Ser Asp Trp Gly Ala His His Ser Gly
                245                 250                 255

Val Gly Ser Ala Leu Ala Gly Leu Asp Met Ser Met Pro Gly Asp Ile
                260                 265                 270

Thr Phe Asp Ser Ala Thr Ser Phe Trp Gly Thr Asn Leu Thr Ile Ala
            275                 280                 285

Val Leu Asn Gly Thr Val Pro Gln Trp Arg Val Asp Asp Met Ala Val
290                 295                 300

Arg Ile Met Ala Ala Tyr Tyr Lys Val Gly Arg Asp Arg Leu Tyr Gln
305                 310                 315                 320

Pro Pro Asn Phe Ser Ser Trp Thr Arg Asp Glu Tyr Gly Phe Lys Tyr
                325                 330                 335

Phe Tyr Pro Gln Glu Gly Pro Tyr Glu Lys Val Asn His Phe Val Asn
                340                 345                 350

Val Gln Arg Asn His Ser Glu Val Ile Arg Lys Leu Gly Ala Asp Ser
            355                 360                 365

Thr Val Leu Leu Lys Asn Asn Asn Ala Leu Pro Leu Thr Gly Lys Glu
370                 375                 380

Arg Lys Val Ala Ile Leu Gly Glu Asp Ala Gly Ser Asn Ser Tyr Gly
385                 390                 395                 400

Ala Asn Gly Cys Ser Asp Arg Gly Cys Asp Asn Gly Thr Leu Ala Met
                405                 410                 415

Ala Trp Gly Ser Gly Thr Ala Glu Phe Pro Tyr Leu Val Thr Pro Glu
                420                 425                 430

Gln Ala Ile Gln Ala Glu Val Leu Lys His Lys Gly Ser Val Tyr Ala
            435                 440                 445

Ile Thr Asp Asn Trp Ala Leu Ser Gln Val Glu Thr Leu Ala Lys Gln
450                 455                 460

Ala Ser Val Ser Leu Val Phe Val Asn Ser Asp Ala Gly Glu Gly Tyr
465                 470                 475                 480

Ile Ser Val Asp Gly Asn Glu Gly Asp Arg Asn Asn Leu Thr Leu Trp
                485                 490                 495

Lys Asn Gly Asp Asn Leu Ile Lys Ala Ala Ala Asn Asn Cys Asn Asn
                500                 505                 510

Thr Ile Val Val Ile His Ser Val Gly Pro Val Leu Val Asp Glu Trp
            515                 520                 525

Tyr Asp His Pro Asn Val Thr Ala Ile Leu Trp Ala Gly Leu Pro Gly
530                 535                 540

Gln Glu Ser Gly Asn Ser Leu Ala Asp Val Leu Tyr Gly Arg Val Asn
545                 550                 555                 560
```

```
Pro Gly Ala Lys Ser Pro Phe Thr Trp Gly Lys Thr Arg Glu Ala Tyr
            565                 570                 575

Gly Asp Tyr Leu Val Arg Glu Leu Asn Asn Gly Asn Gly Ala Pro Gln
            580                 585                 590

Asp Asp Phe Ser Glu Gly Val Phe Ile Asp Tyr Arg Gly Phe Asp Lys
            595                 600                 605

Arg Asn Glu Thr Pro Ile Tyr Glu Phe Gly His Gly Leu Ser Tyr Thr
            610                 615                 620

Thr Phe
625

<210> SEQ ID NO 57
<211> LENGTH: 590
<212> TYPE: PRT
<213> ORGANISM: Aspergillus fumigatus

<400> SEQUENCE: 57

Gly Ser Trp Ala Ala Tyr Ala Lys Ala Lys Lys Phe Val Ala Gln
 1               5                  10                  15

Leu Thr Pro Glu Glu Lys Val Asn Leu Thr Ala Gly Thr Asp Ala Asn
            20                  25                  30

Asn Gly Cys Ser Gly Asn Ile Ala Ala Ile Pro Arg Leu Asn Phe Pro
        35                  40                  45

Gly Leu Cys Val Ser Asp Ala Gly Asn Gly Leu Arg Gly Thr Asp Tyr
    50                  55                  60

Val Ser Ser Trp Pro Ser Gly Leu His Val Gly Ala Ser Trp Asn Lys
65                  70                  75                  80

Ala Leu Ala Arg Gln Arg Ala Val Gln Met Ala Thr Glu Phe Arg Lys
                85                  90                  95

Lys Gly Val Asn Val Leu Leu Gly Pro Val Val Gly Pro Leu Gly Arg
            100                 105                 110

Val Ala Glu Ala Gly Arg Asn Trp Glu Gly Phe Ser Asn Asp Pro Tyr
            115                 120                 125

Leu Ser Gly Ala Leu Val Tyr Glu Thr Val Asp Gly Ala Gln Ser Val
    130                 135                 140

Gly Val Ala Thr Cys Thr Lys His Tyr Ile Leu Asn Glu Gln Glu Thr
145                 150                 155                 160

Asn Arg Asn Pro Gly Met Glu Asp Gly Val Glu Val Ala Ala Val Ser
                165                 170                 175

Ser Asn Ile Asp Asp Lys Thr Met His Glu Leu Tyr Leu Trp Pro Phe
            180                 185                 190

Gln Asp Ala Val Leu Ala Gly Ser Ala Ser Ile Met Cys Ser Tyr Asn
            195                 200                 205

Arg Val Asn Asn Ser Tyr Gly Cys Gln Asn Ser Lys Thr Leu Asn Gly
    210                 215                 220

Leu Leu Lys Thr Glu Leu Gly Phe Gln Gly Tyr Val Met Thr Asp Trp
225                 230                 235                 240

Gly Ala Gln His Ala Gly Ile Ala Gly Ala Asn Ala Gly Leu Asp Met
                245                 250                 255

Val Met Pro Ser Thr Glu Thr Trp Gly Ala Asn Leu Thr Thr Ala Ile
            260                 265                 270

Ser Asn Gly Thr Met Asp Ala Ser Arg Leu Asp Asp Met Ala Thr Arg
            275                 280                 285

Ile Ile Ala Ser Trp Tyr Gln Met Asn Gln Asp Ser Asp Phe Pro Ser
    290                 295                 300
```

```
Pro Gly Ala Gly Met Pro Ser Asp Met Tyr Ala Pro His Gln Arg Val
305                 310                 315                 320

Ile Gly Arg Asp Ala Ser Ser Lys Gln Thr Leu Leu Arg Gly Ala Ile
            325                 330                 335

Glu Gly His Val Leu Val Lys Asn Asn His Ser Ala Leu Pro Leu Lys
            340                 345                 350

Ser Pro Gln Leu Leu Ser Val Phe Gly Tyr Asp Ala Lys Gly Pro Asn
            355                 360                 365

Ala Leu Lys Gln Asn Phe Asn Trp Leu Ser Tyr Ser Pro Ala Ile Gln
370                 375                 380

Glu Asn His Thr Leu Trp Val Gly Gly Ser Gly Ala Asn Asn Ala
385                 390                 395                 400

Ala Tyr Ile Asp Ala Pro Ile Asp Ala Ile Gln Arg Gln Ala Tyr Glu
            405                 410                 415

Asp Gly Thr Ser Val Leu Tyr Asp Ile Ser Ser Glu Asp Pro Glu Val
            420                 425                 430

Asp Pro Thr Thr Asp Ala Cys Leu Val Phe Ile Asn Ser Tyr Ala Thr
            435                 440                 445

Glu Gly Trp Asp Arg Pro Gly Leu Ala Asp Asn Ser Ser Asp Thr Leu
            450                 455                 460

Val Lys Asn Val Ala Arg Lys Cys Ala Asn Thr Ile Val Thr Ile His
465                 470                 475                 480

Asn Ala Gly Ile Arg Val Val Gly Glu Trp Ile Asp His Glu Asn Val
            485                 490                 495

Thr Ala Val Ile Phe Ala His Leu Pro Gly Gln Asp Ser Gly Arg Ala
            500                 505                 510

Leu Val Glu Leu Leu Tyr Gly Arg Ala Asn Pro Ser Gly Lys Leu Pro
            515                 520                 525

Tyr Thr Val Ala Lys Lys Val Glu Asp Tyr Gly Ser Leu Leu His Pro
            530                 535                 540

Ser Leu Pro Glu Thr Pro Tyr Gly Leu Phe Pro Gln Ser Asp Phe Asp
545                 550                 555                 560

Glu Gly Val Tyr Ile Asp Tyr Arg Ala Phe Asp Arg Ala Asn Ile Thr
            565                 570                 575

Ala Gln Phe Glu Phe Gly Phe Gly Leu Ser Tyr Thr Ser Phe
            580                 585                 590

<210> SEQ ID NO 58
<211> LENGTH: 627
<212> TYPE: PRT
<213> ORGANISM: Aspergillus fumigatus

<400> SEQUENCE: 58

Pro Trp Ala Asp Gly Gln Gly Glu Trp Ala Asp Ala His Arg Arg Ala
1               5                   10                  15

Val Glu Ile Val Ser Gln Met Thr Leu Ala Glu Lys Val Asn Leu Thr
            20                  25                  30

Thr Gly Thr Gly Trp Glu Met Asp Arg Cys Val Gly Gln Thr Gly Ser
            35                  40                  45

Val Pro Arg Leu Gly Ile Asn Trp Gly Leu Cys Gly Gln Asp Ser Pro
        50                  55                  60

Leu Gly Ile Arg Phe Ser Asp Leu Asn Ser Ala Phe Pro Ala Gly Thr
65                  70                  75                  80

Asn Val Ala Ala Thr Trp Asp Lys Thr Leu Ala Tyr Leu Arg Gly Lys
            85                  90                  95
```

```
Ala Met Gly Glu Glu Phe Asn Asp Lys Gly Val Asp Ile Leu Leu Gly
            100                 105                 110
Pro Ala Ala Gly Pro Leu Gly Lys Tyr Pro Asp Gly Arg Ile Trp
        115                 120                 125
Glu Gly Phe Ser Pro Asp Pro Ala Leu Thr Gly Val Leu Phe Ala Glu
    130                 135                 140
Thr Ile Lys Gly Ile Gln Asp Ala Gly Val Ile Ala Thr Ala Lys His
145                 150                 155                 160
Tyr Ile Leu Asn Glu Gln Glu His Phe Arg Gln Val Gly Glu Ala Gln
                165                 170                 175
Gly Tyr Gly Tyr Asn Ile Thr Glu Thr Ile Ser Ser Asn Val Asp Asp
            180                 185                 190
Lys Thr Met His Glu Leu Tyr Leu Trp Pro Phe Ala Asp Ala Val Arg
        195                 200                 205
Ala Gly Val Gly Ala Val Met Cys Ser Tyr Asn Gln Ile Asn Asn Ser
    210                 215                 220
Tyr Gly Cys Gln Asn Ser Gln Thr Leu Asn Lys Leu Leu Lys Ala Glu
225                 230                 235                 240
Leu Gly Phe Gln Gly Phe Val Met Ser Asp Trp Ser Ala His His Ser
                245                 250                 255
Gly Val Gly Ala Ala Leu Ala Gly Leu Asp Met Ser Met Pro Gly Asp
            260                 265                 270
Ile Ser Phe Asp Asp Gly Leu Ser Phe Trp Gly Thr Asn Leu Thr Val
        275                 280                 285
Ser Val Leu Asn Gly Thr Val Pro Ala Trp Arg Val Asp Asp Met Ala
    290                 295                 300
Val Arg Ile Met Thr Ala Tyr Tyr Lys Val Gly Arg Asp Arg Leu Arg
305                 310                 315                 320
Ile Pro Pro Asn Phe Ser Ser Trp Thr Arg Asp Glu Tyr Gly Trp Glu
                325                 330                 335
His Ser Ala Val Ser Glu Gly Ala Trp Thr Lys Val Asn Asp Phe Val
            340                 345                 350
Asn Val Gln Arg Ser His Ser Gln Ile Ile Arg Glu Ile Gly Ala Ala
        355                 360                 365
Ser Thr Val Leu Leu Lys Asn Thr Gly Ala Leu Pro Leu Thr Gly Lys
    370                 375                 380
Glu Val Lys Val Gly Val Leu Gly Glu Asp Ala Gly Ser Asn Pro Trp
385                 390                 395                 400
Gly Ala Asn Gly Cys Pro Asp Arg Gly Cys Asp Asn Gly Thr Leu Ala
                405                 410                 415
Met Ala Trp Gly Ser Gly Thr Ala Asn Phe Pro Tyr Leu Val Thr Pro
            420                 425                 430
Glu Gln Ala Ile Gln Arg Glu Val Ile Ser Asn Gly Gly Asn Val Phe
        435                 440                 445
Ala Val Thr Asp Asn Gly Ala Leu Ser Gln Met Ala Asp Val Ala Ser
    450                 455                 460
Gln Ser Ser Val Ser Leu Val Phe Val Asn Ala Asp Ser Gly Glu Gly
465                 470                 475                 480
Phe Ile Ser Val Asp Gly Asn Glu Gly Asp Arg Lys Asn Leu Thr Leu
                485                 490                 495
Trp Lys Asn Gly Glu Ala Val Ile Asp Thr Val Val Ser His Cys Asn
            500                 505                 510
Asn Thr Ile Val Val Ile His Ser Val Gly Pro Val Leu Ile Asp Arg
```

```
                    515                 520                 525
Trp Tyr Asp Asn Pro Asn Val Thr Ala Ile Ile Trp Ala Gly Leu Pro
            530                 535                 540

Gly Gln Glu Ser Gly Asn Ser Leu Val Asp Val Leu Tyr Gly Arg Val
545                 550                 555                 560

Asn Pro Ser Ala Lys Thr Pro Phe Thr Trp Lys Thr Arg Glu Ser
                565                 570                 575

Tyr Gly Ala Pro Leu Leu Thr Glu Pro Asn Asn Gly Asn Gly Ala Pro
            580                 585                 590

Gln Asp Asp Phe Asn Glu Gly Val Phe Ile Asp Tyr Arg His Phe Asp
                595                 600                 605

Lys Arg Asn Glu Thr Pro Ile Tyr Glu Phe Gly His Gly Leu Ser Tyr
            610                 615                 620

Thr Thr Phe
625

<210> SEQ ID NO 59
<211> LENGTH: 626
<212> TYPE: PRT
<213> ORGANISM: Aspergillus kawachii

<400> SEQUENCE: 59

Pro Trp Ala Asn Gly Gln Gly Asp Trp Ala Gln Ala Tyr Gln Arg Ala
1               5                   10                  15

Val Asp Ile Val Ser Gln Met Thr Leu Ala Glu Lys Val Asn Leu Thr
                20                  25                  30

Thr Gly Thr Gly Trp Glu Leu Glu Leu Cys Val Gly Gln Thr Gly Gly
            35                  40                  45

Val Pro Arg Leu Gly Val Pro Gly Met Cys Leu Gln Asp Ser Pro Leu
50                  55                  60

Gly Val Arg Asp Ser Asp Tyr Asn Ser Ala Phe Pro Ser Gly Met Asn
65                  70                  75                  80

Val Ala Ala Thr Trp Asp Lys Asn Leu Ala Tyr Leu Arg Gly Lys Ala
                85                  90                  95

Met Gly Gln Glu Phe Ser Asp Lys Gly Ala Asp Ile Gln Leu Gly Pro
            100                 105                 110

Ala Ala Gly Pro Leu Gly Arg Ser Pro Asp Gly Gly Arg Asn Trp Glu
        115                 120                 125

Gly Phe Ser Pro Asp Pro Ala Leu Ser Gly Val Leu Phe Ala Glu Thr
    130                 135                 140

Ile Lys Gly Ile Gln Asp Ala Gly Val Val Ala Thr Ala Lys His Tyr
145                 150                 155                 160

Ile Ala Tyr Glu Gln Glu His Phe Arg Gln Ala Pro Glu Ala Gln Gly
                165                 170                 175

Tyr Gly Phe Asn Ile Ser Glu Ser Gly Ser Ala Asn Leu Asp Asp Lys
            180                 185                 190

Thr Met His Glu Leu Tyr Leu Trp Pro Phe Ala Asp Ala Ile Arg Ala
        195                 200                 205

Gly Ala Gly Ala Val Met Cys Ser Tyr Asn Gln Ile Asn Asn Ser Tyr
    210                 215                 220

Gly Cys Gln Asn Ser Tyr Thr Leu Asn Lys Leu Leu Lys Ala Glu Leu
225                 230                 235                 240

Gly Phe Gln Gly Phe Val Met Ser Asp Trp Ala Ala His His Ala Gly
                245                 250                 255

Val Ser Gly Ala Leu Ala Gly Leu Asp Met Ser Met Pro Gly Asp Val
```

```
                    260                 265                 270
Asp Tyr Asp Ser Gly Thr Ser Tyr Trp Gly Thr Asn Leu Thr Val Ser
                275                 280                 285
Val Leu Asn Gly Thr Val Pro Gln Trp Arg Val Asp Asp Met Ala Val
            290                 295                 300
Arg Ile Met Ala Ala Tyr Tyr Lys Val Gly Arg Asp Arg Leu Trp Thr
305                 310                 315                 320
Pro Pro Asn Phe Ser Ser Trp Thr Arg Asp Glu Tyr Gly Tyr Lys Tyr
                325                 330                 335
Tyr Tyr Val Ser Glu Gly Pro Tyr Glu Lys Val Asn His Tyr Val Asn
                340                 345                 350
Val Gln Arg Asn His Ser Glu Leu Ile Arg Arg Ile Gly Ala Asp Ser
                355                 360                 365
Thr Val Leu Leu Lys Asn Asp Gly Ala Leu Pro Leu Thr Gly Lys Glu
            370                 375                 380
Arg Leu Val Ala Leu Ile Gly Glu Asp Ala Gly Ser Asn Pro Tyr Gly
385                 390                 395                 400
Ala Asn Gly Cys Ser Asp Arg Gly Cys Asp Asn Gly Thr Leu Ala Met
                405                 410                 415
Gly Trp Gly Ser Gly Thr Ala Asn Phe Pro Tyr Leu Val Thr Pro Glu
                420                 425                 430
Gln Ala Ile Ser Asn Glu Val Leu Lys Asn Lys Asn Gly Val Phe Thr
                435                 440                 445
Ala Thr Asp Asn Trp Ala Ile Asp Gln Ile Glu Ala Leu Ala Lys Thr
            450                 455                 460
Ala Ser Val Ser Leu Val Phe Val Asn Ala Asp Ser Gly Glu Gly Tyr
465                 470                 475                 480
Ile Asn Val Asp Gly Asn Leu Gly Asp Arg Lys Asn Leu Thr Leu Trp
                485                 490                 495
Arg Asn Gly Asp Asn Val Ile Lys Ala Ala Ala Ser Asn Cys Asn Asn
                500                 505                 510
Thr Ile Val Ile His Ser Val Gly Pro Val Leu Val Asn Glu Trp
            515                 520                 525
Tyr Asp Asn Pro Asn Val Thr Ala Ile Leu Trp Gly Gly Leu Pro Gly
            530                 535                 540
Gln Glu Ser Gly Asn Ser Leu Ala Asp Val Leu Tyr Gly Arg Val Asn
545                 550                 555                 560
Pro Gly Ala Lys Ser Pro Phe Thr Trp Gly Lys Thr Arg Glu Ala Tyr
                565                 570                 575
Gln Asp Tyr Leu Val Thr Glu Pro Asn Asn Gly Asn Gly Ala Pro Gln
            580                 585                 590
Glu Asp Phe Val Glu Gly Val Phe Ile Asp Tyr Arg Gly Phe Asp Lys
            595                 600                 605
Arg Asn Glu Thr Pro Ile Tyr Glu Phe Gly Tyr Gly Leu Ser Tyr Thr
            610                 615                 620
Thr Phe
625

<210> SEQ ID NO 60
<211> LENGTH: 585
<212> TYPE: PRT
<213> ORGANISM: Aspergillus nidulans

<400> SEQUENCE: 60

Ala Leu Pro Ile Tyr Lys Asn Ala Ser Tyr Cys Val Asp Glu Arg Val
```

```
             1               5                  10                 15
Arg Asp Leu Leu Ser Arg Met Thr Leu Glu Glu Lys Ala Gly Gln Leu
                    20                 25                 30

Phe His Lys Gln Leu Ser Glu Gly Pro Leu Asp Asp Ser Ser Gly
            35                 40                 45

Asn Ser Thr Glu Thr Met Ile Gly Lys Lys His Met Thr His Phe Asn
        50                 55                 60

Leu Ala Ser Asp Ile Thr Asn Ala Thr Gln Thr Ala Glu Phe Ile Asn
65                  70                 75                      80

Leu Ile Gln Lys Arg Ala Leu Gln Thr Arg Leu Gly Ile Pro Ile Thr
                85                 90                  95

Ile Ser Thr Asp Pro Arg His Ser Phe Thr Glu Asn Val Gly Thr Gly
                100                105                110

Phe Gln Ala Gly Val Phe Ser Gln Trp Pro Glu Ser Leu Gly Leu Ala
            115                120                125

Ala Leu Arg Asp Pro Gln Leu Val Arg Glu Phe Ala Glu Val Ala Arg
        130                135                 140

Glu Glu Tyr Leu Ala Val Gly Ile Arg Ala Ala Leu His Pro Gln Val
145                 150                155                    160

Asp Leu Ser Thr Glu Pro Arg Trp Ala Arg Ile Ser Gly Thr Trp Gly
                165                170                175

Glu Asn Ser Thr Leu Thr Ser Glu Leu Ile Val Glu Tyr Ile Lys Gly
            180                185                190

Phe Gln Gly Glu Gly Lys Leu Gly Pro Lys Ser Val Lys Thr Val Thr
            195                200                205

Lys His Phe Pro Gly Gly Pro Met Glu Asn Gly Glu Asp Ser His
        210                215                220

Phe Tyr Tyr Gly Lys Asn Gln Thr Tyr Pro Gly Asn Asn Ile Asp Glu
225                 230                235                    240

His Leu Ile Pro Phe Lys Ala Ala Leu Ala Gly Ala Thr Glu Ile
                245                250                255

Met Pro Tyr Tyr Ser Arg Pro Ile Gly Thr Asn Trp Glu Ala Val Gly
            260                265                270

Phe Ser Phe Asn Lys Glu Ile Val Thr Asp Leu Leu Arg Gly Glu Leu
        275                280                285

Gly Phe Asp Gly Ile Val Leu Thr Asp Trp Gly Leu Ile Thr Asp Thr
        290                295                300

Tyr Ile Gly Asn Gln Tyr Met Pro Ala Arg Ala Trp Gly Val Glu Tyr
305                 310                315                    320

Leu Ser Glu Leu Gln Arg Ala Ala Arg Ile Leu Asp Ala Gly Cys Asp
                325                330                335

Gln Phe Gly Gly Glu Glu Arg Pro Glu Leu Ile Val Gln Leu Val Arg
            340                345                350

Glu Gly Thr Ile Ser Glu Asp Arg Ile Asp Val Ser Val Ala Arg Leu
            355                360                365

Leu Lys Glu Lys Phe Leu Leu Gly Leu Phe Asp Asn Pro Phe Val Asn
    370                375                380

Ala Ser Ala Ala Asn Asn Ile Val Gly Asn Glu His Phe Val Asn Leu
385                 390                395                    400

Gly Arg Asp Ala Gln Arg Arg Ser Tyr Thr Leu Leu Thr Asn Asn Gln
                405                410                415

Thr Ile Leu Pro Leu Ala Lys Pro Gly Glu Gly Thr Arg Phe Tyr Ile
                420                425                430
```

```
Glu Gly Phe Asp Ser Ala Phe Met Ser Ala Arg Asn Tyr Thr Val Val
        435                 440                 445

Asn Thr Thr Glu Glu Ala Asp Phe Ala Leu Leu Arg Tyr Asn Ala Pro
450                 455                 460

Tyr Glu Pro Arg Asn Gly Thr Phe Glu Ala Asn Phe His Ala Gly Ser
465                 470                 475                 480

Leu Ala Phe Asn Ala Thr Glu Lys Ala Arg Gln Ala Lys Ile Tyr Ser
                485                 490                 495

Ser Leu Pro Thr Ile Val Asp Ile Ile Leu Asp Arg Pro Ala Val Ile
                500                 505                 510

Pro Glu Val Val Glu Gln Ala Gln Ala Val Leu Ala Ser Tyr Gly Ser
                515                 520                 525

Asp Ser Glu Ala Phe Leu Asp Val Val Phe Gly Val Ser Lys Pro Glu
530                 535                 540

Gly Lys Leu Pro Phe Asp Leu Pro Arg Ser Met Asp Ala Val Glu Ala
545                 550                 555                 560

Gln Ala Glu Asp Leu Pro Phe Asp Thr Glu Asn Pro Val Phe Arg Tyr
                565                 570                 575

Gly His Gly Leu Glu Tyr Glu Asp Asn
                580                 585

<210> SEQ ID NO 61
<211> LENGTH: 718
<212> TYPE: PRT
<213> ORGANISM: Aspergillus nidulans

<400> SEQUENCE: 61

Ala Gln Ile Glu Ser Val Leu Ser Lys Leu Thr Leu Glu Glu Lys Ile
1               5                   10                  15

Ser Leu Leu Ala Gly Lys Asn Phe Trp Glu Thr Gln Asp Tyr Pro Glu
            20                  25                  30

Lys Gly Val Pro Pro Val Lys Ser Asp Gly Pro Asn Gly Ala Arg
        35                  40                  45

Gly Ala Thr Phe Lys Gly Gly Val Thr Ala Ala Cys Phe Pro Ala Ser
50                  55                  60

Ser Leu Leu Ala Ala Thr Trp Asp Leu Asp Ala Ala Lys His Ile Gly
65                  70                  75                  80

Glu Ala Leu Ala Asp Glu Thr Arg Ser Lys Gly Ala Arg Val Leu Leu
                85                  90                  95

Ala Pro Thr Val Cys Ile His Arg His Pro Leu Gly Gly Arg Asn Phe
            100                 105                 110

Glu Ser Phe Ser Glu Asp Pro Phe Leu Ala Gly Lys Leu Ala Ala Gln
        115                 120                 125

Tyr Ile Lys Gly Leu Gln Gly Asn Gly Val Ala Ala Thr Ile Lys His
130                 135                 140

Tyr Ala Ala Asn Glu Gln Glu Thr Cys Arg Phe Thr Val Asn Glu His
145                 150                 155                 160

Ile Thr Glu Arg Ala Leu Arg Glu Ile Tyr Leu Lys Pro Phe Glu Ile
                165                 170                 175

Ala Ile Lys Glu Ser Asn Pro Leu Ala Val Met Thr Ala Tyr Asn Ile
            180                 185                 190

Val Asn Gly Thr His Ala Asp Ser Asn Asn Phe Leu Leu Arg Asp Val
        195                 200                 205

Leu Arg Gly Glu Trp Gly Trp Lys Gly Leu Val Met Ser Asp Trp Gly
210                 215                 220
```

```
Gly Thr Asn Ser Thr Ala Asp Ala Leu Asn Ala Gly Leu Asp Leu Glu
225                 230                 235                 240

Met Pro Gly Pro Thr Arg Trp Arg Lys Val Asp Glu Val Leu Ala Val
            245                 250                 255

Val Lys Ser Gly Ala Val Leu Glu Glu Thr Ile Asp Glu Arg Ala Arg
        260                 265                 270

Asn Val Leu Glu Leu Leu Ala Lys Leu Asn Cys Phe Glu Asn Pro Thr
    275                 280                 285

Ile Pro Glu Glu Lys Ala Ile Asn Arg Pro Glu His Gln Lys Leu Ile
290                 295                 300

Arg Ser Val Gly Ser Gln Gly Leu Val Leu Lys Asn Glu Gly Asp
305                 310                 315                 320

Val Leu Pro Leu Arg Lys Glu Ile Leu Thr Asn Lys Lys Val Ala Leu
            325                 330                 335

Leu Gly Phe Ala Arg Glu Ala Leu Ile His Gly Gly Ser Ala Ser
        340                 345                 350

Val Asn Ala His Tyr Arg Val Thr Pro Glu Glu Gly Leu Arg Ala Ala
    355                 360                 365

Leu Gly Asp Thr Val Glu Phe Glu Tyr Ala Lys Gly Ala His Thr Phe
370                 375                 380

Arg Gln Leu Pro Leu Met Ser Asp Asn Val Val Asn Leu Glu Gly Gln
385                 390                 395                 400

Pro Gly Trp Thr Leu Asp Phe Phe Ala Asp Glu Pro Asn Gly Glu
            405                 410                 415

Pro Gly Ser Ser Ile Ser Ser Glu Gln Pro Ser Tyr Ile Pro Leu Phe
        420                 425                 430

Val Lys Glu Ser Trp Gly Ser Val Arg Ala Ser Ala His Phe Thr Pro
    435                 440                 445

Thr Gln Ser Gly Lys His Tyr Phe Gly Met Ser Gly Leu Gly Arg Ser
450                 455                 460

Lys Leu Leu Ile Asp Gly Glu Val Ile Tyr Glu Gln Lys Leu Asn Cys
465                 470                 475                 480

Pro Asp Ser Met Gly Phe Leu Gly Gly Val Glu Glu Pro Glu Ile
            485                 490                 495

Gln Tyr Ser Phe Glu Ala Gly Lys Thr Tyr Ala Val Glu Val Val Ser
        500                 505                 510

Val Lys Pro Thr Ser Lys Gly Leu Ala Leu Leu Asp Gly Phe Ile
    515                 520                 525

Gly Phe Arg Leu Gly Phe Met Thr Glu Glu Glu His Asn Arg Asp Leu
530                 535                 540

Leu Ser Glu Ala Val Asp Val Ala Lys Arg Ser Asp Ile Ala Ile Val
545                 550                 555                 560

Phe Thr Gly His Thr Pro Asp Trp Glu Thr Glu Gly Gln Asp Gln Ile
            565                 570                 575

Ser Phe His Leu Pro Ser Asn Gly Ser Gln Asp Arg Leu Val Ala Ala
        580                 585                 590

Val Gly Ala Ala Asn Pro Asn Thr Val Val Asn Cys Thr Gly Val
    595                 600                 605

Ala Val Ala Met Pro Trp Leu Asp Lys Val Lys Ala Val Gln Ala
610                 615                 620

Trp Phe Pro Gly Gln Glu Ala Gly Asn Ala Ile Ala Asp Val Leu Thr
625                 630                 635                 640

Gly Ala Val Asn Pro Ser Gly Arg Leu Pro Val Ser Phe Pro Arg Ala
            645                 650                 655
```

```
Ile Glu Asp Ala Pro Ala His Gly Asn Phe Pro Gly Asp Tyr Thr Asp
            660                 665                 670

Gly Lys Asp Asn Arg Arg His Leu Glu Val Thr Tyr Lys Glu Gly Val
        675                 680                 685

Phe Val Gly Tyr Arg His Tyr Asp Leu Ser Glu Ala Asn Arg Ala Lys
    690                 695                 700

Val Leu Phe Pro Phe Gly Tyr Gly Leu Ser Tyr Thr Thr Phe
705                 710                 715

<210> SEQ ID NO 62
<211> LENGTH: 626
<212> TYPE: PRT
<213> ORGANISM: Aspergillus niger

<400> SEQUENCE: 62

Pro Trp Ala Asn Gly Gln Gly Asp Trp Ala Gln Ala Tyr Gln Arg Ala
1               5                   10                  15

Val Asp Ile Val Ser Gln Met Thr Leu Asp Glu Lys Val Asn Leu Thr
                20                  25                  30

Thr Gly Thr Gly Trp Glu Leu Glu Leu Cys Val Gly Gln Thr Gly Gly
            35                  40                  45

Val Pro Arg Leu Gly Val Pro Gly Met Cys Leu Gln Asp Ser Pro Leu
        50                  55                  60

Gly Val Arg Asp Ser Asp Tyr Asn Ser Ala Phe Pro Ala Gly Met Asn
65                  70                  75                  80

Val Ala Ala Thr Trp Asp Lys Asn Leu Ala Tyr Leu Arg Gly Lys Ala
                85                  90                  95

Met Gly Gln Glu Phe Ser Asp Lys Gly Ala Asp Ile Gln Leu Gly Pro
            100                 105                 110

Ala Ala Gly Pro Leu Gly Arg Ser Pro Asp Gly Gly Arg Asn Trp Glu
        115                 120                 125

Gly Phe Ser Pro Asp Pro Ala Leu Ser Gly Val Leu Phe Ala Glu Thr
130                 135                 140

Ile Lys Gly Ile Gln Asp Ala Gly Val Val Ala Thr Ala Lys His Tyr
145                 150                 155                 160

Ile Ala Tyr Glu Gln Glu His Phe Arg Gln Ala Pro Glu Ala Gln Gly
                165                 170                 175

Phe Gly Phe Asn Ile Ser Glu Ser Gly Ser Ala Asn Leu Asp Asp Lys
            180                 185                 190

Thr Met His Glu Leu Tyr Leu Trp Pro Phe Ala Asp Ala Ile Arg Ala
        195                 200                 205

Gly Ala Gly Ala Val Met Cys Ser Tyr Asn Gln Ile Asn Asn Ser Tyr
210                 215                 220

Gly Cys Gln Asn Ser Tyr Thr Leu Asn Lys Leu Leu Lys Ala Glu Leu
225                 230                 235                 240

Gly Phe Gln Gly Phe Val Met Ser Asp Trp Ala Ala His His Ala Gly
                245                 250                 255

Val Ser Gly Ala Leu Ala Gly Leu Asp Met Ser Met Pro Gly Asp Val
            260                 265                 270

Asp Tyr Asp Ser Gly Thr Ser Tyr Trp Gly Thr Asn Leu Thr Ile Ser
        275                 280                 285

Val Leu Asn Gly Thr Val Pro Gln Trp Arg Val Asp Asp Met Ala Val
        290                 295                 300

Arg Ile Met Ala Ala Tyr Tyr Lys Val Gly Arg Asp Arg Leu Trp Thr
305                 310                 315                 320
```

```
Pro Pro Asn Phe Ser Ser Trp Thr Arg Asp Glu Tyr Gly Tyr Lys Tyr
            325                 330                 335

Tyr Tyr Val Ser Glu Gly Pro Tyr Glu Lys Val Asn Gln Tyr Val Asn
            340                 345                 350

Val Gln Arg Asn His Ser Glu Leu Ile Arg Arg Ile Gly Ala Asp Ser
            355                 360                 365

Thr Val Leu Leu Lys Asn Asp Gly Ala Leu Pro Leu Thr Gly Lys Glu
        370                 375                 380

Arg Leu Val Ala Leu Ile Gly Glu Asp Ala Gly Ser Asn Pro Tyr Gly
385                 390                 395                 400

Ala Asn Gly Cys Ser Asp Arg Gly Cys Asp Asn Gly Thr Leu Ala Met
            405                 410                 415

Gly Trp Gly Ser Gly Thr Ala Asn Phe Pro Tyr Leu Val Thr Pro Glu
            420                 425                 430

Gln Ala Ile Ser Asn Glu Val Leu Lys His Lys Asn Gly Val Phe Thr
            435                 440                 445

Ala Thr Asp Asn Trp Ala Ile Asp Gln Ile Glu Ala Leu Ala Lys Thr
        450                 455                 460

Ala Ser Val Ser Leu Val Phe Val Asn Ala Asp Ser Gly Glu Gly Tyr
465                 470                 475                 480

Ile Asn Val Asp Gly Asn Leu Gly Asp Arg Arg Asn Leu Thr Leu Trp
            485                 490                 495

Arg Asn Gly Asp Asn Val Ile Lys Ala Ala Ser Asn Cys Asn Asn
            500                 505                 510

Thr Ile Val Val Ile His Ser Val Gly Pro Val Leu Val Asn Glu Trp
        515                 520                 525

Tyr Asp Asn Pro Asn Val Thr Ala Ile Leu Trp Gly Gly Leu Pro Gly
    530                 535                 540

Gln Glu Ser Gly Asn Ser Leu Ala Asp Val Leu Tyr Gly Arg Val Asn
545                 550                 555                 560

Pro Gly Ala Lys Ser Pro Phe Thr Trp Gly Lys Thr Arg Glu Ala Tyr
            565                 570                 575

Gln Asp Tyr Leu Val Thr Glu Pro Asn Asn Gly Asn Gly Ala Pro Gln
            580                 585                 590

Glu Asp Phe Val Glu Gly Val Phe Ile Asp Tyr Arg Gly Phe Asp Lys
            595                 600                 605

Arg Asn Glu Thr Pro Ile Tyr Glu Phe Gly Tyr Gly Leu Ser Tyr Thr
        610                 615                 620

Thr Phe
625

<210> SEQ ID NO 63
<211> LENGTH: 626
<212> TYPE: PRT
<213> ORGANISM: Aspergillus niger

<400> SEQUENCE: 63

Pro Trp Ala Asn Gly Gln Gly Asp Trp Ala Glu Ala Tyr Gln Arg Ala
1               5                   10                  15

Val Asp Ile Val Ser Gln Met Thr Leu Ala Glu Lys Val Asn Leu Thr
            20                  25                  30

Thr Gly Thr Gly Trp Glu Leu Glu Leu Cys Val Gly Gln Thr Gly Gly
        35                  40                  45

Val Pro Arg Leu Gly Ile Pro Gly Met Cys Ala Gln Asp Ser Pro Leu
    50                  55                  60
```

```
Gly Val Arg Asp Ser Asp Tyr Asn Ser Ala Phe Pro Ala Gly Val Asn
 65                  70                  75                  80

Val Ala Ala Thr Trp Asp Lys Asn Leu Ala Tyr Leu Arg Gly Gln Ala
             85                  90                  95

Met Gly Gln Glu Phe Ser Asp Lys Gly Ala Asp Ile Gln Leu Gly Pro
            100                 105                 110

Ala Ala Gly Pro Leu Gly Arg Ser Pro Asp Gly Gly Arg Asn Trp Glu
        115                 120                 125

Gly Phe Ser Pro Asp Pro Ala Leu Ser Gly Val Leu Phe Ala Glu Thr
    130                 135                 140

Ile Lys Gly Ile Gln Asp Ala Gly Val Val Ala Thr Ala Lys His Tyr
145                 150                 155                 160

Ile Ala Tyr Glu Gln Glu His Phe Arg Gln Ala Pro Glu Ala Gln Gly
                165                 170                 175

Tyr Gly Phe Asn Ile Thr Glu Ser Gly Ser Ala Asn Leu Asp Asp Lys
            180                 185                 190

Thr Met His Glu Leu Tyr Leu Trp Pro Phe Ala Asp Ala Ile Arg Ala
        195                 200                 205

Gly Ala Gly Ala Val Met Cys Ser Tyr Asn Gln Ile Asn Asn Ser Tyr
    210                 215                 220

Gly Cys Gln Asn Ser Tyr Thr Leu Asn Lys Leu Leu Lys Ala Glu Leu
225                 230                 235                 240

Gly Phe Gln Gly Phe Val Met Ser Asp Trp Ala Ala His His Ala Gly
                245                 250                 255

Val Ser Gly Ala Leu Ala Gly Leu Asp Met Ser Met Pro Gly Asp Val
            260                 265                 270

Asp Tyr Asp Ser Gly Thr Ser Tyr Trp Gly Thr Asn Leu Thr Ile Ser
        275                 280                 285

Val Leu Asn Gly Thr Val Pro Gln Trp Arg Val Asp Asp Met Ala Val
    290                 295                 300

Arg Ile Met Ala Ala Tyr Tyr Lys Val Gly Arg Asp Arg Leu Trp Thr
305                 310                 315                 320

Pro Pro Asn Phe Ser Ser Trp Thr Arg Asp Glu Tyr Gly Phe Lys Tyr
                325                 330                 335

Tyr Tyr Val Ser Glu Gly Pro Tyr Glu Lys Val Asn Gln Phe Val Asn
            340                 345                 350

Val Gln Arg Asn His Ser Glu Leu Ile Arg Arg Ile Gly Ala Asp Ser
        355                 360                 365

Thr Val Leu Leu Lys Asn Asp Gly Ala Leu Pro Leu Thr Gly Lys Glu
    370                 375                 380

Arg Leu Val Ala Leu Ile Gly Glu Asp Ala Gly Ser Asn Pro Tyr Gly
385                 390                 395                 400

Ala Asn Gly Cys Ser Asp Arg Gly Cys Asp Asn Gly Thr Leu Ala Met
                405                 410                 415

Gly Trp Gly Ser Gly Thr Ala Asn Phe Pro Tyr Leu Val Thr Pro Glu
            420                 425                 430

Gln Ala Ile Ser Asn Glu Val Leu Lys Asn Lys Asn Gly Val Phe Thr
        435                 440                 445

Ala Thr Asp Asn Trp Ala Ile Asp Gln Ile Glu Ala Leu Ala Lys Thr
    450                 455                 460

Ala Ser Val Ser Leu Val Phe Val Asn Ala Asp Ser Gly Glu Gly Tyr
465                 470                 475                 480

Ile Asn Val Asp Gly Asn Leu Gly Asp Arg Arg Asn Leu Thr Leu Trp
```

```
                    485                 490                 495
Arg Asn Gly Asp Asn Val Ile Lys Ala Ala Ser Asn Cys Asn Asn
                500                 505                 510

Thr Ile Val Ile Ile His Ser Val Gly Pro Val Leu Val Asn Glu Trp
            515                 520                 525

Tyr Asp Asn Pro Asn Val Thr Ala Ile Leu Trp Gly Gly Leu Pro Gly
            530                 535                 540

Gln Glu Ser Gly Asn Ser Leu Ala Asp Val Leu Tyr Gly Arg Val Asn
545                 550                 555                 560

Pro Gly Ala Lys Ser Pro Phe Thr Trp Gly Lys Thr Arg Glu Ala Tyr
                565                 570                 575

Gln Asp Tyr Leu Tyr Thr Glu Pro Asn Asn Gly Asn Gly Ala Pro Gln
            580                 585                 590

Glu Asp Phe Val Glu Gly Val Phe Ile Asp Tyr Arg Gly Phe Asp Lys
            595                 600                 605

Arg Asn Glu Thr Pro Ile Tyr Glu Phe Gly Tyr Gly Leu Ser Tyr Thr
            610                 615                 620

Thr Phe
625

<210> SEQ ID NO 64
<211> LENGTH: 626
<212> TYPE: PRT
<213> ORGANISM: Aspergillus oryzae

<400> SEQUENCE: 64

Pro Trp Ala Asp Gly Gln Gly Glu Trp Ala Glu Val Tyr Lys Arg Ala
1               5                   10                  15

Val Asp Ile Val Ser Gln Met Thr Leu Thr Glu Lys Val Asn Leu Thr
                20                  25                  30

Thr Gly Thr Gly Trp Gln Leu Glu Arg Cys Val Gly Gln Thr Gly Ser
            35                  40                  45

Val Pro Arg Leu Asn Ile Pro Ser Leu Cys Leu Gln Asp Ser Pro Leu
    50                  55                  60

Gly Ile Arg Phe Ser Asp Tyr Asn Ser Ala Phe Pro Ala Gly Val Asn
65                  70                  75                  80

Val Ala Ala Thr Trp Asp Lys Thr Leu Ala Tyr Leu Arg Gly Gln Ala
                85                  90                  95

Met Gly Glu Glu Phe Ser Asp Lys Gly Ile Asp Val Gln Leu Gly Pro
                100                 105                 110

Ala Ala Gly Pro Leu Gly Ala His Pro Asp Gly Gly Arg Asn Trp Glu
            115                 120                 125

Gly Phe Ser Pro Asp Pro Ala Leu Thr Gly Val Leu Phe Ala Glu Thr
            130                 135                 140

Ile Lys Gly Ile Gln Asp Ala Gly Val Ile Ala Thr Ala Lys His Tyr
145                 150                 155                 160

Ile Met Asn Glu Gln Glu His Phe Arg Gln Gln Pro Glu Ala Ala Gly
                165                 170                 175

Tyr Gly Phe Asn Val Ser Asp Ser Leu Ser Ser Asn Val Asp Asp Lys
            180                 185                 190

Thr Met His Glu Leu Tyr Leu Trp Pro Phe Ala Asp Ala Val Arg Ala
            195                 200                 205

Gly Val Gly Ala Val Met Cys Ser Tyr Asn Gln Ile Asn Asn Ser Tyr
    210                 215                 220

Gly Cys Glu Asn Ser Glu Thr Leu Asn Lys Leu Leu Lys Ala Glu Leu
```

```
                    225                 230                 235                 240
Gly Phe Gln Gly Phe Val Met Ser Asp Trp Thr Ala His His Ser Gly
                245                 250                 255
Val Gly Ala Ala Leu Ala Gly Leu Asp Met Ser Met Pro Gly Asp Val
            260                 265                 270
Thr Phe Asp Ser Gly Thr Ser Phe Trp Gly Ala Asn Leu Thr Val Gly
        275                 280                 285
Val Leu Asn Gly Thr Ile Pro Gln Trp Arg Val Asp Asp Met Ala Val
290                 295                 300
Arg Ile Met Ala Ala Tyr Tyr Lys Val Gly Arg Asp Thr Lys Tyr Thr
305                 310                 315                 320
Pro Pro Asn Phe Ser Ser Trp Thr Arg Asp Glu Tyr Gly Phe Ala His
                325                 330                 335
Asn His Val Ser Glu Gly Ala Tyr Glu Arg Val Asn Glu Phe Val Asp
            340                 345                 350
Val Gln Arg Asp His Ala Asp Leu Ile Arg Arg Ile Gly Ala Gln Ser
        355                 360                 365
Thr Val Leu Leu Lys Asn Lys Gly Ala Leu Pro Leu Ser Arg Lys Glu
    370                 375                 380
Lys Leu Val Ala Leu Leu Gly Glu Asp Ala Gly Ser Asn Ser Trp Gly
385                 390                 395                 400
Ala Asn Gly Cys Asp Asp Arg Gly Cys Asp Asn Gly Thr Leu Ala Met
                405                 410                 415
Ala Trp Gly Ser Gly Thr Ala Asn Phe Pro Tyr Leu Val Thr Pro Glu
            420                 425                 430
Gln Ala Ile Gln Asn Glu Val Leu Gln Gly Arg Gly Asn Val Phe Ala
        435                 440                 445
Val Thr Asp Ser Trp Ala Leu Asp Lys Ile Ala Ala Ala Arg Gln
    450                 455                 460
Ala Ser Val Ser Leu Val Phe Val Asn Ser Asp Ser Gly Glu Ser Tyr
465                 470                 475                 480
Leu Ser Val Asp Gly Asn Glu Gly Asp Arg Asn Asn Ile Thr Leu Trp
                485                 490                 495
Lys Asn Gly Asp Asn Val Val Lys Thr Ala Ala Asn Cys Asn Asn
            500                 505                 510
Thr Val Ile Ile His Ser Val Gly Pro Val Leu Ile Asp Glu Trp
    515                 520                 525
Tyr Asp His Pro Asn Val Thr Gly Ile Leu Trp Ala Gly Leu Pro Gly
530                 535                 540
Gln Glu Ser Gly Asn Ser Ile Ala Asp Val Leu Tyr Gly Arg Val Asn
545                 550                 555                 560
Pro Gly Ala Lys Ser Pro Phe Thr Trp Gly Lys Thr Arg Glu Ser Tyr
                565                 570                 575
Gly Ser Pro Leu Val Lys Asp Ala Asn Asn Gly Asn Gly Ala Pro Gln
            580                 585                 590
Ser Asp Phe Thr Gln Gly Val Phe Ile Asp Tyr Arg His Phe Asp Lys
        595                 600                 605
Phe Asn Glu Thr Pro Ile Tyr Glu Phe Gly Tyr Gly Leu Ser Tyr Thr
    610                 615                 620
Thr Phe
625

<210> SEQ ID NO 65
<211> LENGTH: 626
```

```
<212> TYPE: PRT
<213> ORGANISM: Aspergillus oryzae

<400> SEQUENCE: 65

Pro Trp Ala Asp Gly Gln Gly Glu Trp Ala Glu Val Tyr Lys Arg Ala
1               5                   10                  15

Val Asp Ile Val Ser Gln Met Thr Leu Thr Glu Lys Val Asn Leu Thr
            20                  25                  30

Thr Gly Thr Gly Trp Gln Leu Glu Arg Cys Val Gly Gln Thr Gly Ser
        35                  40                  45

Val Pro Arg Leu Asn Ile Pro Ser Leu Cys Leu Gln Asp Ser Pro Leu
    50                  55                  60

Gly Ile Arg Phe Ser Asp Tyr Asn Ser Ala Phe Pro Ala Gly Val Asn
65                  70                  75                  80

Val Ala Ala Thr Trp Asp Lys Thr Leu Ala Tyr Leu Arg Gly Gln Ala
                85                  90                  95

Met Gly Glu Glu Phe Ser Asp Lys Gly Ile Asp Val Gln Leu Gly Pro
            100                 105                 110

Ala Ala Gly Pro Leu Gly Ala His Pro Asp Gly Gly Arg Asn Trp Glu
        115                 120                 125

Gly Phe Ser Pro Asp Pro Ala Leu Thr Gly Val Leu Phe Ala Glu Thr
    130                 135                 140

Ile Lys Gly Ile Gln Asp Ala Gly Val Ile Ala Thr Ala Lys His Tyr
145                 150                 155                 160

Ile Met Asn Glu Gln Glu His Phe Arg Gln Gln Pro Glu Ala Ala Gly
                165                 170                 175

Tyr Gly Phe Asn Val Ser Asp Ser Leu Ser Ser Asn Val Asp Asp Lys
            180                 185                 190

Thr Met His Glu Leu Tyr Leu Trp Pro Phe Ala Asp Ala Val Arg Ala
        195                 200                 205

Gly Val Gly Ala Val Met Cys Ser Tyr Asn Gln Ile Asn Asn Ser Tyr
    210                 215                 220

Gly Cys Glu Asn Ser Glu Thr Leu Asn Lys Leu Leu Lys Ala Glu Leu
225                 230                 235                 240

Gly Phe Gln Gly Phe Val Met Ser Asp Trp Thr Ala His His Ser Gly
                245                 250                 255

Val Gly Ala Ala Leu Ala Gly Leu Asp Met Ser Met Pro Gly Asp Val
            260                 265                 270

Thr Phe Asp Ser Gly Thr Ser Phe Trp Gly Ala Asn Leu Thr Val Gly
        275                 280                 285

Val Leu Asn Gly Thr Ile Pro Gln Trp Arg Val Asp Asp Met Ala Val
    290                 295                 300

Arg Ile Met Ala Ala Tyr Tyr Lys Val Gly Arg Asp Thr Lys Tyr Thr
305                 310                 315                 320

Pro Pro Asn Phe Ser Ser Trp Thr Arg Asp Glu Tyr Gly Phe Ala His
                325                 330                 335

Asn His Val Ser Glu Gly Ala Tyr Glu Arg Val Asn Glu Phe Val Asp
            340                 345                 350

Val Gln Arg Asp His Ala Asp Leu Ile Arg Arg Ile Gly Ala Gln Ser
        355                 360                 365

Thr Val Leu Leu Lys Asn Lys Gly Ala Leu Pro Leu Ser Arg Lys Glu
    370                 375                 380

Lys Leu Val Ala Leu Leu Gly Glu Asp Ala Gly Ser Asn Ser Trp Gly
385                 390                 395                 400
```

```
Ala Asn Gly Cys Asp Asp Arg Gly Cys Asp Asn Gly Thr Leu Ala Met
                405                 410                 415

Ala Trp Gly Ser Gly Thr Ala Asn Phe Pro Tyr Leu Val Thr Pro Glu
            420                 425                 430

Gln Ala Ile Gln Asn Glu Val Leu Gln Gly Arg Gly Asn Val Phe Ala
        435                 440                 445

Val Thr Asp Ser Trp Ala Leu Asp Lys Ile Ala Ala Ala Arg Gln
450                 455                 460

Ala Ser Val Ser Leu Val Phe Val Asn Ser Asp Ser Gly Glu Gly Tyr
465                 470                 475                 480

Leu Ser Val Asp Gly Asn Glu Gly Asp Arg Asn Asn Ile Thr Leu Trp
                485                 490                 495

Lys Asn Gly Asp Asn Val Val Lys Thr Ala Ala Asn Asn Cys Asn Asn
            500                 505                 510

Thr Val Ile Ile His Ser Val Gly Pro Val Leu Ile Asp Glu Trp
        515                 520                 525

Tyr Asp His Pro Asn Val Thr Gly Ile Leu Trp Ala Gly Leu Pro Gly
        530                 535                 540

Gln Glu Ser Gly Asn Ser Ile Ala Asp Val Leu Tyr Gly Arg Val Asn
545                 550                 555                 560

Pro Gly Ala Lys Ser Pro Phe Thr Trp Gly Lys Thr Arg Glu Ser Tyr
                565                 570                 575

Gly Ser Pro Leu Val Lys Asp Ala Asn Asn Gly Asn Gly Ala Pro Gln
            580                 585                 590

Ser Asp Phe Thr Gln Gly Val Phe Ile Asp Tyr Arg His Phe Asp Lys
        595                 600                 605

Phe Asn Glu Thr Pro Ile Tyr Glu Phe Gly Tyr Gly Leu Ser Tyr Thr
        610                 615                 620

Thr Phe
625

<210> SEQ ID NO 66
<211> LENGTH: 615
<212> TYPE: PRT
<213> ORGANISM: Aspergillus oryzae

<400> SEQUENCE: 66

Pro Asn Gly Gly Trp Ile Ser Glu Trp Ala Ser Ala Tyr Glu Lys Ala
1               5                   10                  15

His Arg Val Val Ser Asn Met Thr Leu Ala Glu Lys Val Asn Leu Thr
            20                  25                  30

Ser Gly Thr Gly Ile Tyr Met Gly Pro Cys Ala Gly Gln Thr Gly Ser
        35                  40                  45

Val Pro Arg Phe Gly Ile Pro Asn Leu Cys Leu His Asp Ser Pro Leu
50                  55                  60

Gly Val Arg Asn Ser Asp His Asn Thr Ala Phe Pro Ala Gly Ile Thr
65                  70                  75                  80

Val Gly Ala Thr Phe Asp Lys Asp Leu Met Tyr Glu Arg Gly Val Gly
            85                  90                  95

Leu Gly Glu Glu Ala Arg Gly Lys Gly Ile Asn Val Leu Leu Gly Pro
        100                 105                 110

Ser Val Gly Pro Ile Gly Arg Lys Pro Arg Gly Gly Arg Asn Trp Glu
    115                 120                 125

Gly Phe Gly Ala Asp Pro Ser Leu Gln Ala Phe Gly Gly Ser Leu Thr
130                 135                 140
```

-continued

Ile Lys Gly Met Gln Ser Thr Gly Ala Ile Ala Ser Leu Lys His Leu
145                 150                 155                 160

Ile Gly Asn Glu Gln Glu Gln His Arg Met Ser Ser Val Ile Thr Gln
            165                 170                 175

Gly Tyr Ser Ser Asn Ile Asp Asp Arg Thr Leu His Glu Leu Tyr Leu
        180                 185                 190

Trp Pro Phe Ala Glu Ser Val Arg Ala Gly Ala Gly Ser Val Met Ile
    195                 200                 205

Ala Tyr Asn Asp Val Asn Arg Ser Ala Cys Ser Gln Asn Ser Lys Leu
210                 215                 220

Ile Asn Gly Ile Leu Lys Asp Glu Leu Gly Phe Gln Gly Phe Val Val
225                 230                 235                 240

Thr Asp Trp Leu Ala His Ile Gly Gly Val Ser Ser Ala Leu Ala Gly
                245                 250                 255

Leu Asp Met Ser Met Pro Gly Asp Gly Ala Ile Pro Leu Leu Gly Thr
            260                 265                 270

Ser Tyr Trp Ser Trp Glu Leu Ser Arg Ser Val Leu Asn Gly Ser Val
        275                 280                 285

Pro Val Glu Arg Leu Asn Asp Met Val Thr Arg Ile Val Ala Thr Trp
    290                 295                 300

Tyr Lys Met Gly Gln Asp Lys Asp Tyr Pro Leu Pro Asn Phe Ser Ser
305                 310                 315                 320

Asn Thr Glu Asp Glu Thr Gly Pro Leu Tyr Pro Gly Ala Leu Phe Ser
                325                 330                 335

Pro Ser Gly Ile Val Asn Gln Tyr Val Asn Val Gln Gly Asn His Asn
            340                 345                 350

Val Thr Ala Arg Ala Ile Ala Arg Asp Ala Ile Thr Leu Leu Lys Asn
        355                 360                 365

Asn Glu Asn Val Leu Pro Leu Lys Arg Asn Asp Thr Leu Lys Ile Phe
    370                 375                 380

Gly Thr Asp Ala Gly Thr Asn Ser Asp Gly Ile Asn Ser Cys Thr Asp
385                 390                 395                 400

Lys Gly Cys Asn Lys Gly Val Leu Thr Met Gly Trp Gly Ser Gly Thr
                405                 410                 415

Ser Arg Leu Pro Tyr Leu Ile Thr Pro Gln Glu Ala Ile Ala Asn Ile
            420                 425                 430

Ser Ser Asn Ala Glu Phe His Ile Thr Asp Thr Phe Pro Leu Gly Val
        435                 440                 445

Thr Ala Gly Pro Asp Asp Ile Ala Val Phe Ile Asn Ser Asp Ser
    450                 455                 460

Gly Glu Asn Tyr Ile Thr Val Asp Gly Asn Pro Gly Asp Arg Thr Leu
465                 470                 475                 480

Ala Gly Leu His Ala Trp His Asn Gly Asp Asn Leu Val Lys Ala Ala
                485                 490                 495

Ala Glu Lys Phe Ser Asn Val Val Val Val His Thr Val Gly Pro
            500                 505                 510

Ile Leu Met Glu Glu Trp Ile Asp Leu Asp Ser Val Lys Ala Val Leu
        515                 520                 525

Val Ala His Leu Pro Gly Gln Glu Ala Gly Trp Ser Leu Thr Asp Ile
    530                 535                 540

Leu Phe Gly Asp Tyr Ser Pro Ser Gly His Leu Pro Tyr Thr Ile Pro
545                 550                 555                 560

His Ser Glu Ser Asp Tyr Pro Glu Ser Val Gly Leu Ile Ala Gln Pro
                565                 570                 575

```
Phe Gly Gln Ile Gln Asp Asp Tyr Thr Glu Gly Leu Tyr Ile Asp Tyr
            580                 585                 590

Arg His Phe Leu Lys Ala Asn Ile Thr Pro Arg Tyr Pro Phe Gly His
    595                 600                 605

Gly Leu Ser Tyr Thr Thr Phe
    610                 615

<210> SEQ ID NO 67
<211> LENGTH: 631
<212> TYPE: PRT
<213> ORGANISM: Aspergillus oryzae

<400> SEQUENCE: 67

Pro Glu Thr Lys Gly Leu Gly Asp Trp Glu Ala Phe Thr Lys Ala
1               5                   10                  15

Arg Ser Leu Val Ala Gln Met Thr Asp Lys Glu Lys Asn Asn Ile Thr
            20                  25                  30

Tyr Gly Tyr Ser Ser Thr Ala Asn Gly Cys Gly Gly Thr Ser Gly Gly
        35                  40                  45

Val Pro Arg Leu Gly Phe Pro Gly Ile Cys Leu Gln Asp Ala Gly Asn
    50                  55                  60

Gly Val Arg Gly Thr Asp Met Val Asn Ser Tyr Ala Ser Gly Val His
65                  70                  75                  80

Val Gly Ala Ser Trp Asn Arg Asp Leu Thr Tyr Ser Arg Ala Gln Tyr
                85                  90                  95

Met Gly Ala Glu Phe Lys Arg Lys Gly Val Asn Val Ala Leu Gly Pro
            100                 105                 110

Val Ala Gly Pro Ile Gly Arg Ile Ala Arg Gly Gly Arg Asn Trp Glu
        115                 120                 125

Gly Phe Ser Asn Asp Pro Tyr Leu Ser Gly Ala Leu Thr Gly Asp Thr
130                 135                 140

Val Arg Gly Leu Gln Glu Ser Val Ile Ala Cys Val Lys His Leu Ile
145                 150                 155                 160

Gly Asn Glu Gln Glu Thr His Arg Ser Thr Pro Ser Met Leu Ala Asn
                165                 170                 175

Ser Arg Asn Gln Ser Ser Ser Ser Asn Leu Asp Asp Lys Thr Met His
            180                 185                 190

Glu Leu Tyr Leu Trp Pro Phe Gln Asp Ala Val Lys Ala Gly Ala Gly
        195                 200                 205

Ser Val Met Cys Ser Tyr Asn Arg Ile Asn Asn Ser Tyr Gly Cys Gln
    210                 215                 220

Asn Ser Lys Ala Met Asn Gly Leu Leu Lys Gly Glu Leu Gly Phe Gln
225                 230                 235                 240

Gly Phe Val Val Ser Asp Trp Gly Ala Gln His Thr Gly Ile Ala Ser
                245                 250                 255

Ala Ala Ala Gly Leu Asp Met Ala Met Pro Ser Ser Tyr Trp Glu
            260                 265                 270

Asn Gly Thr Leu Ala Leu Ala Val Lys Asn Gly Ser Leu Pro Ser Thr
        275                 280                 285

Arg Leu Asp Asp Met Ala Thr Arg Ile Val Ala Thr Trp Tyr Lys Tyr
    290                 295                 300

Ala Glu Ile Glu Asn Pro Gly His Gly Leu Pro Tyr Ser Leu Leu Ala
305                 310                 315                 320

Pro His Asn Leu Thr Asp Ala Arg Asp Pro Lys Ser Lys Ser Thr Ile
                325                 330                 335
```

Leu Gln Gly Ala Val Glu Gly His Val Leu Val Lys Asn Thr Asn Asn
                340                 345                 350

Ala Leu Pro Leu Lys Lys Pro Gln Phe Leu Ser Leu Phe Gly Tyr Asp
            355                 360                 365

Ala Val Ala Ala Ala Arg Asn Thr Met Asp Asp Leu Asp Trp Asn Met
370                 375                 380

Trp Ser Met Gly Tyr Asp Asn Ser Leu Thr Tyr Pro Asn Gly Ser Ala
385                 390                 395                 400

Val Asp Ala Met Met Leu Lys Tyr Ile Phe Leu Ser Ser Ala Asn Pro
                405                 410                 415

Ser Ala Phe Gly Pro Gly Val Ala Leu Asn Ala Thr Ile Thr Gly
            420                 425                 430

Gly Gly Ser Gly Ala Ser Thr Ala Ser Tyr Ile Asp Ala Pro Phe Asn
                435                 440                 445

Ala Phe Gln Arg Gln Ala Tyr Asp Asp Asp Thr Phe Leu Ala Trp Asp
450                 455                 460

Phe Ala Ser Gln Asn Pro Leu Val Asn Pro Ala Ser Asp Ala Cys Ile
465                 470                 475                 480

Val Phe Ile Asn Glu Gln Ser Ser Glu Gly Trp Asp Arg Pro Tyr Leu
                485                 490                 495

Ala Asp Pro Tyr Ser Asp Thr Leu Val Gln Asn Val Ala Ser Gln Cys
            500                 505                 510

Ser Asn Thr Met Val Val Ile His Asn Ala Gly Val Arg Leu Val Asp
            515                 520                 525

Arg Trp Ile Glu Asn Asp Asn Ile Thr Ala Val Ile Tyr Ala His Leu
530                 535                 540

Pro Gly Gln Asp Ser Gly Arg Ala Leu Val Glu Val Met Tyr Gly Lys
545                 550                 555                 560

Gln Ser Pro Ser Gly Arg Leu Pro Tyr Thr Val Ala Lys Asn Glu Ser
                565                 570                 575

Asp Tyr Gly Ser Leu Leu Asn Pro Val Ile Gln Ser Gly Thr Asp Asp
            580                 585                 590

Ile Tyr Tyr Pro Gln Asp Asn Phe Thr Glu Gly Val Tyr Ile Asp Tyr
            595                 600                 605

Lys Ala Phe Val Ala Ala Asn Ile Thr Pro Arg Tyr Glu Phe Gly Tyr
610                 615                 620

Gly Leu Thr Tyr Ser Thr Phe
625                 630

<210> SEQ ID NO 68
<211> LENGTH: 633
<212> TYPE: PRT
<213> ORGANISM: Botryotinia fuckeliana

<400> SEQUENCE: 68

Arg Ala Ser Thr Ser Phe Gln Asn Trp Thr His Ala His His Leu Ala
1               5                   10                  15

Leu Thr Phe Val Asn Gln Leu Asn Ile Thr Glu Lys Ser Asn Ile Val
                20                  25                  30

Thr Gly Thr Tyr His Thr Ser Thr Leu Asp Gly Lys Pro Met Asn Cys
            35                  40                  45

Ile Gly Asn Ile Gly Pro Ile Pro Arg Leu Asn Phe Thr Gly Ile Cys
        50                  55                  60

Leu Asn Asp Gly Pro Ala Leu Leu Leu Val Arg Asp Leu Ile Ser Val
65                  70                  75                  80

```
Phe Pro Ser Gly Val Thr Leu Ala Ala Thr Trp Asp Arg Glu Leu Val
                85                  90                  95

Tyr Gln Ser Tyr Lys Ala Leu Gly Glu Glu Phe Arg Gly Lys Gly Thr
            100                 105                 110

His Val Ala Leu Gly Pro Val Ala Gly Pro Leu Gly Arg His Pro Leu
        115                 120                 125

Gly Gly Arg Asn Trp Glu Gly Phe Ser Pro Asp Pro Tyr Leu Thr Gly
130                 135                 140

His Leu Met Thr Ala Ser Ile Thr Gly Met Gln Ser Val Gly Val Gln
145                 150                 155                 160

Thr Ser Ser Lys His Phe Ile Gly Asn Glu Gln Glu Thr Gln Arg Ser
                165                 170                 175

Asn Ser Pro Leu Pro Asp Gly Thr Asn Ile Asp Ala Ile Ser Ser Asn
            180                 185                 190

Ile Asp Asp Arg Thr Leu His Glu Leu Tyr Leu Trp Pro Phe Ala Asp
        195                 200                 205

Ala Val Arg Ala Gly Thr Thr Ser Ile Leu Cys Ser Tyr Asn Arg Ile
    210                 215                 220

Asn Glu Thr Tyr Ala Cys Glu Asn Pro His Leu Leu Asn Asn Ile Leu
225                 230                 235                 240

Lys Gly Glu Leu Gly Phe Gln Gly Tyr Val Val Ser Asp Trp Phe Ala
                245                 250                 255

Thr His Ser Gly Tyr Pro Ala Ala Asn Ala Gly Leu Asp Met Asp Met
            260                 265                 270

Pro Gly Tyr Ile Ser Gln Ser Ala Ile Asn Thr Gly Glu Thr Tyr Phe
        275                 280                 285

Gly Pro His Leu Ile Ser Ala Ile Gln Ala Gly Asn Met Thr Glu Asp
    290                 295                 300

Arg Leu Asp Asp Met Val Thr Arg Ile Met Thr Ser Tyr Phe Leu Leu
305                 310                 315                 320

Asn Gln Ser Ser Asn Tyr Pro Thr Pro Asp Pro Ser Gln Thr Tyr Val
                325                 330                 335

Met Ala Asn Met Tyr Gly Tyr Asp Tyr Gly Ala Gln Ile Pro Ala Arg
            340                 345                 350

Asp Val Arg Ala Asn His Ser Ser Leu Ile Arg Gln Ile Gly Ser Ala
        355                 360                 365

Gly Thr Val Leu Leu Lys Asn Thr Asn Asn Ile Leu Pro Leu Ser Lys
    370                 375                 380

Pro Leu Asn Ile Gly Val Phe Gly Asn Ser Ala Pro Asp Pro Thr Asp
385                 390                 395                 400

Gly Leu Thr Trp Pro Gln Ser Asp Leu Gln Thr Gly Phe Asp Ile Gly
                405                 410                 415

Thr Leu Asp Ile Gly Gly Gly Ser Gly Ser Ala Arg His Thr Thr Leu
            420                 425                 430

Ile Ser Pro Leu Thr Ala Leu Arg Thr Arg Ala Ala Thr Tyr Ala Arg
        435                 440                 445

Val Gln Tyr Leu Thr Asn Asn Ala Leu Leu Ser Ser Ser Ser Ser Ser
    450                 455                 460

Ser Phe Ala Gly Ile Tyr Pro Ile Pro Glu Ile Cys Leu Val Phe Leu
465                 470                 475                 480

Lys Thr Phe Ser Ser Glu Gly Val Asp Arg Thr Ser Tyr Pro Leu Asp
                485                 490                 495

Trp Asn Ser Thr Leu Val Val Asn Asn Val Ala Ser Phe Cys Gln Gly
```

```
                500             505                 510
Asn Thr Ile Val Ile Thr His Ser Ser Gly Ile Asn Thr Leu Pro Phe
            515                 520                 525

Ala Gln Asn Pro Asn Val Ser Ala Ile Leu Leu Ala His Tyr Pro Gly
            530                 535                 540

Gln Glu Ser Gly Asn Ser Ile Val Asp Val Leu Phe Gly Val Val Asn
545                 550                 555                 560

Pro Ser Gly Lys Leu Pro Tyr Thr Ile Pro Val His Glu Ser Asp Met
            565                 570                 575

His Ile Pro Val Val Asn Leu Ser Thr Ser Glu Val Leu Ala His His
            580                 585                 590

Gln Ser Gln Asn Ala Trp Gln Ser Asn Phe Thr Glu Lys Leu Ala Ile
            595                 600                 605

Asp Tyr Arg Gly Phe Glu Met Lys Asn Val Thr Pro Leu Tyr Glu Phe
            610                 615                 620

Gly His Gly Leu Ser Tyr Thr Thr Phe
625                 630

<210> SEQ ID NO 69
<211> LENGTH: 626
<212> TYPE: PRT
<213> ORGANISM: Coccidioides posadasii

<400> SEQUENCE: 69

Pro Trp Ala Ser Gly Gln Gly Glu Trp Ser Glu Ala Tyr Asn Lys Ala
1               5                   10                  15

Arg Glu Phe Val Ser Gln Leu Thr Leu Thr Glu Lys Val Asn Leu Thr
            20                  25                  30

Thr Gly Val Gly Trp Met Gln Glu Ala Cys Val Gly Asn Val Gly Ser
        35                  40                  45

Ile Pro Arg Leu Gly Phe Arg Ser Leu Cys Met Gln Asp Gly Pro Leu
    50                  55                  60

Gly Ile Arg Phe Ala Asp His Val Ser Ala Phe Pro Ala Gly Ile Asn
65                  70                  75                  80

Val Gly Ala Thr Trp Ser Lys Ser Leu Ala Tyr Leu Arg Gly Lys Ala
                85                  90                  95

Met Gly Glu Glu His Arg Asp Lys Gly Val Asp Val Gln Leu Gly Pro
            100                 105                 110

Ala Val Gly Pro Leu Gly Arg Ser Pro Asp Gly Gly Arg Asn Trp Glu
            115                 120                 125

Gly Phe Ser Pro Asp Pro Val Leu Ser Gly Tyr Leu Val Ala Glu Thr
        130                 135                 140

Ile Lys Gly Ile Gln Asp Ala Gly Val Ile Ala Cys Val Lys His Phe
145                 150                 155                 160

Ile Val Asn Glu Gln Glu Arg Phe Arg Gln Ala Pro Glu Ala Gln Gly
                165                 170                 175

Tyr Gly Phe Asn Ile Ser Glu Ser Ser Ser Asn Val Asp Asp Val
            180                 185                 190

Thr Met His Glu Leu Tyr Leu Trp Pro Phe Ala Asp Ala Val Arg Ala
            195                 200                 205

Gly Val Gly Ser Val Met Cys Ser Tyr Asn Gln Ile Asn Asn Ser Tyr
        210                 215                 220

Gly Cys Ser Asn Ser Tyr Thr Gln Asn Lys Leu Leu Lys Gly Glu Leu
225                 230                 235                 240

Gly Phe Gln Gly Phe Ile Met Ser Asp Trp Gln Ala His His Ser Gly
```

```
                    245                 250                 255
Val Gly Asp Asp Leu Ala Gly Leu Asp Met Ser Met Pro Gly Asp Thr
            260                 265                 270

Leu Phe Leu Thr Gly Lys Ser Tyr Trp Gly Pro Asn Leu Thr Ile Ala
        275                 280                 285

Val Thr Asn Gly Thr Ile Pro Gln Trp Arg Leu Asp Asp Met Ala Val
    290                 295                 300

Arg Ile Met Ala Ala Tyr Tyr Lys Val Arg Arg Asp Gln Thr Gln Val
305                 310                 315                 320

Pro Ile Asn Phe Asn Ser Trp Thr Arg Asp Glu Phe Gly Tyr Leu His
                325                 330                 335

Ala Gly Gly Gln Glu Gly Tyr Gly Arg Val Asn Gln Met Val Asn Val
            340                 345                 350

Arg Gly Arg His Ala Val Ile Ala Arg Lys Val Ala Ser Ala Ser Thr
        355                 360                 365

Val Leu Leu Lys Asn Arg Gly Val Leu Pro Leu Lys Gly Lys Glu Lys
    370                 375                 380

Leu Thr Ala Val Ile Gly Glu Asp Ala Gly Pro Asn Leu Trp Gly Pro
385                 390                 395                 400

Asn Gly Cys Pro Asp Arg Gly Cys Ala Asn Gly Thr Leu Ala Met Gly
                405                 410                 415

Trp Gly Ser Gly Thr Ala Asp Phe Pro Tyr Leu Val Thr Pro Ala Gln
            420                 425                 430

Ala Ile Glu Asn Glu Val Ile Thr Lys Gly Val Gly Ala Met Ser
        435                 440                 445

Val Phe Asp Asn Tyr Ala Thr Ser Gln Ile Glu Ser Val Ser Gln
    450                 455                 460

Ala Thr Val Ser Leu Val Phe Val Asn Ala Gly Ala Gly Glu Gly Phe
465                 470                 475                 480

Ile Ser Val Asp Gly Asn Glu Gly Asp Arg Lys Asn Leu Thr Leu Trp
                485                 490                 495

Lys Asn Gly Asp Glu Leu Ile Lys Thr Val Ala Ser Met Cys Asn Asn
            500                 505                 510

Thr Val Val Met His Thr Ala Gly Pro Val Leu Val Asn Lys Trp
    515                 520                 525

Tyr Asp His Pro Asn Val Thr Ala Ile Leu Trp Ala Gly Leu Pro Gly
530                 535                 540

Gln Glu Ser Gly Asn Ala Leu Gly Asp Val Ile Tyr Gly Arg Val Asn
545                 550                 555                 560

Pro Gly Ala Lys Ser Pro Phe Thr Trp Ala Ala Thr Ser Glu Asp Tyr
                565                 570                 575

Gly Val Ser Ile Leu Lys Glu Pro Asn Ala Ala Thr Lys Ala Pro Gln
            580                 585                 590

Ile Asp Phe Glu Glu Gly Ile Phe Ile Asp Tyr Arg Ala Phe Asp Lys
        595                 600                 605

Ser Asn Thr Lys Pro Ile Tyr Glu Phe Gly Phe Gly Leu Ser Tyr Thr
    610                 615                 620

Thr Phe
625

<210> SEQ ID NO 70
<211> LENGTH: 604
<212> TYPE: PRT
<213> ORGANISM: Coccidioides posadasii
```

-continued

```
<400> SEQUENCE: 70

Glu Ala Tyr Ser Lys Ala His Thr Val Val Ser Lys Met Thr Leu Ala
1               5                   10                  15

Gly Lys Val Asn Leu Thr Thr Gly Thr Gly Phe Leu Met Ala Leu Val
            20                  25                  30

Gly Gln Thr Gly Ser Ala Leu Arg Phe Gly Ile Pro Arg Leu Cys Leu
        35                  40                  45

Gln Asp Gly Pro Leu Gly Leu Arg Asn Thr Asp His Asn Thr Ala Phe
    50                  55                  60

Pro Ala Gly Ile Ser Val Gly Ala Thr Phe Asp Lys Lys Leu Met Tyr
65                  70                  75                  80

Glu Arg Gly Cys Ala Met Gly Glu Glu Phe Arg Gly Lys Gly Ala Asn
                85                  90                  95

Val His Leu Gly Pro Ser Val Gly Pro Leu Gly Arg Lys Pro Arg Gly
            100                 105                 110

Gly Arg Asn Trp Glu Gly Phe Gly Ser Asp Pro Ser Leu Gln Ala Ile
        115                 120                 125

Ala Ala Val Glu Thr Ile Lys Gly Val Gln Ser Lys Gly Val Ile Ala
    130                 135                 140

Thr Ile Lys His Leu Val Gly Asn Glu Gln Glu Met Tyr Arg Met Thr
145                 150                 155                 160

Asn Ile Val Gln Arg Ala Tyr Ser Ala Asn Ile Asp Asp Arg Thr Met
                165                 170                 175

His Glu Leu Tyr Leu Trp Pro Phe Ala Glu Ser Val Arg Ala Gly Val
            180                 185                 190

Gly Ala Val Met Met Ala Tyr Asn Asp Val Asn Gly Ser Ala Ser Cys
        195                 200                 205

Gln Asn Ser Lys Leu Ile Asn Gly Ile Leu Lys Asp Glu Leu Gly Phe
    210                 215                 220

Gln Gly Phe Val Met Thr Asp Trp Tyr Ala Gln Ile Gly Gly Val Ser
225                 230                 235                 240

Ser Ala Leu Ala Gly Leu Asp Met Ser Met Pro Gly Asp Gly Ser Val
                245                 250                 255

Pro Leu Ser Gly Thr Ser Phe Trp Ala Ser Glu Leu Ser Arg Ser Ile
            260                 265                 270

Leu Asn Gly Thr Val Ala Leu Asp Arg Leu Asn Asp Met Val Thr Arg
        275                 280                 285

Ile Val Ala Thr Trp Phe Lys Phe Gly Gln Asp Lys Asp Phe Pro Leu
    290                 295                 300

Pro Asn Phe Ser Ser Tyr Thr Gln Asn Ala Lys Gly Leu Leu Tyr Pro
305                 310                 315                 320

Gly Ala Leu Phe Ser Pro Leu Gly Val Val Asn Gln Phe Val Asn Val
                325                 330                 335

Gln Ala Asp His His Lys Leu Ala Arg Val Ile Ala Arg Glu Ser Ile
            340                 345                 350

Thr Leu Leu Lys Asn Glu Asp Asn Leu Leu Pro Leu Asp Pro Asn Arg
        355                 360                 365

Ala Ile Lys Tyr Ser Glu Gln Met Pro Gly Thr Asn Pro Arg Gly Ile
    370                 375                 380

Asn Ala Cys Pro Asp Lys Gly Cys Asn Lys Gly Val Leu Thr Met Gly
385                 390                 395                 400

Trp Gly Ser Gly Thr Ser Asn Leu Pro Tyr Leu Val Thr Pro Glu Asp
                405                 410                 415
```

-continued

```
Ala Ile Arg Asn Ile Ser Lys Asn Thr Glu Phe His Ile Thr Asp Lys
            420                 425                 430

Phe Pro Asn Asn Val Gln Pro Gly Pro Asp Asp Val Ala Ile Val Phe
                435                 440                 445

Val Asn Ala Asp Ser Gly Glu Asn Tyr Ile Ile Val Glu Ser Asn Pro
450                 455                 460

Gly Asp Arg Thr Val Ala Gln Met Lys Leu Trp His Asn Gly Asp Glu
465                 470                 475                 480

Leu Ile Glu Ser Ala Ala Lys Lys Phe Ser Asn Val Val Val Val
                485                 490                 495

Val His Thr Val Gly Pro Ile Ile Met Glu Lys Trp Ile Asp Leu Leu
            500                 505                 510

Arg Ser Arg Val Ser Cys Leu Pro Asp Phe Gln Asp Lys Lys Leu Glu
            515                 520                 525

Ile Leu Leu Leu Ile Ser Cys Ser Glu Thr Ser Val Arg Val Ala Ala
            530                 535                 540

Ser Ile Tyr Asp Thr Glu Ser Arg Ile Gly Leu Ser Asp Ser Val Ser
545                 550                 555                 560

Leu Ile Asn Gln Arg Phe Gly Gln Ile Gln Asp Thr Phe Thr Glu Gly
                565                 570                 575

Leu Phe Ile Asp Tyr Arg His Phe Gln Lys Glu Asn Ile Thr Pro Arg
                580                 585                 590

Tyr His Phe Gly Tyr Gly Leu Ser Tyr Thr Thr Phe
            595                 600

<210> SEQ ID NO 71
<211> LENGTH: 644
<212> TYPE: PRT
<213> ORGANISM: Dictyostelium discoideum

<400> SEQUENCE: 71

Ser Gln Ile Tyr Pro Lys Lys Gln Leu Asn Gln Glu Asn Ile Asn Phe
1               5                   10                  15

Met Ser Ala Arg Asp Thr Phe Val Asp Asn Leu Met Ser Lys Met Ser
                20                  25                  30

Ile Thr Glu Lys Ile Gly Gln Met Thr Gln Leu Asp Ile Thr Thr Leu
            35                  40                  45

Thr Ser Pro Asn Thr Ile Thr Ile Asn Glu Thr Thr Leu Ala Tyr Tyr
50                  55                  60

Ala Lys Thr Tyr Tyr Ile Gly Ser Tyr Leu Asn Ser Pro Val Ser Gly
65                  70                  75                  80

Gly Leu Ala Gly Asp Ile His His Ile Asn Ser Ser Val Trp Leu Asp
                85                  90                  95

Met Ile Asn Thr Ile Gln Thr Ile Val Ile Glu Gly Ser Pro Asn Lys
            100                 105                 110

Ile Pro Met Ile Tyr Gly Leu Asp Ser Val His Gly Ala Asn Tyr Val
            115                 120                 125

His Lys Ala Thr Leu Phe Pro His Asn Thr Gly Leu Ala Ala Thr Phe
        130                 135                 140

Asn Ile Glu His Ala Thr Thr Ala Ala Gln Ile Thr Ser Lys Asp Thr
145                 150                 155                 160

Val Ala Val Gly Ile Pro Trp Val Phe Ala Pro Val Leu Gly Ile Gly
                165                 170                 175

Val Gln Pro Leu Trp Ser Arg Ile Tyr Glu Thr Phe Gly Glu Asp Pro
            180                 185                 190
```

-continued

Tyr Val Ala Ser Met Met Gly Ala Ala Val Arg Gly Phe Gln Gly
    195                 200                 205

Gly Asn Asn Ser Phe Asp Gly Pro Ile Asn Ala Pro Ser Ala Val Cys
    210                 215                 220

Thr Ala Lys His Tyr Phe Gly Tyr Ser Asn Pro Thr Ser Gly Lys Asp
225                 230                 235                 240

Arg Thr Ala Ala Trp Ile Pro Glu Arg Met Leu Arg Arg Tyr Phe Leu
                245                 250                 255

Pro Ser Phe Ala Glu Ala Ile Thr Gly Ala Gly Ala Gly Thr Ile Met
                260                 265                 270

Ile Asn Ser Gly Glu Val Asn Gly Val Pro Met His Thr Ser Tyr Lys
            275                 280                 285

Tyr Leu Thr Glu Val Leu Arg Gly Glu Leu Gln Phe Glu Gly Val Ala
    290                 295                 300

Val Thr Asp Trp Gln Asp Ile Glu Lys Leu Val Tyr Phe His His Thr
305                 310                 315                 320

Ala Gly Ser Ala Glu Glu Ala Ile Leu Gln Ala Leu Asp Ala Gly Ile
                325                 330                 335

Ile Cys Leu Cys His Asp Leu Leu Ser Gln Leu Phe Ser Leu Glu Ile
                340                 345                 350

Leu Ala Ala Gly Thr Val Pro Glu Ser Arg Leu Asp Leu Ser Val Arg
            355                 360                 365

Arg Ile Leu Asn Leu Lys Tyr Ala Leu Gly Leu Phe Ser Asn Pro Tyr
    370                 375                 380

Pro Asn Pro Asn Ala Ala Ile Val Asp Thr Ile Gly Gln Val Gln Asp
385                 390                 395                 400

Arg Glu Ala Ala Ala Thr Ala Glu Glu Ser Ile Thr Leu Leu Leu
                405                 410                 415

Phe Lys Asn Asn Ile Leu Pro Leu Asn Thr Asn Thr Ile Lys Asn Val
                420                 425                 430

Leu Leu Thr Gly Pro Ser Ala Asp Ser Ile Arg Asn Leu Asn Gly Gly
            435                 440                 445

Trp Ser Val His Trp Gln Gly Ala Tyr Glu Asp Ser Glu Phe Pro Phe
    450                 455                 460

Gly Thr Ser Ile Leu Thr Gly Leu Arg Glu Ile Thr Asn Asp Thr Ala
465                 470                 475                 480

Asp Phe Asn Ile Gln Tyr Thr Ile Gly His Glu Ile Gly Val Pro Thr
                485                 490                 495

Asn Gln Thr Ser Ile Asp Glu Ala Val Glu Leu Ala Gln Ser Ser Asp
                500                 505                 510

Val Val Val Val Ile Gly Glu Leu Pro Glu Ala Glu Thr Pro Gly
            515                 520                 525

Asp Ile Tyr Asp Leu Ser Met Asp Pro Asn Glu Val Leu Leu Leu Gln
    530                 535                 540

Gln Leu Val Asp Thr Gly Lys Pro Val Val Leu Ile Leu Val Glu Ala
545                 550                 555                 560

Arg Pro Arg Ile Leu Pro Pro Asp Leu Val Tyr Ser Cys Ala Ala Val
                565                 570                 575

Leu Met Ala Tyr Leu Pro Gly Ser Glu Gly Gly Lys Pro Ile Ala Asn
                580                 585                 590

Ile Leu Met Gly Asn Val Asn Pro Ser Gly Arg Leu Pro Leu Thr Tyr
            595                 600                 605

Pro Gly Thr Gly Asp Ile Gly Val Pro Tyr His Lys Tyr Ser
    610                 615                 620

```
Glu Asn Gly Val Thr Thr Pro Leu Phe Gln Phe Gly Asp Gly Leu Ser
625                 630                 635                 640

Tyr Thr Thr Phe

<210> SEQ ID NO 72
<211> LENGTH: 600
<212> TYPE: PRT
<213> ORGANISM: Hordeum vulgare

<400> SEQUENCE: 72

Asp Tyr Leu Lys Tyr Lys Asp Pro Lys Gln Pro Leu Gly Val Arg Ile
1               5                   10                  15

Lys Asp Leu Leu Gly Arg Met Thr Leu Ala Glu Lys Ile Gly Gln Met
            20                  25                  30

Thr Gln Ile Glu Arg Glu Asn Ala Thr Ala Glu Ala Met Ser Lys Tyr
        35                  40                  45

Phe Ile Gly Ser Val Leu Ser Gly Gly Ser Val Pro Ser Pro Gln
    50                  55                  60

Ala Ser Ala Ala Ala Trp Gln Ser Met Val Asn Glu Met Gln Lys Gly
65                  70                  75                  80

Ala Leu Ser Thr Arg Leu Gly Ile Pro Met Ile Tyr Gly Ile Asp Ala
                85                  90                  95

Val His Gly His Asn Asn Val Tyr Lys Ala Thr Ile Phe Pro His Asn
            100                 105                 110

Val Gly Leu Gly Ala Thr Arg Asp Pro Met Leu Val Lys Arg Ile Gly
        115                 120                 125

Glu Ala Thr Ala Leu Glu Val Arg Ala Thr Gly Ile Pro Tyr Ala Phe
    130                 135                 140

Ala Pro Cys Ile Ala Val Cys Arg Asp Pro Arg Trp Gly Arg Cys Tyr
145                 150                 155                 160

Glu Ser Tyr Ser Glu Asp Pro Lys Val Val Gln Ser Met Thr Thr Leu
                165                 170                 175

Ile Ser Gly Leu Gln Gly Asp Val Pro Ala Gly Ser Glu Gly Arg Pro
            180                 185                 190

Tyr Val Gly Gly Ser Lys Lys Val Ala Ala Cys Ala Lys His Tyr Val
        195                 200                 205

Gly Asp Gly Gly Thr Phe Met Gly Ile Asn Glu Asn Asp Thr Ile Ile
    210                 215                 220

Asp Ala His Gly Leu Met Thr Ile His Met Pro Ala Tyr Tyr Asn Ser
225                 230                 235                 240

Ile Ile Arg Gly Val Ser Thr Val Met Thr Ser Tyr Ser Ser Trp Asn
                245                 250                 255

Gly Lys Lys Met His Ala Asn His Phe Leu Val Thr Asp Phe Leu Lys
            260                 265                 270

Asn Lys Leu Lys Phe Arg Gly Phe Val Ile Ser Asp Trp Gln Gly Ile
        275                 280                 285

Asp Arg Ile Thr Ser Pro Pro Gly Val Asn Tyr Ser Tyr Ser Val Glu
    290                 295                 300

Ala Gly Val Gly Ala Gly Ile Asp Met Ile Met Val Pro Phe Ala Tyr
305                 310                 315                 320

Thr Glu Phe Ile Asp Asp Leu Thr Tyr Gln Val Lys Asn Asn Ile Ile
                325                 330                 335

Pro Met Ser Arg Ile Asn Asp Ala Val Tyr Arg Ile Leu Arg Val Lys
            340                 345                 350
```

```
Phe Thr Met Gly Leu Phe Glu Ser Pro Tyr Ala Asp Pro Ser Leu Val
            355                 360                 365

Gly Glu Leu Gly Lys Gln Glu His Arg Asp Leu Ala Arg Glu Ala Val
    370                 375                 380

Arg Lys Ser Leu Val Leu Leu Lys Asn Gly Lys Ser Ala Ser Thr Pro
385                 390                 395                 400

Leu Leu Pro Leu Pro Lys Lys Ala Gly Lys Ile Leu Val Ala Gly Ser
                405                 410                 415

His Ala Asp Asp Leu Gly Asn Gln Cys Gly Gly Trp Thr Ile Thr Trp
                420                 425                 430

Gln Gly Gln Thr Gly Asn Asp Lys Thr Ala Gly Thr Thr Ile Leu Ser
            435                 440                 445

Ala Ile Lys Ser Thr Val Asp Pro Ser Thr Glu Val Val Phe Ser Glu
    450                 455                 460

Asn Pro Asp Ser Ala Ala Val Asp Ser Gly Lys Tyr Asp Tyr Ala Ile
465                 470                 475                 480

Val Val Val Gly Glu Pro Pro Tyr Ala Glu Thr Phe Gly Asp Asn Leu
                485                 490                 495

Asn Leu Thr Ile Pro Ala Pro Gly Pro Ser Val Ile Gln Asn Val Cys
            500                 505                 510

Lys Ser Val Arg Cys Val Val Val Leu Ile Ser Gly Arg Pro Leu Val
    515                 520                 525

Val Glu Pro Tyr Ile Ser Ala Met Asp Ala Phe Val Ala Ala Trp Leu
530                 535                 540

Pro Gly Ser Glu Gly Gln Gly Val Ala Asp Val Leu Phe Gly Asp Tyr
545                 550                 555                 560

Gly Phe Ser Gly Lys Leu Ala Arg Thr Trp Phe Lys Ser Ala Asp Gln
                565                 570                 575

Leu Pro Met Asn Val Gly Asp Lys His Tyr Asp Pro Leu Phe Pro Phe
                580                 585                 590

Gly Phe Gly Leu Thr Thr Glu Ala
            595                 600

<210> SEQ ID NO 73
<211> LENGTH: 703
<212> TYPE: PRT
<213> ORGANISM: Hypocrea jecorina

<400> SEQUENCE: 73

Val Glu Ala Ile Leu Lys Lys Leu Thr Leu Ala Glu Lys Val Asp Leu
1               5                   10                  15

Leu Ala Gly Ile Asp Phe Trp His Thr Lys Ala Leu Pro Lys His Gly
                20                  25                  30

Val Pro Ser Leu Arg Phe Thr Asp Gly Pro Asn Gly Val Arg Gly Thr
            35                  40                  45

Lys Phe Phe Asn Gly Val Pro Ala Ala Cys Phe Pro Cys Gly Thr Ser
    50                  55                  60

Leu Gly Ser Thr Phe Asn Gln Thr Leu Leu Glu Glu Ala Gly Lys Met
65                  70                  75                  80

Met Gly Lys Glu Ala Ile Ala Lys Ser His Val Ile Leu Gly Pro
                85                  90                  95

Thr Ile Asn Met Gln Arg Ser Pro Leu Gly Gly Arg Gly Phe Glu Ser
            100                 105                 110

Ile Gly Glu Asp Pro Phe Leu Ala Gly Leu Gly Ala Ala Ala Leu Ile
        115                 120                 125
```

```
Arg Gly Ile Gln Ser Thr Gly Val Gln Ala Thr Ile Lys His Phe Leu
    130                 135                 140

Cys Asn Asp Gln Glu Asp Arg Arg Met Met Val Gln Ser Ile Val Thr
145                 150                 155                 160

Glu Arg Ala Leu Arg Glu Ile Tyr Ala Leu Pro Phe Gln Ile Ala Val
                165                 170                 175

Arg Asp Ser Gln Pro Gly Ala Phe Met Thr Ala Tyr Asn Gly Ile Asn
            180                 185                 190

Gly Val Ser Cys Ser Glu Asn Pro Lys Tyr Leu Asp Gly Met Leu Arg
        195                 200                 205

Lys Glu Trp Gly Trp Asp Gly Leu Ile Met Ser Asp Trp Tyr Gly Thr
    210                 215                 220

Tyr Ser Thr Thr Glu Ala Val Val Ala Gly Leu Asp Leu Glu Met Pro
225                 230                 235                 240

Gly Pro Pro Arg Phe Arg Gly Glu Thr Leu Lys Phe Asn Val Ser Asn
                245                 250                 255

Gly Lys Pro Phe Ile His Val Ile Asp Gln Arg Ala Arg Glu Val Leu
            260                 265                 270

Gln Phe Val Lys Lys Cys Ala Ala Ser Gly Val Thr Glu Asn Gly Pro
        275                 280                 285

Glu Thr Thr Val Asn Asn Thr Pro Glu Thr Ala Ala Leu Leu Arg Lys
    290                 295                 300

Val Gly Asn Glu Gly Ile Val Leu Leu Lys Asn Glu Asn Asn Val Leu
305                 310                 315                 320

Pro Leu Ser Lys Lys Lys Thr Leu Ile Val Gly Pro Asn Ala Lys
                325                 330                 335

Gln Ala Thr Tyr His Gly Gly Ser Ala Ala Leu Arg Ala Tyr Tyr
        340                 345                 350

Ala Val Thr Pro Phe Asp Gly Leu Ser Lys Gln Leu Glu Thr Pro Pro
    355                 360                 365

Ser Tyr Thr Val Gly Ala Tyr Thr Thr Val Pro Pro Ile Leu Gly Glu
    370                 375                 380

Gln Cys Leu Thr Pro Asp Gly Ala Pro Gly Met Arg Trp Arg Val Phe
385                 390                 395                 400

Asn Glu Pro Pro Gly Thr Pro Asn Arg Gln His Ile Asp Glu Leu Phe
                405                 410                 415

Phe Thr Lys Thr Asp Met His Leu Val Asp Tyr Tyr His Pro Lys Ala
            420                 425                 430

Ala Asp Thr Trp Tyr Ala Asp Met Glu Gly Thr Tyr Thr Ala Asp Glu
        435                 440                 445

Asp Cys Thr Tyr Glu Leu Gly Leu Val Val Cys Gly Thr Ala Lys Ala
    450                 455                 460

Tyr Val Asp Asp Gln Leu Val Val Asp Asn Ala Thr Lys Gln Val Pro
465                 470                 475                 480

Gly Asp Ala Phe Phe Gly Ser Ala Thr Arg Glu Thr Gly Arg Ile
                485                 490                 495

Asn Leu Val Lys Gly Asn Thr Tyr Lys Phe Lys Ile Glu Phe Gly Ser
            500                 505                 510

Ala Pro Thr Tyr Thr Leu Lys Gly Asp Thr Ile Val Pro Gly His Gly
        515                 520                 525

Ser Leu Arg Val Gly Gly Cys Lys Val Ile Asp Asp Gln Ala Glu Ile
    530                 535                 540

Glu Lys Ser Val Ala Leu Ala Lys Glu His Asp Gln Val Ile Ile Cys
545                 550                 555                 560
```

```
Ala Gly Leu Asn Ala Asp Trp Glu Thr Glu Gly Ala Asp Arg Ala Ser
            565                 570                 575

Met Lys Leu Pro Gly Val Leu Asp Gln Leu Ile Ala Asp Val Ala Ala
            580                 585                 590

Ala Asn Pro Asn Thr Val Val Met Gln Thr Gly Thr Pro Glu Glu
            595                 600                 605

Met Pro Trp Leu Asp Ala Thr Pro Ala Val Ile Gln Ala Trp Tyr Gly
    610                 615                 620

Gly Asn Glu Thr Gly Asn Ser Ile Ala Asp Val Val Phe Gly Asp Tyr
625                 630                 635                 640

Asn Pro Ser Gly Lys Leu Ser Leu Ser Phe Pro Lys Arg Leu Gln Asp
                645                 650                 655

Asn Pro Ala Phe Leu Asn Phe Arg Thr Glu Ala Gly Arg Thr Leu Tyr
            660                 665                 670

Gly Glu Asp Val Tyr Val Gly Tyr Arg Tyr Tyr Glu Phe Ala Asp Lys
            675                 680                 685

Asp Val Asn Phe Pro Phe Gly His Gly Leu Ser Tyr Thr Thr Phe
    690                 695                 700

<210> SEQ ID NO 74
<211> LENGTH: 602
<212> TYPE: PRT
<213> ORGANISM: Hypocrea jecorina

<400> SEQUENCE: 74

Gly Pro Trp Ala His Ala Tyr Arg Arg Ala Glu Lys Leu Val Arg Gln
1               5                   10                  15

Met Thr Leu Glu Glu Lys Ala Asn Ile Thr Arg Gly Phe Thr Gly Asp
            20                  25                  30

Asn Val Cys Ala Gly Asn Thr Gly Ser Val Pro Arg Leu Gly Trp Pro
        35                  40                  45

Gly Met Cys Val His Asp Ala Gly Asn Gly Val Arg Ala Thr Asp Leu
    50                  55                  60

Val Asn Ser Tyr Pro Ser Gly Ile His Val Gly Ala Ser Trp Asp Arg
65                  70                  75                  80

Asn Leu Thr Tyr Glu Arg Gly Leu His Met Gly Gly Glu Phe Lys Ala
                85                  90                  95

Lys Gly Val Asn Val Pro Leu Gly Pro Asn Ala Gly Pro Leu Gly Arg
            100                 105                 110

Thr Pro Leu Gly Gly Arg Asn Trp Glu Gly Phe Ser Ile Asp Pro Tyr
        115                 120                 125

Leu Ser Gly Gln Leu Asn Ala Glu Thr Ile Thr Gly Met Gln Asp Ala
    130                 135                 140

Gly Val Ile Ala Asn Ile Lys His Phe Ile Ala Asn Glu Gln Glu Thr
145                 150                 155                 160

Leu Arg Arg Pro Tyr Phe Gly Val Glu Ala Val Ser Ala Asn Ile Asp
                165                 170                 175

Asp Arg Thr Leu His Glu Tyr Tyr Leu Trp Pro Phe Met Asp Ser Val
            180                 185                 190

His Ala Gly Val Gly Ser Val Met Cys Ser Tyr Asn Arg Ile Asn Asn
        195                 200                 205

Thr Tyr Gly Cys Met Asn Asp Lys Leu Met Asn Gly Ile Leu Lys Ala
    210                 215                 220

Glu Leu Gly Phe Gln Gly Phe Val Met Leu Asp Trp Asn Ala Gln His
225                 230                 235                 240
```

Asp Leu Gln Ser Ala Asn Ala Gly Leu Asp Met Val Met Pro Leu Gly
                245                 250                 255

Gly Ser Trp Gly Lys Asn Leu Thr Asp Ala Val Ala Asn Gly Thr Val
            260                 265                 270

Ser Glu Ser Arg Ile Thr Asp Met Ala Thr Arg Ile Ile Ala Ala Trp
        275                 280                 285

Tyr Leu Val Gly Gln Asp Gly Asn Asn Phe Pro Val Pro Gly Ile Gly
    290                 295                 300

Leu Lys Gln Leu Thr Lys Pro His Glu Gln Val Asp Ala Arg Asp Pro
305                 310                 315                 320

Ala Ser Lys Pro Val Leu Leu Glu Gly Ala Ile Ala Gly His Val Leu
                325                 330                 335

Val Lys Asn Glu Asn Asn Ala Leu Pro Phe Asn Lys Lys Leu Thr Met
            340                 345                 350

Ile Ser Val Phe Gly Tyr Asp Ala Thr Ile Pro Arg Thr Lys Asn Thr
        355                 360                 365

Asp Ile Leu Phe Gln Leu Gly Tyr Thr Ser Ser Pro Glu Met Ala Gln
    370                 375                 380

Ala Val Leu Gly Asn Glu Ala His Phe Asp Gln Ala Ala Lys Gly Gly
385                 390                 395                 400

Thr Ile Met Thr Gly Gly Arg Ala Gly Ala Asn Ala Pro Ser Tyr Ile
                405                 410                 415

Asp Asp Pro Leu Ala Ala Ile Gln Arg Arg Ala Arg Lys Asp Asp Thr
            420                 425                 430

Trp Val Asn Trp Asp Leu Asp Ser Phe Asn Pro Glu Val Asn Ala Ala
        435                 440                 445

Ser Asp Ala Cys Leu Val Phe Ile Asn Ala Ile Ala Thr Glu Gly Trp
    450                 455                 460

Asp Arg Asp Gly Leu His Asp Phe Ser Asp Gly Leu Val Leu Asn
465                 470                 475                 480

Val Ala Ala Asn Cys Ser Asn Thr Ile Val Val His Ala Ala Gly
                485                 490                 495

Thr Arg Leu Val Asp Gln Trp Ile Glu His Pro Asn Val Thr Ala Ala
            500                 505                 510

Val Ile Ala His Leu Pro Gly Gln Asp Ser Gly Arg Ala Leu Val Lys
        515                 520                 525

Leu Leu Tyr Gly Glu Ala Asn Phe Ser Gly Lys Leu Pro Tyr Thr Ile
    530                 535                 540

Ala Lys Asn Glu Ser Asp Tyr Ser Val Tyr Thr Pro Cys Gln Arg Arg
545                 550                 555                 560

Ser Pro Glu Asp Thr Asp Pro Gln Cys Asp Phe Thr Glu Gly Val Tyr
                565                 570                 575

Leu Asp Tyr Arg Ala Phe Asp Ala Asn Asn Met Thr Pro Arg Phe Glu
            580                 585                 590

Phe Gly Tyr Gly Leu Ser Tyr Thr Ser Phe
        595                 600

<210> SEQ ID NO 75
<211> LENGTH: 574
<212> TYPE: PRT
<213> ORGANISM: Hypocrea jecorina

<400> SEQUENCE: 75

Met Ile Leu Gly Cys Glu Ser Thr Gly Val Ile Ser Ala Val Lys His
1               5                   10                  15

| | | | | | | | | | | | |
|---|---|---|---|---|---|---|---|---|---|---|---|
|Phe|Val|Ala|Asn|Asp|Gln|Glu|His|Glu|Arg|Ala|Val|Asp|Cys|Leu|
| | | |20| | |25| | |30| | |

Ile Thr Gln Arg Ala Leu Arg Glu Val Tyr Leu Arg Pro Phe Gln Ile
            35                  40                  45

Val Ala Arg Asp Ala Arg Pro Gly Ala Leu Met Thr Ser Tyr Asn Lys
 50                  55                  60

Val Asn Gly Lys His Val Ala Asp Ser Ala Glu Phe Leu Gln Gly Ile
 65                  70                  75                  80

Leu Arg Thr Glu Trp Asn Trp Asp Pro Leu Ile Val Ser Asp Trp Tyr
                85                  90                  95

Gly Thr Tyr Thr Thr Ile Asp Ala Ile Lys Ala Gly Leu Asp Leu Glu
                100                 105                 110

Met Pro Gly Val Ser Arg Tyr Arg Gly Lys Tyr Ile Glu Ser Ala Leu
                115                 120                 125

Gln Ala Arg Leu Leu Lys Gln Ser Thr Ile Asp Glu Arg Ala Arg Arg
130                 135                 140

Val Leu Arg Phe Ala Gln Lys Ala Ser His Leu Lys Val Ser Glu Val
145                 150                 155                 160

Glu Gln Gly Arg Asp Phe Pro Glu Asp Arg Val Leu Asn Arg Gln Ile
                165                 170                 175

Cys Gly Ser Ser Ile Val Leu Leu Lys Asn Glu Asn Ser Ile Leu Pro
                180                 185                 190

Leu Pro Lys Ser Val Lys Lys Val Ala Leu Val Gly Ser His Val Arg
                195                 200                 205

Leu Pro Ala Ile Ser Gly Gly Ser Ala Ser Leu Val Pro Tyr Tyr
                210                 215                 220

Ala Ile Ser Leu Tyr Asp Ala Val Ser Glu Val Leu Ala Gly Ala Thr
225                 230                 235                 240

Ile Thr His Glu Val Gly Ala Tyr Ala His Gln Met Leu Pro Val Ile
                245                 250                 255

Asp Ala Met Ile Ser Asn Ala Val Ile His Phe Tyr Asn Asp Pro Ile
                260                 265                 270

Asp Val Lys Asp Arg Lys Leu Leu Gly Ser Glu Asn Val Ser Ser Thr
                275                 280                 285

Ser Phe Gln Leu Met Asp Tyr Asn Asn Ile Pro Thr Leu Asn Lys Ala
                290                 295                 300

Met Phe Trp Gly Thr Leu Val Gly Glu Phe Ile Pro Thr Ala Thr Gly
305                 310                 315                 320

Ile Trp Glu Phe Gly Leu Ser Val Phe Gly Thr Ala Asp Leu Tyr Ile
                325                 330                 335

Asp Asn Glu Leu Val Ile Glu Asn Thr Thr His Gln Thr Arg Gly Thr
                340                 345                 350

Ala Phe Phe Gly Lys Gly Thr Thr Glu Lys Val Ala Thr Arg Arg Met
                355                 360                 365

Val Ala Gly Ser Thr Tyr Lys Leu Arg Leu Glu Phe Gly Ser Ala Asn
                370                 375                 380

Thr Thr Lys Met Glu Thr Thr Gly Val Val Asn Phe Gly Gly Gly Ala
385                 390                 395                 400

Val His Leu Gly Ala Cys Leu Lys Val Asp Pro Gln Glu Met Ile Ala
                405                 410                 415

Arg Ala Val Lys Ala Ala Ala Asp Ala Asp Tyr Thr Ile Ile Cys Thr
                420                 425                 430

Gly Leu Ser Gly Glu Trp Glu Ser Glu Gly Phe Asp Arg Pro His Met

```
                435                 440                 445
Asp Leu Pro Pro Gly Val Asp Thr Met Ile Ser Gln Val Leu Asp Ala
    450                 455                 460

Ala Pro Asn Ala Val Val Asn Gln Ser Gly Thr Pro Val Thr Met
465                 470                 475                 480

Ser Trp Ala His Lys Ala Lys Ala Ile Val Gln Ala Trp Tyr Gly Gly
                485                 490                 495

Asn Glu Thr Gly His Gly Ile Ser Asp Val Leu Phe Gly Asn Val Asn
                500                 505                 510

Pro Ser Gly Lys Leu Ser Leu Ser Trp Pro Val Asp Val Lys His Asn
            515                 520                 525

Pro Ala Tyr Leu Asn Tyr Ala Ser Val Gly Gly Arg Val Leu Tyr Gly
        530                 535                 540

Glu Asp Val Tyr Val Gly Tyr Lys Phe Tyr Asp Lys Thr Glu Arg Glu
545                 550                 555                 560

Val Leu Phe Pro Phe Gly His Gly Leu Ser Tyr Ala Thr Phe
                565                 570

<210> SEQ ID NO 76
<211> LENGTH: 633
<212> TYPE: PRT
<213> ORGANISM: Hypocrea jecorina

<400> SEQUENCE: 76

Trp Met Asp Pro Ser Ala Pro Gly Trp Glu Gln Ala Tyr Ala Gln Ala
1               5                   10                  15

Lys Glu Phe Val Ser Gly Leu Thr Leu Leu Glu Lys Val Asn Leu Thr
            20                  25                  30

Thr Gly Val Gly Trp Met Gly Glu Lys Cys Val Gly Asn Val Gly Thr
        35                  40                  45

Val Pro Arg Leu Gly Met Arg Ser Leu Cys Met Gln Asp Gly Pro Leu
    50                  55                  60

Gly Leu Arg Phe Asn Thr Tyr Asn Ser Ala Phe Ser Val Gly Leu Thr
65                  70                  75                  80

Ala Ala Ala Ser Trp Ser Arg His Leu Trp Val Asp Arg Gly Thr Ala
                85                  90                  95

Leu Gly Ser Glu Ala Lys Gly Lys Gly Val Asp Val Leu Leu Gly Pro
            100                 105                 110

Val Ala Gly Pro Leu Gly Arg Asn Pro Asn Gly Gly Arg Asn Val Glu
        115                 120                 125

Gly Phe Gly Ser Asp Pro Tyr Leu Ala Gly Leu Ala Leu Ala Asp Thr
    130                 135                 140

Val Thr Gly Ile Gln Asn Ala Gly Thr Ile Ala Cys Ala Lys His Phe
145                 150                 155                 160

Leu Leu Asn Glu Gln Glu His Phe Arg Gln Val Gly Glu Ala Asn Gly
                165                 170                 175

Tyr Gly Tyr Pro Ile Thr Glu Ala Leu Ser Ser Asn Val Asp Asp Lys
            180                 185                 190

Thr Ile His Glu Val Tyr Gly Trp Pro Phe Gln Asp Ala Val Lys Ala
        195                 200                 205

Gly Val Gly Ser Phe Met Cys Ser Tyr Asn Gln Val Asn Asn Ser Tyr
    210                 215                 220

Ala Cys Gln Asn Ser Lys Leu Ile Asn Gly Leu Leu Lys Glu Glu Tyr
225                 230                 235                 240

Gly Phe Gln Gly Phe Val Met Ser Asp Trp Gln Ala Gln His Thr Gly
```

```
                    245                 250                 255
Val Ala Ser Ala Val Gly Leu Asp Met Thr Met Pro Gly Asp Thr
                260                 265                 270

Ala Phe Asn Thr Gly Ala Ser Tyr Phe Gly Ser Asn Leu Thr Leu Ala
            275                 280                 285

Val Leu Asn Gly Thr Val Pro Glu Trp Arg Ile Asp Asp Met Val Met
        290                 295                 300

Arg Ile Met Ala Pro Phe Lys Val Gly Lys Thr Val Asp Ser Leu
305                 310                 315                 320

Ile Asp Thr Asn Phe Asp Ser Trp Thr Asn Gly Glu Tyr Gly Tyr Val
                325                 330                 335

Gln Ala Ala Val Asn Glu Asn Trp Glu Lys Val Asn Tyr Gly Val Asp
                340                 345                 350

Val Arg Ala Asn His Ala Asn His Ile Arg Glu Val Gly Ala Lys Gly
            355                 360                 365

Thr Val Ile Phe Lys Asn Asn Gly Ile Leu Pro Leu Lys Lys Pro Lys
        370                 375                 380

Phe Leu Thr Val Ile Gly Glu Asp Ala Gly Asn Pro Ala Gly Pro
385                 390                 395                 400

Asn Gly Cys Gly Asp Arg Gly Cys Asp Asp Gly Thr Leu Ala Met Glu
                405                 410                 415

Trp Gly Ser Gly Thr Thr Asn Phe Pro Tyr Leu Val Thr Pro Asp Ala
                420                 425                 430

Ala Leu Gln Ser Gln Ala Leu Gln Asp Gly Thr Arg Tyr Glu Ser Ile
            435                 440                 445

Leu Ser Asn Tyr Ala Ile Ser Gln Thr Gln Ala Leu Val Ser Gln Pro
        450                 455                 460

Asp Ala Ile Ala Ile Val Phe Ala Asn Ser Asp Ser Gly Glu Gly Tyr
465                 470                 475                 480

Ile Asn Val Asp Gly Asn Glu Gly Asp Arg Lys Asn Leu Thr Leu Trp
                485                 490                 495

Lys Asn Gly Asp Asp Leu Ile Lys Thr Val Ala Ala Val Asn Pro Lys
            500                 505                 510

Thr Ile Val Val Ile His Ser Thr Gly Pro Val Ile Leu Lys Asp Tyr
        515                 520                 525

Ala Asn His Pro Asn Ile Ser Ala Ile Leu Trp Ala Gly Ala Pro Gly
530                 535                 540

Gln Glu Ser Gly Asn Ser Leu Val Asp Ile Leu Tyr Gly Lys Gln Ser
545                 550                 555                 560

Pro Gly Arg Thr Pro Phe Thr Trp Gly Pro Ser Leu Glu Ser Tyr Gly
                565                 570                 575

Val Ser Val Met Thr Thr Pro Asn Asn Gly Asn Gly Ala Pro Gln Asp
            580                 585                 590

Asn Phe Asn Glu Gly Ala Phe Ile Asp Tyr Arg Tyr Phe Asp Lys Val
        595                 600                 605

Ala Pro Gly Lys Pro Arg Ser Ser Asp Lys Ala Pro Thr Tyr Glu Phe
610                 615                 620

Gly Phe Gly Leu Ser Trp Ser Thr Phe
625                 630

<210> SEQ ID NO 77
<211> LENGTH: 586
<212> TYPE: PRT
<213> ORGANISM: Hypocrea jecorina
```

<400> SEQUENCE: 77

```
Lys Asn Asn Leu Val Cys Asp Ser Ser Ala Gly Tyr Val Glu Arg Ala
1               5                   10                  15
Gln Ala Leu Ile Ser Leu Phe Thr Leu Glu Glu Leu Ile Leu Asn Thr
            20                  25                  30
Gln Asn Ser Gly Pro Gly Val Pro Arg Leu Gly Leu Pro Asn Tyr Gln
        35                  40                  45
Val Trp Asn Glu Ala Leu His Gly Leu Asp Arg Ala Asn Phe Ala Thr
50                  55                  60
Lys Gly Gly Gln Phe Glu Trp Ala Thr Ser Phe Pro Met Pro Ile Leu
65                  70                  75                  80
Thr Thr Ala Ala Leu Asn Arg Thr Leu Ile His Gln Ile Ala Asp Ile
            85                  90                  95
Ile Ser Thr Gln Ala Arg Ala Phe Ser Asn Ser Gly Arg Tyr Gly Leu
            100                 105                 110
Asp Val Tyr Ala Pro Asn Val Asn Gly Phe Arg Ser Pro Leu Trp Gly
        115                 120                 125
Arg Gly Gln Glu Thr Pro Gly Glu Asp Ala Phe Phe Leu Ser Ser Ala
130                 135                 140
Tyr Thr Tyr Glu Tyr Ile Thr Gly Ile Gln Gly Gly Val Asp Pro Glu
145                 150                 155                 160
His Leu Lys Val Ala Ala Thr Val Lys His Phe Ala Gly Tyr Asp Leu
            165                 170                 175
Glu Asn Trp Asn Asn Gln Ser Arg Leu Gly Phe Asp Ala Ile Ile Thr
            180                 185                 190
Gln Gln Asp Leu Ser Glu Tyr Tyr Thr Pro Gln Phe Leu Ala Ala Ala
        195                 200                 205
Arg Tyr Ala Lys Ser Arg Ser Leu Met Cys Ala Tyr Asn Ser Val Asn
210                 215                 220
Gly Val Pro Ser Cys Ala Asn Ser Phe Phe Leu Gln Thr Leu Leu Arg
225                 230                 235                 240
Glu Ser Trp Gly Phe Pro Glu Trp Gly Tyr Val Ser Ser Asp Cys Asp
            245                 250                 255
Ala Val Tyr Asn Val Phe Asn Pro His Asp Tyr Ala Ser Asn Gln Ser
            260                 265                 270
Ser Ala Ala Ala Ser Ser Leu Arg Ala Gly Thr Asp Ile Asp Cys Gly
        275                 280                 285
Gln Thr Tyr Pro Trp His Leu Asn Glu Ser Phe Val Ala Gly Glu Val
        290                 295                 300
Ser Arg Gly Glu Ile Glu Arg Ser Val Thr Arg Leu Tyr Ala Asn Leu
305                 310                 315                 320
Val Arg Leu Gly Tyr Phe Asp Lys Lys Asn Gln Tyr Arg Ser Leu Gly
            325                 330                 335
Trp Lys Asp Val Val Lys Thr Asp Ala Trp Asn Ile Ser Tyr Glu Ala
            340                 345                 350
Ala Val Glu Gly Ile Val Leu Leu Lys Asn Asp Gly Thr Leu Pro Leu
        355                 360                 365
Ser Lys Lys Val Arg Ser Ile Ala Leu Ile Gly Pro Trp Ala Asn Ala
370                 375                 380
Thr Thr Gln Met Gln Gly Asn Tyr Gly Pro Ala Pro Tyr Leu Ile
385                 390                 395                 400
Ser Pro Leu Glu Ala Ala Lys Lys Ala Gly Tyr His Val Asn Phe Glu
            405                 410                 415
```

```
Leu Gly Thr Glu Ile Ala Gly Asn Ser Thr Thr Gly Phe Ala Lys Ala
            420                 425                 430

Ile Ala Ala Ala Lys Lys Ser Asp Ala Ile Ile Tyr Leu Gly Gly Ile
        435                 440                 445

Asp Asn Thr Ile Glu Gln Glu Gly Ala Asp Arg Thr Asp Ile Ala Trp
    450                 455                 460

Pro Gly Asn Gln Leu Asp Leu Ile Lys Gln Leu Ser Glu Val Gly Lys
465                 470                 475                 480

Pro Leu Val Val Leu Gln Met Gly Gly Gln Val Asp Ser Ser Ser
                485                 490                 495

Leu Lys Ser Asn Lys Lys Val Asn Ser Leu Val Trp Gly Gly Tyr Pro
            500                 505                 510

Gly Gln Ser Gly Gly Val Ala Leu Phe Asp Ile Leu Ser Gly Lys Arg
        515                 520                 525

Ala Pro Ala Gly Arg Leu Val Thr Thr Gln Tyr Pro Ala Glu Tyr Val
    530                 535                 540

His Gln Phe Pro Gln Asn Asp Met Asn Leu Arg Pro Asp Gly Lys Ser
545                 550                 555                 560

Asn Pro Gly Gln Thr Tyr Ile Trp Tyr Thr Gly Lys Pro Val Tyr Glu
                565                 570                 575

Phe Gly Ser Gly Leu Phe Tyr Thr Thr Phe
            580                 585

<210> SEQ ID NO 78
<211> LENGTH: 718
<212> TYPE: PRT
<213> ORGANISM: Kluyveromyces fragilis

<400> SEQUENCE: 78

Val Glu Gln Leu Leu Ser Glu Leu Asn Gln Asp Glu Lys Ile Ser Leu
1               5                   10                  15

Leu Ser Ala Val Asp Phe Trp His Thr Lys Lys Ile Glu Arg Leu Gly
            20                  25                  30

Ile Pro Ala Val Arg Val Ser Asp Gly Pro Asn Gly Ile Arg Gly Thr
        35                  40                  45

Lys Phe Phe Asp Gly Val Pro Ser Gly Cys Phe Pro Asn Gly Thr Gly
    50                  55                  60

Leu Ala Ser Thr Phe Asp Arg Asp Leu Leu Glu Thr Ala Gly Lys Leu
65                  70                  75                  80

Met Ala Lys Glu Ser Ile Ala Lys Asn Ala Ala Val Ile Leu Gly Pro
                85                  90                  95

Thr Thr Asn Met Gln Arg Gly Pro Leu Gly Gly Arg Gly Phe Glu Ser
            100                 105                 110

Phe Ser Glu Asp Pro Tyr Leu Ala Gly Met Ala Thr Ser Ser Val Val
        115                 120                 125

Lys Gly Met Gln Gly Glu Gly Ile Ala Ala Thr Val Lys His Phe Val
    130                 135                 140

Cys Asn Asp Leu Glu Asp Gln Arg Phe Ser Ser Asn Ser Ile Val Ser
145                 150                 155                 160

Glu Arg Ala Leu Arg Glu Ile Tyr Leu Glu Pro Phe Arg Leu Ala Val
                165                 170                 175

Lys His Ala Asn Pro Val Cys Ile Met Thr Ala Tyr Asn Lys Val Asn
            180                 185                 190

Gly Asp His Cys Ser Gln Ser Lys Lys Leu Leu Ile Asp Ile Leu Arg
        195                 200                 205
```

```
Asp Glu Trp Lys Trp Asp Gly Met Leu Met Ser Asp Trp Phe Gly Thr
    210                 215                 220
Tyr Thr Thr Ala Ala Ala Ile Lys Asn Gly Leu Asp Ile Glu Phe Pro
225                 230                 235                 240
Gly Pro Thr Arg Trp Arg Thr Arg Ala Leu Val Ser His Ser Leu Asn
                245                 250                 255
Ser Arg Glu Gln Ile Thr Thr Glu Asp Val Asp Arg Val Arg Gln
            260                 265                 270
Val Leu Lys Met Ile Lys Phe Val Asp Asn Leu Glu Lys Thr Gly
        275                 280                 285
Ile Val Glu Asn Gly Pro Glu Ser Thr Ser Asn Asn Thr Lys Glu Thr
    290                 295                 300
Ser Asp Leu Leu Arg Glu Ile Ala Ala Asp Ser Ile Val Leu Leu Lys
305                 310                 315                 320
Asn Lys Asn Asn Tyr Leu Thr Ser Lys Glu Arg Arg Gln Tyr His Val
                325                 330                 335
Ile Gly Pro Asn Ala Lys Ala Lys Thr Ser Ser Gly Gly Ser Ala
            340                 345                 350
Ser Met Asn Ser Tyr Tyr Val Val Ser Pro Tyr Glu Gly Ile Val Asn
    355                 360                 365
Lys Leu Gly Lys Glu Val Asp Tyr Thr Val Gly Ala Tyr Ser His Lys
    370                 375                 380
Ser Ile Gly Gly Leu Ala Glu Ser Ser Leu Ile Asp Ala Ala Lys Pro
385                 390                 395                 400
Ala Asp Ala Glu Asn Ala Gly Leu Ile Ala Lys Phe Tyr Ser Asn Pro
                405                 410                 415
Val Glu Glu Arg Ser Glu Asp Glu Pro Phe His Val Thr Lys Val
            420                 425                 430
Asn Arg Ser Asn Val His Leu Phe Asp Phe Lys His Glu Lys Val Asp
435                 440                 445
Pro Lys Asn Pro Tyr Phe Phe Val Thr Leu Thr Gly Gln Tyr Val Pro
    450                 455                 460
Gln Glu Asp Gly Asp Tyr Ile Phe Ser Leu Gln Val Tyr Gly Ser Gly
465                 470                 475                 480
Leu Phe Tyr Leu Asn Asp Glu Leu Ile Ile Asp Gln Lys His Asn Gln
                485                 490                 495
Glu Arg Gly Ser Phe Cys Phe Gly Ala Gly Thr Lys Glu Arg Thr Lys
            500                 505                 510
Lys Leu Thr Leu Lys Lys Gly Gln Val Tyr Asn Val Arg Val Glu Tyr
        515                 520                 525
Gly Ser Gly Pro Thr Ser Gly Leu Val Gly Glu Phe Gly Ala Gly Gly
    530                 535                 540
Phe Gln Ala Gly Val Ile Lys Ala Ile Asp Asp Glu Glu Ile Arg
545                 550                 555                 560
Asn Ala Ala Glu Leu Ala Ala Lys His Asp Lys Ala Val Leu Ile Ile
                565                 570                 575
Gly Leu Asn Gly Glu Trp Glu Thr Glu Gly Tyr Asp Arg Glu Asn Met
            580                 585                 590
Asp Leu Pro Lys Arg Thr Asn Glu Leu Val Arg Ala Val Leu Lys Ala
        595                 600                 605
Asn Pro Asn Thr Val Ile Val Asn Gln Ser Gly Thr Pro Val Glu Phe
    610                 615                 620
Pro Trp Leu Glu Glu Ala Asn Ala Leu Val Gln Ala Trp Tyr Gly Gly
625                 630                 635                 640
```

```
Asn Glu Leu Gly Asn Ala Ile Ala Asp Val Leu Tyr Gly Asp Val Val
                645                 650                 655

Pro Asn Gly Lys Leu Ser Leu Ser Trp Pro Phe Lys Leu Gln Asp Asn
            660                 665                 670

Pro Ala Phe Leu Asn Phe Lys Thr Glu Phe Gly Arg Val Val Tyr Gly
        675                 680                 685

Glu Asp Ile Phe Val Gly Tyr Arg Tyr Tyr Glu Lys Leu Gln Arg Lys
    690                 695                 700

Val Ala Phe Pro Phe Gly Tyr Gly Leu Ser Tyr Thr Thr Phe
705                 710                 715

<210> SEQ ID NO 79
<211> LENGTH: 591
<212> TYPE: PRT
<213> ORGANISM: Kuraishia capsulata

<400> SEQUENCE: 79

Pro Glu Ile Ser Gly Leu Gly Asp Trp Gln Phe Ala Tyr Gln Arg Ala
1               5                   10                  15

Arg Glu Ile Val Ala Leu Met Thr Asn Glu Glu Lys Thr Asn Leu Thr
            20                  25                  30

Phe Gly Ser Ser Gly Asp Thr Gly Cys Ser Gly Met Ile Ser Asp Val
        35                  40                  45

Pro Asp Val Asp Phe Pro Gly Leu Cys Leu Gln Asp Ala Gly Asn Gly
    50                  55                  60

Val Arg Gly Thr Asp Met Val Asn Ala Tyr Ala Ser Gly Leu His Val
65                  70                  75                  80

Gly Ala Ser Trp Asn Arg Gln Leu Ala Tyr Asp Arg Ala Val Tyr Met
                85                  90                  95

Gly Ala Glu Phe Arg His Lys Gly Val Asn Val Leu Leu Gly Pro Val
            100                 105                 110

Val Gly Pro Ile Gly Arg Val Ala Thr Gly Gly Arg Asn Trp Glu Gly
        115                 120                 125

Phe Thr Asn Asp Pro Tyr Leu Ala Gly Ala Leu Val Tyr Glu Thr Thr
    130                 135                 140

Lys Gly Ile Gln Glu Asn Val Ile Ala Cys Thr Lys His Phe Ile Gly
145                 150                 155                 160

Asn Glu Gln Glu Thr Asn Arg Asn Pro Ser Gly Thr Tyr Asn Gln Ser
                165                 170                 175

Val Ser Ala Asn Ile Asp Asp Lys Thr Met His Glu Leu Tyr Leu Trp
            180                 185                 190

Pro Phe Gln Asp Ser Val Arg Ala Gly Leu Gly Ser Ile Met Gly Ser
        195                 200                 205

Tyr Asn Arg Val Asn Asn Ser Tyr Ala Cys Lys Asn Ser Lys Val Leu
    210                 215                 220

Asn Gly Leu Leu Lys Ser Glu Leu Gly Phe Gln Gly Phe Val Val Ser
225                 230                 235                 240

Asp Trp Gly Gly Gln His Thr Gly Ile Ala Ser Ala Asn Ala Gly Leu
                245                 250                 255

Asp Met Ala Met Pro Ser Ser Thr Tyr Trp Glu Glu Gly Leu Ile Glu
            260                 265                 270

Ala Val Lys Asn Gly Thr Val Asp Gln Ser Arg Leu Asp Asp Met Ala
        275                 280                 285

Thr Arg Ile Ile Ala Ala Trp Tyr Lys Tyr Ala Arg Leu Asp Asp Pro
    290                 295                 300
```

Gly Phe Gly Met Pro Val Ser Leu Ala Glu Asp His Glu Leu Val Asp
305                 310                 315                 320

Ala Arg Asp Pro Ala Ala Ser Thr Ile Phe Gln Gly Ala Val Glu
            325                 330                 335

Gly His Val Leu Val Lys Asn Glu Asn Ala Leu Pro Leu Lys Lys Pro
            340                 345                 350

Lys Tyr Ile Ser Leu Phe Gly Tyr Asp Gly Val Ser Thr Asp Val Asn
                355                 360                 365

Thr Val Gly Gly Phe Ser Phe Ser Phe Asp Val Lys Ala Ile
        370                 375                 380

Glu Asn Lys Thr Leu Ile Ser Gly Gly Ser Gly Thr Asn Thr Pro
385                 390                 395                 400

Ser Tyr Val Asp Ala Pro Phe Asn Ala Phe Val Ala Lys Ala Arg Glu
                405                 410                 415

Asp Asn Thr Phe Leu Ser Trp Asp Phe Thr Ser Ala Glu Pro Val Ala
                420                 425                 430

Asn Pro Ala Ser Asp Ala Cys Ile Asp Phe Ile Asn Ala Ala Ala Ser
                435                 440                 445

Glu Gly Tyr Asp Arg Pro Asn Leu Ala Asp Lys Tyr Ser Asp Lys Leu
    450                 455                 460

Val Glu Ala Val Ala Ser Gln Cys Ser Asn Thr Ile Val Val Ile His
465                 470                 475                 480

Asn Ala Gly Ile Arg Leu Val Asp Asn Trp Ile Glu His Glu Asn Val
                485                 490                 495

Thr Gly Val Ile Leu Ala His Leu Pro Gly Gln Asp Thr Gly Thr Ser
                500                 505                 510

Leu Ile Glu Val Leu Tyr Gly Asn Gln Ser Pro Ser Gly Arg Leu Pro
            515                 520                 525

Tyr Thr Val Ala Lys Lys Ala Ser Asp Tyr Gly Gly Leu Leu Trp Pro
    530                 535                 540

Thr Glu Pro Glu Gly Asp Leu Asp Leu Tyr Phe Pro Gln Ser Asn Phe
545                 550                 555                 560

Thr Glu Gly Val Tyr Ile Asp Tyr Lys Tyr Phe Ile Gln Lys Asn Ile
                565                 570                 575

Thr Pro Arg Tyr Glu Phe Gly Tyr Gly Leu Thr Tyr Thr Thr Phe
            580                 585                 590

<210> SEQ ID NO 80
<211> LENGTH: 605
<212> TYPE: PRT
<213> ORGANISM: Nicotiana tabacum

<400> SEQUENCE: 80

Glu Tyr Val Lys Tyr Lys Asp Pro Lys Gln Pro Val Gly Ala Arg Ile
1               5                   10                  15

Lys Asp Leu Met Lys Arg Met Thr Leu Glu Glu Lys Ile Gly Gln Met
            20                  25                  30

Thr Gln Ile Glu Arg Lys Val Ala Thr Ala Asp Val Met Lys Gln Asn
        35                  40                  45

Phe Ile Gly Ser Val Leu Ser Gly Gly Ser Val Pro Ala Pro Lys
    50                  55                  60

Ala Ser Ala Gln Val Trp Thr Asn Met Val Asp Glu Ile Gln Lys Gly
65                  70                  75                  80

Ser Leu Ser Thr Arg Leu Gly Ile Pro Met Ile Tyr Gly Ile Asp Ala
                85                  90                  95

```
Val His Gly His Asn Asn Val Tyr Gly Ala Thr Ile Phe Pro His Asn
            100                 105                 110
Val Gly Leu Gly Val Thr Arg Asp Pro Asp Leu Val Lys Arg Ile Gly
            115                 120                 125
Ala Ala Thr Ala Leu Glu Val Arg Ala Thr Gly Ile Pro Tyr Ala Phe
130                 135                 140
Ala Pro Cys Ile Ala Val Cys Arg Asn Pro Arg Trp Gly Arg Cys Tyr
145                 150                 155                 160
Glu Ser Tyr Ser Glu Asp His Arg Ile Val Arg Ser Met Thr Glu Ile
                165                 170                 175
Ile Pro Gly Leu Gln Gly Asp Leu Pro Ala Lys Ser Lys Asn Gly Val
            180                 185                 190
Pro Tyr Val Gly Gly Lys Thr Lys Val Ala Ala Cys Ala Lys His Phe
            195                 200                 205
Val Gly Asp Gly Gly Thr Leu His Gly Val Asp Glu Ser Asn Thr Val
            210                 215                 220
Ile Ser Ser Asn Ser Leu Phe Ser Ile His Met Pro Ala Tyr Tyr Asp
225                 230                 235                 240
Ser Leu Arg Lys Gly Val Ala Thr Val Met Val Ser Tyr Ser Ser Trp
                245                 250                 255
Asn Gly Arg Lys Met His Ala Asn Arg Asp Leu Val Thr Gly Phe Leu
            260                 265                 270
Lys Asp Lys Leu Lys Phe Arg Gly Phe Val Ile Ser Asp Trp Gln Gly
            275                 280                 285
Ile Asp Arg Ile Thr Asp Pro Pro His Ala Asn Tyr Ser Tyr Ser Val
            290                 295                 300
Gln Ala Gly Ile Met Ala Gly Ile Asp Met Ile Met Val Pro Glu Asn
305                 310                 315                 320
Tyr Arg Glu Phe Ile Asp Thr Leu Thr Ser Gln Val Lys Ala Asn Ile
                325                 330                 335
Ile Pro Met Ser Arg Ile Asp Asp Ala Val Lys Arg Ile Leu Arg Val
            340                 345                 350
Lys Phe Val Met Gly Leu Phe Glu Asn Pro Met Ser Asp Pro Ser Leu
            355                 360                 365
Ala Asn Gln Leu Gly Ser Gln Glu His Arg Glu Leu Ala Arg Glu Ala
            370                 375                 380
Val Arg Lys Ser Leu Val Leu Leu Lys Asn Gly Lys Thr Pro Ser Gln
385                 390                 395                 400
Pro Leu Leu Pro Leu Pro Lys Lys Ala Pro Lys Ile Leu Val Ala Gly
                405                 410                 415
Thr His Ala Asp Asn Leu Gly Tyr Gln Cys Gly Gly Trp Thr Ile Glu
            420                 425                 430
Trp Gln Gly Val Ala Gly Asn Asp Leu Thr Ile Gly Thr Thr Ile Leu
            435                 440                 445
Thr Ala Ile Lys Lys Thr Val Asp Pro Ser Thr Gln Val Val Tyr Gln
            450                 455                 460
Gln Asn Pro Asp Ala Asn Phe Val Lys Ser Asn Lys Phe Ser Tyr Ala
465                 470                 475                 480
Ile Val Val Val Gly Glu Val Pro Tyr Ala Glu Met Phe Gly Asp Ser
                485                 490                 495
Ser Asn Leu Thr Ile Ala Glu Pro Gly Pro Ser Thr Ile Ser Asn Ile
            500                 505                 510
Cys Gly Ser Val Lys Cys Val Val Val Val Val Ser Gly Arg Pro Val
```

```
            515                 520                 525
Val Leu Glu Pro Tyr Val Ser Lys Met Asp Ala Leu Val Ala Ala Trp
530                 535                 540

Leu Pro Gly Thr Glu Gly Gln Gly Val Ala Asp Ala Leu Phe Gly Asp
545                 550                 555                 560

Tyr Gly Phe Thr Gly Lys Leu Ala Arg Thr Trp Phe Lys Arg Val Asp
                565                 570                 575

Gln Leu Pro Met Asn Phe Asp Asp Ala His Val Asp Pro Leu Phe Pro
            580                 585                 590

Phe Gly Phe Gly Ile Thr Thr Lys Pro Val Lys Gly Tyr
        595                 600                 605

<210> SEQ ID NO 81
<211> LENGTH: 601
<212> TYPE: PRT
<213> ORGANISM: Periconia sp.

<400> SEQUENCE: 81

Pro Trp Met Asp Pro Ser Ala Ala Gly Trp Ala Glu Ala Tyr Thr Lys
1               5                   10                  15

Ala Gln Ala Phe Val Arg Gln Leu Thr Leu Leu Glu Lys Val Asn Leu
            20                  25                  30

Thr Thr Gly Val Gly Trp Glu Gly Glu Ala Cys Val Gly Asn Thr Gly
        35                  40                  45

Ser Ile Pro Arg Leu Gly Phe Pro Gly Phe Cys Thr Gln Asp Ser Pro
50                  55                  60

Leu Gly Val Arg Phe Ala Asp Tyr Val Ser Ala Phe Thr Ala Gly Gly
65                  70                  75                  80

Thr Ile Ala Ala Ser Trp Asp Arg Ser Glu Phe Tyr Arg Arg Gly Tyr
                85                  90                  95

Gln Met Gly Val Glu His Arg Gly Lys Gly Val Asp Val Gln Leu Gly
            100                 105                 110

Pro Val Val Gly Pro Ile Gly Arg His Pro Lys Gly Gly Arg Asn Trp
        115                 120                 125

Glu Gly Phe Ser Pro Asp Pro Val Leu Ser Gly Ile Ala Val Ala Glu
130                 135                 140

Thr Val Lys Gly Ile Gln Asp Ala Gly Val Ile Ala Cys Thr Lys His
145                 150                 155                 160

Phe Ile Leu Asn Glu Gln Glu His Phe Arg Gln Pro Gly Asn Val Gly
                165                 170                 175

Asp Phe Gly Phe Val Asp Ala Val Ser Ala Asn Leu Ala Asp Lys Thr
            180                 185                 190

Leu His Glu Leu Tyr Leu Trp Pro Phe Ala Asp Ala Val Arg Ala Gly
        195                 200                 205

Thr Gly Ser Ile Met Cys Ser Tyr Asn Lys Ala Asn Asn Ser Gln Val
210                 215                 220

Cys Gln Asn Ser Tyr Leu Gln Asn Tyr Ile Leu Lys Gly Glu Leu Gly
225                 230                 235                 240

Phe Gln Gly Phe Thr Met Ser Asp Trp Asp Ala Gln His Ser Gly Val
                245                 250                 255

Ala Ser Thr Leu Ala Gly Leu Asp Met Asn Met Pro Gly Asp Thr Asp
            260                 265                 270

Phe Asp Ser Gly Phe Ser Phe Trp Gly Pro Asn Met Thr Leu Ser Ile
        275                 280                 285

Ile Asn Gly Thr Val Pro Glu Trp Arg Leu Asp Asp Ala Ala Thr Arg
```

```
            290                 295                 300
Ile Met Ala Ala Tyr Tyr Leu Val Gly Arg Asp Arg His Ala Val Pro
305                 310                 315                 320

Val Asn Phe Asn Ser Trp Ser Lys Asp Thr Tyr Gly Tyr Gln His Ala
                325                 330                 335

Tyr Ala Lys Val Gly Tyr Gly Leu Ile Asn Gln His Val Asp Val Arg
            340                 345                 350

Ala Asp His Phe Lys Ser Ile Arg Thr Ala Ala Lys Ser Thr Val
            355                 360                 365

Leu Leu Lys Asn Gly Val Leu Pro Leu Lys Gly Thr Glu Lys Tyr
370                 375                 380

Thr Ala Val Phe Gly Asn Asp Ala Gly Glu Ala Gln Tyr Gly Pro Asn
385                 390                 395                 400

Gly Cys Ala Asp His Gly Cys Asp Asn Gly Thr Leu Ala Met Gly Trp
                405                 410                 415

Gly Ser Gly Thr Ala Asp Tyr Pro Tyr Leu Val Thr Pro Leu Glu Ala
            420                 425                 430

Ile Lys Arg Thr Val Gly Asp His Gly Gly Val Ile Ala Ser Val Thr
            435                 440                 445

Asp Asn Tyr Ala Phe Ser Gln Ile Met Ala Leu Ala Lys Gln Ala Thr
450                 455                 460

His Ala Ile Val Phe Val Asn Ala Asp Ser Gly Glu Gly Tyr Ile Thr
465                 470                 475                 480

Val Asp Gly Asn Glu Gly Asp Arg Asn Asn Leu Thr Leu Trp Gln Asn
                485                 490                 495

Gly Glu Glu Leu Val Arg Asn Val Ser Gly Tyr Cys Asn Asn Thr Ile
            500                 505                 510

Val Val Ile His Ser Val Gly Pro Val Leu Val Asp Ser Phe Asn Asn
            515                 520                 525

Ser Pro Asn Val Ser Ala Ile Leu Trp Ala Gly Leu Pro Gly Gln Glu
530                 535                 540

Ser Gly Asn Ala Ile Thr Asp Val Leu Tyr Gly Arg Val Asn Pro Gly
545                 550                 555                 560

Gly Lys Leu Pro Phe Thr Ile Gly Lys Ser Ala Glu Glu Tyr Gly Pro
                565                 570                 575

Asp Ile Ile Tyr Glu Pro Thr Ala Gly His Gly Ser Pro Gln Ala Asn
            580                 585                 590

Phe Glu Glu Gly Val Phe Ile Asp Tyr
            595                 600

<210> SEQ ID NO 82
<211> LENGTH: 623
<212> TYPE: PRT
<213> ORGANISM: Phaeosphaeria avenaria

<400> SEQUENCE: 82

Pro Trp Ile Glu Gly Leu Gly Asp Trp Glu Ala Ala Tyr Gln Lys Ala
1               5                   10                  15

Gln Ala Phe Val Ser Gln Leu Thr Leu Leu Glu Lys Val Asn Leu Thr
            20                  25                  30

Thr Gly Thr Gly Trp Gln Ser Asp His Cys Val Gly Asn Thr Gly Gly
        35                  40                  45

Val Pro Arg Leu Asn Phe Thr Gly Ile Cys Asn Gln Asp Ala Pro Leu
    50                  55                  60

Gly Val Arg Phe Ala Asp Tyr Val Ser Ala Phe Pro Ser Gly Gly Thr
```

```
                65                  70                  75                  80
Ile Ala Ala Ala Trp Asp Arg Gly Glu Trp Tyr Leu Arg Gly Tyr Gln
                    85                  90                  95

Met Gly Ser Glu His Arg Ser Lys Gly Val Asp Val Gln Leu Gly Pro
                100                 105                 110

Val Val Gly Pro Leu Gly Arg Asn Pro Lys Gly Gly Arg Asn Trp Glu
                115                 120                 125

Gly Phe Ser Pro Asp Pro Tyr Leu Ser Gly Ile Ala Ser Ala Glu Ser
                130                 135                 140

Val Arg Gly Ile Gln Asp Ala Gly Val Ile Ala Cys Thr Lys His Tyr
145                 150                 155                 160

Ile Met Asn Glu Gln Glu His Phe Arg Gln Pro Gly Asn Phe Glu Asp
                165                 170                 175

Gln Gly Phe Val Asp Ala Leu Ser Ser Asn Leu Asp Asp Lys Thr Leu
                180                 185                 190

His Glu Leu Tyr Leu Trp Pro Phe Ala Asp Ala Val Arg Ala Gly Thr
                195                 200                 205

Gly Ser Ile Met Cys Ser Tyr Asn Lys Val Asn Asn Ser Gln Ala Cys
                210                 215                 220

Gln Asn Ser Tyr Leu Gln Asn Tyr Ile Leu Lys Gly Glu Leu Gly Phe
225                 230                 235                 240

Gln Gly Phe Ile Met Ser Asp Trp Asp Ala Gln His Ser Gly Val Ala
                245                 250                 255

Ser Thr Phe Ala Gly Leu Asp Met Thr Met Pro Gly Asp Thr Asp Phe
                260                 265                 270

Asn Ser Gly Lys Thr Phe Trp Gly Thr Asn Phe Thr Thr Ser Ile Leu
                275                 280                 285

Asn Gly Thr Val Pro Gln Trp Arg Leu Asp Asp Ala Val Thr Arg Ile
                290                 295                 300

Met Ala Ala Phe Tyr Tyr Val Gly Arg Asp Lys Ala Arg Ile Pro Val
305                 310                 315                 320

Asn Phe Asp Ser Trp Ser Arg Asp Thr Tyr Gly Phe Asp His Tyr Tyr
                325                 330                 335

Gly Lys Ala Gly Tyr Ser Gln Ile Asn Ser His Val Asp Val Arg Ala
                340                 345                 350

Asp His Phe Arg Ser Ile Arg Arg Thr Ala Ala Met Ser Thr Val Leu
                355                 360                 365

Leu Lys Asn Glu Gly Ala Leu Pro Leu Thr Gly Ser Glu Lys Trp Thr
                370                 375                 380

Ala Val Phe Gly Asp Asp Ala Gly Glu Gly Gln Leu Gly Pro Asn Gly
385                 390                 395                 400

Phe Pro Asp His Gly Gly Asn Asn Gly Thr Leu Ala Met Gly Trp Gly
                405                 410                 415

Ser Gly Thr Ser Asp Tyr Pro Tyr Leu Val Thr Pro Leu Glu Ser Ile
                420                 425                 430

Lys Ala Thr Val Ala Gln Asn Gly Gly Ile Val Thr Ser Val Thr Asp
                435                 440                 445

Asn Trp Ala Tyr Thr Gln Ile Gln Thr Leu Ala Lys Gln Ala Ser Val
                450                 455                 460

Ala Ile Val Phe Val Asn Ala Asp Ser Gly Glu Gly Tyr Ile Thr Val
465                 470                 475                 480

Asp Gly Asn Ala Gly Asp Arg Asn Asn Leu Thr Leu Trp Gln Asp Gly
                485                 490                 495
```

```
Asp Thr Leu Ile Lys Asn Val Ser Ser Leu Cys Asn Asn Thr Ile Val
                500                 505                 510

Val Ile His Ser Val Gly Pro Val Leu Val Asn Ser Phe Tyr Asp Ser
        515                 520                 525

Glu Asn Val Thr Ala Ile Leu Trp Ala Gly Leu Pro Gly Gln Glu Ser
    530                 535                 540

Gly Asn Ala Ile Ala Asp Ile Leu Tyr Gly Arg His Asn Pro Gly Gly
545                 550                 555                 560

Lys Leu Pro Phe Thr Ile Gly Ser Asp Ala Ala Glu Tyr Gly Pro Asp
                565                 570                 575

Leu Ile Tyr Glu Pro Thr Asn Asn Ser Ser Pro Gln Asp Asn Phe
        580                 585                 590

Glu Glu Gly Val Phe Ile Asp Tyr Arg Ala Phe Asp Lys Gln Asn Val
    595                 600                 605

Thr Pro Ile Tyr Glu Phe Gly Phe Gly Leu Ser Tyr Thr Lys Phe
        610                 615                 620

<210> SEQ ID NO 83
<211> LENGTH: 594
<212> TYPE: PRT
<213> ORGANISM: Phanerochaete chrysosporium

<400> SEQUENCE: 83

Thr Val Ala Asn Val Ser Pro Glu Trp Ala Ala Tyr Val Lys Ala
1               5                   10                  15

Gln Ala Ala Val Ala Lys Leu Ser Val Thr Asp Met Val Asn Leu Ala
                20                  25                  30

Thr Gly Val Gln Trp Glu Lys Gly Pro Cys Val Gly Asn Thr Pro Ala
            35                  40                  45

Ile Ser Ser Ile Pro Gly Phe Thr Gly Leu Cys Leu Gln Asp Ser Pro
    50                  55                  60

Val Gly Val Arg Tyr Ala Asp Gly Thr Ser Val Phe Pro Pro Glu Ile
65                  70                  75                  80

Asn Val Ala Ala Thr Trp Asn Arg Thr Leu Met Arg Gln Arg Gly Ala
                85                  90                  95

Ala Met Gly Ala Glu Phe Lys Gly Lys Gly Val His Val Ala Leu Gly
            100                 105                 110

Pro Met Met Asn Leu Met Arg Val Pro Ala Ala Gly Arg Asn Trp Glu
    115                 120                 125

Gly Gly Gly Gly Asp Pro Phe Leu Ser Gly Glu Leu Ala Phe Glu Thr
130                 135                 140

Ile Thr Gly Ile Gln Ser Ser Gly Ala Gln Ala Cys Ala Lys His Phe
145                 150                 155                 160

Ile Asn Asn Glu Gln Glu His Phe Arg Asp Ser Ser Ser Asn Val
                165                 170                 175

Asp Asp Arg Thr Glu His Glu Leu Tyr Gly His Pro Phe Leu Arg Ser
            180                 185                 190

Val Gln Ala Asn Val Ala Ser Val Met Cys Ser Tyr Asn Gln Ile Asn
    195                 200                 205

Gly Thr Phe Ser Cys Glu Asn Glu Lys Thr Leu Ser Gly Leu Leu Lys
210                 215                 220

Gly Glu Tyr Gly Phe Gln Gly Tyr Val Met Ser Asp Trp Trp Ala Thr
225                 230                 235                 240

His Ser Gly Ala Pro Ala Val Asn Ala Gly Leu Asp Met Thr Met Pro
                245                 250                 255
```

```
Gly Asp Glu Thr Thr Asn Ser Gly Thr Thr Tyr Phe Gly Gln Asn Leu
            260                 265                 270

Val Asn Ala Val Asn Ser Gly Gln Val Ser Gln Ala Arg Ile Lys Asp
            275                 280                 285

Met Ala Thr Arg Ile Leu Ala Ala Trp Tyr Leu Leu Gly Gln Asp Gln
290                 295                 300

Asn Phe Pro Ala Val Asn Phe Asn Ser Trp Asn Ser Gly Gln Gly Gln
305                 310                 315                 320

His Val Asn Val Ser Gly Asn His Ala Ser Leu Ile Arg Thr Ile Gly
            325                 330                 335

Ala Ala Ser Gln Ile Leu Leu Lys Asn Val Asn Gly Ala Leu Pro Leu
            340                 345                 350

Lys Lys Pro Lys Thr Ile Gly Ile Ile Gly Asn Gly Ala Gly Ser Asn
            355                 360                 365

Pro Ser Gly Pro Asn Ala Phe Ser Asp Arg Ala Gly Asp Val Gly Val
            370                 375                 380

Leu Ala Leu Gly Trp Gly Ser Gly Thr Ala Asn Phe Pro Tyr Leu Val
385                 390                 395                 400

Ala Pro Val Asp Ala Ile Thr Ala Arg Ala Ser Gln Asp Gly Thr Thr
            405                 410                 415

Val Ser Ser Ser Leu Ser Asp Thr Asp Leu Thr Gly Ala Ala Asn Thr
            420                 425                 430

Ala Thr Gly Lys Asp Val Ala Met Val Phe Ile Thr Ala Asp Ser Gly
            435                 440                 445

Glu Gly Tyr Leu Thr Val Glu Gly Asn Ala Gly Asp Arg Asn Asp Leu
            450                 455                 460

Gln Ala Trp His Gly Gly Asp Ala Leu Val Gln Gln Val Ala Ser His
465                 470                 475                 480

Asn Lys Asn Thr Ile Val Val Ile Asn Ser Val Gly Pro Ile Asn Met
            485                 490                 495

Glu Ala Trp Val Asn His Pro Asn Val Thr Ala Ile Val Trp Ser Gly
            500                 505                 510

Leu Pro Gly Gln Glu Ala Gly Asn Ala Val Thr Asp Val Leu Phe Gly
            515                 520                 525

Ala Val Asn Pro Gly Gly Lys Leu Pro Phe Thr Ile Gly Lys Ser Ile
            530                 535                 540

Ser Asp Tyr Ser Ala Gln Ile Ile Thr Thr Gly Ser Gly Ile Val Pro
545                 550                 555                 560

Ile Pro Tyr Asn Glu Gly Leu Phe Ile Asp Tyr Arg His Phe Asp Gln
            565                 570                 575

Ala Gly Ile Ala Pro Arg Phe Glu Phe Gly Phe Gly Leu Ser Tyr Thr
            580                 585                 590

Thr Phe

<210> SEQ ID NO 84
<211> LENGTH: 594
<212> TYPE: PRT
<213> ORGANISM: Phanerochaete chrysosporium

<400> SEQUENCE: 84

Thr Val Ala Asn Val Ser Pro Glu Trp Ala Ala Ala Tyr Val Lys Ala
1               5                   10                  15

Gln Ala Ala Val Ala Lys Leu Ser Val Thr Asp Met Val Asn Leu Ala
            20                  25                  30

Thr Gly Val Gln Trp Gln Lys Gly Pro Cys Val Gly Asn Thr Pro Ala
```

```
                35                  40                  45
Ile Ser Ser Ile Pro Gly Phe Thr Gly Leu Cys Leu Gln Asp Ser Pro
 50                  55                  60
Val Gly Val Arg Tyr Ala Asp Gly Thr Ser Val Phe Pro Pro Glu Ile
 65                  70                  75                  80
Asn Val Ala Ala Thr Trp Asn Arg Thr Leu Met Arg Gln Arg Gly Ala
                 85                  90                  95
Ala Met Gly Ala Glu Phe Lys Gly Lys Gly Val His Val Ala Leu Gly
                100                 105                 110
Pro Met Met Asn Leu Met Arg Val Pro Ala Ala Gly Arg Asn Trp Glu
            115                 120                 125
Gly Gly Gly Gly Asp Pro Phe Leu Ser Gly Glu Val Ala Phe Glu Thr
        130                 135                 140
Ile Thr Gly Ile Gln Ser Ser Gly Ala Gln Ala Cys Ala Lys His Phe
145                 150                 155                 160
Ile Asn Asn Glu Gln Glu His Phe Arg Asp Ser Ser Ser Asn Val
                165                 170                 175
Asp Asp Arg Thr Glu His Glu Leu Tyr Gly His Pro Phe Leu Arg Ser
            180                 185                 190
Val Gln Ala Asn Val Ala Ser Val Met Cys Ser Tyr Asn Gln Ile Asn
        195                 200                 205
Gly Thr Phe Ser Cys Glu Asn Glu Lys Thr Leu Ser Gly Leu Leu Lys
    210                 215                 220
Gly Glu Tyr Gly Phe Gln Gly Tyr Val Met Ser Asp Trp Trp Ala Thr
225                 230                 235                 240
His Ser Gly Ala Pro Ala Val Asn Ala Gly Leu Asp Met Thr Met Pro
                245                 250                 255
Gly Asp Glu Thr Leu Ser Ser Gly Thr Thr Tyr Phe Gly Gln Asn Leu
            260                 265                 270
Val Asn Ala Val Asn Ser Gly Gln Val Ser Gln Ala Arg Val Lys Asp
        275                 280                 285
Met Ala Thr Arg Ile Leu Ala Ala Trp Tyr Leu Leu Gly Gln Asp Gln
    290                 295                 300
Asn Phe Pro Ala Val Asn Phe Asn Ser Trp Asn Ser Gly Gln Gly Gln
305                 310                 315                 320
His Val Asn Val Ser Gly Asn His Ala Ser Leu Ile Arg Thr Ile Gly
                325                 330                 335
Ala Ala Ser Gln Ile Leu Leu Lys Asn Val Asn Ser Ala Leu Pro Leu
            340                 345                 350
Lys Lys Pro Lys Thr Ile Gly Ile Ile Gly Asn Gly Ala Gly Ser Asn
        355                 360                 365
Pro Asn Gly Pro Asn Ala Phe Ser Asp Arg Ala Gly Asp Val Gly Val
    370                 375                 380
Leu Ala Leu Gly Trp Gly Ser Gly Thr Ala Asn Phe Pro Tyr Leu Val
385                 390                 395                 400
Ala Pro Val Asp Ala Ile Thr Ala Arg Ala Ser Gln Asp Gly Thr Thr
                405                 410                 415
Val Ser Ser Ser Leu Ser Asp Thr Asp Leu Thr Gly Ala Ala Asn Thr
            420                 425                 430
Ala Thr Gly Lys Asp Val Ala Met Val Phe Ile Thr Ala Asp Ser Gly
        435                 440                 445
Glu Gly Tyr Leu Thr Val Glu Gly Asn Ala Gly Asp Arg Asn Asp Leu
    450                 455                 460
```

-continued

```
Gln Ala Trp His Gly Gly Asp Ala Leu Val Gln Gln Val Ala Ser His
465                 470                 475                 480

Asn Lys Asn Thr Ile Val Val Ile Asn Ser Val Gly Pro Ile Asn Met
            485                 490                 495

Glu Ala Trp Val Asn His Pro Asn Val Thr Ala Ile Val Trp Ser Gly
        500                 505                 510

Leu Pro Gly Gln Glu Ala Gly Asn Ala Val Thr Asp Val Leu Phe Gly
            515                 520                 525

Ala Val Asn Pro Gly Gly Lys Leu Pro Phe Thr Ile Gly Lys Ser Ile
530                 535                 540

Ser Asp Tyr Ser Ala Gln Ile Ile Thr Thr Gly Ser Gly Ile Val Pro
545                 550                 555                 560

Ile Pro Tyr Asn Glu Gly Leu Phe Ile Asp Tyr Arg His Phe Asp Gln
                565                 570                 575

Ala Gly Ile Ala Pro Arg Phe Glu Phe Gly Phe Gly Leu Ser Tyr Thr
            580                 585                 590

Thr Phe
```

<210> SEQ ID NO 85
<211> LENGTH: 618
<212> TYPE: PRT
<213> ORGANISM: Pichia anomala

<400> SEQUENCE: 85

```
Gly Lys Trp Gln Ala Ala Phe Tyr Arg Ala Arg Glu Leu Val Asp Gln
1               5                   10                  15

Met Ser Ile Ala Glu Lys Val Asn Leu Thr Thr Gly Val Gly Ser Ala
            20                  25                  30

Ser Gly Pro Cys Ser Gly Asn Thr Gly Ser Val Pro Arg Leu Asn Ile
        35                  40                  45

Ser Ser Ile Cys Val Gln Asp Gly Pro Leu Ser Val Arg Ala Ala Asp
    50                  55                  60

Leu Thr Asp Val Phe Pro Cys Gly Met Ala Ala Ser Ser Ser Phe Asn
65                  70                  75                  80

Lys Gln Leu Ile Tyr Asp Arg Ala Val Ala Ile Gly Ser Glu Phe Lys
                85                  90                  95

Gly Lys Gly Ala Asp Ala Ile Leu Gly Pro Val Tyr Gly Pro Met Gly
            100                 105                 110

Val Lys Ala Ala Gly Gly Arg Gly Trp Glu Gly His Gly Pro Asp Pro
        115                 120                 125

Tyr Leu Glu Gly Val Ile Ala Tyr Leu Gln Thr Ile Gly Ile Gln Ser
    130                 135                 140

Gln Gly Val Val Ser Thr Ala Lys His Leu Ile Gly Asn Glu Gln Glu
145                 150                 155                 160

His Phe Arg Phe Ala Lys Lys Asp Lys His Ala Gly Lys Ile Asp Pro
                165                 170                 175

Gly Met Phe Asn Thr Ser Ser Leu Ser Ser Glu Ile Asp Asp Arg
            180                 185                 190

Ala Met His Glu Ile Tyr Leu Trp Pro Phe Ala Glu Ala Val Arg Gly
        195                 200                 205

Gly Val Ser Ser Ile Met Cys Ser Tyr Asn Lys Leu Asn Gly Ser His
    210                 215                 220

Ala Cys Gln Asn Ser Tyr Leu Leu Asn Tyr Leu Leu Lys Glu Glu Leu
225                 230                 235                 240

Gly Phe Gln Gly Phe Val Met Thr Asp Trp Gly Ala Leu Tyr Ser Gly
```

```
                    245                 250                 255
Ile Asp Ala Ala Asn Ala Gly Leu Asp Met Asp Met Pro Cys Glu Ala
                260                 265                 270

Gln Tyr Phe Gly Gly Asn Leu Thr Thr Ala Val Leu Asn Gly Thr Leu
            275                 280                 285

Pro Gln Asp Arg Leu Asp Met Ala Thr Arg Ile Leu Ser Ala Leu
        290                 295                 300

Ile Tyr Ser Gly Val His Asn Pro Asp Gly Pro Asn Tyr Asn Ala Gln
305                 310                 315                 320

Thr Phe Leu Thr Glu Gly His Glu Tyr Phe Lys Gln Gln Gly Asp
                325                 330                 335

Ile Val Val Leu Asn Lys His Val Asp Val Arg Ser Asp Ile Asn Arg
            340                 345                 350

Ala Val Ala Leu Arg Ser Ala Val Glu Gly Val Val Leu Leu Lys Asn
            355                 360                 365

Glu His Glu Thr Leu Pro Leu Gly Arg Glu Lys Val Lys Arg Ile Ser
        370                 375                 380

Ile Leu Gly Gln Ala Ala Gly Asp Asp Ser Lys Gly Thr Ser Cys Ser
385                 390                 395                 400

Leu Arg Gly Cys Gly Ser Gly Ala Ile Gly Thr Gly Tyr Gly Ser Gly
                405                 410                 415

Ala Gly Thr Phe Ser Tyr Phe Val Thr Pro Ala Asp Gly Ile Gly Ala
            420                 425                 430

Arg Ala Gln Gln Glu Lys Ile Ser Tyr Glu Phe Ile Gly Asp Ser Trp
        435                 440                 445

Asn Gln Ala Ala Ala Met Asp Ser Ala Leu Tyr Ala Asp Ala Ile
        450                 455                 460

Glu Val Ala Asn Ser Val Ala Gly Glu Glu Ile Gly Asp Val Asp Gly
465                 470                 475                 480

Asn Tyr Gly Asp Leu Asn Asn Leu Thr Leu Trp His Asn Ala Val Pro
                485                 490                 495

Leu Ile Lys Asn Ile Ser Ser Ile Asn Asn Thr Ile Val Ile Val
            500                 505                 510

Thr Ser Gly Gln Gln Ile Asp Leu Glu Pro Phe Ile Asp Asn Glu Asn
        515                 520                 525

Val Thr Ala Val Ile Tyr Ser Ser Tyr Leu Gly Gln Asp Phe Gly Thr
            530                 535                 540

Val Leu Ala Lys Val Leu Phe Gly Asp Glu Asn Pro Ser Gly Lys Leu
545                 550                 555                 560

Pro Phe Thr Ile Ala Lys Asp Val Asn Asp Tyr Ile Pro Val Ile Glu
                565                 570                 575

Lys Val Asp Val Pro Asp Pro Val Asp Lys Phe Thr Glu Ser Ile Tyr
            580                 585                 590

Val Asp Tyr Arg Tyr Phe Asp Lys Tyr Asn Lys Pro Val Arg Tyr Glu
            595                 600                 605

Phe Gly Tyr Gly Leu Ser Tyr Ser Asn Phe
    610                 615

<210> SEQ ID NO 86
<211> LENGTH: 585
<212> TYPE: PRT
<213> ORGANISM: Piromyces sp.

<400> SEQUENCE: 86

Val Ser Gln Val Phe Ala Thr Ser Trp Ser Glu Ala Asp Glu Lys Ala
```

```
               1               5              10              15
Lys Ser Phe Met Ser Asp Leu Ser Glu Ser Glu Lys Ile Asp Ile Val
                       20                  25                  30

Thr Gly Tyr Met Asn Met Gln Gly Thr Cys Val Gly Asn Ile Lys Pro
                       35                  40                  45

Leu Asp Arg Lys Asn Phe Lys Gly Leu Cys Leu Gln Asp Gly Pro Ala
 50                      55                  60

Gly Val Arg Phe Asn Gly Gly Thr Ser Thr Thr Trp Gln Ala Gly Ile
 65                      70                  75                  80

Asn Asn Ala Ala Thr Phe Asn Lys Asp Leu Leu Tyr Lys Ile Gly Lys
                       85                  90                  95

Asp Gln Gly Ala Glu Phe Tyr Ala Lys Gly Ile Asn Ile Ala Leu Ala
                      100                 105                 110

Pro Ser Met Asn Ile Leu Arg Ala Pro Ala Ser Gly Arg Val Trp Glu
                      115                 120                 125

Asn Phe Gly Glu Asp Pro Tyr Leu Ser Gly Val Cys Gly Ala Gln Ile
                      130                 135                 140

Thr Lys Gly Tyr Gln Asp Ser Gly Val Ile Val Ala Ala Lys His Tyr
145                     150                 155                 160

Val Ala Asn Asp Ile Glu His Asn Arg Glu Ala Ser Ser Ser Asn Met
                      165                 170                 175

Asp Asp Gln Thr Leu Met Glu Ile His Val Glu Pro Phe Tyr Arg Thr
                      180                 185                 190

Ile Lys Asp Gly Asp Ala Gly Ser Val Met Ala Ser Tyr Asn Ala Val
                      195                 200                 205

Asn Asn Ile Tyr Val Val Gln Asn Lys Lys Val Leu Thr Glu Ile Leu
                      210                 215                 220

Lys Glu Gly Ile Gly Phe Gln Gly Phe Val Met Ser Asp Trp Trp Ala
225                     230                 235                 240

Ile His Asp Leu Glu Gly Ser Phe Asn Ala Gly Met Asp Met Asn Met
                      245                 250                 255

Pro Gly Gly Lys Ala Trp Gly Pro Asp Tyr Val Asn Asn Ser Phe Trp
                      260                 265                 270

Gly Ser Asn Ile Ser Asn Ala Ile Arg Ser Gly Gln Val Ser Ser Ser
                      275                 280                 285

Arg Leu Asp Asp Ala Val Arg Arg Ile Ile Arg Thr Leu Tyr Arg Phe
                      290                 295                 300

Asp Gln Met Ser Gly Tyr Pro Asn Val Asn Leu Lys Ala Pro Ser Met
305                     310                 315                 320

His Ala Asp Thr Asn Arg Gln Ala Ala Ile Glu Ser Ser Val Leu Leu
                      325                 330                 335

Lys Asn Ala Asp Asp Ile Leu Pro Leu Thr Lys Lys Tyr Arg Lys Ile
                      340                 345                 350

Ala Ile Ile Gly Lys Asp Ala Asp Lys Ala Gln Ser Cys Thr Asp Thr
                      355                 360                 365

Ala Cys Ser Gly Gly Asn Ile Ile Gln Gly Trp Gly Ser Gly Thr Thr
                      370                 375                 380

Asp Phe Thr Gly Ile Ser Asp Pro Ile Thr Ala Ile Lys Asn Arg Ala
385                     390                 395                 400

Ser Lys Glu Gly Ile Ser Ile Val Ser Ser Ile Ser Asp Ser Ala Asn
                      405                 410                 415

Glu Gly Ala Asn Val Ala Lys Asp Ala Asp Val Ala Val Val Phe Val
                      420                 425                 430
```

```
Arg Ala Thr Ser Gly Glu Glu Tyr Ile Val Val Asp Asn Asn Lys Gly
            435                 440                 445

Asp Arg Asn Asn Leu Asp Leu Trp His Gly Gly Asn Asp Leu Val Lys
        450                 455                 460

Ser Val Ala Ala Val Asn Lys Asn Thr Val Val Ile His Ala Pro
465                 470                 475                 480

Ala Thr Val Asn Leu Pro Phe Leu Asn Asn Val Lys Ala Ile Ile His
            485                 490                 495

Ala Gly Met Pro Gly Ala Glu Ser Gly Asn Ala Ile Ala Ser Ile Leu
            500                 505                 510

Phe Gly Asp Ser Asn Pro Ser Gly His Leu Pro Phe Thr Trp Ala Ala
            515                 520                 525

Arg Glu Asp Tyr Cys Cys Asp Val Ser Tyr Pro Ala Glu Leu Pro His
            530                 535                 540

Gly Gly Asn Ser Lys Thr Ala Tyr Asp Tyr Lys Glu Gly Leu Phe Val
545                 550                 555                 560

Gly Tyr Arg Trp Phe Asp Lys Lys Asn Lys Thr Pro Ile Phe Pro Phe
                565                 570                 575

Gly His Gly Leu Ser Tyr Thr Thr Phe
            580                 585

<210> SEQ ID NO 87
<211> LENGTH: 635
<212> TYPE: PRT
<213> ORGANISM: Saccharomycopsis fibuligera

<400> SEQUENCE: 87

Gln Gly Gly Arg Leu Gln Gly Val Trp Gln Asp Ala Tyr Thr Lys Ala
1               5                   10                  15

Lys Ala Leu Val Ser Gln Met Thr Ile Val Glu Lys Val Asn Leu Thr
            20                  25                  30

Thr Gly Thr Gly Trp Gln Leu Gly Pro Cys Val Gly Asn Thr Gly Ser
        35                  40                  45

Val Pro Arg Phe Gly Ile Pro Asn Leu Cys Leu Gln Asp Gly Pro Leu
50                  55                  60

Gly Val Arg Leu Thr Asp Phe Ser Thr Gly Tyr Pro Ser Gly Met Ala
65                  70                  75                  80

Thr Gly Ala Thr Phe Asn Lys Asp Leu Phe Leu Gln Arg Gly Gln Ala
            85                  90                  95

Leu Gly His Glu Phe Asn Ser Lys Gly Val His Ile Ala Leu Gly Pro
            100                 105                 110

Ala Val Gly Pro Leu Gly Val Lys Ala Arg Gly Gly Arg Asn Phe Glu
        115                 120                 125

Ala Phe Gly Ser Asp Pro Tyr Leu Gln Gly Ile Ala Ala Ala Ala Thr
130                 135                 140

Ile Lys Gly Leu Gln Glu Asn Asn Val Met Ala Cys Val Lys His Phe
145                 150                 155                 160

Ile Gly Asn Glu Gln Asp Ile Tyr Arg Gln Pro Ser Asn Ser Lys Val
            165                 170                 175

Asp Pro Glu Tyr Asp Pro Ala Thr Lys Glu Ser Ile Ser Ala Asn Ile
        180                 185                 190

Pro Asp Arg Ala Met His Glu Leu Tyr Leu Trp Pro Phe Ala Asp Ser
        195                 200                 205

Ile Arg Ala Gly Val Gly Ser Val Met Cys Ser Tyr Asn Arg Val Asn
210                 215                 220
```

```
Asn Thr Tyr Ser Cys Glu Asn Ser Tyr Met Ile Asn His Leu Leu Lys
225                 230                 235                 240

Glu Glu Leu Gly Phe Gln Gly Phe Val Val Ser Asp Trp Ala Ala Gln
            245                 250                 255

Met Ser Gly Ala Tyr Ser Ala Ile Ser Gly Leu Asp Met Ser Met Pro
        260                 265                 270

Gly Glu Leu Leu Gly Gly Trp Asn Thr Gly Lys Ser Tyr Trp Gly Gln
    275                 280                 285

Asn Leu Thr Lys Ala Val Tyr Asn Glu Thr Val Pro Ile Glu Arg Leu
290                 295                 300

Asp Asp Met Ala Thr Arg Ile Leu Ala Ala Leu Tyr Ala Thr Asn Ser
305                 310                 315                 320

Phe Pro Thr Lys Asp Arg Leu Pro Asn Phe Ser Ser Phe Thr Thr Lys
            325                 330                 335

Glu Tyr Gly Asn Glu Phe Phe Val Asp Lys Thr Ser Pro Val Val Lys
        340                 345                 350

Val Asn His Phe Val Asp Pro Ser Asn Asp Phe Thr Glu Asp Thr Ala
    355                 360                 365

Leu Lys Val Ala Glu Glu Ser Ile Val Leu Leu Lys Asn Glu Lys Asn
370                 375                 380

Thr Leu Pro Ile Ser Pro Asn Lys Val Arg Lys Leu Leu Leu Ser Gly
385                 390                 395                 400

Ile Ala Ala Gly Pro Asp Pro Lys Gly Tyr Glu Cys Ser Asp Gln Ser
            405                 410                 415

Cys Val Asp Gly Ala Leu Phe Glu Gly Trp Gly Ser Gly Ser Val Gly
        420                 425                 430

Tyr Pro Lys Tyr Gln Val Thr Pro Phe Glu Glu Ile Ser Ala Asn Ala
    435                 440                 445

Arg Lys Asn Lys Met Gln Phe Asp Tyr Ile Arg Glu Ser Phe Asp Leu
            450                 455                 460

Thr Gln Val Ser Thr Val Ala Ser Asp Ala His Met Ser Ile Val Val
465                 470                 475                 480

Val Ser Ala Val Ser Gly Glu Gly Tyr Leu Ile Ile Asp Gly Asn Arg
            485                 490                 495

Gly Asp Lys Asn Asn Val Thr Leu Trp His Asn Ser Asp Asn Leu Ile
        500                 505                 510

Lys Ala Val Ala Glu Asn Cys Ala Asn Thr Val Val Ile Thr Ser
    515                 520                 525

Thr Gly Gln Val Asp Val Ser Phe Ala Asp His Pro Asn Val Thr
530                 535                 540

Ala Ile Val Trp Ala Gly Pro Leu Gly Asp Arg Ser Gly Thr Ala Ile
545                 550                 555                 560

Ala Asn Ile Leu Phe Gly Asn Ala Asn Pro Ser Gly His Leu Pro Phe
            565                 570                 575

Thr Val Ala Lys Ser Asn Asp Asp Tyr Ile Pro Ile Val Thr Tyr Asn
        580                 585                 590

Pro Pro Asn Gly Glu Pro Glu Asp Asn Thr Leu Ala Glu His Asp Leu
    595                 600                 605

Leu Val Asp Tyr Arg Tyr Phe Glu Glu Lys Asn Ile Glu Pro Arg Tyr
610                 615                 620

Ala Phe Gly Tyr Gly Leu Ser Tyr Asn Glu Tyr
625                 630                 635

<210> SEQ ID NO 88
```

```
<211> LENGTH: 633
<212> TYPE: PRT
<213> ORGANISM: Saccharomycopsis fibuligera

<400> SEQUENCE: 88

Gln Gly Gly Arg Leu Gln Asp Val Trp Gln Glu Ala Tyr Ala Arg Ala
1               5                   10                  15

Lys Ala Ile Val Gly Gln Met Thr Ile Val Glu Lys Val Asn Leu Thr
            20                  25                  30

Thr Gly Thr Gly Trp Gln Leu Asp Pro Cys Val Gly Asn Thr Gly Ser
        35                  40                  45

Val Pro Arg Phe Gly Ile Pro Asn Leu Cys Leu Gln Asp Gly Pro Leu
    50                  55                  60

Gly Val Arg Phe Ala Asp Phe Val Thr Gly Tyr Pro Ser Gly Leu Ala
65                  70                  75                  80

Thr Gly Ala Thr Phe Asn Lys Asp Leu Phe Leu Gln Arg Gly Gln Ala
                85                  90                  95

Leu Gly His Glu Phe Asn Ser Lys Gly Val His Ile Ala Leu Gly Pro
            100                 105                 110

Ala Val Gly Pro Leu Gly Val Lys Ala Arg Gly Gly Arg Asn Phe Glu
        115                 120                 125

Ala Phe Gly Ser Asp Pro Tyr Leu Gln Gly Thr Ala Ala Ala Ala Thr
    130                 135                 140

Ile Lys Gly Leu Gln Glu Asn Asn Val Met Ala Cys Val Lys His Phe
145                 150                 155                 160

Ile Gly Asn Glu Gln Glu Lys Tyr Arg Gln Pro Asp Asp Ile Asn Pro
                165                 170                 175

Ala Thr Asn Gln Thr Thr Lys Glu Ala Ile Ser Ala Asn Ile Pro Asp
            180                 185                 190

Arg Ala Met His Ala Leu Tyr Leu Trp Pro Phe Ala Asp Ser Val Arg
        195                 200                 205

Ala Gly Val Gly Ser Val Met Cys Ser Tyr Asn Arg Val Asn Asn Thr
    210                 215                 220

Tyr Ala Cys Glu Asn Ser Tyr Met Met Asn His Leu Leu Lys Glu Glu
225                 230                 235                 240

Leu Gly Phe Gln Gly Phe Val Val Ser Asp Trp Gly Ala Gln Leu Ser
                245                 250                 255

Gly Val Tyr Ser Ala Ile Ser Gly Leu Asp Met Ser Met Pro Gly Glu
            260                 265                 270

Val Tyr Gly Gly Trp Asn Thr Gly Thr Ser Phe Trp Gly Gln Asn Leu
        275                 280                 285

Thr Lys Ala Ile Tyr Asn Glu Thr Val Pro Ile Glu Arg Leu Asp Asp
    290                 295                 300

Met Ala Thr Arg Ile Leu Ala Ala Leu Tyr Ala Thr Asn Ser Phe Pro
305                 310                 315                 320

Thr Glu Asp His Leu Pro Asn Phe Ser Ser Trp Thr Lys Glu Tyr
                325                 330                 335

Gly Asn Lys Tyr Tyr Ala Asp Asn Thr Thr Glu Ile Val Lys Val Asn
            340                 345                 350

Tyr Asn Val Asp Pro Ser Asn Asp Phe Thr Glu Asp Thr Ala Leu Lys
        355                 360                 365

Val Ala Glu Glu Ser Ile Val Leu Leu Lys Asn Glu Asn Asn Thr Leu
    370                 375                 380

Pro Ile Ser Pro Glu Lys Ala Lys Arg Leu Leu Leu Ser Gly Ile Ala
385                 390                 395                 400
```

Ala Gly Pro Asp Pro Ile Gly Tyr Gln Cys Glu Asp Gln Ser Cys Thr
            405                 410                 415

Asn Gly Ala Leu Phe Gln Gly Trp Gly Ser Gly Ser Val Gly Ser Pro
        420                 425                 430

Lys Tyr Gln Val Thr Pro Phe Glu Ile Ser Tyr Leu Ala Arg Lys
    435                 440                 445

Asn Lys Met Gln Phe Asp Tyr Ile Arg Glu Ser Tyr Asp Leu Ala Gln
450                 455                 460

Val Thr Lys Val Ala Ser Asp Ala His Leu Ser Ile Val Val Ser
465                 470                 475                 480

Ala Ala Ser Gly Glu Gly Tyr Ile Thr Val Asp Gly Asn Gln Gly Asp
                485                 490                 495

Arg Lys Asn Leu Thr Leu Trp Asn Asn Gly Asp Lys Leu Ile Glu Thr
                500                 505                 510

Val Ala Glu Asn Cys Ala Asn Thr Val Val Val Thr Ser Thr Gly
            515                 520                 525

Gln Ile Asn Phe Glu Gly Phe Ala Asp His Pro Asn Val Thr Ala Ile
        530                 535                 540

Val Trp Ala Gly Pro Leu Gly Asp Arg Ser Gly Thr Ala Ile Ala Asn
545                 550                 555                 560

Ile Leu Phe Gly Lys Ala Asn Pro Ser Gly His Leu Pro Phe Thr Ile
                565                 570                 575

Ala Lys Thr Asp Asp Asp Tyr Ile Pro Ile Glu Thr Tyr Ser Pro Ser
            580                 585                 590

Ser Gly Glu Pro Glu Asp Asn His Leu Val Glu Asn Asp Leu Leu Val
        595                 600                 605

Asp Tyr Arg Tyr Phe Glu Glu Lys Asn Ile Glu Pro Arg Tyr Ala Phe
    610                 615                 620

Gly Tyr Gly Leu Ser Tyr Asn Glu Tyr
625                 630

<210> SEQ ID NO 89
<211> LENGTH: 711
<212> TYPE: PRT
<213> ORGANISM: Schizosaccharomyces pombe

<400> SEQUENCE: 89

Met Met Glu His Asp Val Glu Asp Leu Ile Asn Gln Leu Asp Ile Ser
1               5                   10                  15

Glu Lys Ala Met Leu Leu Ser Gly Thr Asp Leu Trp His Thr Ala Ala
            20                  25                  30

Ile Pro Arg Leu Asn Ile Pro Ser Ile Arg Leu Ser Asp Gly Pro Asn
        35                  40                  45

Gly Ile Arg Gly Thr Ser Phe Phe Asn Ser Ser Pro Ser Ala Cys Phe
    50                  55                  60

Pro Cys Gly Thr Ala Leu Gly Ala Thr Phe Asp Lys Lys Leu Leu Phe
65                  70                  75                  80

Glu Val Gly Glu Tyr Leu Ala Glu Glu Ala Lys Ala Lys Gly Val Ser
            85                  90                  95

Val Val Leu Gly Pro Thr Val Asn Ile His Arg Gly Pro Leu Asn Gly
            100                 105                 110

Arg Gly Phe Glu Ser Phe Ser Glu Asp Ser Thr Leu Ser Gly Leu Ala
        115                 120                 125

Ala Ser Tyr Val Ile Leu Gly Leu Gln Ser Lys Asn Val Gln Ala Cys
    130                 135                 140

```
Ile Lys His Phe Val Cys Asn Asp Met Glu Asp Arg Asn Ser Val
145                 150                 155                 160

Ser Ile Asp Val Ser Gln Arg Ala Leu Arg Glu Val Tyr Leu Met Pro
            165                 170                 175

Phe Gln Leu Ala Cys Lys Tyr Ser Asn Phe Lys Ser Leu Met Thr Ser
                180                 185                 190

Tyr Asn Lys Val Asn Gly Glu His Val Ser Gln Ser Arg Ile Leu Leu
        195                 200                 205

Asp Asn Ile Leu Arg Lys Glu Trp Glu Trp Lys Gly Thr Ile Ile Ser
    210                 215                 220

Asp Trp Phe Gly Thr Tyr Ser Leu Lys Lys Ala Ile Asp Ala Gly Leu
225                 230                 235                 240

Asp Leu Glu Met Pro Gly Lys Pro Arg Phe Arg Asn Val Asn Thr Ile
                245                 250                 255

Gln His Leu Val Gly Ser Lys Glu Leu Ser Glu Ser Ile Leu Asp Glu
            260                 265                 270

Arg Ala Lys Asn Val Leu Lys Leu Val Lys His Ser Trp Gln Asn Thr
        275                 280                 285

Glu Ala Glu Asn His Cys Glu Leu Asn Asn Asp Ser Ser Cys Leu Arg
    290                 295                 300

Glu Ala Leu Lys Lys Phe Ala Ser Gln Ser Ile Val Leu Leu Lys Asn
305                 310                 315                 320

Lys Lys Lys Leu Leu Pro Leu Ser Arg Lys Gly Thr Phe Ala Val Ile
                325                 330                 335

Gly Pro Asn Ala Lys Val Cys Asn Tyr Ser Gly Gly Ser Ala Asn
            340                 345                 350

Leu Lys Pro Tyr Tyr Thr Val Ser Met Tyr Asp Gly Ile Ala Ala Lys
        355                 360                 365

Ile Asp Gly Val Pro Glu Tyr Ala Leu Gly Cys His Asn Tyr Leu Asn
    370                 375                 380

Leu Pro Asn Ile Ala Asn Leu Val Asn Pro Arg Thr Gly Lys His
385                 390                 395                 400

Gly Tyr Val Ala Lys Phe Tyr Leu Glu Pro Ala Thr Ser Glu Asn Arg
                405                 410                 415

Thr Leu Ile Asp Asp Tyr Asp Leu Glu Asp Gly Val Val Arg Phe Tyr
            420                 425                 430

Asp Tyr Cys Asn Asp Lys Met Lys Asp Gly Tyr Phe Tyr Ile Asp Ile
        435                 440                 445

Glu Gly Tyr Leu Ile Pro Asp Glu Asp Ala Val Tyr Glu Phe Gly Ile
    450                 455                 460

Ser Val Phe Gly Thr Ala Leu Leu Phe Ile Asp Asp Val Leu Leu Ile
465                 470                 475                 480

Asp Asn Lys Thr Lys Gln Thr Pro Thr Asn His Thr Phe Glu Phe Gly
                485                 490                 495

Thr Ile Glu Glu Arg Asn Ser Ile Tyr Leu Lys Lys Gly Arg Lys Tyr
            500                 505                 510

Asn Val Arg Val Glu Tyr Gly Ser Ala Ala Thr Tyr Thr Leu Ser Thr
        515                 520                 525

Asn Leu Ser Pro Ser Thr Gly Gly Arg Tyr Ser Ile Gly Cys Val Lys
    530                 535                 540

Val Ile Asp Pro Glu Thr Glu Ile Asp Tyr Ala Val Arg Val Ala Lys
545                 550                 555                 560

Ser Val Asp Cys Val Ile Leu Cys Val Gly Leu Thr Ala Glu Trp Glu
```

-continued

```
                565                 570                 575
Thr Glu Gly Glu Asp Arg Lys Thr Met Thr Leu Pro Ser Leu Ser Asp
            580                 585                 590
Lys Leu Val Tyr Ser Ile Leu Gln Ser Asn Pro Asn Thr Val Val Val
            595                 600                 605
Thr Gln Ser Gly Thr Pro Ile Glu Met Pro Trp Ile Ser Glu Ala His
            610                 615                 620
Thr Leu Leu His Ile Trp Tyr Asn Gly Asn Leu Gly Asn Ala Leu
625                 630                 635                 640
Ala Asn Ile Ile Phe Gly Glu Gln Asn Pro Cys Gly Lys Leu Pro Ile
                645                 650                 655
Thr Phe Pro Lys Lys Leu Lys Asp Asn Pro Ala Tyr Leu Ser Phe Arg
                660                 665                 670
Ser Ser Arg Gly His Cys Val Tyr Gly Glu Asp Val Phe Val Gly Tyr
                675                 680                 685
Lys Tyr Tyr Glu Ala Val Glu Arg Glu Val Leu Phe Pro Phe Gly Tyr
                690                 695                 700
Gly Leu Ser Tyr Thr Thr Phe
705                 710

<210> SEQ ID NO 90
<211> LENGTH: 623
<212> TYPE: PRT
<213> ORGANISM: Septoria lycopersici

<400> SEQUENCE: 90

Trp Lys Ala Ala Phe Glu Lys Ala Ala Asp Ala Val Ser Arg Leu Asn
1               5                   10                  15
Leu Thr Gln Lys Val Ala Leu Thr Thr Gly Thr Thr Ala Gly Leu Ser
                20                  25                  30
Cys Asn Gly Asn Ile Ala Pro Ile Pro Glu Ile Asn Phe Ser Gly Leu
                35                  40                  45
Cys Leu Ala Asp Gly Pro Val Ser Val Arg Ile Ala Asp Leu Ala Thr
            50                  55                  60
Val Phe Pro Ala Gly Leu Thr Ala Ala Ala Thr Trp Asp Arg Gln Leu
65              70                  75                  80
Ile Tyr Glu Arg Ala Arg Ala Leu Gly Ser Glu Phe Arg Gly Lys Gly
                85                  90                  95
Ser Gln Val His Leu Gly Pro Ala Ser Gly Ala Leu Gly Arg His Pro
                100                 105                 110
Leu Gly Gly Arg Asn Trp Glu Ser Phe Ser Pro Asp Pro Tyr Leu Ser
                115                 120                 125
Gly Val Ala Met Asp Phe Ser Ile Arg Gly Ile Gln Glu Met Gly Val
            130                 135                 140
Gln Ala Asn Arg Lys His Phe Ile Gly Asn Glu Gln Glu Thr Gln Arg
145                 150                 155                 160
Ser Asn Thr Phe Thr Asp Asp Gly Thr Glu Ile Gln Ala Ile Ser Ser
                165                 170                 175
Asn Ile Asp Asp Arg Thr Met His Glu Leu Tyr Leu Trp Pro Phe Ala
                180                 185                 190
Asn Ala Val Arg Ser Gly Val Ala Ser Val Met Cys Ser Tyr Asn Arg
                195                 200                 205
Leu Asn Gln Thr Tyr Ala Cys Glu Asn Ser Lys Leu Met Asn Gly Ile
            210                 215                 220
Leu Lys Gly Glu Leu Gly Phe Gln Gly Tyr Val Val Ser Asp Trp Tyr
```

```
            225                 230                 235                 240
        Ala Thr His Ser Gly Val Glu Ser Val Asn Ala Gly Leu Asp Met Thr
                        245                 250                 255

Met Pro Gly Pro Leu Asp Ser Pro Ser Thr Ala Leu Arg Pro Pro Pro
                        260                 265                 270

Ser Tyr Leu Gly Gly Asn Leu Thr Glu Ala Val Leu Asn Gly Thr Ile
                        275                 280                 285

Pro Glu Ala Arg Val Asp Met Ala Arg Arg Ile Leu Met Pro Tyr
                290                 295                 300

Phe Phe Leu Gly Gln Asp Thr Asp Phe Pro Thr Val Asp Pro Ser Thr
        305                 310                 315                 320

Gly Phe Val Phe Ala Arg Thr Tyr Asn Tyr Pro Asp Glu Tyr Leu Thr
                        325                 330                 335

Leu Gly Gly Leu Asp Pro Tyr Asn Pro Pro Ala Arg Asp Val Arg
                        340                 345                 350

Gly Asn His Ser Asp Ile Val Arg Lys Val Ala Ala Gly Thr Val
                        355                 360                 365

Leu Leu Lys Asn Val Asn Asn Val Leu Pro Leu Lys Glu Pro Lys Ser
        370                 375                 380

Val Gly Ile Phe Gly Asn Gly Ala Ala Asp Val Thr Glu Gly Leu Thr
        385                 390                 395                 400

Phe Thr Gly Asp Asp Ser Gly Pro Trp Gly Ala Asp Ile Gly Ala Leu
                        405                 410                 415

Ser Val Gly Gly Gly Ser Gly Ala Gly Arg His Thr His Leu Val Ser
                        420                 425                 430

Pro Leu Ala Ala Ile Arg Lys Arg Thr Glu Ser Val Gly Gly Arg Val
                        435                 440                 445

Gln Tyr Leu Leu Ser Asn Ser Arg Ile Val Asn Asp Asp Phe Thr Ser
                        450                 455                 460

Ile Tyr Pro Thr Pro Glu Val Cys Leu Val Phe Leu Lys Thr Trp Ala
        465                 470                 475                 480

Arg Glu Gly Thr Asp Arg Leu Ser Tyr Glu Asn Asp Trp Asn Ser Thr
                        485                 490                 495

Ala Val Val Asn Asn Val Ala Arg Arg Cys Pro Asn Thr Ile Val Val
                        500                 505                 510

Thr His Ser Gly Gly Ile Asn Thr Met Pro Trp Ala Asp Asn Ala Asn
                        515                 520                 525

Val Thr Ala Ile Leu Ala Ala His Tyr Pro Gly Gln Glu Asn Gly Asn
                        530                 535                 540

Ser Ile Met Asp Ile Leu Tyr Gly Asp Val Asn Pro Ser Gly Arg Leu
        545                 550                 555                 560

Pro Tyr Thr Ile Pro Lys Leu Ala Thr Asp Tyr Asp Phe Pro Val Val
                        565                 570                 575

Asn Ile Thr Asn Glu Ala Gln Asp Pro Tyr Val Trp Gln Ala Asp Phe
                        580                 585                 590

Thr Glu Gly Leu Leu Ile Asp Tyr Arg His Phe Asp Ala Arg Asn Ile
                        595                 600                 605

Thr Pro Leu Tyr Glu Phe Gly Tyr Gly Leu Ser Tyr Thr Thr Phe
                        610                 615                 620

<210> SEQ ID NO 91
<211> LENGTH: 621
<212> TYPE: PRT
<213> ORGANISM: Talaromyces emersonii
```

```
<400> SEQUENCE: 91

Pro Trp Ala Asn Gly Gln Gly Asp Trp Ala Glu Ala Tyr Gln Lys Ala
1               5                   10                  15

Val Gln Phe Val Ser Gln Leu Thr Leu Ala Glu Lys Val Asn Leu Thr
            20                  25                  30

Thr Gly Thr Gly Trp Glu Gln Asp Arg Cys Val Gly Gln Val Gly Ser
        35                  40                  45

Ile Pro Arg Leu Gly Phe Pro Gly Leu Cys Met Gln Asp Ser Pro Leu
    50                  55                  60

Gly Val Arg Asp Thr Asp Tyr Asn Ser Ala Phe Pro Ala Gly Val Asn
65                  70                  75                  80

Val Ala Ala Thr Trp Asp Arg Asn Leu Ala Tyr Arg Arg Gly Val Ala
                85                  90                  95

Met Gly Glu Glu His Arg Gly Lys Gly Val Asp Val Gln Leu Gly Pro
            100                 105                 110

Val Ala Gly Pro Leu Gly Arg Ser Pro Asp Ala Gly Arg Asn Trp Glu
        115                 120                 125

Gly Phe Ala Pro Asp Pro Val Leu Thr Gly Asn Met Met Ala Ser Thr
130                 135                 140

Ile Gln Gly Ile Gln Asp Ala Gly Val Ile Ala Cys Ala Lys His Phe
145                 150                 155                 160

Ile Leu Tyr Glu Gln Glu His Phe Arg Gln Gly Ala Gln Asp Gly Tyr
                165                 170                 175

Asp Ile Ser Asp Ser Ile Ser Ala Asn Ala Asp Asp Lys Thr Met His
            180                 185                 190

Glu Leu Tyr Leu Trp Pro Phe Ala Asp Ala Val Arg Ala Gly Val Gly
        195                 200                 205

Ser Val Met Cys Ser Tyr Asn Gln Val Asn Asn Ser Tyr Ala Cys Ser
210                 215                 220

Asn Ser Tyr Thr Met Asn Lys Leu Leu Lys Ser Glu Leu Gly Phe Gln
225                 230                 235                 240

Gly Phe Val Met Thr Asp Trp Gly Gly His His Ser Gly Val Gly Ser
                245                 250                 255

Ala Leu Ala Gly Leu Asp Met Ser Met Pro Gly Asp Ile Ala Phe Asp
            260                 265                 270

Ser Gly Thr Ser Phe Trp Gly Thr Asn Leu Thr Val Ala Val Leu Asn
        275                 280                 285

Gly Ser Ile Pro Glu Trp Arg Val Asp Asp Met Ala Val Arg Ile Met
290                 295                 300

Ser Ala Tyr Tyr Lys Val Gly Arg Asp Arg Tyr Ser Val Pro Ile Asn
305                 310                 315                 320

Phe Asp Ser Trp Thr Leu Asp Thr Tyr Gly Pro Glu His Tyr Ala Val
                325                 330                 335

Gly Gln Gly Gln Thr Lys Ile Asn Glu His Val Asp Val Arg Gly Asn
            340                 345                 350

His Ala Glu Ile Ile His Glu Ile Gly Ala Ala Ser Ala Val Leu Leu
        355                 360                 365

Lys Asn Lys Gly Gly Leu Pro Leu Thr Gly Thr Glu Arg Phe Val Gly
370                 375                 380

Val Phe Gly Lys Asp Ala Gly Ser Asn Pro Trp Gly Val Asn Gly Cys
385                 390                 395                 400

Ser Asp Arg Gly Cys Asp Asn Gly Thr Leu Ala Met Gly Trp Gly Ser
                405                 410                 415
```

```
Gly Thr Ala Asn Phe Pro Tyr Leu Val Thr Pro Glu Gln Ala Ile Gln
        420                 425                 430

Arg Glu Val Leu Ser Arg Asn Gly Thr Phe Thr Gly Ile Thr Asp Asn
            435                 440                 445

Gly Ala Leu Ala Glu Met Ala Ala Ala Ser Gln Ala Asp Thr Cys
        450                 455                 460

Leu Val Phe Ala Asn Ala Asp Ser Gly Glu Gly Tyr Ile Thr Val Asp
465                 470                 475                 480

Gly Asn Glu Gly Asp Arg Lys Asn Leu Thr Leu Trp Gln Gly Ala Asp
                485                 490                 495

Gln Val Ile His Asn Val Ser Ala Asn Cys Asn Thr Val Val
            500                 505                 510

Leu His Thr Val Gly Pro Val Leu Ile Asp Asp Trp Tyr Asp His Pro
        515                 520                 525

Asn Val Thr Ala Ile Leu Trp Ala Gly Leu Pro Gly Gln Glu Ser Gly
        530                 535                 540

Asn Ser Leu Val Asp Val Leu Tyr Gly Arg Val Asn Pro Gly Lys Thr
545                 550                 555                 560

Pro Phe Thr Trp Gly Arg Ala Arg Asp Asp Tyr Gly Ala Pro Leu Ile
                565                 570                 575

Val Lys Pro Asn Asn Gly Lys Gly Ala Pro Gln Gln Asp Phe Thr Glu
            580                 585                 590

Gly Ile Phe Ile Asp Tyr Arg Arg Phe Asp Lys Tyr Asn Ile Thr Pro
        595                 600                 605

Ile Tyr Glu Phe Gly Phe Gly Leu Ser Tyr Thr Thr Phe
    610                 615                 620

<210> SEQ ID NO 92
<211> LENGTH: 611
<212> TYPE: PRT
<213> ORGANISM: Thermoascus aurantiacus

<400> SEQUENCE: 92

Trp Val Ser Asp Trp Ala Pro Ala Tyr Ala Lys Ala Tyr Glu Val Val
1               5                   10                  15

Ser Asn Met Thr Leu Ala Glu Lys Val Asn Met Thr Thr Gly Thr Gly
            20                  25                  30

Ile Phe Met Gly Pro Cys Val Gly Gln Thr Gly Ser Ala Leu Arg Phe
        35                  40                  45

Gly Ile Pro Asn Leu Cys Leu Met Asp Ser Pro Leu Gly Ile Arg Asn
    50                  55                  60

Thr Asp His Asn Thr Ala Phe Pro Ala Gly Ile Thr Val Gly Ala Thr
65                  70                  75                  80

Phe Asp Lys Glu Leu Met Tyr Ala Arg Gly Val Ala Leu Gly Glu Glu
                85                  90                  95

Ala Arg Gly Lys Gly Val Asn Val Leu Met Gly Pro Met Val Gly Pro
            100                 105                 110

Ile Gly Arg Lys Pro Arg Gly Gly Arg Asn Trp Glu Gly Phe Gly Ala
        115                 120                 125

Asp Pro Thr Leu Gln Ala Ile Gly Gly Ala Gln Thr Ile Lys Gly Met
    130                 135                 140

Gln Ser Thr Gly Val Ile Ala Thr Leu Lys His Phe Ile Gly Asn Glu
145                 150                 155                 160

Gln Glu Met Tyr Arg Met Thr Ser Val Ile Gln Arg Gly Tyr Ser Ser
                165                 170                 175
```

```
Asn Ile Asp Asp Arg Thr Leu His Glu Leu Tyr Leu Trp Pro Phe Ala
            180                 185                 190

Glu Gly Val Arg Ala Gly Val Gly Ser Val Met Met Ala Tyr Asn Asp
        195                 200                 205

Val Asn Gly Ser Ala Cys Ser Gln Asn Ser Lys Leu Ile Asn Gly Ile
    210                 215                 220

Leu Lys Asp Glu Leu Gly Phe Gln Gly Phe Val Met Thr Asp Trp Leu
225                 230                 235                 240

Thr Gln Ile Gly Gly Val Ser Ser Ala Leu Ala Gly Leu Asp Met Ala
                245                 250                 255

Met Pro Gly Asp Gly Pro Ile Pro Leu Phe Gly Asp Ser Tyr Trp Gly
            260                 265                 270

Ser Glu Leu Ser Arg Ala Val Leu Asn Gly Thr Val Pro Val Asp Arg
        275                 280                 285

Leu Asn Asp Met Val Thr Arg Ile Val Ala Thr Trp Tyr Lys Phe Gly
    290                 295                 300

Gln Asp Lys Asp Phe Pro Leu Pro Asn Phe Ser Ser Asn Thr Asp Ala
305                 310                 315                 320

Ala Thr Gly Leu Leu Tyr Pro Gly Ala Val Phe Ser Pro Ile Gly Val
                325                 330                 335

Val Asn Gln Phe Val Asp Val Gln Gly Asp His Lys Val Val Ala Arg
            340                 345                 350

Ala Ile Ala Arg Asp Ala Ile Thr Leu Leu Lys Asn Glu Asp Asn Ala
        355                 360                 365

Leu Pro Leu Lys Arg Asn Asp Ser Leu Lys Ile Phe Gly Thr Asp Ala
    370                 375                 380

Gly Thr Asn Pro Asp Gly Ile Asn Ser Cys Ala Asp Lys Gly Cys Asp
385                 390                 395                 400

Lys Gly Val Leu Thr Met Gly Trp Gly Ser Gly Thr Ser Lys Leu Pro
                405                 410                 415

Tyr Leu Asn Thr Pro Gln Glu Ala Ile Ala Asn Ala Ser Ser Asn Ala
            420                 425                 430

Glu Phe Phe Val Thr Asp Ser Phe Pro Ser Asn Val Asn Ala Asn Pro
        435                 440                 445

Glu Asp Ile Ala Ile Val Phe Ile Asn Ala Asp Ser Gly Glu Asn Tyr
    450                 455                 460

Ile Thr Val Glu Gly Asn Tyr Gly Asp Arg Ser Ala Ala Gly Leu Tyr
465                 470                 475                 480

Ala Trp His Asn Gly Asp Asp Leu Val Lys Ala Ala Ala Lys Phe
                485                 490                 495

Ser Lys Val Val Val Val His Thr Val Gly Pro Ile Ile Leu Glu
            500                 505                 510

Asn Trp Ile Asp Leu Pro Ser Val Lys Ser Val Val Phe Ala His Leu
        515                 520                 525

Pro Gly Gln Glu Ala Gly Asp Ser Leu Val Asp Val Leu Phe Gly Asp
    530                 535                 540

Tyr Ser Pro Ser Gly His Leu Pro Tyr Thr Ile Pro Arg Ser Glu Asp
545                 550                 555                 560

Gln Tyr Pro Ser Ser Val Ser Leu Ile Asn Gln Pro Phe Gly Gln Ile
                565                 570                 575

Gln Asp Thr Phe Thr Glu Gly Leu Tyr Ile Asp Tyr Arg His Phe Leu
            580                 585                 590

His Ala Asn Leu Thr Pro Arg Tyr Pro Phe Gly His Gly Leu Ser Tyr
        595                 600                 605
```

Thr Thr Phe
    610

<210> SEQ ID NO 93
<211> LENGTH: 626
<212> TYPE: PRT
<213> ORGANISM: Thermoascus aurantiacus

<400> SEQUENCE: 93

```
Pro Trp Met Asp Gly Asn Gly Glu Trp Ala Glu Ala Tyr Arg Arg Ala
1               5                   10                  15

Val Asp Phe Val Ser Gln Leu Thr Leu Ala Glu Lys Val Asn Leu Thr
            20                  25                  30

Thr Gly Val Gly Trp Met Gln Glu Lys Cys Val Gly Glu Thr Gly Ser
        35                  40                  45

Ile Pro Arg Leu Gly Phe Arg Gly Leu Cys Leu Gln Asp Ser Pro Leu
    50                  55                  60

Gly Val Arg Phe Ala Asp Tyr Val Ser Ala Phe Pro Ala Gly Val Asn
65                  70                  75                  80

Val Ala Ala Thr Trp Asp Lys Asn Leu Ala Tyr Leu Arg Gly Lys Ala
                85                  90                  95

Met Gly Glu Glu His Arg Gly Lys Gly Val Asp Val Gln Leu Gly Pro
            100                 105                 110

Val Ala Gly Pro Leu Gly Arg His Pro Asp Gly Gly Arg Asn Trp Glu
        115                 120                 125

Gly Phe Ser Pro Asp Pro Val Leu Thr Gly Val Leu Met Ala Glu Thr
    130                 135                 140

Ile Lys Gly Ile Gln Asp Ala Gly Val Ile Ala Cys Ala Lys His Phe
145                 150                 155                 160

Ile Gly Asn Glu Met Glu His Phe Arg Gln Ala Ser Glu Ala Val Gly
                165                 170                 175

Tyr Gly Phe Asp Ile Thr Glu Ser Val Ser Ser Asn Ile Asp Asp Lys
            180                 185                 190

Thr Leu His Glu Leu Tyr Leu Trp Pro Phe Ala Asp Ala Val Arg Ala
        195                 200                 205

Gly Val Gly Ser Phe Met Cys Ser Tyr Asn Gln Val Asn Asn Ser Tyr
    210                 215                 220

Ser Cys Ser Asn Ser Tyr Leu Leu Asn Lys Leu Leu Lys Ser Glu Leu
225                 230                 235                 240

Asp Phe Gln Gly Phe Val Met Ser Asp Trp Ala His His Ser Gly
                245                 250                 255

Val Gly Ala Ala Leu Ala Gly Leu Asp Met Ser Met Pro Gly Asp Thr
            260                 265                 270

Ala Phe Gly Thr Gly Lys Ser Phe Trp Gly Thr Asn Leu Thr Ile Ala
        275                 280                 285

Val Leu Asn Gly Thr Val Pro Glu Trp Arg Val Asp Asp Met Ala Val
    290                 295                 300

Arg Ile Met Ala Ala Phe Tyr Lys Val Gly Arg Asp Arg Tyr Gln Val
305                 310                 315                 320

Pro Val Asn Phe Asp Ser Trp Thr Lys Asp Glu Tyr Gly Tyr Glu His
                325                 330                 335

Ala Leu Val Gly Gln Asn Tyr Val Lys Val Asn Asp Lys Val Asp Val
            340                 345                 350

Arg Ala Asp His Ala Asp Ile Ile Arg Gln Ile Gly Ser Ala Ser Val
        355                 360                 365
```

Val Leu Leu Lys Asn Asp Gly Leu Pro Leu Thr Gly Tyr Glu Lys
    370                 375                 380

Phe Thr Gly Val Phe Gly Glu Asp Ala Gly Ser Asn Arg Trp Gly Ala
385                 390                 395                 400

Asp Gly Cys Ser Asp Arg Gly Cys Asp Asn Gly Thr Leu Ala Met Gly
            405                 410                 415

Trp Gly Ser Gly Thr Ala Asp Phe Pro Tyr Leu Val Thr Pro Glu Gln
            420                 425                 430

Ala Ile Gln Asn Glu Ile Leu Ser Lys Gly Lys Gly Leu Val Ser Ala
            435                 440                 445

Val Thr Asp Asn Gly Ala Leu Asp Gln Met Glu Gln Val Ala Ser Gln
    450                 455                 460

Ala Ser Val Ser Ile Val Phe Val Asn Ala Asp Ser Gly Glu Gly Tyr
465                 470                 475                 480

Ile Asn Val Asp Gly Asn Glu Gly Asp Arg Lys Asn Leu Thr Leu Trp
            485                 490                 495

Lys Gly Gly Glu Glu Val Ile Lys Thr Val Ala Ala Asn Cys Asn Asn
            500                 505                 510

Thr Ile Val Val Met His Thr Val Gly Pro Val Leu Ile Asp Glu Trp
    515                 520                 525

Tyr Asp Asn Pro Asn Val Thr Ala Ile Val Trp Ala Gly Leu Pro Gly
    530                 535                 540

Gln Glu Ser Gly Asn Ser Leu Val Asp Val Leu Tyr Gly Arg Val Ser
545                 550                 555                 560

Pro Gly Gly Lys Thr Pro Phe Thr Trp Gly Lys Thr Arg Glu Ser Tyr
            565                 570                 575

Gly Ala Pro Leu Leu Thr Lys Pro Asn Asn Gly Lys Gly Ala Pro Gln
            580                 585                 590

Asp Asp Phe Thr Glu Gly Val Phe Ile Asp Tyr Arg Arg Phe Asp Lys
            595                 600                 605

Tyr Asn Glu Thr Pro Ile Tyr Glu Phe Gly Phe Gly Leu Ser Tyr Thr
    610                 615                 620

Thr Phe
625

<210> SEQ ID NO 94
<211> LENGTH: 626
<212> TYPE: PRT
<213> ORGANISM: Thermoascus aurantiacus

<400> SEQUENCE: 94

Pro Trp Met Asn Gly Asn Gly Glu Trp Ala Glu Ala Tyr Arg Arg Ala
1               5                   10                  15

Val Asp Phe Val Ser Gln Leu Thr Leu Ala Glu Lys Val Asn Leu Thr
            20                  25                  30

Thr Gly Val Gly Trp Met Gln Glu Lys Cys Val Gly Glu Thr Gly Ser
        35                  40                  45

Ile Pro Arg Leu Gly Phe Arg Gly Leu Cys Leu Gln Asp Ser Pro Leu
    50                  55                  60

Gly Val Arg Phe Ala Asp Tyr Ile Ser Ala Phe Pro Ala Gly Val Asn
65              70                  75                  80

Val Ala Ala Thr Trp Asp Lys Asn Leu Ala Tyr Leu Arg Gly Lys Ala
            85                  90                  95

Met Gly Glu Glu His Arg Gly Lys Gly Val Asp Val Gln Leu Gly Pro
            100                 105                 110

Val Ala Gly Pro Leu Gly Arg His Pro Asp Gly Gly Arg Asn Trp Glu
    115                 120                 125

Gly Phe Ser Pro Asp Pro Val Leu Thr Gly Val Leu Met Ala Glu Thr
    130                 135                 140

Ile Lys Gly Ile Gln Asp Ala Gly Val Ile Ala Cys Ala Lys His Phe
145                 150                 155                 160

Ile Gly Asn Glu Met Glu His Phe Arg Gln Ala Ser Glu Ala Val Gly
                165                 170                 175

Tyr Gly Phe Asp Ile Thr Glu Ser Val Ser Ser Asn Ile Asp Asp Lys
                180                 185                 190

Thr Leu His Glu Leu Tyr Leu Trp Pro Phe Ala Asp Ala Val Arg Ala
                195                 200                 205

Gly Val Gly Ser Phe Met Cys Ser Tyr Asn Gln Val Asn Asn Ser Tyr
    210                 215                 220

Ser Cys Ser Asn Ser Tyr Leu Leu Asn Lys Leu Leu Lys Ser Glu Leu
225                 230                 235                 240

Asp Phe Gln Gly Phe Val Met Ser Asp Trp Gly Ala His His Ser Gly
                245                 250                 255

Val Gly Ala Ala Leu Ala Gly Leu Asp Met Ser Met Pro Gly Asp Thr
                260                 265                 270

Ala Phe Gly Thr Gly Lys Ser Phe Trp Gly Thr Asn Leu Thr Ile Ala
                275                 280                 285

Val Leu Asn Gly Thr Val Pro Glu Trp Arg Val Asp Asp Met Ala Val
    290                 295                 300

Arg Ile Met Ala Ala Phe Tyr Lys Val Gly Arg Asp Arg Tyr Gln Val
305                 310                 315                 320

Pro Val Asn Phe Asp Ser Trp Thr Lys Asp Glu His Gly Tyr Glu His
                325                 330                 335

Ala Leu Val Gly Gln Asp Tyr Val Lys Val Asn Asp Lys Val Asp Val
                340                 345                 350

Arg Ala Asp His Ala Asp Ile Ile Arg Gln Ile Gly Ser Ala Ser Val
                355                 360                 365

Val Leu Leu Lys Asn Asp Gly Gly Leu Pro Leu Thr Gly Tyr Glu Lys
    370                 375                 380

Phe Thr Gly Val Phe Gly Glu Asp Ala Gly Ser Asn Arg Trp Gly Ala
385                 390                 395                 400

Asp Gly Cys Ser Asp Arg Gly Cys Asp Asn Gly Thr Leu Ala Met Gly
                405                 410                 415

Trp Gly Ser Gly Thr Ala Asp Phe Pro Tyr Leu Val Thr Pro Glu Gln
                420                 425                 430

Ala Ile Gln Asn Glu Ile Leu Ser Lys Gly Lys Gly Leu Val Ser Ala
                435                 440                 445

Val Thr Asp Asn Gly Ala Leu Asp Gln Met Glu Gln Val Ala Ser Gln
    450                 455                 460

Ala Ser Val Ser Ile Val Phe Val Asn Ala Asp Ser Gly Glu Gly Tyr
465                 470                 475                 480

Ile Asn Val Asp Gly Asn Glu Gly Asp Arg Lys Asn Leu Thr Leu Trp
                485                 490                 495

Lys Gly Gly Glu Glu Val Ile Lys Thr Val Ala Ala Asn Cys Asn Asn
                500                 505                 510

Thr Ile Val Val Met His Thr Val Gly Pro Val Leu Ile Asp Glu Trp
                515                 520                 525

Tyr Asp Asn Pro Asn Val Thr Ala Ile Val Trp Ala Gly Leu Pro Gly

```
                530             535             540
Gln Glu Ser Gly Asn Ser Leu Val Asp Val Leu Tyr Gly Arg Val Ser
545                 550                 555                 560

Pro Gly Gly Lys Thr Pro Phe Thr Trp Gly Lys Thr Arg Glu Ser Tyr
                565                 570                 575

Gly Ala Pro Leu Leu Thr Lys Pro Asn Asn Gly Lys Gly Ala Pro Gln
                580                 585                 590

Asp Asp Phe Thr Glu Gly Val Phe Ile Asp Tyr Arg Arg Phe Asp Lys
                595                 600                 605

Tyr Asn Glu Thr Pro Ile Tyr Glu Phe Gly Phe Gly Leu Ser Tyr Thr
                610                 615                 620

Thr Phe
625

<210> SEQ ID NO 95
<211> LENGTH: 615
<212> TYPE: PRT
<213> ORGANISM: Thermoascus aurantiacus

<400> SEQUENCE: 95

Pro Pro Gly Gly Trp Val Ser Asp Trp Ala Pro Ala Tyr Ala Lys Ala
1               5                   10                  15

Tyr Glu Val Val Ser Asn Met Thr Leu Ala Glu Lys Val Asn Met Thr
                20                  25                  30

Thr Gly Thr Gly Ile Phe Met Gly Pro Cys Val Gly Gln Thr Gly Ser
            35                  40                  45

Ala Leu Arg Phe Gly Ile Pro Asn Leu Cys Leu Met Asp Ser Pro Leu
50                  55                  60

Gly Ile Arg Asn Thr Asp His Asn Thr Ala Phe Pro Ala Gly Ile Thr
65                  70                  75                  80

Val Gly Ala Thr Phe Asp Lys Glu Leu Met Tyr Ala Arg Gly Val Ala
                85                  90                  95

Leu Gly Glu Glu Ala Arg Gly Lys Gly Val Asn Val Leu Met Gly Pro
            100                 105                 110

Met Val Gly Pro Ile Gly Arg Lys Pro Arg Gly Gly Arg Asn Trp Glu
        115                 120                 125

Gly Phe Gly Ala Asp Pro Thr Leu Gln Ala Ile Gly Gly Ala Gln Thr
130                 135                 140

Ile Lys Gly Met Gln Ser Thr Gly Val Ile Ala Thr Leu Lys His Phe
145                 150                 155                 160

Ile Gly Asn Glu Gln Glu Met Tyr Arg Met Thr Ser Val Ile Gln Arg
                165                 170                 175

Gly Tyr Ser Ser Asn Ile Asp Asp Arg Thr Leu His Glu Leu Tyr Leu
            180                 185                 190

Trp Pro Phe Ala Glu Gly Val Arg Ala Gly Val Gly Ser Val Met Met
        195                 200                 205

Ala Tyr Asn Asp Val Asn Gly Ser Ala Cys Ser Gln Asn Ser Lys Leu
210                 215                 220

Ile Asn Gly Ile Leu Lys Asp Glu Leu Gly Phe Gln Gly Phe Val Met
225                 230                 235                 240

Thr Asp Trp Leu Thr Gln Ile Gly Gly Val Ser Ser Ala Leu Ala Gly
                245                 250                 255

Leu Asp Met Ala Met Pro Gly Asp Gly Pro Ile Pro Leu Phe Gly Asp
            260                 265                 270

Ser Tyr Trp Gly Ser Glu Leu Ser Arg Ala Val Leu Asn Gly Thr Val
```

```
            275                 280                 285
Pro Val Asp Arg Leu Asn Asp Met Val Thr Arg Ile Val Ala Thr Trp
        290                 295                 300
Tyr Lys Phe Gly Gln Asp Lys Asp Phe Pro Leu Pro Asn Phe Ser Ser
305                 310                 315                 320
Asn Thr Asp Ala Ala Thr Gly Leu Leu Tyr Pro Gly Ala Val Phe Ser
                325                 330                 335
Pro Ile Gly Val Val Asn Gln Phe Val Asp Val Gln Gly Asp His Lys
                340                 345                 350
Val Val Ala Arg Ala Ile Ala Arg Asp Ala Ile Thr Leu Leu Lys Asn
            355                 360                 365
Glu Asp Asn Ala Leu Pro Leu Lys Arg Asn Asp Ser Leu Lys Ile Phe
    370                 375                 380
Gly Thr Asp Ala Gly Thr Asn Pro Asp Gly Ile Asn Ser Cys Ala Asp
385                 390                 395                 400
Lys Gly Cys Asp Lys Gly Val Leu Thr Met Gly Trp Gly Ser Gly Thr
                405                 410                 415
Ser Lys Leu Pro Tyr Leu Asn Thr Pro Gln Glu Ala Ile Ala Asn Ala
            420                 425                 430
Ser Ser Asn Ala Glu Phe Phe Val Thr Asp Ser Phe Pro Ser Asn Val
        435                 440                 445
Asn Ala Asn Pro Glu Asp Ile Ala Ile Val Phe Ile Asn Ala Asp Ser
    450                 455                 460
Gly Glu Asn Tyr Ile Thr Val Glu Gly Asn Tyr Gly Asp Arg Ser Ala
465                 470                 475                 480
Ala Gly Leu Tyr Ala Trp His Asn Gly Asp Asp Leu Val Lys Ala Ala
                485                 490                 495
Ala Ala Lys Phe Ser Lys Val Val Val Val His Thr Val Gly Pro
            500                 505                 510
Ile Ile Leu Glu Asn Trp Ile Asp Leu Pro Ser Val Lys Ser Val Val
            515                 520                 525
Phe Ala His Leu Pro Gly Gln Glu Ala Gly Asp Ser Leu Val Asp Val
        530                 535                 540
Leu Phe Gly Asp Tyr Ser Pro Ser Gly His Leu Pro Tyr Thr Ile Pro
545                 550                 555                 560
Arg Ser Glu Asp Gln Tyr Pro Ser Ser Val Ser Leu Ile Asn Gln Pro
                565                 570                 575
Phe Gly Gln Ile Gln Asp Thr Phe Ile Glu Gly Leu Tyr Ile Asp Tyr
            580                 585                 590
Arg His Phe Leu His Ala Asn Leu Thr Pro Arg Tyr Pro Phe Gly His
        595                 600                 605
Gly Leu Ser Tyr Thr Thr Phe
    610                 615

<210> SEQ ID NO 96
<211> LENGTH: 577
<212> TYPE: PRT
<213> ORGANISM: Trichoderma viride

<400> SEQUENCE: 96

Val Val Leu Pro Ala Gly Thr Pro Trp Gly Thr Ala Tyr Asp Lys Ala
1               5                   10                  15
Lys Ala Ala Leu Ala Lys Leu Asn Leu Gln Asp Lys Val Gly Ile Val
            20                  25                  30
Ser Gly Val Gly Trp Asn Gly Gly Pro Cys Val Gly Asn Thr Ser Pro
```

-continued

```
                35                  40                  45
Ala Ser Lys Phe Ser Tyr Pro Ser Leu Cys Leu Gln Asp Gly Pro Leu
 50                  55                  60
Gly Val Arg Tyr Ser Thr Gly Ser Thr Ala Phe Thr Pro Gly Val Gln
 65                  70                  75                  80
Ala Ala Ser Thr Trp Asp Val Asn Leu Ile Arg Glu Arg Gly Gln Phe
                 85                  90                  95
Ile Gly Glu Val Lys Ala Ser Gly Ile His Val Ile Leu Gly Pro
            100                 105                 110
Val Ala Gly Pro Leu Gly Lys Thr Pro Gln Gly Gly Arg Asn Trp Glu
            115                 120                 125
Gly Phe Gly Val Asp Pro Tyr Leu Thr Gly Ile Ala Met Gly Gln Thr
            130                 135                 140
Ile Asn Gly Ile Gln Ser Val Gly Val Gln Ala Thr Ala Lys His Tyr
145                 150                 155                 160
Ile Leu Asn Glu Gln Glu Leu Asn Arg Glu Thr Ile Ser Ser Asn Pro
                165                 170                 175
Asp Asp Arg Thr Leu His Glu Leu Tyr Thr Trp Pro Phe Ala Asp Ala
            180                 185                 190
Val Gln Ala Asn Val Ala Ser Val Met Cys Ser Tyr Asn Lys Val Asn
            195                 200                 205
Thr Thr Trp Ala Cys Glu Asp Gln Tyr Thr Leu Gln Thr Val Leu Lys
            210                 215                 220
Asp Gln Leu Gly Phe Pro Gly Tyr Val Met Thr Asp Trp Asn Ala Gln
225                 230                 235                 240
His Ala Thr Val Gln Ser Ala Asn Ser Gly Leu Asp Val Ser Met Pro
                245                 250                 255
Gly Thr Asp Phe Asn Gly Asn Asn Arg Leu Trp Gly Pro Ala Leu Thr
            260                 265                 270
Asn Ala Val Asn Ser Asn Gln Val Pro Thr Ser Arg Val Asp Asp Met
            275                 280                 285
Val Thr Arg Ile Leu Ala Ala Trp Tyr Leu Thr Gly Gln Asp Gln Ala
            290                 295                 300
Gly Tyr Pro Ser Phe Asn Ile Ser Arg Asn Val Gln Gly Asn His Lys
305                 310                 315                 320
Thr Asn Val Arg Ala Ile Ala Arg Asp Gly Ile Val Leu Leu Lys Asn
                325                 330                 335
Asp Ala Asn Ile Leu Pro Leu Lys Lys Pro Ala Ser Ile Ala Val Val
            340                 345                 350
Gly Ser Ala Ala Ile Ile Gly Asn His Ala Arg Asn Ser Pro Ser Cys
            355                 360                 365
Asn Asp Lys Gly Cys Asp Asp Gly Ala Leu Gly Met Gly Trp Gly Ser
            370                 375                 380
Gly Ala Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
Asn Thr Ser Ser Gly Ala Ser Ala Ala Arg Gly Lys Asp Val Ala Ile
            420                 425                 430
Val Phe Ile Thr Ala Asp Ser Gly Glu Gly Tyr Ile Thr Val Glu Gly
            435                 440                 445
Asn Ala Gly Asp Arg Asn Asn Leu Asp Pro Trp His Asn Gly Asn Ala
450                 455                 460
```

```
Leu Val Gln Ala Val Ala Gly Ala Asn Ser Asn Val Ile Val Val
465                 470                 475                 480

His Ser Val Gly Ala Ile Ile Leu Glu Gln Ile Leu Ala Leu Pro Gln
                    485                 490                 495

Val Lys Ala Val Val Trp Thr Gly Leu Pro Ser Gln Glu Ser Gly Asn
                500                 505                 510

Ala Leu Val Asp Val Leu Trp Gly Asp Val Ser Pro Ser Gly Lys Leu
                515                 520                 525

Val Tyr Thr Ile Ala Lys Ser Pro Asn Asp Tyr Asn Thr Arg Ile Val
            530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu

<210> SEQ ID NO 97
<211> LENGTH: 602
<212> TYPE: PRT
<213> ORGANISM: Tropaeolum majus

<400> SEQUENCE: 97

Glu Tyr Met Arg Tyr Lys Asp Pro Lys Lys Pro Leu Asn Val Arg Ile
1               5                   10                  15

Lys Asp Leu Met Ser Arg Met Thr Leu Ala Glu Lys Ile Gly Gln Met
                20                  25                  30

Thr Gln Ile Glu Arg Lys Glu Ala Thr Pro Asp Val Ile Ser Lys Tyr
            35                  40                  45

Phe Ile Gly Ser Val Leu Ser Gly Gly Ser Val Pro Ala Pro Lys
    50                  55                  60

Ala Ser Pro Glu Ala Trp Val Asp Leu Val Asn Gly Met Gln Lys Ala
65                  70                  75                  80

Ala Leu Ser Thr Arg Leu Gly Ile Pro Met Ile Tyr Gly Ile Asp Ala
                85                  90                  95

Val His Gly His Asn Asn Val Tyr Asn Ala Thr Ile Phe Pro His Asn
                100                 105                 110

Val Gly Leu Gly Val Thr Arg Asp Pro Ala Leu Ile Lys Arg Ile Gly
            115                 120                 125

Glu Ala Thr Ala Leu Glu Cys Arg Ala Thr Gly Ile Pro Tyr Ala Phe
130                 135                 140

Ala Pro Cys Ile Ala Val Cys Arg Asp Pro Arg Trp Gly Arg Cys Tyr
145                 150                 155                 160

Glu Ser Tyr Ser Glu Asp His Thr Ile Val Gln Ala Met Thr Glu Ile
                165                 170                 175

Ile Pro Gly Leu Gln Gly Asp Val Pro Pro Asp Val Lys Lys Gly Val
            180                 185                 190

Pro Phe Val Gly Gly Lys Thr Lys Val Ala Ala Cys Ala Lys His Phe
        195                 200                 205

Val Gly Asp Gly Gly Thr Thr Lys Gly Ile Asp Glu Asn Asn Thr Val
    210                 215                 220

Ile Asp Ser Arg Gly Leu Phe Ser Ile His Met Pro Ala Tyr His Asp
225                 230                 235                 240

Ser Ile Lys Lys Gly Val Ala Thr Val Met Val Ser Tyr Ser Ser Trp
                245                 250                 255

Asn Gly Leu Arg Met His Ala Asn Arg Asp Leu Val Thr Gly Tyr Leu
```

```
                    260                 265                 270
Lys Asn Lys Leu Lys Phe Arg Gly Phe Val Ile Ser Asp Trp Glu Gly
                275                 280                 285

Ile Asp Arg Ile Thr Asp Pro Pro Gly Arg Asn Tyr Ser Tyr Ser Val
            290                 295                 300

Glu Ala Gly Val Gly Ala Gly Ile Asp Met Ile Met Val Pro Glu Asp
305                 310                 315                 320

Phe Thr Lys Phe Leu Asn Glu Leu Thr Ser Gln Val Lys Lys Asn Ile
                325                 330                 335

Ile Pro Met Ser Arg Ile Asp Asp Ala Val Lys Arg Ile Leu Arg Val
            340                 345                 350

Lys Phe Val Met Gly Leu Phe Glu Ser Pro Leu Ala Asp Tyr Ser Leu
                355                 360                 365

Ala Asn Gln Leu Gly Ser Gln Glu His Arg Asp Leu Ala Arg Glu Ala
            370                 375                 380

Val Arg Lys Ser Leu Val Leu Leu Lys Asn Gly Glu Ser Ala Asp Lys
385                 390                 395                 400

Pro Phe Val Pro Leu Pro Lys Asn Ala Lys Lys Ile Leu Val Ala Gly
                405                 410                 415

Ser His Ala Asp Asn Leu Gly Arg Gln Cys Gly Gly Trp Thr Ile Glu
            420                 425                 430

Trp Gln Gly Val Asn Gly Asn Asp Leu Thr Thr Gly Thr Ile Leu
                435                 440                 445

Asn Ala Ile Lys Lys Thr Val Asp Pro Thr Thr Gln Val Ile Tyr Asn
450                 455                 460

Glu Asn Pro Asp Ser Asn Tyr Val Lys Thr Asn Ser Phe Asp Tyr Ala
465                 470                 475                 480

Ile Val Val Val Gly Glu Pro Pro Tyr Ala Glu Met Gln Gly Asp Ser
                485                 490                 495

Phe Asn Leu Thr Ile Pro Glu Pro Gly Pro Thr Thr Ile Ser Ser Val
            500                 505                 510

Cys Gly Ala Val Lys Cys Val Val Val Ile Ser Gly Arg Pro Val
                515                 520                 525

Val Leu Gln Pro Tyr Val Ser Tyr Met Asp Ala Leu Val Ala Ala Trp
530                 535                 540

Leu Pro Gly Thr Glu Gly Gln Gly Val Thr Asp Val Leu Phe Gly Asp
545                 550                 555                 560

Tyr Gly Phe Thr Gly Lys Leu Ala Arg Thr Trp Phe Lys Thr Val Asp
                565                 570                 575

Gln Leu Pro Met Asn Val Gly Asp Lys His Tyr Asp Pro Leu Phe Pro
            580                 585                 590

Phe Gly Phe Gly Leu Thr Thr Lys Pro Ser
                595                 600
```

<210> SEQ ID NO 98
<211> LENGTH: 621
<212> TYPE: PRT
<213> ORGANISM: Uromyces viciae-fabae

<400> SEQUENCE: 98

```
Pro Val Gln Ser Gly Leu Ser Pro Trp Ser Glu Ser Ile Val Arg Ala
1               5                   10                  15

Arg Ala Phe Val Ala Gln Leu Thr Ile Glu Glu Lys Val Asn Leu Thr
            20                  25                  30

Thr Gly Ala Gly Thr Gln Gly Arg Cys Val Gly Glu Thr Gly Thr Val
```

-continued

```
              35                  40                  45
Pro Arg Leu Gly Phe Asn Gln Pro Ile Cys Leu Gln Asp Gly Pro Val
 50                  55                  60
Gly Ile Arg Tyr Thr Asp Phe Asn Ser Val Phe Pro Ala Ala Ile Asn
 65                  70                  75                  80
Val Ala Ala Thr Phe Asp Lys Gln Leu Met Phe Lys Arg Ala Gln Ala
                 85                  90                  95
Met Ala Glu Glu Phe Arg Gly Lys Gly Ala Asn Val Val Leu Ala Pro
                100                 105                 110
Met Thr Asn Leu Met Arg Thr Pro Gln Ala Gly Arg Ala Trp Glu Gly
                115                 120                 125
Tyr Gly Ser Asp Pro Tyr Leu Ser Gly Val Ala Thr Val Gln Ser Val
130                 135                 140
Leu Gly Ile Gln Ser Thr Arg Ala Ser Ala Cys Val Lys His Tyr Ile
145                 150                 155                 160
Gly Asn Glu Gln Glu His Tyr Arg Gly Ser Gly Ala Thr Ala Ser
                165                 170                 175
Ser Ser Asn Ile Asp Asp Arg Thr Leu Arg Glu Leu Tyr Glu Trp Pro
                180                 185                 190
Phe Ala Glu Ala Ile His Ala Gly Val Asp Tyr Ile Met Cys Ser Tyr
                195                 200                 205
Asn Arg Val Asn Gln Thr Tyr Ala Cys Glu Asn Ser Lys Leu Ile Asn
                210                 215                 220
Gly Ile Ala Lys Gly Glu His Lys Phe Gln Gly Val Met Val Thr Asp
225                 230                 235                 240
Trp Ala Ala Ala Glu Ser Gly Val Arg Thr Ala Leu Ala Gly Thr Asp
                245                 250                 255
Met Asn Met Pro Gly Phe Met Ala Tyr Gly Gln Pro Ser Glu Pro Asn
                260                 265                 270
Pro Ser Thr Ala Asn Gly Ser Tyr Trp Gly Leu Arg Met Ile Glu Ala
                275                 280                 285
Val Lys Asn Gly Thr Val Pro Met Glu Arg Leu Asp Asp Met Val Thr
                290                 295                 300
Arg Val Ile Ser Thr Tyr Tyr Lys Gln Gly Gln Asp Lys Ser Asp Tyr
305                 310                 315                 320
Pro Lys Leu Asn Phe Met Ser Met Gly Gln Gly Thr Pro Ala Glu Gln
                325                 330                 335
Ala Val Ser Asn His His Val Asn Val Gln Lys Asp His Tyr Leu Ile
                340                 345                 350
Ile Arg Gln Ile Ala Thr Ala Ser Thr Ile Leu Leu Lys Asn Val Asn
                355                 360                 365
His Thr Leu Pro Leu Lys Ser Pro Asp Lys Met Arg Ser Val Val Val
                370                 375                 380
Val Gly Ser Asp Ala Gly Asp Asn Pro Gln Gly Pro Asn Ser Cys Val
385                 390                 395                 400
Asp Arg Gly Cys Asn Arg Gly Ile Leu Ala Ile Gly Trp Gly Ser Gly
                405                 410                 415
Thr Ala Asn Phe Ala His Leu Thr Ala Pro Ala Thr Ser Ile Gln Asn
                420                 425                 430
Tyr Leu Leu Gln Ser Asn Pro Thr Ile Thr Tyr Arg Ser Ile Phe Asp
                435                 440                 445
Asp Tyr Ala Tyr Asp Glu Ile Ala Lys Ala Ala Ser Thr Ala Asp Val
                450                 455                 460
```

```
Ser Ile Val His Val Ser Ser Asp Ser Gly Glu Gly Tyr Leu Thr Val
465                 470                 475                 480

Glu Gly Asn Gln Gly Asp Arg Ser Asn Thr Ser Leu Trp Asn Lys Gly
            485                 490                 495

Asp Glu Leu Ile Leu Lys Ala Ala Glu Ala Cys Asn Asn Val Val Val
        500                 505                 510

Val Ile His Ser Val Gly Pro Val Asp Met Glu Ala Trp Ile Asn His
    515                 520                 525

Pro Asn Val Thr Ala Val Leu Leu Ala Gly Leu Pro Gly Gln Glu Ala
530                 535                 540

Gly Ser Ala Glu Val Asp Val Leu Trp Gly Ser Thr Asn Pro Ser Gly
545                 550                 555                 560

Arg Leu Pro Tyr Thr Ile Ala Lys Lys Pro Ser Asp Tyr Pro Ala Glu
                565                 570                 575

Leu Leu Tyr Glu Ser Asn Met Thr Val Pro Gln Ile Asn Tyr Ser Glu
            580                 585                 590

Arg Leu Asn Ile Asp Tyr Arg His Phe Asp Thr Tyr Asn Ile Glu Pro
        595                 600                 605

Arg Phe Glu Phe Gly Phe Gly Leu Ser Tyr Thr Thr Phe
610                 615                 620

<210> SEQ ID NO 99
<211> LENGTH: 731
<212> TYPE: PRT
<213> ORGANISM: Volvariella volvacea

<400> SEQUENCE: 99

Met Pro Pro Ser Asp Phe Ala Lys Ala Asn Ile Asp Glu Ile Val Glu
1               5                   10                  15

Gln Leu Thr Leu Asp Glu Ala Ile Ser Leu Thr Ala Gly Val Gly Phe
            20                  25                  30

Trp His Thr His Ala Ile Glu Arg Leu Gly Val Pro Ala Val Lys Val
        35                  40                  45

Ser Asp Gly Pro Asn Gly Ile Arg Gly Asn His Phe Phe Met Gly Thr
50                  55                  60

Pro Ala Lys Cys Leu Pro Ser Ser Thr Ala Leu Gly Ala Thr Trp Asp
65                  70                  75                  80

Pro Glu Val Val Glu Val Gly Leu Lys Leu Leu Ala Pro Glu Ala
                85                  90                  95

Lys Leu Arg Ala Ala Ser Leu Val Leu Ala Pro Thr Ser Asn Ile Gln
            100                 105                 110

Arg Asn Pro Leu Gly Gly Arg Ser Phe Glu Ser Phe Ser Glu Asp Pro
        115                 120                 125

Tyr Leu Ser Gly Ile Ile Ser Ala Ser Tyr Val Asn Gly Val Gln Lys
130                 135                 140

Gly Gly Ile Gly Ala Thr Ile Lys His Phe Val Gly Asn Asp Lys Glu
145                 150                 155                 160

Asp Asp Arg Gln Gly Tyr Asp Ser Ile Ile Ser Glu Arg Ala Leu Arg
                165                 170                 175

Glu Ile Tyr Leu Leu Pro Phe Met Leu Thr Gln Lys Tyr Ala Ala Pro
            180                 185                 190

Trp Ala Ile Met Thr Ala Tyr Asn Arg Val Asn Gly His Val Ala
        195                 200                 205

Glu Asp Pro Phe Leu Leu Lys Gln Val Leu Arg Asn Glu Trp Lys Tyr
210                 215                 220
```

```
Lys Gly Leu Ile Met Ser Asp Trp Phe Gly Met Tyr Ser Val Asp His
225                 230                 235                 240

Gly Ile Lys Ala Gly Leu Asp Leu Glu Met Pro Gly Ile Asn Lys Trp
            245                 250                 255

Arg Thr Leu Asp Leu Val Asn Arg Thr Ile Gln Ala Arg Lys Leu Thr
                260                 265                 270

Pro Arg Asp Ile Lys Asp Arg Ala Arg Val Val Leu Glu Leu Val Lys
            275                 280                 285

Lys Cys Ala Gln Gly Ala Pro Glu Ile Leu Asp Gly Asp Gly Glu
            290                 295                 300

Arg Thr Val Glu Leu Glu Ser Asp Lys Leu Leu Met Arg Arg Ile Ala
305                 310                 315                 320

Ser Glu Ser Ile Val Leu Leu Lys Asn Asp Asn Val Leu Pro Leu Lys
                325                 330                 335

Pro Glu Gly Gly Ala Ile Lys Lys Ile Ala Val Val Gly Gly Asn Ala
            340                 345                 350

Lys Ala Gln Val Leu Ser Gly Gly Ser Ala Ala Leu Lys Ala Ser
            355                 360                 365

Tyr Phe Ile Ser Pro Tyr Asp Gly Ile Lys Ala Ala Leu Glu Pro His
370                 375                 380

Gly Val Glu Val Thr Phe Ser Glu Gly Ala Arg Ala Tyr Lys Thr Leu
385                 390                 395                 400

Pro Thr Leu Glu Trp Asp Leu Glu Thr Glu Thr Gly Glu Arg Gly Trp
                405                 410                 415

Ile Gly Thr Trp His Thr His Glu Ser Asp Ser Met Thr Ala Leu
            420                 425                 430

Asp Gln Pro Phe Ile Ala Pro Arg Leu Val Asp Glu Thr Arg Ile Phe
            435                 440                 445

Ile Ser Thr Ser Tyr Pro Lys Gly Ile Thr Lys Arg Trp Thr Met Arg
            450                 455                 460

Leu Lys Gly Tyr Leu Lys Pro Arg Glu Lys Asp Thr Asn Phe Glu Phe
465                 470                 475                 480

Gly Leu Ile Ala Ala Gly Arg Ala Lys Leu Trp Val Asp Gly Gln Leu
                485                 490                 495

Val Ile Asp Asn Trp Thr Arg Gln Arg Arg Gly Glu Ala Phe Phe Gly
            500                 505                 510

Ser Gly Ser Gln Glu Glu Thr Gly Val Tyr Leu Leu Lys Ala Gly Lys
            515                 520                 525

Lys His Glu Ile Tyr Val Glu Tyr Cys Asn Val Arg Ala Pro Ala Asp
            530                 535                 540

Gly Asp Glu Asp Glu Ala Ile Met Asp Ser Asn Pro Gly Val Arg Leu
545                 550                 555                 560

Gly Gly Ala Glu Val Ala Asn Ala Asp Leu Leu Ser Glu Ala Val
            565                 570                 575

Lys Leu Ala Ser Glu Ala Asp Ala Val Ile Ala Val Gly Leu Asn
            580                 585                 590

Ala Asp Trp Glu Thr Glu Gly Asn Asp Arg Arg Thr Leu Ala Leu Pro
            595                 600                 605

Gly Arg Thr Asp Glu Leu Val Glu Lys Val Ala Lys Val Asn Ser Lys
610                 615                 620

Thr Val Val Val Thr Gln Ala Gly Ser Ala Ile Thr Leu Pro Trp Leu
625                 630                 635                 640

Asp Ser Val Ala Ala Val Val His Ala Trp Tyr Leu Gly Asn Ala Thr
                645                 650                 655
```

```
Gly Asp Ala Ile Ala Asp Val Leu Phe Gly Lys Gln Asn Pro Ser Gly
                660                 665                 670

Lys Leu Ser Leu Thr Phe Pro Lys Arg Leu Glu Asp Val Pro Ser His
            675                 680                 685

Gly His Phe Gly Ser Glu Asn Gly Lys Val Arg Tyr Ala Glu Asp Leu
        690                 695                 700

Phe Val Gly Tyr Lys His Tyr His Arg Asn Ile Glu Pro Leu Phe
705                 710                 715                 720

Pro Phe Gly Phe Gly Leu Ser Tyr Thr Thr Phe
                725                 730

<210> SEQ ID NO 100
<211> LENGTH: 713
<212> TYPE: PRT
<213> ORGANISM: Trichoderma reesei

<400> SEQUENCE: 100

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300
```

```
Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
            325                 330                 335

Asp Ala Asn Ile Leu Pro Leu Lys Lys Pro Ala Ser Ile Ala Val Val
                340                 345                 350

Gly Ser Ala Ala Ile Ile Gly Asn His Ala Arg Asn Ser Pro Ser Cys
        355                 360                 365

Asn Asp Lys Gly Cys Asp Asp Gly Ala Leu Gly Met Gly Trp Gly Ser
    370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
            405                 410                 415

Asn Thr Ser Ser Gly Ala Ser Ala Ala Arg Gly Lys Asp Val Ala Ile
                420                 425                 430

Val Phe Ile Thr Ala Asp Ser Gly Glu Gly Tyr Ile Thr Val Glu Gly
                435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
                515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
            595                 600                 605

Asp Leu Phe Gln Asn Val Ala Thr Val Thr Val Asp Ile Ala Asn Ser
610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
            690                 695                 700

Arg Leu Thr Ser Thr Leu Ser Val Ala
705                 710
```

<210> SEQ ID NO 101
<211> LENGTH: 713
<212> TYPE: PRT
<213> ORGANISM: Trichoderma reesei

<400> SEQUENCE: 101

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Ile Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Asn Asp Lys Gly Cys Asp Asp Gly Ala Leu Gly Met Gly Trp Gly Ser
    370                 375                 380

Gly Ala Val Asn Tyr Pro Tyr Phe Val Ala Pro Tyr Asp Ala Ile Asn

```
                385                 390                 395                 400
Thr Arg Ala Ser Ser Gln Gly Thr Gln Val Thr Leu Ser Asn Thr Asp
                    405                 410                 415
Asn Thr Ser Ser Gly Ala Ser Ala Ala Arg Gly Lys Asp Val Ala Ile
                420                 425                 430
Val Phe Ile Thr Ala Asp Ser Gly Glu Gly Tyr Ile Thr Val Glu Gly
            435                 440                 445
Asn Ala Gly Asp Arg Asn Leu Asp Pro Trp His Asn Gly Asn Ala
        450                 455                 460
Leu Val Gln Ala Val Ala Gly Ala Asn Ser Asn Val Ile Val Val Val
465                 470                 475                 480
His Ser Val Gly Ala Ile Ile Leu Glu Gln Ile Leu Ala Leu Pro Gln
                485                 490                 495
Val Lys Ala Val Val Trp Ala Gly Leu Pro Ser Gln Glu Ser Gly Asn
                500                 505                 510
Ala Leu Val Asp Val Leu Trp Gly Asp Val Ser Pro Ser Gly Lys Leu
            515                 520                 525
Val Tyr Thr Ile Ala Lys Ser Pro Asn Asp Tyr Asn Thr Arg Ile Val
530                 535                 540
Ser Gly Gly Ser Asp Ser Phe Ser Glu Gly Leu Phe Ile Asp Tyr Lys
545                 550                 555                 560
His Phe Asp Asp Ala Asn Ile Thr Pro Arg Tyr Glu Phe Gly Tyr Gly
                565                 570                 575
Leu Ser Tyr Thr Lys Phe Asn Tyr Ser Arg Leu Ser Val Leu Ser Thr
                580                 585                 590
Ala Lys Ser Gly Pro Ala Thr Gly Ala Val Val Pro Gly Gly Pro Ser
            595                 600                 605
Asp Leu Phe Gln Asn Val Ala Thr Val Thr Val Asp Ile Ala Asn Ser
        610                 615                 620
Gly Gln Val Thr Gly Ala Glu Val Ala Gln Leu Tyr Ile Thr Tyr Pro
625                 630                 635                 640
Ser Ser Ala Pro Arg Thr Pro Pro Lys Gln Leu Arg Gly Phe Ala Lys
                645                 650                 655
Leu Asn Leu Thr Pro Gly Gln Ser Gly Thr Ala Thr Phe Asn Ile Arg
                660                 665                 670
Arg Arg Asp Leu Ser Tyr Trp Asp Thr Ala Ser Gln Lys Trp Val Val
            675                 680                 685
Pro Ser Gly Ser Phe Gly Ile Ser Val Gly Ala Ser Ser Arg Asp Ile
        690                 695                 700
Arg Leu Thr Ser Thr Leu Ser Val Ala
705                 710

<210> SEQ ID NO 102
<211> LENGTH: 713
<212> TYPE: PRT
<213> ORGANISM: Trichoderma reesei

<400> SEQUENCE: 102

Val Val Pro Pro Ala Gly Thr Pro Trp Gly Thr Ala Tyr Asp Lys Ala
1               5                   10                  15
Lys Ala Ala Leu Ala Lys Leu Asn Leu Gln Asp Lys Val Gly Ile Val
                20                  25                  30
Ser Gly Val Gly Trp Asn Gly Gly Pro Cys Val Gly Asn Thr Ser Pro
            35                  40                  45
Ala Ser Lys Ile Ser Tyr Pro Ser Leu Cys Leu Gln Asp Gly Pro Leu
```

```
                50                  55                  60
Gly Val Arg Tyr Ser Thr Gly Asn Thr Ala Phe Thr Pro Gly Val Gln
 65                  70                  75                  80

Ala Ala Ser Thr Trp Asp Val Asn Leu Ile Arg Glu Arg Gly Gln Phe
                     85                  90                  95

Ile Gly Glu Glu Val Lys Ala Ser Gly Ile His Val Ile Leu Gly Pro
                100                 105                 110

Val Ala Gly Pro Leu Gly Lys Thr Pro Gln Gly Gly Arg Asn Trp Glu
                115                 120                 125

Gly Phe Gly Val Asp Pro Tyr Leu Thr Gly Ile Ala Met Gly Gln Thr
            130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
                260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
            290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
                340                 345                 350

Gly Ser Ala Ala Ile Ile Gly Asn His Ala Arg Asn Ser Pro Ser Cys
            355                 360                 365

Asn Asp Lys Gly Cys Asp Asp Gly Ala Leu Gly Met Gly Trp Gly Ser
370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
            450                 455                 460

Leu Val Gln Ala Val Ala Gly Ala Asn Ser Asn Val Ile Val Val Val
465                 470                 475                 480
```

```
His Ser Val Gly Ala Ile Ile Leu Glu Gln Ile Leu Ala Leu Pro Gln
            485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
            530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
            595                 600                 605

Asp Leu Phe Gln Asn Val Ala Thr Val Thr Val Asp Ile Ala Asn Ser
            610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
            690                 695                 700

Arg Leu Thr Ser Thr Leu Ser Val Ala
705                 710

<210> SEQ ID NO 103
<211> LENGTH: 713
<212> TYPE: PRT
<213> ORGANISM: Trichoderma reesei

<400> SEQUENCE: 103

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Glu Thr Ala Phe Thr Pro Gly Val Gln
65                  70                  75                  80

Ala Ala Ser Thr Trp Asp Val Asn Leu Ile Arg Glu Arg Gly Gln Leu
                85                  90                  95

Ile Gly Glu Glu Met Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140
```

```
Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
            165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
            245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
            325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
            355                 360                 365

Lys Asp Lys Gly Cys Asp Asp Gly Ala Leu Gly Met Gly Trp Gly Ser
            370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
            405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
            485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
            530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
            565                 570                 575
```

```
Leu Ser Tyr Thr Lys Phe Asn Tyr Ser Arg Leu Ser Val Leu Ser Thr
                580                 585                 590

Ala Lys Ser Gly Pro Ala Thr Gly Ala Val Val Pro Gly Gly Pro Ser
            595                 600                 605

Asp Leu Phe Gln Asn Val Ala Thr Val Thr Val Asp Ile Ala Asn Ser
610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
                660                 665                 670

Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
690                 695                 700

Arg Leu Thr Ser Thr Leu Ser Val Ala
705                 710

<210> SEQ ID NO 104
<211> LENGTH: 713
<212> TYPE: PRT
<213> ORGANISM: Trichoderma reesei

<400> SEQUENCE: 104

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
                20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
        50                  55                  60

Gly Val Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Met Lys Ala Ser Gly Ile His Val Ile Leu Gly Pro
                100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240
```

-continued

His Thr Thr Val Gln Ser Ala Asn Ser Gly Leu Asp Met Ser Met Pro
            245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
            355                 360                 365

Asn Asp Lys Gly Cys Asp Asp Gly Ala Leu Gly Met Gly Trp Gly Ser
            370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
            450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
            595                 600                 605

Asp Leu Phe Gln Asn Val Ala Thr Val Thr Val Asp Ile Ala Asn Ser
            610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg

```
                   660                 665                 670
Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
        690                 695                 700

Arg Leu Thr Ser Thr Leu Ser Val Ala
705                 710

<210> SEQ ID NO 105
<211> LENGTH: 713
<212> TYPE: PRT
<213> ORGANISM: Trichoderma reesei

<400> SEQUENCE: 105

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Ser Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
```

```
                      325                 330                 335
Asp Ala Asn Ile Leu Pro Leu Lys Lys Pro Ala Ser Ile Ala Val Val
            340                 345                 350
Gly Ser Ala Ala Ile Ile Gly Asn His Ala Arg Asn Ser Pro Ser Cys
        355                 360                 365
Asn Asp Lys Gly Cys Asp Asp Gly Ala Leu Gly Met Gly Trp Gly Ser
    370                 375                 380
Gly Ala Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
Asn Thr Ser Ser Gly Ala Ser Ala Ala Arg Gly Lys Asp Val Ala Ile
            420                 425                 430
Val Phe Ile Thr Ala Asp Ser Gly Glu Gly Tyr Ile Thr Val Glu Gly
        435                 440                 445
Asn Ala Gly Asp Arg Asn Asn Leu Asp Pro Trp His Asn Gly Asn Ala
    450                 455                 460
Leu Val Gln Ala Val Ala Gly Ala Asn Ser Asn Val Ile Val Val Val
465                 470                 475                 480
His Ser Val Gly Ala Ile Ile Leu Glu Gln Ile Leu Ala Leu Pro Gln
                485                 490                 495
Val Lys Ala Val Val Trp Ala Gly Leu Pro Ser Gln Glu Ser Gly Asn
            500                 505                 510
Ala Leu Val Asp Val Leu Trp Gly Asp Val Ser Pro Ser Gly Lys Leu
        515                 520                 525
Val Tyr Thr Ile Ala Lys Ser Pro Asn Asp Tyr Asn Thr Arg Ile Val
    530                 535                 540
Ser Gly Gly Ser Asp Ser Phe Ser Glu Gly Leu Phe Ile Asp Tyr Lys
545                 550                 555                 560
His Phe Asp Asp Ala Asn Ile Thr Pro Arg Tyr Glu Phe Gly Tyr Gly
                565                 570                 575
Leu Ser Tyr Thr Lys Phe Asn Tyr Ser Arg Leu Ser Val Leu Ser Thr
            580                 585                 590
Ala Lys Ser Gly Pro Ala Thr Gly Ala Val Val Pro Gly Gly Pro Ser
        595                 600                 605
Asp Leu Phe Gln Asn Val Ala Thr Val Thr Val Asp Ile Ala Asn Ser
    610                 615                 620
Gly Gln Val Thr Gly Ala Glu Val Ala Gln Leu Tyr Ile Thr Tyr Pro
625                 630                 635                 640
Ser Ser Ala Pro Arg Thr Pro Lys Gln Leu Arg Gly Phe Ala Lys
                645                 650                 655
Leu Asn Leu Thr Pro Gly Gln Ser Gly Thr Ala Thr Phe Asn Ile Arg
            660                 665                 670
Arg Arg Asp Leu Ser Tyr Trp Asp Thr Ala Ser Gln Lys Trp Val Val
        675                 680                 685
Pro Ser Gly Ser Phe Gly Ile Ser Val Gly Ala Ser Ser Arg Asp Ile
    690                 695                 700
Arg Leu Thr Ser Thr Leu Ser Val Ala
705                 710

<210> SEQ ID NO 106
<211> LENGTH: 713
<212> TYPE: PRT
<213> ORGANISM: Trichoderma reesei
```

<400> SEQUENCE: 106

```
Val Val Pro Pro Ala Gly Thr Pro Trp Gly Thr Ala Tyr Asp Lys Ala
1               5                   10                  15
Lys Ala Ala Leu Ala Lys Leu Asn Leu Gln Asp Lys Val Gly Ile Val
            20                  25                  30
Ser Gly Val Gly Trp Asn Gly Gly Pro Cys Val Gly Asn Thr Ser Pro
        35                  40                  45
Ala Ser Lys Ile Ser Tyr Pro Ser Leu Cys Leu Gln Asp Gly Pro Leu
    50                  55                  60
Gly Val Arg Tyr Ser Thr Gly Ser Thr Ala Phe Thr Pro Gly Val Gln
65                  70                  75                  80
Ala Ala Ser Thr Trp Asp Val Asn Leu Ile Arg Glu Arg Gly Gln Phe
                85                  90                  95
Ile Gly Glu Glu Val Lys Ala Ser Gly Ile His Val Ile Leu Gly Pro
            100                 105                 110
Val Ala Gly Pro Leu Gly Lys Thr Pro Gln Gly Gly Arg Asn Trp Glu
        115                 120                 125
Gly Phe Gly Val Asp Pro Tyr Leu Thr Gly Ile Ala Met Gly Gln Thr
    130                 135                 140
Ile Asn Gly Ile Gln Ser Val Gly Val Gln Ala Thr Ala Lys His Tyr
145                 150                 155                 160
Ile Leu Asn Glu Gln Glu Leu Asn Arg Glu Thr Ile Ser Ser Asn Pro
                165                 170                 175
Asp Asp Arg Thr Leu His Glu Leu Tyr Thr Trp Pro Phe Ala Asp Ala
            180                 185                 190
Val Gln Ala Asn Val Ala Ser Val Met Cys Ser Tyr Asn Lys Val Asn
        195                 200                 205
Thr Thr Trp Ala Cys Glu Asp Gln Tyr Thr Leu Gln Thr Val Leu Lys
    210                 215                 220
Asp Gln Leu Gly Phe Pro Gly Tyr Val Met Thr Asp Trp Asn Ala Gln
225                 230                 235                 240
His Thr Thr Val Gln Ser Ala Lys Ser Gly Leu Asp Met Ser Met Pro
                245                 250                 255
Gly Thr Asp Phe Asn Gly Asn Asn Arg Leu Trp Gly Pro Ala Leu Thr
            260                 265                 270
Asn Ala Val Asn Ser Asn Gln Val Pro Thr Ser Arg Val Asp Asp Met
        275                 280                 285
Val Thr Arg Ile Leu Ala Ala Trp Tyr Leu Thr Gly Gln Asp Gln Ala
    290                 295                 300
Gly Tyr Pro Ser Phe Asn Ile Ser Arg Asn Val Gln Gly Asn His Lys
305                 310                 315                 320
Thr Asn Val Arg Ala Ile Ala Arg Asp Gly Ile Val Leu Leu Lys Asn
                325                 330                 335
Asp Ala Asn Ile Leu Pro Leu Lys Lys Pro Ala Ser Ile Ala Val Val
            340                 345                 350
Gly Ser Ala Ala Ile Gly Asn His Ala Arg Asn Ser Pro Ser Cys
        355                 360                 365
Asn Asp Lys Gly Cys Asp Asp Gly Ala Leu Gly Met Gly Trp Gly Ser
    370                 375                 380
Gly Ala Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
```

```
Asn Thr Ser Ser Gly Ala Ser Ala Arg Gly Lys Asp Val Ala Ile
            420                 425                 430

Val Phe Ile Thr Ala Asp Ser Glu Gly Tyr Ile Thr Val Glu Gly
            435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val
465                 470                 475                 480

His Ser Val Gly Ala Ile Ile Leu Glu Gln Ile Leu Ala Leu Pro Gln
            485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
            530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
            595                 600                 605

Asp Leu Phe Gln Asn Val Ala Thr Val Thr Val Asp Ile Ala Asn Ser
610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
690                 695                 700

Arg Leu Thr Ser Thr Leu Ser Val Ala
705                 710

<210> SEQ ID NO 107
<211> LENGTH: 713
<212> TYPE: PRT
<213> ORGANISM: Trichoderma reesei

<400> SEQUENCE: 107

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
50                  55                  60

Gly Val Arg Tyr Ser Thr Gly Ser Thr Ala Phe Thr Pro Gly Val Gln
65                  70                  75                  80
```

-continued

Ala Ala Ser Thr Trp Asp Val Asn Leu Ile Arg Glu Arg Gly Gln Phe
            85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
        130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
        210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
        290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Lys Asp Lys Gly Cys Asp Asp Gly Ala Leu Gly Met Gly Trp Gly Ser
            370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
            450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

```
Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
    530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
        595                 600                 605

Asp Leu Phe Gln Asn Val Ala Thr Val Thr Val Asp Ile Ala Asn Ser
    610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
        675                 680                 685

Pro Ser Gly Ser Phe Gly Ile Ser Val Gly Ala Ser Ser Arg Asp Ile
    690                 695                 700

Arg Leu Thr Ser Thr Leu Ser Val Ala
705                 710

<210> SEQ ID NO 108
<211> LENGTH: 713
<212> TYPE: PRT
<213> ORGANISM: Trichoderma reesei

<400> SEQUENCE: 108

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Ser Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175
```

-continued

```
Asp Asp Arg Thr Leu His Glu Leu Tyr Thr Trp Pro Phe Ala Asp Ala
            180                 185                 190
Val Gln Ala Asn Val Ala Ser Val Met Cys Ser Tyr Asn Lys Val Asn
            195                 200                 205
Thr Thr Trp Ala Cys Glu Asp Gln Tyr Thr Leu Gln Thr Val Leu Lys
        210                 215                 220
Asp Gln Leu Gly Phe Pro Gly Tyr Val Met Thr Asp Trp Asn Ala Gln
225                 230                 235                 240
His Thr Thr Val Gln Ser Ala Asn Ser Gly Leu Asp Met Ser Met Pro
                245                 250                 255
Gly Thr Asp Phe Asn Gly Asn Asn Arg Leu Trp Gly Pro Ala Leu Thr
            260                 265                 270
Asn Ala Val Asn Ser Asn Gln Val Pro Thr Ser Arg Val Asp Asp Met
            275                 280                 285
Val Thr Arg Ile Leu Ala Ala Trp Tyr Leu Thr Gly Gln Asp Gln Ala
        290                 295                 300
Gly Tyr Pro Ser Phe Asn Ile Ser Arg Asn Val Gln Gly Asn His Lys
305                 310                 315                 320
Thr Asn Val Arg Ala Ile Ala Arg Asp Gly Ile Val Leu Leu Lys Asn
                325                 330                 335
Asp Ala Asn Ile Leu Pro Leu Lys Lys Pro Ala Ser Ile Ala Val Val
            340                 345                 350
Gly Ser Ala Ala Ile Ile Gly Asn His Ala Arg Asn Ser Pro Ser Cys
        355                 360                 365
Asn Asp Lys Gly Cys Asp Asp Gly Ala Leu Gly Met Gly Trp Gly Ser
370                 375                 380
Gly Thr Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
Asn Thr Ser Ser Gly Ala Ser Ala Ala Arg Gly Lys Asp Val Ala Ile
            420                 425                 430
Val Phe Ile Thr Ala Asp Ser Gly Glu Gly Tyr Ile Thr Val Glu Gly
        435                 440                 445
Asn Ala Gly Asp Arg Asn Asn Leu Asp Pro Trp His Asn Gly Asn Ala
450                 455                 460
Leu Val Gln Ala Val Ala Gly Ala Asn Ser Asn Val Ile Val Val Val
465                 470                 475                 480
His Ser Val Gly Ala Ile Ile Leu Glu Gln Ile Leu Ala Leu Pro Gln
                485                 490                 495
Val Lys Ala Val Val Trp Ala Gly Leu Pro Ser Gln Glu Ser Gly Asn
            500                 505                 510
Ala Leu Val Asp Val Leu Trp Gly Asp Val Ser Pro Ser Gly Lys Leu
        515                 520                 525
Val Tyr Thr Ile Ala Lys Ser Pro Asn Asp Tyr Asn Thr Arg Ile Val
530                 535                 540
Ser Gly Gly Ser Asp Ser Phe Ser Glu Gly Leu Phe Ile Asp Tyr Lys
545                 550                 555                 560
His Phe Asp Asp Ala Asn Ile Thr Pro Arg Tyr Glu Phe Gly Tyr Gly
                565                 570                 575
Leu Ser Tyr Thr Lys Phe Asn Tyr Ser Arg Leu Ser Val Leu Ser Thr
            580                 585                 590
Ala Lys Ser Gly Pro Ala Thr Gly Ala Val Val Pro Gly Gly Pro Ser
```

```
            595                 600                 605
Asp Leu Phe Gln Asn Val Ala Thr Val Thr Val Asp Ile Ala Asn Ser
        610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
                660                 665                 670

Arg Arg Asp Leu Ser Tyr Trp Asp Thr Ala Ser Gln Lys Trp Val Val
                675                 680                 685

Pro Ser Gly Ser Phe Gly Ile Ser Val Gly Ala Ser Ser Arg Asp Ile
690                 695                 700

Arg Leu Thr Ser Thr Leu Ser Val Ala
705                 710

<210> SEQ ID NO 109
<211> LENGTH: 713
<212> TYPE: PRT
<213> ORGANISM: Trichoderma reesei

<400> SEQUENCE: 109

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
                20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
        50                  55                  60

Gly Ile Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Val Lys Ala Ser Gly Ile His Val Ile Leu Gly Pro
                100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
                180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
```

```
                     260                 265                 270
Asn Ala Val Asn Ser Asn Gln Val Pro Thr Ser Arg Val Asp Asp Met
            275                 280                 285
Val Thr Arg Ile Leu Ala Ala Trp Tyr Leu Thr Gly Gln Asp Gln Ala
            290                 295                 300
Gly Tyr Pro Ser Phe Asn Ile Ser Arg Asn Val Gln Gly Asn His Lys
305                 310                 315                 320
Thr Asn Val Arg Ala Ile Ala Arg Asp Gly Ile Val Leu Leu Lys Asn
                325                 330                 335
Asp Ala Asn Ile Leu Pro Leu Lys Lys Pro Ala Ser Ile Ala Val Val
            340                 345                 350
Gly Ser Ala Ala Ile Ile Gly Asn His Ala Arg Asn Ser Pro Ser Cys
            355                 360                 365
Asn Asp Lys Gly Cys Asp Asp Gly Ala Leu Gly Met Gly Trp Gly Ser
            370                 375                 380
Gly Ala Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
Asn Thr Ser Ser Gly Ala Ser Ala Ala Arg Gly Lys Asp Val Ala Ile
                420                 425                 430
Val Phe Ile Thr Ala Asp Ser Gly Glu Gly Tyr Ile Thr Val Glu Gly
            435                 440                 445
Asn Ala Gly Asp Arg Asn Asn Leu Asp Pro Trp His Asn Gly Asn Ala
450                 455                 460
Leu Val Gln Ala Val Ala Gly Ala Asn Ser Asn Val Ile Val Val Val
465                 470                 475                 480
His Ser Val Gly Ala Ile Ile Leu Glu Gln Ile Leu Ala Leu Pro Gln
                485                 490                 495
Val Lys Ala Val Val Trp Ala Gly Leu Pro Ser Gln Glu Ser Gly Asn
            500                 505                 510
Ala Leu Val Asp Val Leu Trp Gly Asp Val Ser Pro Ser Gly Lys Leu
            515                 520                 525
Val Tyr Thr Ile Ala Lys Ser Pro Asn Asp Tyr Asn Thr Arg Ile Val
            530                 535                 540
Ser Gly Gly Ser Asp Ser Phe Ser Glu Gly Leu Phe Ile Asp Tyr Lys
545                 550                 555                 560
His Phe Asp Asp Ala Asn Ile Thr Pro Arg Tyr Glu Phe Gly Tyr Gly
                565                 570                 575
Leu Ser Tyr Thr Lys Phe Asn Tyr Ser Arg Leu Ser Val Leu Ser Thr
            580                 585                 590
Ala Lys Ser Gly Pro Ala Thr Gly Ala Val Val Pro Gly Gly Pro Ser
            595                 600                 605
Asp Leu Phe Gln Asn Val Ala Thr Val Thr Val Asp Ile Ala Asn Ser
            610                 615                 620
Gly Gln Val Thr Gly Ala Glu Val Ala Gln Leu Tyr Ile Thr Tyr Pro
625                 630                 635                 640
Ser Ser Ala Pro Arg Thr Pro Pro Lys Gln Leu Arg Gly Phe Ala Lys
                645                 650                 655
Leu Asn Leu Thr Pro Gly Gln Ser Gly Thr Ala Thr Phe Asn Ile Arg
                660                 665                 670
Arg Arg Asp Leu Ser Tyr Trp Asp Thr Ala Ser Gln Lys Trp Val Val
                675                 680                 685
```

```
Pro Ser Gly Ser Phe Gly Ile Ser Val Gly Ala Ser Ser Arg Asp Ile
        690                 695                 700

Arg Leu Thr Ser Thr Leu Ser Val Ala
705                 710
```

<210> SEQ ID NO 110
<211> LENGTH: 713
<212> TYPE: PRT
<213> ORGANISM: Trichoderma reesei

<400> SEQUENCE: 110

```
Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
                20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
    50                  55                  60

Gly Val Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Leu
                85                  90                  95

Ile Gly Glu Glu Met Lys Ala Ser Gly Ile His Val Ile Leu Gly Pro
                100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
                180                 185                 190

Val Gln Ala Asn Val Ala Ser Val Met Cys Ser Tyr Asn Lys Val Asn
            195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
                260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
                340                 345                 350
```

-continued

```
Gly Ser Ala Ala Ile Ile Gly Asn His Ala Arg Asn Ser Pro Ser Cys
            355                 360                 365

Asn Asp Lys Gly Cys Asp Asp Gly Ala Leu Gly Met Gly Trp Gly Ser
370                 375                 380

Gly Ala Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Arg Gly Lys Asp Val Ala Ile
                420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
            595                 600                 605

Asp Leu Phe Gln Asn Val Ala Thr Val Thr Val Asp Ile Ala Asn Ser
610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
690                 695                 700

Arg Leu Thr Ser Thr Leu Ser Val Ala
705                 710
```

<210> SEQ ID NO 111
<211> LENGTH: 713
<212> TYPE: PRT
<213> ORGANISM: Trichoderma reesei

<400> SEQUENCE: 111

```
Val Val Pro Pro Ala Gly Thr Pro Trp Gly Thr Ala Tyr Asp Lys Ala
1               5                   10                  15
```

```
Lys Ala Ala Leu Ala Lys Leu Asn Leu Gln Asp Lys Val Gly Ile Val
             20                  25                  30
Ser Gly Val Gly Trp Asn Gly Pro Cys Val Gly Asn Thr Ser Pro
         35                  40                  45
Ala Ser Lys Ile Ser Tyr Pro Ser Leu Cys Leu Gln Asp Gly Pro Leu
 50                  55                  60
Gly Val Arg Tyr Ser Thr Gly Asn Thr Ala Phe Thr Pro Gly Val Gln
 65                  70                  75                  80
Ala Ala Ser Thr Trp Asp Val Asn Leu Ile Arg Glu Arg Gly Gln Leu
             85                  90                  95
Ile Gly Glu Glu Met Lys Ala Ser Gly Ile His Val Ile Leu Gly Pro
            100                 105                 110
Val Ala Gly Pro Leu Gly Lys Thr Pro Gln Gly Gly Arg Asn Trp Glu
        115                 120                 125
Gly Phe Gly Val Asp Pro Tyr Leu Thr Gly Ile Ala Met Gly Gln Thr
        130                 135                 140
Ile Asn Gly Ile Gln Ser Val Gly Val Gln Ala Thr Ala Lys His Tyr
145                 150                 155                 160
Ile Leu Asn Glu Gln Glu Leu Asn Arg Glu Thr Ile Ser Ser Asn Pro
                165                 170                 175
Asp Asp Arg Thr Leu His Glu Leu Tyr Thr Trp Pro Phe Ala Asp Ala
        180                 185                 190
Val Gln Ala Asn Val Ala Ser Val Met Cys Ser Tyr Asn Lys Val Asn
        195                 200                 205
Thr Thr Trp Ala Cys Glu Asp Gln Tyr Thr Leu Gln Thr Val Leu Lys
        210                 215                 220
Asp Gln Leu Gly Phe Pro Gly Tyr Val Met Thr Asp Trp Asn Ala Gln
225                 230                 235                 240
His Thr Thr Val Gln Ser Ala Asn Ser Gly Leu Asp Met Ser Met Pro
                245                 250                 255
Gly Thr Asp Phe Asn Gly Asn Asn Arg Leu Trp Gly Pro Ala Leu Thr
            260                 265                 270
Asn Ala Val Asn Ser Asn Gln Val Pro Thr Ser Arg Val Asp Asp Met
        275                 280                 285
Val Thr Arg Ile Leu Ala Ala Trp Tyr Leu Thr Gly Gln Asp Gln Ala
        290                 295                 300
Gly Tyr Pro Ser Phe Asn Ile Ser Arg Asn Val Gln Gly Asn His Lys
305                 310                 315                 320
Thr Asn Val Arg Ala Ile Ala Arg Asp Gly Ile Val Leu Leu Lys Asn
                325                 330                 335
Asp Ala Asn Ile Leu Pro Leu Lys Lys Pro Ala Ser Ile Ala Val Val
            340                 345                 350
Gly Ser Ala Ala Ile Ile Gly Asn His Ala Arg Asn Ser Pro Ser Cys
        355                 360                 365
Lys Asp Lys Gly Cys Asp Asp Gly Ala Leu Gly Met Gly Trp Gly Ser
        370                 375                 380
Gly Ala Val Asn Tyr Pro Tyr Phe Val Ala Pro Tyr Asp Ala Ile Asn
385                 390                 395                 400
Thr Arg Ala Ser Ser Gln Gly Thr Gln Val Thr Leu Ser Asn Thr Asp
                405                 410                 415
Asn Thr Ser Ser Gly Ala Ser Ala Ala Arg Gly Lys Asp Val Ala Ile
            420                 425                 430
Val Phe Ile Thr Ala Asp Ser Gly Glu Gly Tyr Ile Thr Val Glu Gly
        435                 440                 445
```

```
Asn Ala Gly Asp Arg Asn Asn Leu Asp Pro Trp His Asn Gly Asn Ala
    450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
    530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
        595                 600                 605

Asp Leu Phe Gln Asn Val Ala Thr Val Thr Val Asp Ile Ala Asn Ser
    610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
        675                 680                 685

Pro Ser Gly Ser Phe Gly Ile Ser Val Gly Ala Ser Ser Arg Asp Ile
    690                 695                 700

Arg Leu Thr Ser Thr Leu Ser Val Ala
705                 710

<210> SEQ ID NO 112
<211> LENGTH: 713
<212> TYPE: PRT
<213> ORGANISM: Trichoderma reesei

<400> SEQUENCE: 112

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Met Lys Ala Ser Gly Ile His Val Ile Leu Gly Pro
            100                 105                 110
```

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
            245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
            325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Lys Asp Lys Gly Cys Asp Asp Gly Ala Leu Gly Met Gly Trp Gly Ser
    370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
            405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
    450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
            485                 490                 495

Val Lys Ala Val Val Trp Ala Gly Leu Pro Ser Gln Glu Ser Gly Asn
        500                 505                 510

Ala Leu Val Asp Val Leu Trp Gly Asp Val Ser Pro Ser Gly Lys Leu
    515                 520                 525

Val Tyr Thr Ile Ala Lys Ser Pro Asn Asp Tyr Asn Thr Arg Ile Val

```
                    530                 535                 540
Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Pro Gly Gly Pro Ser
        595                 600                 605

Asp Leu Phe Gln Asn Val Ala Thr Val Thr Val Asp Ile Ala Asn Ser
    610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
        675                 680                 685

Pro Ser Gly Ser Phe Gly Ile Ser Val Gly Ala Ser Ser Arg Asp Ile
    690                 695                 700

Arg Leu Thr Ser Thr Leu Ser Val Ala
705                 710

<210> SEQ ID NO 113
<211> LENGTH: 713
<212> TYPE: PRT
<213> ORGANISM: Trichoderma reesei

<400> SEQUENCE: 113

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Ile Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Phe
                85                  90                  95

Ile Gly Glu Glu Met Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
```

-continued

```
                 195                 200                 205
Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
                260                 265                 270

Asn Ala Val Asn Ser Asn Gln Val Pro Thr Ser Arg Val Asp Asp Met
            275                 280                 285

Val Thr Arg Ile Leu Ala Ala Trp Tyr Leu Thr Gly Gln Asp Gln Ala
290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
                340                 345                 350

Gly Ser Ala Ala Ile Ile Gly Asn His Ala Arg Asn Ser Pro Ser Cys
            355                 360                 365

Lys Asp Lys Gly Cys Asp Asp Gly Ala Leu Gly Met Gly Trp Gly Ser
370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
                420                 425                 430

Val Phe Ile Thr Ala Asp Ser Gly Glu Gly Tyr Ile Thr Val Glu Gly
            435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
                500                 505                 510

Ala Leu Val Asp Val Leu Trp Gly Asp Val Ser Pro Ser Gly Lys Leu
            515                 520                 525

Val Tyr Thr Ile Ala Lys Ser Pro Asn Asp Tyr Asn Thr Arg Ile Val
530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
                580                 585                 590

Ala Lys Ser Gly Pro Ala Thr Gly Ala Val Val Pro Gly Gly Pro Ser
            595                 600                 605

Asp Leu Phe Gln Asn Val Ala Thr Val Thr Val Asp Ile Ala Asn Ser
610                 615                 620
```

```
Gly Gln Val Thr Gly Ala Glu Val Ala Gln Leu Tyr Ile Thr Tyr Pro
625                 630                 635                 640

Ser Ser Ala Pro Arg Thr Pro Lys Gln Leu Arg Gly Phe Ala Lys
            645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
            690                 695                 700

Arg Leu Thr Ser Thr Leu Ser Val Ala
705                 710

<210> SEQ ID NO 114
<211> LENGTH: 713
<212> TYPE: PRT
<213> ORGANISM: Trichoderma reesei

<400> SEQUENCE: 114

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
                20                  25                  30

Ser Gly Val Gly Trp Asn Gly Gly Pro Cys Val Gly Asn Thr Ser Pro
            35                  40                  45

Ala Ser Lys Ile Ser Tyr Pro Ser Leu Cys Leu Gln Asp Gly Pro Leu
        50                  55                  60

Gly Val Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Leu
                85                  90                  95

Ile Gly Glu Glu Met Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285
```

```
Val Thr Arg Ile Leu Ala Ala Trp Tyr Leu Thr Gly Gln Asp Gln Ala
        290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
                340                 345                 350

Gly Ser Ala Ala Ile Ile Gly Asn His Ala Arg Asn Ser Pro Ser Cys
        355                 360                 365

Lys Asp Lys Gly Cys Asp Gly Ala Leu Gly Met Gly Trp Gly Ser
370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
                420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
450                 455                 460

Leu Val Gln Ala Val Ala Gly Ala Asn Ser Asn Val Ile Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
                500                 505                 510

Ala Leu Val Asp Val Leu Trp Gly Asp Val Ser Pro Ser Gly Lys Leu
                515                 520                 525

Val Tyr Thr Ile Ala Lys Ser Pro Asn Asp Tyr Asn Thr Arg Ile Val
        530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
                580                 585                 590

Ala Lys Ser Gly Pro Ala Thr Gly Ala Val Val Pro Gly Gly Pro Ser
                595                 600                 605

Asp Leu Phe Gln Asn Val Ala Thr Val Thr Val Asp Ile Ala Asn Ser
        610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
                660                 665                 670

Arg Arg Asp Leu Ser Tyr Trp Asp Thr Ala Ser Gln Lys Trp Val Val
                675                 680                 685

Pro Ser Gly Ser Phe Gly Ile Ser Val Gly Ala Ser Ser Arg Asp Ile
        690                 695                 700

Arg Leu Thr Ser Thr Leu Ser Val Ala
705                 710
```

<210> SEQ ID NO 115
<211> LENGTH: 713
<212> TYPE: PRT
<213> ORGANISM: Trichoderma reesei

<400> SEQUENCE: 115

```
Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Ile Arg Tyr Ser Thr Gly Asn Thr Ala Phe Thr Pro Gly Val Gln
65                  70                  75                  80

Ala Ala Ser Thr Trp Asp Val Asn Leu Ile Arg Glu Arg Gly Gln Leu
                85                  90                  95

Ile Gly Glu Glu Met Lys Ala Ser Gly Ile His Val Ile Leu Gly Pro
            100                 105                 110

Val Ala Gly Pro Leu Gly Lys Thr Pro Gln Gly Gly Arg Asn Trp Glu
        115                 120                 125

Gly Phe Gly Val Asp Pro Tyr Leu Thr Gly Ile Ala Met Gly Gln Thr
    130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Lys Asp Lys Gly Cys Asp Asp Gly Ala Leu Gly Met Gly Trp Gly Ser
    370                 375                 380
```

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
            405                 410                 415

Asn Thr Ser Ser Gly Ala Ser Ala Arg Gly Lys Asp Val Ala Ile
        420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
        450                 455                 460

Leu Val Gln Ala Val Ala Gly Ala Asn Ser Asn Val Ile Val Val Val
465                 470                 475                 480

His Ser Val Gly Ala Ile Ile Leu Glu Gln Ile Leu Ala Leu Pro Gln
                485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
        530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
            580                 585                 590

Ala Lys Ser Gly Pro Ala Thr Gly Ala Val Val Pro Gly Gly Pro Ser
        595                 600                 605

Asp Leu Phe Gln Asn Val Ala Thr Val Thr Val Asp Ile Ala Asn Ser
        610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
            660                 665                 670

Arg Arg Asp Leu Ser Tyr Trp Asp Thr Ala Ser Gln Lys Trp Val Val
        675                 680                 685

Pro Ser Gly Ser Phe Gly Ile Ser Val Gly Ala Ser Ser Arg Asp Ile
        690                 695                 700

Arg Leu Thr Ser Thr Leu Ser Val Ala
705                 710

<210> SEQ ID NO 116
<211> LENGTH: 713
<212> TYPE: PRT
<213> ORGANISM: Trichoderma reesei

<400> SEQUENCE: 116

Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Gly Pro Cys Val Gly Asn Thr Ser Pro
        35                  40                  45

```
Ala Ser Lys Ile Ser Tyr Pro Ser Leu Cys Leu Gln Asp Gly Pro Leu
         50                  55                  60

Gly Val Arg Tyr Ser Thr Gly Asn Thr Ala Phe Thr Pro Gly Val Gln
 65                  70                  75                  80

Ala Ala Ser Thr Trp Asp Val Asn Leu Ile Arg Glu Arg Gly Gln Leu
                     85                  90                  95

Ile Gly Glu Glu Met Lys Ala Ser Gly Ile His Val Ile Leu Gly Pro
                100                 105                 110

Val Ala Gly Pro Leu Gly Lys Thr Pro Gln Gly Gly Arg Asn Trp Glu
            115                 120                 125

Gly Phe Gly Val Asp Pro Tyr Leu Thr Gly Ile Ala Met Gly Gln Thr
        130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
    195                 200                 205

Thr Thr Trp Ala Cys Glu Asp Gln Tyr Thr Leu Gln Thr Val Leu Lys
210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Pro Asp Lys Gly Cys Asp Gly Ala Leu Gly Met Gly Trp Gly Ser
    370                 375                 380

Gly Thr Val Asn Tyr Pro Tyr Phe Val Ala Pro Tyr Asp Ala Ile Asn
385                 390                 395                 400

Thr Arg Ala Ser Ser Gln Gly Thr Gln Val Thr Leu Ser Asn Thr Asp
                405                 410                 415

Asn Thr Ser Ser Gly Ala Ser Ala Ala Arg Gly Lys Asp Val Ala Ile
            420                 425                 430

Val Phe Ile Thr Ala Asp Ser Gly Glu Gly Tyr Ile Thr Val Glu Gly
        435                 440                 445

Asn Ala Gly Asp Arg Asn Asn Leu Asp Pro Trp His Asn Gly Asn Ala
    450                 455                 460

Leu Val Gln Ala Val Ala Gly Ala Asn Ser Asn Val Ile Val Val Val
465                 470                 475                 480
```

-continued

```
His Ser Val Gly Ala Ile Ile Leu Glu Gln Ile Leu Ala Leu Pro Gln
            485                 490                 495

Val Lys Ala Val Val Trp Ala Gly Leu Pro Ser Gln Glu Ser Gly Asn
            500                 505                 510

Ala Leu Val Asp Val Leu Trp Gly Asp Val Ser Pro Ser Gly Lys Leu
        515                 520                 525

Val Tyr Thr Ile Ala Lys Ser Pro Asn Asp Tyr Asn Thr Arg Ile Val
        530                 535                 540

Ser Gly Gly Ser Asp Ser Phe Ser Glu Gly Leu Phe Ile Asp Tyr Lys
545                 550                 555                 560

His Phe Asp Asp Ala Asn Ile Thr Pro Arg Tyr Glu Phe Gly Tyr Gly
                565                 570                 575

Leu Ser Tyr Thr Lys Phe Asn Tyr Ser Arg Leu Ser Val Leu Ser Thr
                580                 585                 590

Ala Lys Ser Gly Pro Ala Thr Gly Ala Val Val Pro Gly Gly Pro Ser
        595                 600                 605

Asp Leu Phe Gln Asn Val Ala Thr Val Thr Val Asp Ile Ala Asn Ser
        610                 615                 620

Gly Gln Val Thr Gly Ala Glu Val Ala Gln Leu Tyr Ile Thr Tyr Pro
625                 630                 635                 640

Ser Ser Ala Pro Arg Thr Pro Pro Lys Gln Leu Arg Gly Phe Ala Lys
                645                 650                 655

Leu Asn Leu Thr Pro Gly Gln Ser Gly Thr Ala Thr Phe Asn Ile Arg
                660                 665                 670

Arg Arg Asp Leu Ser Tyr Trp Asp Thr Ala Ser Gln Lys Trp Val Val
            675                 680                 685

Pro Ser Gly Ser Phe Gly Ile Ser Val Gly Ala Ser Ser Arg Asp Ile
        690                 695                 700

Arg Leu Thr Ser Thr Leu Ser Val Ala
705             710
```

MODIFIED BETA-GLUCOSIDASES WITH IMPROVED STABILITY

TECHNICAL FIELD

This invention relates to a modified beta-glucosidase of *Trichoderma reesei*. More specifically, the invention relates to a modified *Trichoderma reesei* beta-glucosidase with improved stability. The present invention also relates to a genetic construct comprising nucleotide sequences encoding a modified beta-glucosidase, methods for the production of a modified beta-glucosidase from host strains and the use of a modified beta-glucosidase in the hydrolysis of cellulose and in the production of compounds such as those used in the medical and food industries.

BACKGROUND OF THE INVENTION

Beta-glucosidases comprise members of Glycosyl Hydrolase Families 1 and 3 whose primary enzymatic function is the hydrolysis of the beta-glycosidic bonds linking carbohydrate residues in cellobiose or soluble cellodextrins. Some beta-glucosidases are specific for cellobiose or aryl glucosides, most of those characterized have broad specificity and can hydrolyse a broad range of substrates (Bhatia et al., 2002). Under certain conditions, these enzymes can also catalyze the synthesis of glycosidic linkages through the reverse reaction or through transglycosylation (Sinnott, 1990). Both the hydrolytic and synthetic capabilities of this enzyme class can be employed in biotechnological applications.

One major application of the hydrolytic activity of beta-glucosidase is the alleviation of product inhibition of cellulase systems. Cellobiose, a major product of cellulose hydrolysis, strongly inhibits the activity of cellobiohydrolases (EC 3.2.1.91). The inclusion of sufficient beta-glucosidase to hydrolyse cellobiose to glucose, which is less inhibitory, results in significant gains in activity at higher degrees of substrate conversion (U.S. Pat. No. 6,015,703).

Numerous other biotechnological applications of beta-glucosidase have been reviewed by Bhatia et al. (2002). Examples of applications that depend on its hydrolytic activity include the release of medically important compounds from flavanoid and isoflavanoid glycosides and the liberation of fragrant compounds in fruit juices and wines (U.S. Pat. No. 6,087,131). A representative use of the synthetic activity is the production of alkyl-glucosides for use as a detergent (Ducret et al., 2002).

The activity of glycosyl hydrolases, including beta-glucosidases, is dependent on specific protonation states of the catalytic amino acids (glutamate or aspartate) in the active site of the enzyme, which are influenced by pH. For example, beta-glucosidase I from *Trichoderma reesei* is most active in the pH range 5.0-5.5 and dramatically less so under more acidic or basic conditions (Woodward and Arnold, 1981).

The pH dependencies of the activity and stability of a protein are not necessarily related. The destabilizing effects of acidic or alkaline conditions result from protonation or deprotonation of amino acid sidechains which may not be catalytic or even in close proximity to the active site. pH-dependent denaturation primarily results from the differing $pK_a$ values of specific amino acid sidechains in the native and denatured states, which introduce pH dependence to the free energy difference between states. Additionally, proteins can become highly charged at extremes of pH and experience increased intramolecular electrostatic repulsion (Fersht, 1998).

An engineered enzyme with an altered pH optimum will not necessarily be stable at the new pH for extended periods. Several glycoside hydrolases have undergone mutagenesis to alter their activity or stability at pH values important for industrial applications. For a starch processing application, an alpha-amylase from *Bacillus licheniformis* was engineered to include two amino acid replacements, M15T and N188S, which increased its low pH (5.2) activity to 140% of wild-type (U.S. Pat. No. 5,958,739). The addition of a third mutation, H133Y, further increased the activity to more than 150% of the double mutant. Replacement of a loop in a *Bacillus* endoglucanase, identified with a rational design approach, shifted its pH optimum for a textiles application. With an Ala-Gly-Ala replacement, the pH optimum was shifted up by more than 1 pH unit (U.S. Publication No. 2005/0287656). A further example is the incorporation of amino acid replacements A162P and W62E into Cel45 endoglucanase from *Humicola insolens*. These mutations increased activity at alkaline conditions (pH 10) to 124-144% of that of the wild-type (U.S. Pat. No. 5,792,641). As a final example, the activity of a recombinant *Trichoderma* xylanase at pH above 5.5 was significantly improved by incorporation of various combinations of the replacements N10H, N11D, Y27M, and N29L (U.S. Pat. No. 5,866,408).

There are few reports of engineering beta-glucosidases though mutagenesis to modulate properties of these enzymes. For example, the thermostability of a quadruple mutant A16T/G142S/H226Q/D703G of an *Aspergillus* beta-glucosidase was increased such that it retained ~50% of its activity after one hour of incubation at 65° C. vs. 0-5% for wild-type variants. This enzyme was constructed using a combination of random mutagenesis, site-saturation and shuffling (U.S. Publication No. 2004/013401). Amino acid substitutions at one or more of positions 43, 101, 260 and 543 of *Trichoderma reesei* beta-glucosidase I resulted in modified beta-glucosidase with increased catalytic efficiency (U.S. Provisional Application No. 61/182,275). The following mutations were found to be particularly advantageous for increasing the catalytic efficiency of *Trichoderma reesei* beta-glucosidase I: V43I, V43C, V101A, V101G, F260I, F260V, F260Q, F260D, I543N, I543W, I543A, I543S, I543G, and I543L.

It is also noted that enzymes with altered pH stability profiles do not necessarily require altered pH optima to be of utility. For example, the pH of a cell culture used to express an enzyme may be different than the intended working pH of the enzyme in its application as a biocatalyst. If the stability of the enzyme is compromised at the expression pH, the overall yield of enzymatic activity will be reduced. This has been observed with *Trichoderma reesei* beta-glucosidase expressed in *Saccharomyces cerevisiae* (Cummings and Fowler, 1996). An unbuffered expression medium was observed to become more acidic over time, dropping from pH 6.0 to 2.0-3.0; this pH drop was correlated to a sharp decline in beta-glucosidase activity.

Instability can be further exacerbated by hydrodynamic shear arising from mixing of the cell culture, particularly in the presence of gas-liquid interfaces such as those produced by aeration (Weijers and Van't Riet, 1992; Elias and Joshi, 1998). Some enzymes may be further inactivated by shear stresses present during post-production processes such as ultrafiltration or in their final applications.

Shear inactivation of glycosyl hydrolases has been reported in the literature: Jones and Lee (1988) described the inactivation of a *T. reesei* cellulase mixture in a reactor system incorporating a high speed impeller, but only in the presence of air; Sachse et al. (1990) reported a higher specific activity of *T. reesei* cellulase produced in a low-shear vs. a conventional stirred reactor; Reese (1980) also reported the inactivation of *T. reesei* cellulase by shaking during hydrolysis and observed that the effect could be ameliorated by the use of surfactants; finally, Gunjikar et al. (2001) reported deactivation of exoglucanases, endoglucanases and beta-glucosidase in mixed reactors, the magnitude of which was proportionate to the mixing energy applied.

SUMMARY OF THE INVENTION

This invention relates to a modified beta-glucosidase of *Trichoderma reesei*. More specifically, the invention relates to a modified *Trichoderma reesei* beta-glucosidase with improved stability.

It is an object of the present invention to present variants of beta-glucosidase with improved stability.

The present invention provides a modified beta-glucosidase with improved stability in aqueous solution at low pH, at low pH with high agitation, low pH with high agitation, or low pH and elevated temperature. Beta-glucosidases of the present invention find utility in industrial processes requiring maintenance of activity under conditions of low pH and high aeration or high agitation, such as microbial fermentation, or low pH and elevated temperature, such as in the production of fermentable sugars by the enzymatic hydrolysis of cellulosic feedstocks.

This invention relates specifically to a modified beta-glucosidase of *Trichoderma reesei* produced by substitution of the amino acid at one or more of positions 66, 72, 101, 235, 248, 369 and 386 in the beta-glucosidase I or TrCel3A sequence (SEQ ID NO: 100). The inventors discovered that substitution of the native amino acid at one or more of these positions results in at least a 2-fold improvement, for example, from about 2-fold to about 500-fold improvement, in the stability of the beta-glucosidase in aqueous solution at low pH, at low pH and elevated temperature, at low pH with high agitation, or low pH with high aeration.

The modified TrCel3A beta-glucosidase may be derived from a parental TrCel3A beta-glucosidase that is otherwise identical to the modified TrCel3A beta-glucosidase except for the substitution of the naturally occurring amino acid at one or more of positions 66, 72, 101, 235, 248, 369, and 386. Furthermore, the modified TrCel3A beta-glucosidase may contain additional amino acid substitutions at positions other than at positions 66, 72, 101, 235, 248, 369, and 386, provided that these additional substitutions are also present in the corresponding parental TrCel3A. The modified TrCel3A beta-glucosidase may contain additional amino acid substitutions at one or more of positions 43, 96, 260 and 543.

The modified TrCel3A beta-glucosidase of the present invention exhibits from about 80% to about 99.9% amino acid sequence identity to native TrCel3A of SEQ ID NO: 1 or 100. For example, the modified TrCel3A exhibits from about 90% to 99.9% amino acid identity to the native TrCel3A of SEQ ID NO: 1 or 100 or from about 95% to 99.9% amino acid identity to the native TrCel3A of SEQ ID NO: 1 or 100.

Further, the modified TrCel3A beta-glucosidase, as defined above, exhibits at least a 2-fold improvement, for example, from about a 2-fold to about a 500-fold improvement, in stability in an aqueous solution (a) from about pH 2 to about 4.5, (b) from about pH 2 to about 4.5 aerated at a superficial gas velocity of from about 0.1 to about 100 cm/s, or from about 0.5 to 5 vvm (c) from about pH 2 to about 4.5 with agitation by shaking from about 300 to about 1000 rpm, (d) from about pH 2 to about 4.5 with agitation by impeller stifling with a tip speed of from about 0.5 to about 10 m/s; (e) from about pH 2 to about 4.5 in a bioreactor agitated at from about 0.2 to about 15 hp/100 gallons; or (f) from about pH 2 to about 4.5 at a temperature between 30° C. and 60° C.

The present invention also relates to a modified TrCel3A comprising an amino acid sequence as defined by
V661 SEQ ID NO: 2 or SEQ ID NO: 101;
SEQ ID NO: 3 or SEQ ID NO: 102;
SEQ ID NO: 5 or SEQ ID NO: 104;
SEQ ID NO: 6 or SEQ ID NO: 105;
SEQ ID NO: 7 or SEQ ID NO: 106;
SEQ ID NO: 8 or SEQ ID NO: 107;
SEQ ID NO: 9 or SEQ ID NO: 108;
SEQ ID NO: 10 or SEQ ID NO: 109;
SEQ ID NO: 11 or SEQ ID NO: 110;
SEQ ID NO: 12 or SEQ ID NO: 111;
SEQ ID NO: 13 or SEQ ID NO: 112;
SEQ ID NO: 14 or SEQ ID NO: 113;
SEQ ID NO: 15 or SEQ ID NO: 114;
SEQ ID NO: 16 or SEQ ID NO: 115;
SEQ ID NO: 4 or SEQ ID NO: 103; or
SEQ ID NO: 55 or SEQ ID NO: 116.

The invention also relates to a genetic construct for directing expression and secretion of the modified TrCel3A from a host microbe including, but not limited to, strains of *Trichoderma reesei*.

The genetic construct of the present invention comprise a nucleic acid sequence encoding a modified TrCel3A that is from about 80% to about 99.9% identical to SEQ ID NO: 1 or 100 and that comprises an amino acid substitution at one or more of positions 66, 72, 101, 235, 248, 369 and 386, which nucleic acid sequence is operably linked to nucleic acid sequences regulating its expression and secretion from a host microbe. For example, the nucleic acid sequences regulating the expression and secretion of the modified TrCel3A beta-glucosidase may be derived from the host microbe used for expression of the modified TrCel3A beta-glucosidase. The host microbe may be a yeast, such as *Saccharomyces cerevisiae*, or a filamentous fungus, such as *Trichoderma reesei*.

The invention also relates to a genetic construct as defined above, wherein the modified TrCel3A beta-glucosidase encoded by the genetic construct further comprises additional amino acid substitutions at positions other than 66, 72, 101, 235, 248, 369 and 386. The modified TrCel3A beta-glucosidase encoded by the genetic construct may contain additional amino acid substitutions at one or more of positions 43, 96, 260 and 543.

The invention also relates to a genetically modified microbe comprising a genetic construct encoding the modified TrCel3A beta-glucosidase the genetically modified microbe being capable of expression and secretion of a modified TrCel3A beta-glucosidase exhibiting from about 80% to about 99.9% amino acid sequence identity to SEQ ID NO: 1 or 100 and comprising an amino acid substitution at one or more of positions 66, 72, 101, 235, 248, 369 and 386. The genetically modified microbe may be capable of expression and secretion of a modified TrCel3A beta-glucosidase further comprising additional amino acid substitutions at positions other than 66, 72, 101, 235, 248, 369 and 386. The modified TrCel3A beta-glucosidase expressed and secreted by the genetically modified microbe may contain additional amino acid substitutions at one or more of positions 43, 96, 260 and 543. The genetically modified microbe may be a yeast or filamentous fungus. For example, the genetically modified microbe may be a species of *Saccharomyces, Pichia, Hansenula, Trichoderma, Hypocrea, Aspergillus, Fuscarium, Humicola* or *Neursopora*.

The present invention also relates to the use of a modified TrCel3A beta-glucosidase, as defined above, in a hydrolysis reaction containing a cellulosic substrate and a cellulase mixture comprising the modified TrCel3A beta-glucosidase.

The invention also relates to a process of producing a modified TrCel3A beta-glucosidase, as defined above, including transformation of a yeast or fungal host with a genetic construct comprising a nucleic acid sequence encoding the modified TrCel3A beta-glucosidase, selection of recombinant yeast or fungal strains expressing the modified TrCel3A beta-glucosidase, culturing the selected recombinant strains in submerged liquid fermentations under conditions that induce the expression of the modified TrCel3A beta-glucosidase and recovering the modified TrCel3A beta-glucosidase by separation of the culture filtrate from the host microbe.

The modified TrCel3A beta-glucosidase of the present invention finds use in a variety of applications in industry that require stability at low pH, a combination of low pH and high aeration, a combination of low pH and high agitation or a combination of low pH and elevated temperature. For example, modified *Trichoderma reesei* TrCel3A beta-glucosidase, as described herein, may be used in industrial processes in which lignocellulosic substrates are converted to fermentable sugars for the production of ethanol or other products, or microbial fermentation processes.

BRIEF DESCRIPTION OF THE DRAWINGS

FIG. 11 shows an alignment of the amino acid sequences of 45 fungal Family 3 beta-glucosidases, including TrCel3A, a consensus Family 3 beta-glucosidase sequence, and the % sequence identity of each amino acid sequence to that of TrCel3A. A graphical representation of the frequency of occurrence of the amino acid at each position of the consensus Family 3 beta-glucosidase sequence of FIG. 11 among the 45 fungal Family 3 beta-glucosidases is shown underneath the aligned sequences.

DETAILED DESCRIPTION OF THE INVENTION

Figure 1:
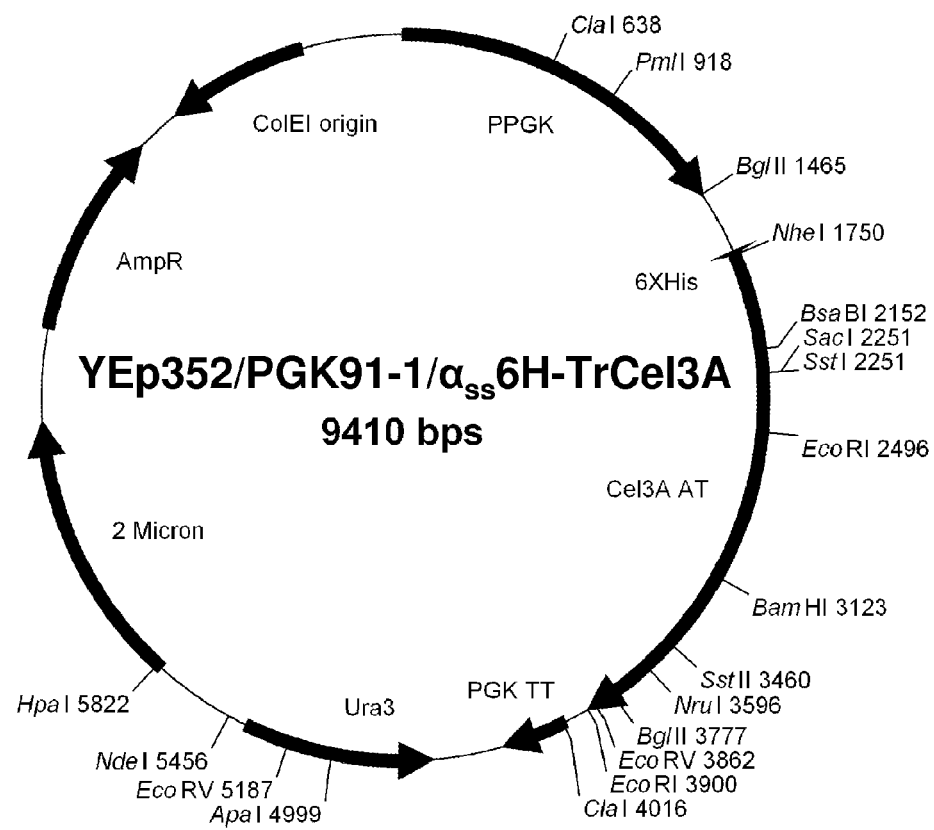
FIG. 1 depicts plasmid vector YEp352/PGK91-1/$\alpha_{ss}$6H-TrCel3A directing the expression and secretion of native and modified TrCel3A from recombinant *Saccharomyces cerevisiae*.

The present invention relates to modified beta-glucosidase. More specifically, the invention relates to modified beta-glucosidase I of *Trichoderma reesei* (hereinafter TrCel3A) with increased stability in aqueous solutions at low pH, at low pH with high aeration, low pH with high agitation, or low pH and elevated temperature relative to the parental TrCel3A from which it is derived. The present invention also relates to genetic constructs comprising nucleotide sequences encoding for modified TrCel3A, methods for the production of the modified TrCel3A from host strains and the use of the modified TrCel3A to alleviate product inhibition of cellulases in the hydrolysis of cellulose. The present invention also relates to the use of the modified TrCel3A to catalyze the production of other chemical compounds, including but not limited to those from the medical or food industries, either through hydrolysis, reverse hydrolysis or transglycosylation.

The following description is of a preferred embodiment by way of example only and without limitation to the combination of features necessary for carrying the invention into effect.

Modified Beta-glucosidases

The term "beta-glucosidases" refers to enzymes classified in EC3.2.1.21 and that transfer a glycosyl group between oxygen nucleophiles, generally resulting in the hydrolysis of a beta-glucosidic bond linking carbohydrate residues in aryl, amino-, alkyl-beta-D-glucosides, cyanogenic-glucosides, short chain oligosaccharides and disaccharides. In oligosaccharides containing more than two glucosides, beta-glucosidase activity decreases as chain length increases. Beta-glucosidases hydrolyze beta-1,4-glucosidic bonds via a double displacement reaction, resulting in a net retention of anomeric configuration. Two acidic amino acids, aspartic (D) and/or glutamic (E) acid, are directly involved in substrate catalysis. One of these residues acts as a nucleophile and forms an enzyme-glycosyl intermediate. The other acidic residue acts as an acid-base catalyst. In the *Trichoderma reesei* beta-glucosidase 1, herein referred to as TrCel3A whose amino acid sequence is presented in SEQ ID NO: 100, the aspartic acid at position 236 serves as the nucleophile and the glutamic acid at position 447 is the acid-base catalyst.

Beta-glucosidases are a subset of beta-glycosidases belonging to glycosyl hydrolase (GH) Families 1 and 3, using the classification system developed by Henrissat and coworkers (Henrissat, B. (1991); Henrissat, B. and Bairoch, A. (1996)). There are currently 115 GH families that have been identified using this classification system, which are listed in the database of Carbohydrate Active Enzymes (CAZy) Family 1 comprises beta-glucosidases from archaebacteria, plants and animals. Beta-glucosidases from some bacteria, mold and yeast belong to Family 3. For the purpose of this invention, a "beta-glucosidase" is therefore defined as any protein that is classified in EC 3.2.1.21 and categorized as a Family 3 glycosyl hydrolase according to the CAZy system.

The three dimensional structure of beta-D-glucan exohydrolase, a Family 3 glycosyl hydrolase, was described by Varghese et al. (1999). The structure was of a two domain globular protein comprising a N-terminal (alpha/beta)$_8$ TIM-barrel domain and a C-terminal a six-stranded beta-sandwich, which contains a beta-sheet of five parallel beta-strands and one antiparallel beta-strand, with three alpha-helices on either side of the sheet. This structure is likely shared by other Family 3 enzymes.

Figures 1, 11B:
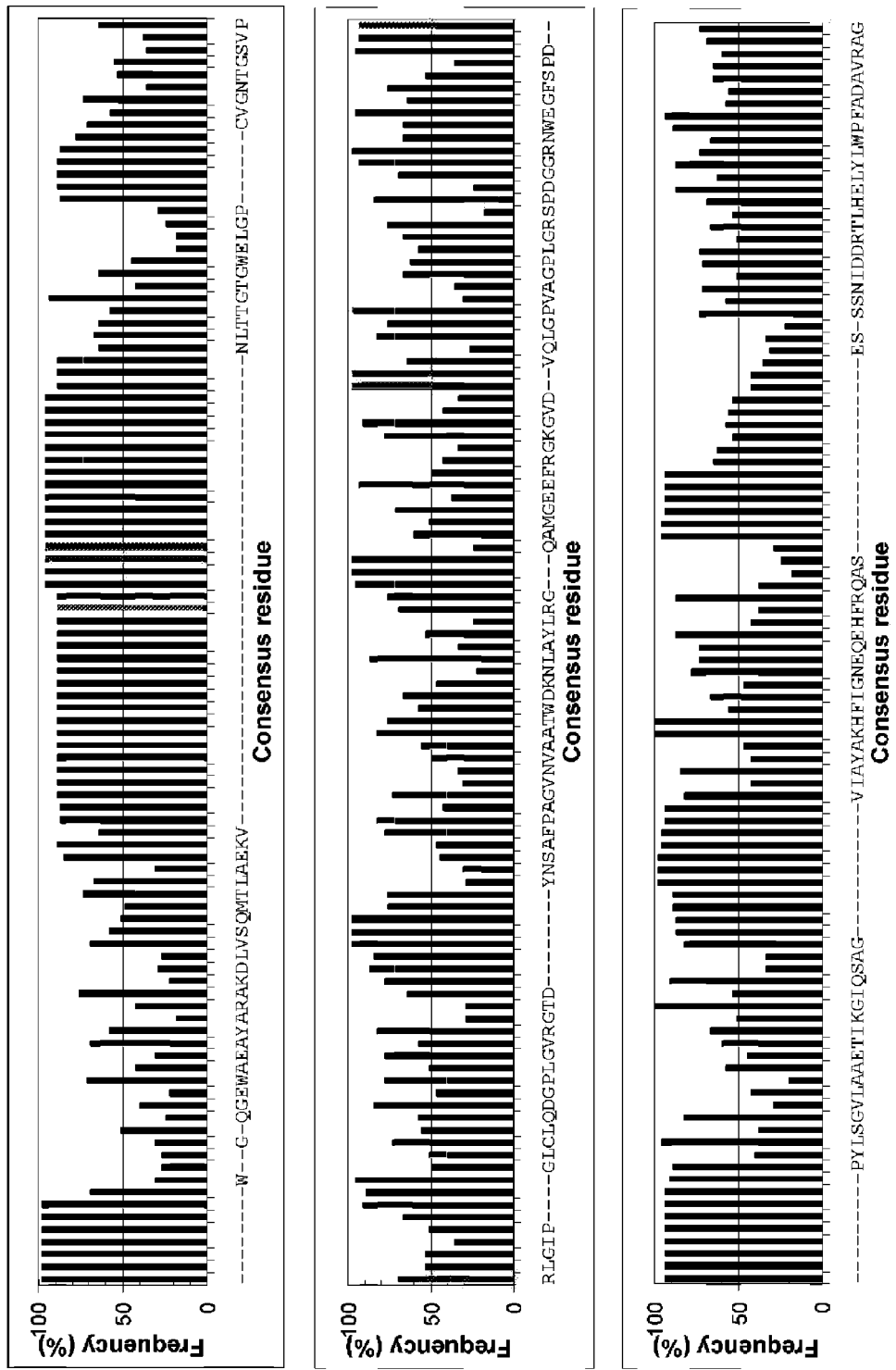
Figures 2, 11B:
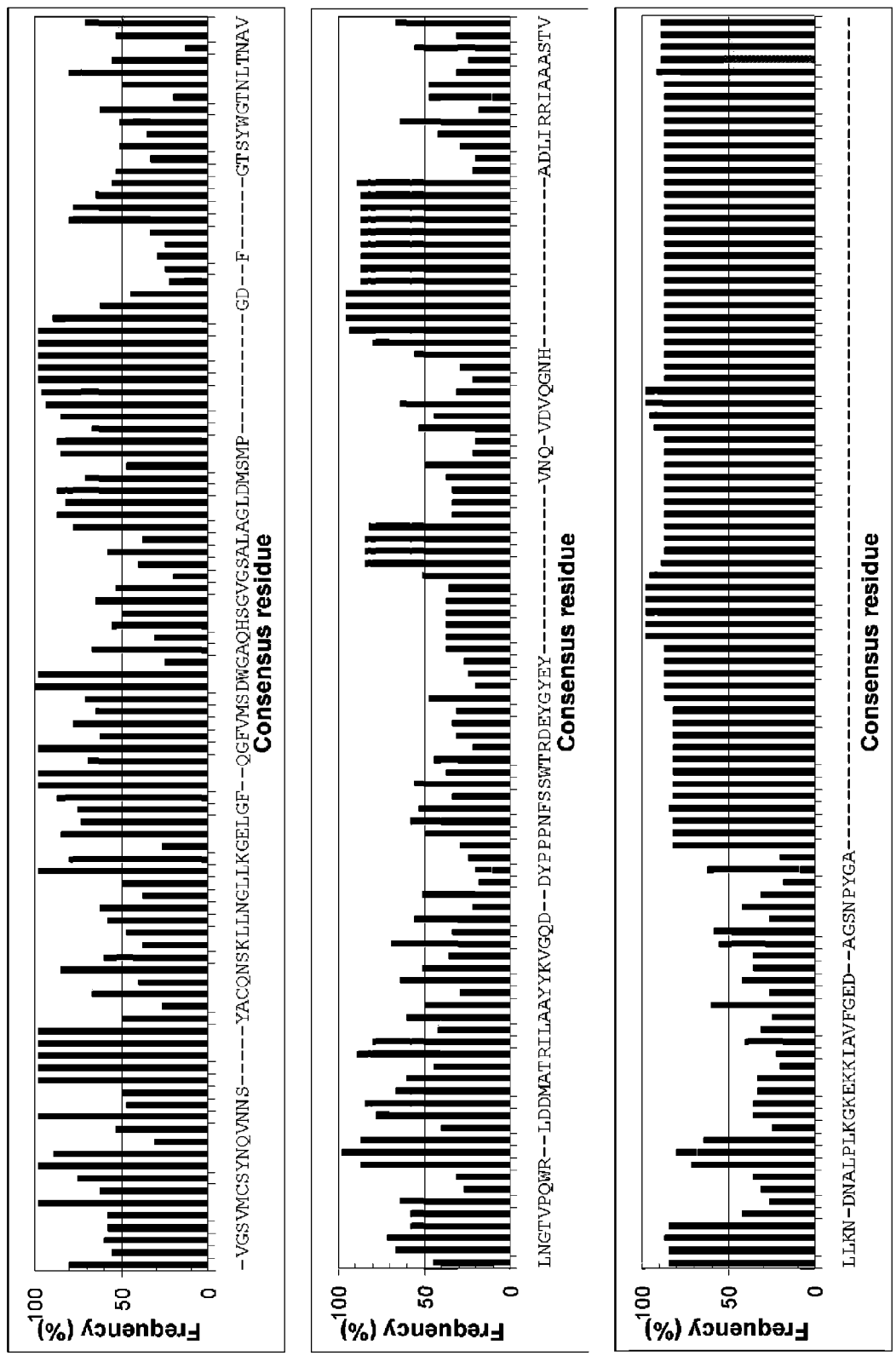
Figures 3, 11B:
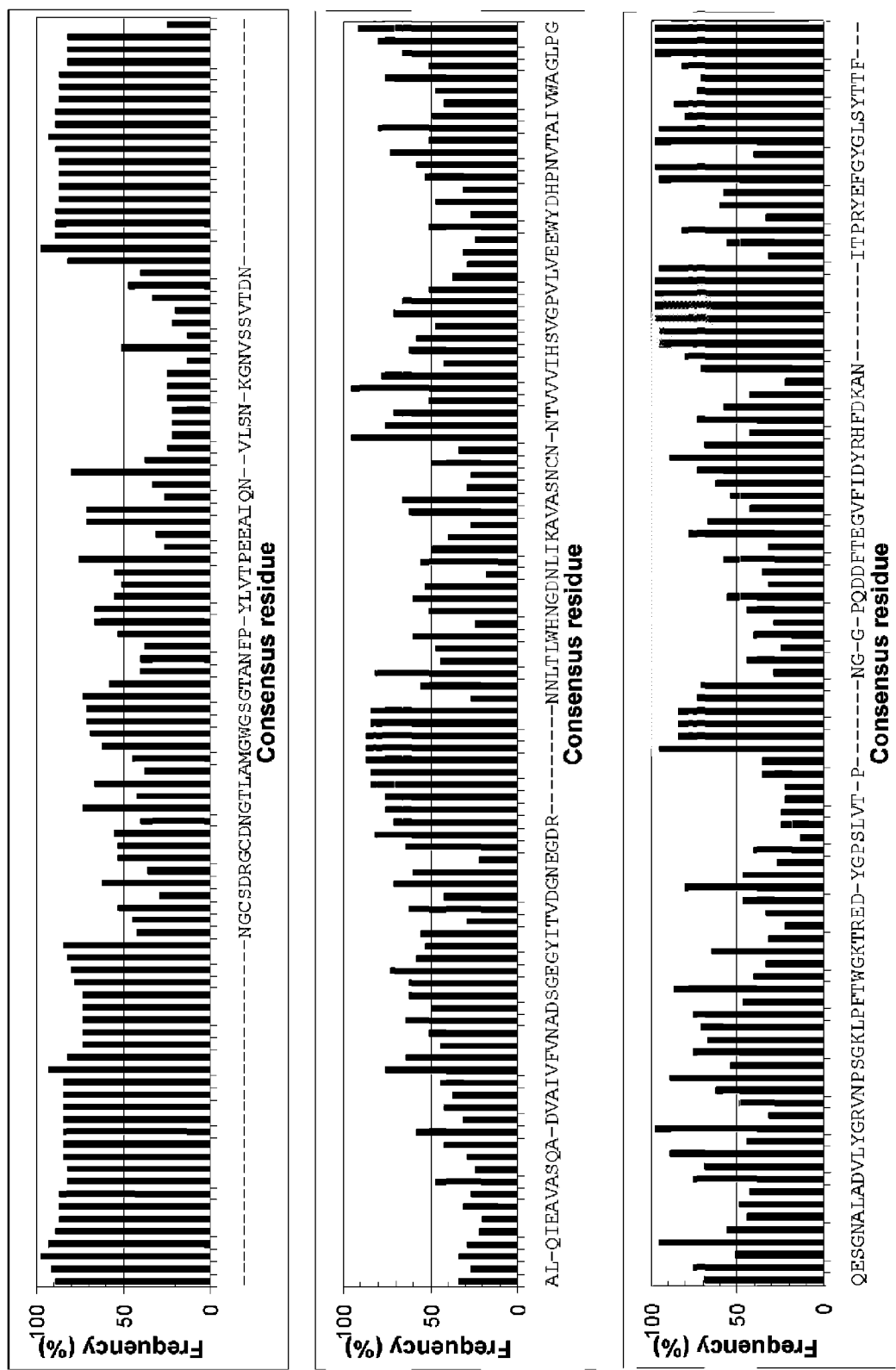

As shown in FIG. 11, the primary amino acid sequence of Family 3 beta-glucosidases show a high degree of similarity. Multiple alignment across 45 Family 3 beta-glucosidase amino acid sequences shows that the most naturally occurring Family 3 beta-glucosidases of fungal origin show from about 40% to about 100% amino acid sequence identity to the amino acid sequence of TrCel3A (FIG. 11). In particular, there are several regions of very high amino acid sequence conservation within the Family 3 beta-glucosidases including, for example, from amino acids 225-256 and 439-459, containing the catalytic amino acids D236 and E447, respectively.

By "TrCel3A" it is meant the Family 3 glycosyl hydrolase produced by *Trichoderma reesei* defined by the amino acid sequence in SEQ ID NO: 100. TrCel3A is also known as *Trichoderma reesei* β-glucosidase or BGL1. By "native" or ild-type" TrCel3A, it is meant the TrCel3A of SEQ ID NO: 100 without any amino acid substitutions. By "modified TrCel3A", it is meant a TrCel3A which comprises one or more amino acid substitutions, introduced by genetic engineering techniques, selected from the group consisting of V66X (i.e., Val at position 66 is replaced by any amino acid X), S72X, V101X, T235X, N248X, N369X, A386X. Genetic engineering techniques for altering amino acid sequences include, but are not limited to, site-directed mutagenesis, cassette mutagenesis, random mutagenesis, synthetic oligonucleotide construction, cloning and other genetic engineering techniques as would be known by those of skill in the art (Eijsink V G, et al. 2005.). It will be understood that a modified TrCel3A may be derived from wild-type TrCel3A or from a TrCel3A that already contains other amino acid substitutions. Modified TrCel3A beta-glucosidases of the present invention include those comprising amino acid substitutions at any one of V66X, S72X, V101X, T235X, N248X, N369X and A386X, at any two of V66X, S72X, V101X, T235X, N248X, N369X and A386X, at any three of V66X, S72X, V101X, T235X, N248X, N369X and A386X, at any four of V66X, S72X, V101X, T235X, N248X, N369X and A386X, at any five of V66X, S72X, V101X, T235X, N248X, N369X and A386X, at any six of V66X, S72X, V101X, T235X, N248X, N369X and A386X, or at all seven of V66X, S72X, V101X, T235X, N248X, N369X and A386X.

It will be understood that the modified TrCel3A beta-glucosidase may be derived from wild-type TrCel3A beta-glucosidase or from a TrCel3A beta-glucosidase that contains other amino acid substitutions. For example, the modified TrCel3A beta-glucosidase may contain amino acid substitution at one or more of positions 43, 96 260 and 543. Alternatively, after production of a modified TrCel3A beta-glucosidase comprising mutations at one or more of positions 66, 72, 101, 235, 248, 369 and 386, it may be subsequently further modified to contain additional amino acid substitutions, including but not limited to those set forth above.

As used herein in respect of modified TrCel3A beta-glucosidase amino acid sequences, "derived from" refers to the isolation of a target nucleic acid sequence element encoding the desired modified TrCel3A beta-glucosidase using genetic material or nucleic acid or amino acid sequence information specific to the corresponding parental TrCel3A beta-glucosidase. As is known by one of skill in the art, such material or sequence information can be used to generate a nucleic acid sequence encoding the desired modified TrCel3A beta-glucosidase using one or more molecular biology techniques including, but not limited to, cloning, sub-cloning, amplification by PCR, in vitro synthesis, and the like.

In a first embodiment of the invention, the modified TrCel3A, as defined above, exhibits from about 80% to about 99.9% amino acid sequence identity to SEQ ID NO: 1 or 100, or any amount therebetween. For example, the modified TrCel3A may exhibit from about 90% to about 99.9% amino acid sequence identity to SEQ ID NO: 1 or 100 or from about 95% to about 99.9% amino acid sequence identity to SEQ ID NO: 1 or 100. Methods to align amino acid sequences are well known and available to those of skill in the art and include BLAST (Basic Local Alignment Search Tool, see Altschul et al., J. Mol. Biol. 215:403-410, 1990) which is useful for aligning two sequences and CLUSTALW for alignment of two or more sequences. Sequence identity may also be determined by manual alignment and visual inspection.

In other embodiments of the invention, the modified TrCel3A exhibits from about 80% to about 99.9% amino acid sequence identity to SEQ ID NO: 1 or 100 and at least a 2-fold improvement in stability in an aqueous solution a) from about pH 2 to about 4.5, (b) from about pH 2 to about 4.5 aerated at a superficial gas velocity of from about 0.1 to about 100 cm/s, or (c) from about pH 2 to about 4.5 with agitation by shaking from about 300 to about 1000 rpm, (d) from about pH 2 to about 4.5 with agitation by impeller stirring with a tip speed of from about 0.5 to about 10 m/s, (e) from about pH 2 to about 4.5 in a bioreactor agitated at from about 0.2 to about 15 hp/100 gallons, or (f) from about pH 2 to about 4.5 at a temperature between 30° C. and 60° C.

By "parental TrCel3A", it is meant a TrCel3A that that does not contain a substitution of its original amino acid(s) at positions 66, 72, 101, 235, 248, 369 or 386 and that is otherwise identical to the modified TrCel3A. As such, the parental TrCel3A may contain amino acid substitutions at as many as 116 (i.e, 20% of 582 amino acids) other positions that have been introduced by genetic engineering or other techniques. For example, the parental TrCel3A may comprise amino acid substitutions at one or more of positions 43, 96, 260 and 543.

In order to assist one of skill in the art regarding those amino acid positions of the TrCel3A beta-glucosidase at which amino acid substitutions (other than V66X, S72X, V101X, T235X, N248X, N369X and A386X) may be made and produce an active beta-glucosidase, an alignment of 45 Family 3 beta-glucosidases derived from fungal sources along with a consensus beta-glucosidase sequence consisting of the amino acids that naturally occur with the highest frequency at each position is provided in FIG. 11 along with a graph showing the frequency of occurrence of each amino acid of the consensus sequence at each position. Using the information provided in FIG. 11, one of skill in the art would recognize regions of low sequence conservation to other Family 3 beta-glucosidases. Non-limiting examples of such regions include, for example, the regions between positions 1-20, 303-323 and 403-414 and select amino acid positions within these regions.

As described in more detail herein, several modified TrCel3A beta-glucosidases have been prepared that exhibit increased stability under conditions of low pH and agitation. A list of several mutants, which is not to be considered limiting in any manner, is presented in Table 1.

TABLE 1

TrCel3A beta-glucosidases with improved stability

| New mutant TrCel6A-S413P | SEQ ID NO: |
|---|---|
| TrCel3A-V66I | 2 |
| TrCel3A-S72N | 3 |
| TrCel3A-V101M | 4 |
| TrCel3A-T235S | 5 |
| TrCel3A-N248K | 6 |
| TrCel3A-N369K | 7 |
| TrCel3A-A386T | 8 |
| TrCel3A-V66I-S72N | 9 |
| TrCel3A-S72N-F96L-V101M | 10 |
| TrCel3A-S72N-F96L-V101M-N369K | 11 |
| TrCel3A-S72N-V101M-N369K-A386T | 12 |
| TrCel3A-V66I-S72N-V101M-N369K-A386T | 13 |
| TrCel3A-S72N-F96L-V101M-N369K-A386T | 14 |
| TrCel3A-V66I-S72N-F96L-V101M-N369K-A386T | 15 |
| TrCel3A-S72E-F96L-V101M-N369K-A386T | 16 |
| TrCel3A-S72N-F96L-V101M-N369P-A386T | 55 |
| TrCel3A-V66I full | 101 |
| TrCel3A-S72N full | 102 |
| TrCel3A-V101M full | 104 |
| TrCel3A-T235S full | 105 |
| TrCel3A-N248K full | 106 |
| TrCel3A-N369K full | 107 |
| TrCel3A-A386T full | 108 |
| TrCel3A-V66I-S72N full | 109 |
| TrCel3A-S72N-F96L-V101M full | 110 |
| TrCel3A-S72N-F96L-V101M-N369K full | 111 |
| TrCel3A-S72N-V101M-N369K-A386T full | 112 |
| TrCel3A-V66I-S72N-V101M-N369K-A386T full | 113 |
| TrCel3A-S72N-F96L-V101M-N369K-A386T full | 114 |
| TrCel3A-V66I-S72N-F96L-V101M-N369K-A386T full | 115 |
| TrCel3A-S72E-F96L-V101M-N369K-A386T full | 103 |
| TrCel3A-S72N-F96L-V101M-N369P-A386T full | 116 |

Modified TrCel3A beta-glucosidases with Improved Stability.

Functional inactivation of enzymes is measured by determination of the inactivation rate constant, $k_i$, a parameter with units of inverse time which determines the instantaneous rate of decrease of enzyme activity in the equation $A_t/A_0 = e^{-k_i \cdot t}$ where $A_t$ is the activity at time t and $A_0$ is the initial activity of the system. This parameter can be equivalently expressed as tau, the mean active lifetime of a given enzyme, by taking the inverse of ki, or as a half-life by multiplying tau by the natural logarithm of 2. Enzymes which are more stable have a smaller value of $k_i$ and corresponding larger values of tau and half-life. As defined herein, therefore, "improved stability" means a larger, higher or increased value of tau, expressed in units of time, such as hours.

For the purposes of the present invention, a modified TrCel3A exhibits improved stability (i.e, a larger value of tau) with respect to the corresponding parental Family 3 glycosyl hydrolase or parental TrCel3A in aqueous solution (a) with a low pH, (b with low pH and high aeration, (c) with low pH and high agitation or (d) with low pH and elevated temperature.

By "low pH", it is meant any pH from about 2 to about 4.5, or any pH therebetween, for example any pH from about 2.5 to about 4.0, or any pH therebetween; for example pH 2.0, 2.2, 2.4, 2.6, 2.8, 3.0, 3.2, 3.4, 3.6, 3.8, 4.0, 4.2, 4.4, 4.5 or any pH therebetween.

By "high aeration", it is meant provision of a gas to the aqueous solution at a superficial gas velocity of from about 0.1 to about 100 cm/s, or any rate therebetween, for example any rate from about 0.1 to about 1 cm/s, or any rate therebetween. An alternative parameter to measure aeration rate that is known to one of skill in the art is vessel volumes per minute (vvm). In the context of the present invention, therefore, "high aeration" may also be defined as provision of a gas to the aqueous solution at a rate of from about 0.5 to about 5 vvm, or any rate therebetween. The gas may be a single gas, such as oxygen, nitrogen, and carbon dioxide, or a mixture of gases such as air.

By high agitation, it is meant mixing of the aqueous solution by shaking from about 300 to about 1000 rpm, or any rate therebetween, or by impeller stifling with a tip speed of from about 0.5 to about 10 m/s, or any rate therebetween, for example from about 0.5 to about 3 m/s. An alternative parameter to measure agitation that is known to one of skill in the art, particularly as it relates to agitation in bioreactors, is horse power (hp) per 100 gallons. In the context of the present invention, therefore, "high agitation" may also be defined as mixing of the aqueous solution at from about 0.2 hp/100 gallons to about 15 hp/100 gallons.

By elevated temperature, it is meant any temperature from about 30° C. to about 60° C., or any temperature therebetween, for example any temperature from about 40° C. to about 60° C., or any temperature therebetween, for example 30, 35, 40, 45, 50, 52, 54, 56, 58, 60° C., or any temperature therebetween.

The modified TrCel3A exhibits improved stability relative to a parental TrCel3A from which it is derived when the tau of the modified TrCel3A is at least 2-fold, for example from about 2-fold to about 500-fold, higher than the tau of the parental TrCel3A under identical conditions of low pH, low pH and high aeration, low pH and high agitation, or low pH and elevated temperature. For example, the tau of the modified TrCel3A may be from about 2-fold to 250-fold higher than the tau of the corresponding parental TrCel3A, or any value in between, from about 3-fold to about 200-fold higher than the tau of the corresponding parental TrCel3A, or any value in between, or for example the tau may be from about 2-, 3-, 5- 10-, 20-, 30-, 40-, 50-, 60-, 70-, 80-, 90-, 100-, 120-, 140-, 160-, 180-, 200-, 220-, 240-, 250-, 300-, 350-, 400-, 450-, or 500-fold higher, or any value therebetween, than the tau of the corresponding parental TrCel3A under identical conditions. Example 8 details an assay for measuring the tau of native and modified TrCel3A beta-glucosidases.

The stability of several modified TrCel6A beta-glucosidases were compared by incubation of the enzymes at low pH (3.0) under conditions of severe agitation produced by swirling the enzyme solution in baffled flasks at 400 rpm and measuring the residual activity at several time points taken over a period of 30 minutes. The residual beta-glucosidase activity was determined via a chromogenic assay using para-nitrophenyl-beta-D-glucopyranoside as a substrate as described in Example 1

Figure 5:
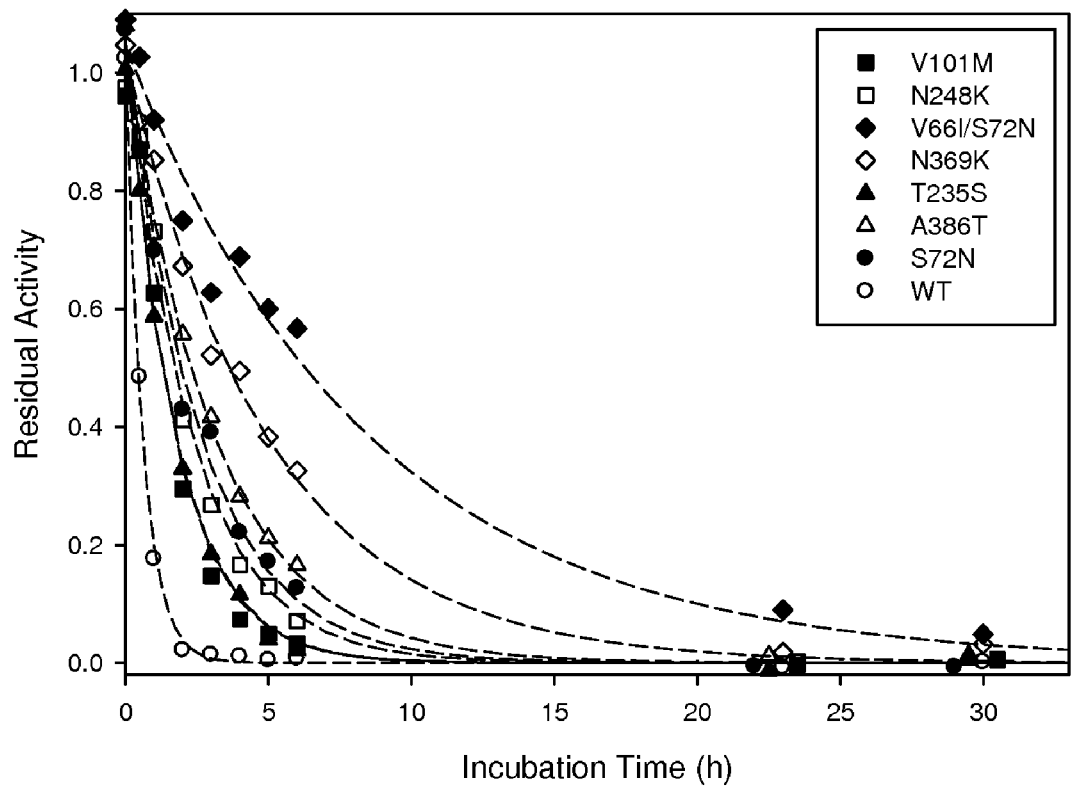
FIG. 5 shows the inactivation of parental and modified TrCel3A beta-glucosidases at pH 3.0 and 30° C. shaken at 400 rpm in baffled flasks for 0 to 30 hours. The concentration of TrCel3A in these assays ranged from 4.8-10.8 μg/mL and the residual activity at each time interval was measured as described in Example 1.
Figure 7:
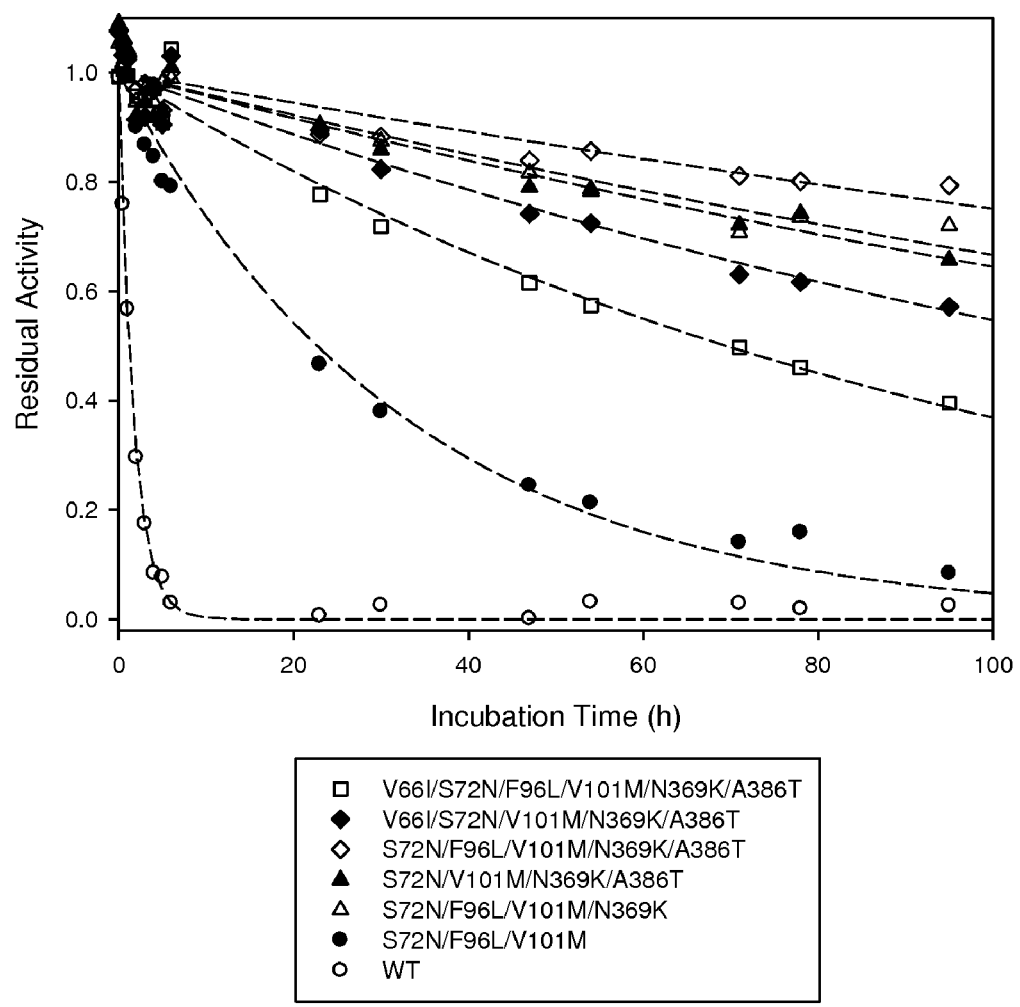
FIG. 7 depicts the inactivation of parental and modified TrCel3A beta-glucosidases at pH 3.0 and 30° C. shaken at 400 rpm in baffled flasks for 0 to 100 hours. The concentration of TrCel3A in these assays ranged from 4.8-10.8 μg/mL and the residual activity at each time interval was measured as described in Example 1.
Figure 8:
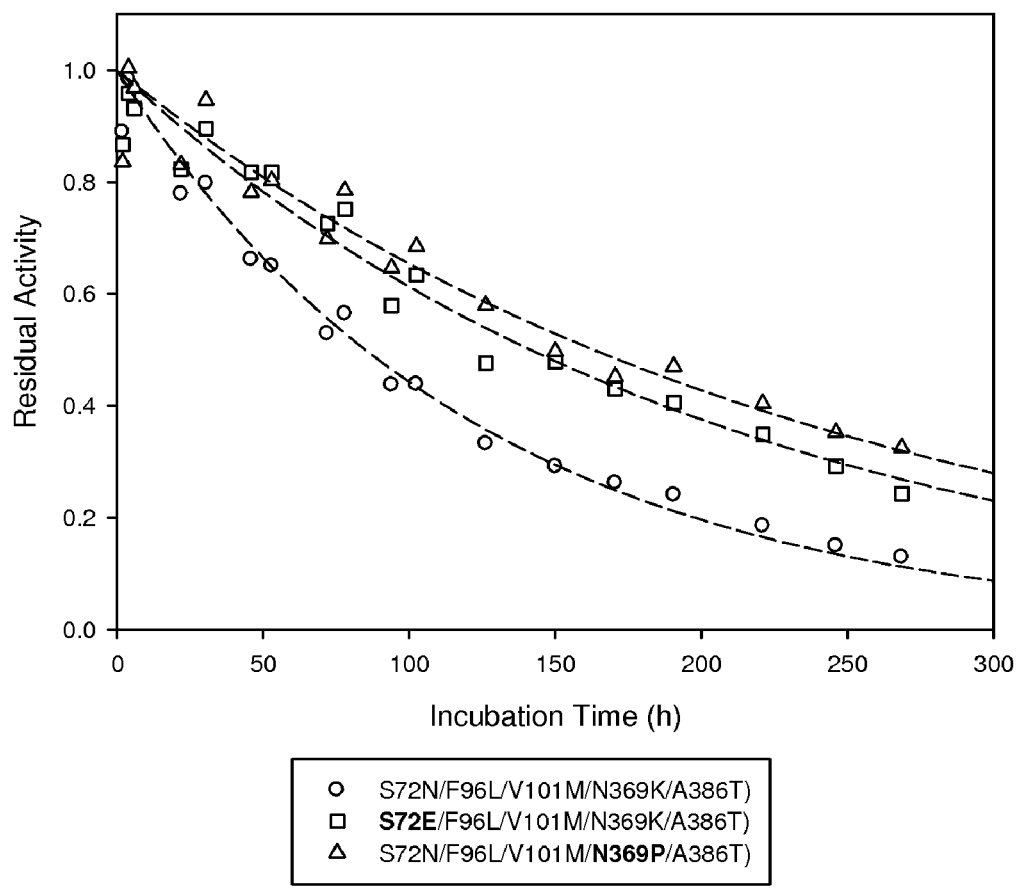
FIG. 8 depicts the inactivation of modified TrCel3A beta-glucosidases at pH 3.0 and 30° C. shaken at 400 rpm in baffled flasks for 0 to 300 hours. The concentration of modified TrCel3A in these assays ranged from 4.8-10.8 μg/mL and the residual activity at each time interval was measured as described in Example 1.

The effect of amino acid substitutions at positions 66, 72, 101, 235, 248, 369 and 386, was determined via a comparative study of the modified TrCel3A and the parental wild-type TrCel3A. The relative increase in tau over that of the parental TrCel3A (where the value of tau for the parental TrCel3A is set to 1.0) is shown in Table 2 below. Inactivation curves for these variants are shown in FIGS. 5, 7 and 8.

TABLE 2

Increased stability of Modified TrCel3A

| Amino acid substitution | Relative Tau |
|---|---|
| None (TrCel3A) | 1.0 |
| S72N | 4.3 |
| V66I-S72N | 13.9 |
| V101M | 2.9 |
| T235S | 2.9 |
| N248K | 3.8 |
| N369K | 8.2 |
| A386T | 5.1 |
| S72N-F96L-V101M | 19.4 |
| S72N-F96L-V101M-N369K | 145 |
| S72N-F96L-V101M-N369K-A386T | 134 |
| S72N-V101M-N369K-A386T | 205 |
| V66I-S72N-V101M-N369K-A386T | 97 |
| V66I-S72N-F96L-V101M-N369K-A386T | 59 |
| S72E-F96L-V101M-N369K-A386T | 194 |
| S72N-F96L-V101M-N369P-A386T | 330 |

Genetic Constructs Encoding Modified TrCel3A

The present invention also relates to a genetic construct comprising a nucleic acid sequence encoding the modified TrCel3A operably linked to regulatory nucleic acid sequences directing the expression and secretion of the modified TrCel3A from a host microbe. By "regulatory nucleic acid sequences" it is meant nucleic acid sequences directing the transcription and translation of the modified TrCel3A-encoding nucleic acid sequence and a nucleic acid sequence encoding a secretion signal peptide capable of directing the secretion of the modified TrCel3A from the host microbe. The regulatory nucleic acid sequences are preferably functional in a fungal host. The regulatory nucleic acid sequences may be derived from genes that are highly expressed and secreted in the host microbe under industrial fermentation conditions. For example, the regulatory nucleic acid sequences may be derived from any one or more of the Trichoderma reesei cellulase or hemicellulase genes.

The genetic construct may further comprise a selectable marker gene to enable isolation of a genetically modified microbe transformed with the construct as is commonly known to those of skill in the art. The selectable marker gene may confer resistance to an antibiotic or the ability to grow on medium lacking a specific nutrient to the host organism that otherwise could not grow under these conditions. The present invention is not limited by the choice of selectable marker gene, and one of skill in the art may readily determine an appropriate gene. For example, the selectable marker gene may confer resistance to hygromycin, phleomycin, kanamycin, geneticin, or G418, or may complement a deficiency of the host microbe in one of the trp, arg, leu, pyr4, pyr, ura3, ura5, his, or ade genes or may confer the ability to grow on acetamide as a sole nitrogen source.

The genetic construct may further comprise other nucleic acid sequences, for example, transcriptional terminators, nucleic acid sequences encoding peptide tags, synthetic sequences to link the various other nucleic acid sequences together, origins of replication, and the like. The practice of the present invention is not limited by the presence of any one or more of these other nucleic acid sequences.

Genetically Modified Microbes Producing Modified TrCel3A

The modified TrCel3A may be expressed and secreted from a genetically modified microbe produced by transformation of a host microbe with a genetic construct encoding the modified TrCel3A. The host microbe may be a yeast or a filamentous fungus, particularly those microbes that are members of the phylum Ascomycota. Genera of yeasts useful as host microbes for the expression of modified TrCel3A beta-glucosidase of the present invention include *Saccharomyces, Pichia, Hansenula, Kluyveromyces, Yarrowia,* and *Arxula*. Genera of fungi useful as microbes for the expression of modified TrCel3A beta-glucosidases of the present invention include *Trichoderma, Hypocrea, Aspergillus, Fusarium, Humicola, Neurospora,* and *Penicillium*. For example, the host microbe may be an industrial strain of *Trichoderma reesei*. Typically, the host microbe is one which does not express a parental TrCel3A.

The genetic construct may be introduced into the host microbe by any number of methods known by one skilled in the art of microbial transformation, including but not limited to, treatment of cells with $CaCl_2$, electroporation, biolistic bombardment, PEG-mediated fusion of protoplasts (e.g. White et al., WO 2005/093072). After selecting the recombinant fungal strains expressing the modified TrCel3A, the selected recombinant strains may be cultured in submerged liquid fermentations under conditions that induce the expression of the modified TrCel3A.

Production of Modified TrCel3A

The modified TrCel3A of the present invention may be produced in a fermentation process using a genetically modified microbe comprising a genetic construct encoding the modified TrCel3A in submerged liquid culture fermentation.

Submerged liquid fermentations of microorganisms, including *Trichoderma* and related filamentous fungi, as one of skill in the art would know are typically conducted as a batch, fed-batch or continuous process. In a batch process, all the necessary materials, with the exception of oxygen for aerobic processes, are placed in a reactor at the start of the operation and the fermentation is allowed to proceed until completion, at which point the product is harvested. In a fed-batch process, the culture is fed continuously or sequentially with one or more media components without the removal of the culture fluid. In a continuous process, fresh medium is supplied and culture fluid is removed continuously at volumetrically equal rates to maintain the culture at a steady growth rate, The process for producing the modified TrCel3A of the present invention may be performed as a batch, fed-batch, a repeated fed-batch, a continuous process or any combination thereof. For example, the process may be a fed-batch process.

One of skill in the art is aware that fermentation medium comprises a carbon source, a nitrogen source and other nutrients, vitamins and minerals can be added to the fermentation media to improve growth and enzyme production of the host cell. These other media components may be added prior to, simultaneously with or after inoculation of the culture with the host cell.

For the process for producing the modified TrCel3A of the present invention, the carbon source may comprise a carbohydrate that will induce the expression of the modified TrCel3A from a genetic construct in a genetically modified microbe. For example, if the genetically modified microbe is a strain of *Trichoderma* and the genetic construct comprises a cellulase or hemicellulase promoter operably linked of the modified TrCel3A nucleic acid sequence, the carbon source may comprise one or more of cellulose, cellobiose, sophorose, xylan, xylose, xylobiose and related oligo- or poly-saccharides known to induce expression of cellulases, hemicellulases and beta-glucosidase in *Trichoderma*.

In the case of batch fermentation, the carbon source may be added to the fermentation medium prior to or simultaneously with inoculation. In the cases of fed-batch or continuous operations, the carbon source may also be supplied continuously or intermittently during the fermentation process.

The process for producing the modified TrCel3A of the present invention may be carried at a temperature from about 20° C. to about 40° C., or any temperature therebetween, or from 20, 22, 25, 26, 27, 28, 29, 30, 32, 35, 37, 40° C. or any temperature therebetween.

The process for producing the modified TrCel3A of the present invention may be carried out at a pH from about 3.0 to 6.5, or any pH therebetween, for example from about pH 3.0, 3.2, 3.4, 3.5, 3.7, 3.8, 4.0, 4.1, 4.2, 4.3, 4.4, 4.5, 4.6, 4.7, 4.8, 4.9, 5.0, 5.2, 5.4, 5.5, 5.7, 5.8, 6.0, 6.2, 6.5 or any pH therebetween.

The process for producing the modified TrCel3A of the present invention may be carried out aerobically, with a superficial gas velocity of from about 0.1 to about 100 cm/s. For example, the superficial gas velocity may be from about 0.1 to about 1.0 cm/s. Alternatively, the superficial gas velocity used in the process for producing the modified TrCel3A of the present invention may be from about 0.5 to about 5 vvm, or any rate therebetween.

The process for producing the modified TrCel3A of the present invention may be carried out in a shakeflask which is shaken from about 300 to about 1000 rpm, or in a bioreactor which is agitated by impeller with an impeller tip speed of from about 0.5 to about 10.0 m/s, or any speed therebetween for example at an impeller tip speed from about 0.5 to 3 m/s, or any speed therebetween. Alternatively, the bioreactor may be agitated at a power from about 0.2 hp/100 gallons to about 15 hp/100 gallons, or any power therebetween.

Following fermentation, the fermentation broth containing the cellulase enzyme may be used directly, or the cellulase enzyme may be separated from the fungal cells, for example by filtration or centrifigation. Low molecular solutes such as unconsumed components of the fermentation medium may be removed by ultrafiltration. The cellulase enzyme maybe concentrated, for example, by evaporation, precipitation, sedimentation or filtration. Chemicals such as glycerol, sucrose, sorbitol and the like may be added to stabilize the cellulase enzyme. Other chemicals, such as sodium benzoate or potassium sorbate, may be added to the cellulase enzyme to prevent growth of microbial contamination.

The Use of Modified TrCel3A for the Hydrolysis of Cellulosic Substrates

The modified TrCel3A of the invention, may be combined with one or more cellulases to produce a cellulase mixture for use in the enzymatic hydrolysis of cellulose. For the purpose of the present invention, cellulases include all enzymes and proteins known to participate in the conversion of cellulose to soluble sugars, including but not limited to cellobiohydrolases (EC 3.2.1.91), endoglucanases (E.C 3.2.1.4), and other accessory enzymes that enhance the enzymatic conversion of cellulose to soluble sugars such as swollenins, expansins, and the like. In addition to the modified TrCel3A and cellulases, the cellulase mixture may comprise other enzymes such as other beta-glucosidases, hemicellulases, glucuronidases, galacturonases, esterases, galactosidases, amylases, and glucoamylases. It is understood that the enzymatic hydrolysis of cellulose by cellulase mixtures comprising the modified TrCel3A beta-glucosidases of the present invention is not limited by the composition of the cellulase mixture.

The cellulase mixture comprising the modified TrCel3A of the present invention may be used for enzymatic hydrolysis of cellulose present in "pretreated lignocellulosic feedstock." A pretreated lignocellulosic feedstock is a material of plant origin that, prior to pretreatment, contains at least 20% cellulose (dry wt), more preferably greater than about 30% cellulose, even more preferably greater than 40% cellulose, for example 20, 22, 24, 26, 28, 30, 32, 34, 36, 38, 40, 42, 44, 46, 48, 50, 55, 60, 65, 70, 75, 80, 85, 90% or any % therebetween, and at least 10% lignin (dry wt), more typically at least 12% (dry wt) and that has been subjected to physical and/or chemical processes to make the fiber more accessible and/or receptive to the actions of cellulolytic enzymes.

After pretreatment, the lignocellulosic feedstock may contain higher levels of cellulose. For example, if acid pretreatment is employed, the hemicellulose component is hydrolyzed, which increases the relative level of cellulose. In this case, the pretreated feedstock may contain greater than about 20% cellulose and greater than about 12% lignin. Lignocellulosic feedstocks that may be used in the invention include, but are not limited to, agricultural residues such as corn stover, wheat straw, barley straw, rice straw, oat straw, canola straw, and soybean stover; fiber process residues such as corn fiber, sugar beet pulp, pulp mill fines and rejects or sugar cane bagasse; forestry residues such as aspen wood, other hardwoods, softwood, and sawdust; or grasses such as switch grass, miscanthus, cord grass, and reed canary grass. The lignocellulosic feedstock may be first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, a hammer mill.

Non-limiting examples of pretreatment processes include chemical treatment of a lignocellulosic feedstock with sulfuric or sulfurous acid, or other acids; ammonia, lime, ammonium hydroxide, or other alkali; ethanol, butanol, or other organic solvents; or pressurized water (See U.S. Pat. Nos. 4,461,648, 5,916,780, 6,090,595, 6,043,392, and 4,600,590).

The pretreatment may be carried out to hydrolyze the hemicellulose, or a portion thereof, that is present in the lignocellulosic feedstock to monomeric sugars, for example xylose, arabinose, mannose, galactose, or a combination thereof. Preferably, the pretreatment is carried out so that nearly complete hydrolysis of the hemicellulose and a small amount of conversion of cellulose to glucose occurs. During the pretreatment, typically an acid concentration in the aqueous slurry from about 0.02% (w/w) to about 2% (w/w), or any amount therebetween, is used for the treatment of the lignocellulosic feedstock. The acid may be, but is not limited to, hydrochloric acid, nitric acid, or sulfuric acid. For example, the acid used during pretreatment is sulfuric acid.

One method of performing acid pretreatment of the feedstock is steam explosion using the process conditions set out in U.S. Pat. No. 4,461,648. Another method of pretreating the feedstock slurry involves continuous pretreatment, meaning that the lignocellulosic feedstock is pumped through a reactor continuously. Continuous acid pretreatment is familiar to those skilled in the art; see, for example, U.S. Pat. No. 5,536, 325; WO 2006/128304; and U.S. Pat. No. 4,237,226. Additional techniques known in the art may be used as required such as the process disclosed in U.S. Pat. No. 4,556,430.

As noted above, the pretreatment may be conducted with alkali. In contrast to acid pretreatment, pretreatment with alkali does not hydrolyze the hemicellulose component of the feedstock, but rather the alkali reacts with acidic groups present on the hemicellulose to open up the surface of the substrate. The addition of alkali may also alter the crystal structure of the cellulose so that it is more amenable to hydrolysis. Examples of alkali that may be used in the pretreatment include ammonia, ammonium hydroxide, potassium hydroxide, and sodium hydroxide. The pretreatment is preferably not conducted with alkali that is insoluble in water, such as lime and magnesium hydroxide.

The pretreated lignocellulosic feedstock may be processed after pretreatment but prior to the enzymatic hydrolysis by any of several steps, such as dilution with water, washing with water, buffering, filtration, or centrifugation, or a combination of these processes, prior to enzymatic hydrolysis, as is familiar to those skilled in the art.

The pretreated lignocellulosic feedstock is next subjected to enzymatic hydrolysis. By the term "enzymatic hydrolysis", it is meant a process by which cellulase enzymes act on cellulose to convert all or a portion thereof to soluble sugars. Soluble sugars are meant to include water-soluble hexose monomers and oligomers of up to six monomer units that are derived from the cellulose portion of the pretreated lignocellulosic feedstock. Examples of soluble sugars include, but are not limited to, glucose, cellobiose, cellodextrins, or mixtures thereof. The soluble sugars may be predominantly cellobiose and glucose. The soluble sugars may be predominantly glucose.

The enzymatic hydrolysis process preferably converts about 80% to about 100% of the cellulose to soluble sugars, or any range therebetween. More preferably, the enzymatic hydrolysis process converts about 90% to about 100% of the cellulose to soluble sugars, or any range therebetween. In the most preferred embodiment, the enzymatic hydrolysis process converts about 98% to about 100% of the cellulose to soluble sugars, or any range therebetween. The enzymatic hydrolysis process may be batch hydrolysis, continuous hydrolysis, or a combination thereof. The hydrolysis process may be agitated, unmixed, or a combination thereof.

The enzymatic hydrolysis of cellulase using a cellulase mixture comprising the modified TrCel3A may be batch hydrolysis, continuous hydrolysis, or a combination thereof. The hydrolysis may be agitated, unmixed, or a combination thereof.

The enzymatic hydrolysis may be carried out at a temperature of about 45° C. to about 75° C., or any temperature therebetween, for example a temperature of 45, 50, 55, 60, 65, 70, 75° C., or any temperature therebetween, and a pH of about 3.0 to about 7.5, or any pH therebetween, for example a pH of about 3.0 to about 5.5, or any pH therebetween, for example a pH of 3.0, 3.5, 4.0, 4.5, 5.0, 5.5, 6.0, 6.5, 7.0, 7.5, or pH therebetween. The initial concentration of cellulose in the hydrolysis reactor, prior to the start of hydrolysis, is preferably about 4% (w/w) to about 15% (w/w), or any amount therebetween, for example 4, 6, 8, 10, 12, 14, 15% or any amount therebetween. The dosage of the cellulase enzyme mixture comprising the modified TrCel3A may be about 1 to about 100 mg protein per gram cellulose, or any amount therebetween, for example 1, 5, 10, 15, 20, 25, 30, 40, 50, 60, 70, 80, 90, 100 mg protein per gram cellulose or any amount therebetween. The hydrolysis may be carried out for a time period of about 12 hours to about 200 hours, or any time therebetween, for example, the hydrolysis may be carried out for a period of 15 hours to 100 hours, or any time therebetween, or it may be carried out for 12, 14, 15, 20, 25, 30, 35, 40, 45, 50, 55, 60, 65, 70, 75, 80, 85, 90, 95, 100, 120, 140, 160, 180, 200 hours, or any time therebetween. It should be appreciated that the reaction conditions are not meant to limit the invention in any manner and may be adjusted as desired by those of skill in the art.

The enzymatic hydrolysis is typically carried out in a hydrolysis reactor. The enzyme mixture is added to the pretreated lignocellulosic feedstock (also referred to as the "substrate") prior to, during, or after the addition of the substrate to the hydrolysis reactor.

All of the enzymes in the cellulase mixture may be secreted from one strain of an organism, referred to herein as a "complete blend" of secreted enzymes. By the term "complete blend", it is meant all proteins secreted extracellularly into the growth medium by a specific microorganism. The enzyme mixture may include the complete blend of enzymes secreted by *Trichoderma reesei*.

The individual enzymes of the cellulase mixture comprising the modified TrCel3A beta-glucosidase may be expressed individually or in sub-groups from different strains of different organisms and the enzymes combined to make the cellulase enzyme mixture. It is also contemplated that the individual enzymes of the cellulase mixture may be expressed individually or in sub-groups from different strains of a single organism, such as from different strains of *Trichoderma reesei*, and the enzymes combined to make the cellulase mixture. Preferably, all of the enzymes are expressed from a single strain of *Trichoderma reesei*.

EXAMPLES

The present invention will be further illustrated in the following examples. However, it is to be understood that these examples are for illustrative purposes only and should not be used to limit the scope of the present invention in any manner.

Example 1 describes evaluation of the stability of parental TrCel3A at different pH conditions with low and high agitation/aeration. Example 2 describes the strains and vectors used in the following examples. Example 3 describes the cloning of the TrCel3A gene and transformation of yeast. Example 4 describes the making of error prone-PCR libraries. Examples 5 and 6 describe the expression of parental and modified TrCel3A beta-glucosidases from yeast microculture and the high-throughput screening to identify modified TrCel3As with improved stability. Examples 7 and 8 describe the larger-scale expression and characterization of modified and native TrCel3A beta-glucosidases. Example 9 describes evaluation of the activity of parental and modified TrCel3A beta-glucosidases. Examples 10 and 11 describe the generation of an aggregate modified TrCel3A with multiple amino acid substitution and the preparation and screening of site-saturation mutagenesis libraries of the aggregate modified TrCel3A. Examples 12 and 13 describe the production of a modified TrCel3A beta-glucosidase from *Trichoderma reesei*. Example 14 describes the assay of the relative specific activity of the parental and modified TrCel3A beta-glucosidases. Examples 15 and 16 describe stability assays for parental and modified TrCel3A beta-glucosidases.

Example 1

Inactivation of TrCel3A in a *Trichoderma reesei* Cellulase Mixture

This example demonstrates that parental TrCel3A is inactivated under conditions of low pH, low pH and high agitation, low pH and high aeration, or low pH and elevated temperature Samples of a cellulase mixture with enhanced levels of parental TrCel3A produced by *T. reesei* strain P59G were adjusted to pH 3.0, 3.5, 4.0 and 5.0 (FIG. 3A) and mixed at 30° C. or 50° C. in unbaffled flasks by orbital shaking at 200 rpm for up to 80 hours. Samples of a cellulase mixture with enhanced levels of parental TrCel3A produced by *T. reesei* strain P59G were adjusted to pH 3.0 or pH 5.0 (FIG. 3B) and incubated at 30° C. in unbaffled flask with no shaking or stiffing, in unbaffled flasks with orbital shaking at 200 rpm ("Shaking") or in baffled flasks with a magnetic stirrer ("Stirring") for up to 400 hours (FIG. 3B). Samples of the cellulase mixture containing the parental TrCel3A were removed at various time points and assayed for residual beta-glucosidase activity using a para-nitrophenyl-beta-D-glucoside (pNPG) as substrate.

Release of para-nitrophenol from pNPG is readily detected by its absorbance at 340 nm. The pNPGase assay is carried out at 50° C. in a Cary300 spectrophotometer, the concentration of substrate is 0.4 mM in 3 mL, to which 2 µg of a cellulase mixture comprising the parental TrCel3A (P59G cellulase) is added. The total protein concentration was also measured at each time point using the method of Bradford et al. (*Analytical Biochemistry*, 72:248-254, (1976)). For the P59G cellulase, this represents the addition of roughly 0.4 µg of TrCel3A. The TrCel3A activity is taken as the slope of the initial increase in A340. The pNPG activity at each time point was divided by the activity at t=0h in order to calculate the relative specific pNPG activity at each time point.

Figure 3:
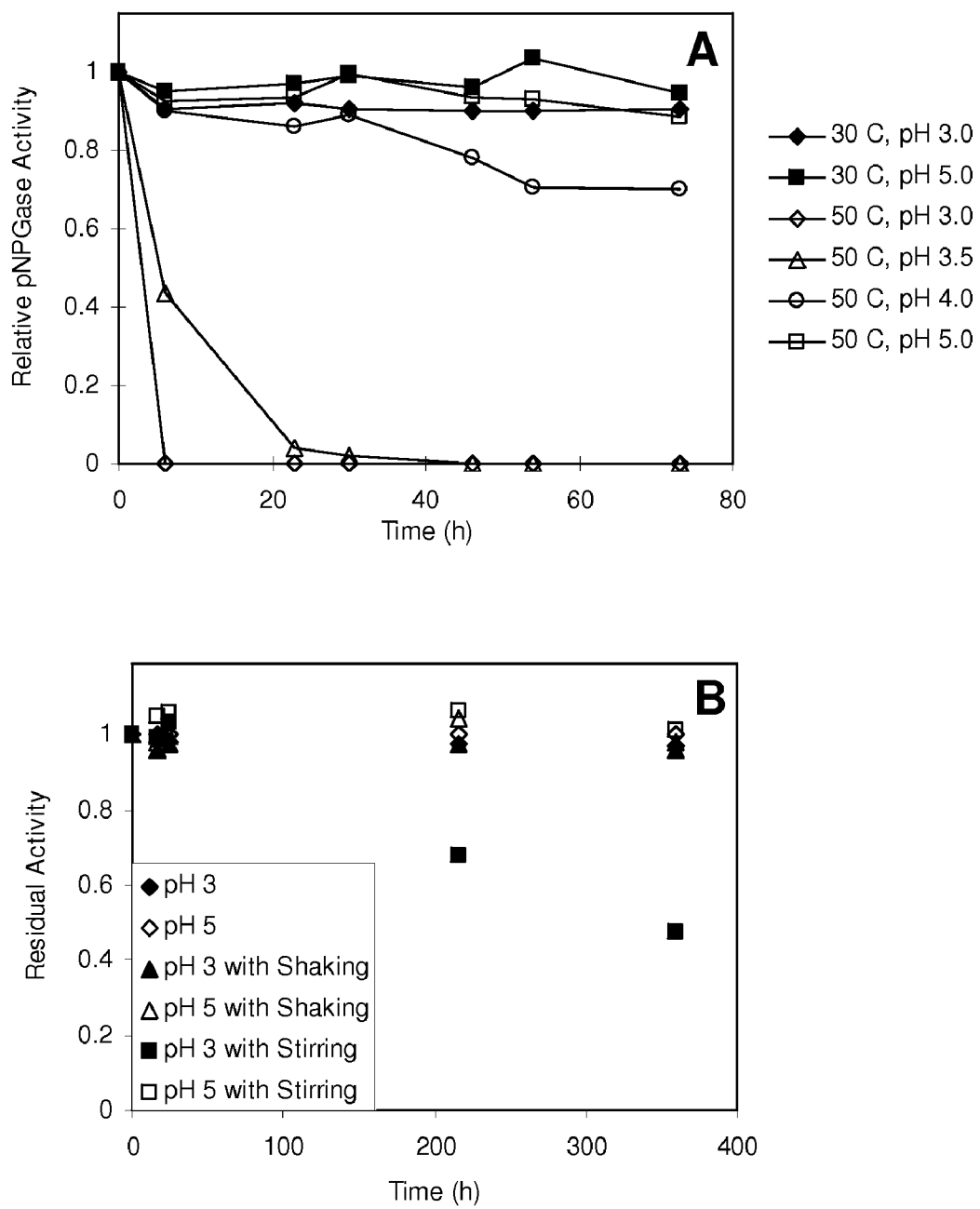
FIG. 3 shows the inactivation of wild-type TrCel3A as a function of pH and temperature. (A) Plot of residual beta-glucosidase activity vs incubation time in aqueous solution with mild shaking (200 rpm) at pH 3.0, 4.0 or 5.0 at 30° C. or at 50° C. (B) Plot of residual beta-glucosidase activity vs incubation time in aqueous solution at 30° C. and pH 3.0 or pH 5.0 in unbaffled flasks with mild shaking (200 rpm), in baffled flasks with shaking at 200 rpm ("shaking"), or in unbaffled flasks with mechanical stifling ("stirring").

The results in FIG. 3 show that the parental TrCel3A is sensitive to inactivation under conditions of low pH and high agitation. FIG. 3A shows that at 50° C., the beta-glucosidase activity is essentially stable at pH 5, inactivates slowly at pH 4 and inactivates rapidly at pH 3.5 and 3.0 under conditions of low agitation (shaking at 200 rpm in unbaffled flask). At 30° C., the enzyme is stable at both pH 3 and 5 under these shaking conditions. The results shown in FIG. 3B demonstrate that parental TrCel3A is sensitive to inactivation in aqueous solution at low pH with high agitation even at 30° C. In the aqueous solution at pH 3.0 with stiffing in a baffled flask, inactivation of the TrCel3A was observed; however, the parental TrCel3A is stable in aqueous solutions at low pH with low agitation (pH 3.0 with 200 rpm shaking in an unbaffled flask) and in aqueous solutions at higher pH with high agitation (pH 5.0 with stiffing in a baffled flask).

Example 2

Strains and Vectors

*Saccharomyces cerevisiae* strain BJ3505 (pep4::HIS3 prb-Δ1.6R HIS3 lys2-208 trp1-Δ101 ura3-52 gal2 can 1) was obtained from Sigma and was a part of the Amino-Terminal Yeast FLAG Expression Kit. *Escherichia coli* strain DH5α (F⁻φ80lacZΔM15 Δ(lacZYA-argF)U169 recA1 endA1 hsdR17($r_k^-$, $m_k^+$) phoA supE44 thi-1 gyrA96 relA1λ⁻) was obtained from Invitrogen. The YEp352/PGK91-1 vector was obtained from the National Institute of Health. The pGEM T-easy vector was obtained from Promega.

*Trichoderma reesei* strain P59G is a genetically modified strain that produces and secretes high levels of the TrCel3A beta-glucosidase, encoded by *T. reesei* bgl1, as described in U.S. Pat. No. 6,015,703. BTR213 is a derivative of RutC30 (ATCC #56765; Montenecourt and Eveleigh, 1979) produced by random mutagenesis and first selected for ability to produce larger clearing zones on minimal media agar containing 1% acid swollen cellulose and 4 g/L 2-deoxyglucose, and then selected for the ability to grow on lactose media containing 0.2 µg/ml carbendazim. Strain P107B is a derivative of strain BTR213 generated by replacing the cel6a gene with the *Neurospora crassa* pyr4 gene. The BTR213aux and P107Baux strains, deficient in uridine production, were isolated by the ability to grow on 5-FOA (5-fluororotic acid) and inability to grow prototrophically in the absence of uridine.

Example 3

Cloning of the Parental TrCel3A Gene into YEp352/PGK91-1 and Transformation in Yeast The TrCel3A gene contains two introns. One intron is located in the secretion signal at position 323 bp to 391 bp, while the other is located within the gene at position 2152 bp to 2215 bp. The TrCel3A gene contains a unique NheI site located at position 1203 bp. In order to facilitate expression from yeast and cloning using NheI and KpnI restriction enzymes, the unique NheI located within TrCel3A at position 1203 bp and the second intron were removed by a three step PCR. The TrCel3A gene was amplified in three segments from a plasmid containing TrCel3A, $p^c/_xBG(XbaI)$-TV (U.S. Pat. No. 6,015,703) using iPROOF DNA polymerase (Bio-Rad). The first fragment (A) was amplified using primers which introduced an NheI site at the 5' end of the gene downstream of the secretion signal (AT048) and which removed the internal NheI site (AT051). The second fragment (B) was amplified using primers which removed the internal NheI site (AT050) and the intron at position 2152 to 2215 bp (AT053). The third fragment (C) was amplified using primers which removed the intron at position 2152 to 2215 bp (AT052) and introduced a KpnI site at the 3' end of the gene, downstream of the stop codon (AT049). Gene products B and C were joined together (to make gene product D) using PCR with primers AT050 and AT049. Gene product D was joined with gene product A using PCR with primers AT048 and AT049 to obtain TrCel3A without introns and with unique NheI and KpnI sites at the 5' and 3' ends, respectively. The final gene product was cloned into the pGEM T-easy vector (Promega) as per the manufacturer's instructions to make plasmid pGEM-TrCel3A. Primer sequences are shown below:

AT048:
(SEQ ID NO: 17)
5' CGC CAG GCT AGC GTT GTA CCT CCT GC

AT049:
(SEQ ID NO: 18)
5' CTG AGG GTA CCG CTA CGC TAC CGA C

```
AT050:
                                     (SEQ ID NO: 19)
5' CCC GCT AGT ATT GCC GTC GTT GGA TC

AT051:
                                     (SEQ ID NO: 20)
5' CCA ACG ACG GCA ATA CTA GCG GGC TTC

AT052:
                                     (SEQ ID NO: 21)
5' GTT CGG CTA TGG ACT GTC TTA CAC CAA GTT CAA CTA
C

AT053:
                                     (SEQ ID NO: 22)
5' GTT GAA CTT GGT GTA AGA CAG TCC ATA GCC GAA CTC
```

A DNA adapter containing NheI, KpnI, and EcoRI restriction sites was prepared by annealing primers AT046 and AT047 together. The adapter was inserted into a YEp based-plasmid containing the pgk1 promoter, alpha mating factor secretion signal, and pgk1 terminator sequences to make plasmid YEp352/PGK91-1/α$_{ss}$NKE. Specifically, the adapter was inserted as an NheI/EcoRI fragment into the NheI and EcoRI sites located downstream of the alpha mating factor secretion signal and upstream of the pgk1 terminator. Primer sequences are shown below:

```
AT046:
5' CTA GCT GAT CAC TGA GGT ACC G    (SEQ ID NO: 23)

AT047:
5' AAT TCG GTA CCT CAG TGA TCA G    (SEQ ID NO: 24)
```

Plasmid pGEM-TrCel3A was digested with NheI and EcoRI to release the 2235 bp TrCel3A gene. The fragment was purified and ligated into the NheI and EcoRI sites of YEp352/PGK91-1/α$_{ss}$NKE to obtain YEp352/PGK91-1/α$_{ss}$Cel3A.

A DNA adapter containing SpeI, NheI, KpnI, and EcoRI restriction sites was prepared by annealing primers AT044 and AT045 together. The adapter contains sequences coding for six histidine residues downstream of the SpeI site and upstream of the NheI site. The adapter was inserted into a YEp based-plasmid containing the pgk1 promoter, alpha mating factor secretion signal, and pgk1 terminator sequences to make plasmid YEp352/PGK91-1/α$_{ss}$6HNKE. Specifically, the linker was inserted as an NheI/EcoRI fragment into the NheI and EcoRI sites located downstream of the alpha mating factor secretion signal and upstream of the pgk1 terminator. Primer sequences are shown below:

```
AT044:
                                     (SEQ ID NO: 25)
5' CTA GTC ATC ACC ATC ACC ATC ACG CTA GCT GAT CAC
TGA GGT ACC G

AT045:
                                     (SEQ ID NO: 26)
5' AAT TCG GTA CCT CAG TGA TCA GCT AGC GTG ATG GTG
ATG GTG ATG A
```

Plasmid pGEM-TrCel3A was digested with NheI and EcoRI to release the 2235 bp TrCel3A gene. The fragment was purified and ligated into the NheI and EcoRI sites of YEp352/PGK91-1/α$_{ss}$6HNKE to obtain YEp352/PGK91-1/α$_{ss}$6H-TrCel3A (FIG. 1). The vector YEp352/PGK91-1/α$_{ss}$6H-TrCel3A has been deposited with the American Type Culture Collection (ATCC®), 10801 University Boulevard, Manassas, Va. 20110-2209. The deposit was made on Dec. 22, 2010, and was assigned ATCC Deposit No. PTA-11562.

A random mutagenesis library was generated using a Mutazyme® II DNA polymerase method. A series of four independent PCR were performed using 5, 10, 15, 20 ng of YEp352/PGK91-1/α$_{ss}$6H-TrCel3A vector and the Mutazyme® II DNA polymerase with primers YalphaN21 and 3'PGK-term. Annealing temperature was set to 50° C. The amplification was done for 20 cycles. The four PCR products were pooled and diluted to 16 ng/µL. The YEp352/PGK91-1/α$_{ss}$6H-TrCel3A vector was digested with NheI and KpnI and the empty vector fragment was isolated. This linear fragment and the final amplicon were transformed simultaneously and cloned by in vivo recombination into yeast strain BJ3505 (Butler, T. and Alcalde, M. 2003).

```
YalphaN21:
5'AGC ACA AAT AAC GGG TTA TTG      (SEQ ID NO: 27)

3'PGK-term:
5'GCA ACA CCT GGC AAT TCC TTA CC   (SEQ ID NO: 28)
```

Example 5

Expression of Parental and Modified TrCel3A Beta-glucosidases from Microplate Cultures This example describes the selection and expression of TrCel3A from *Saccharomyces cerevisiae* for use in a high-throughput screening assay.

*S. cerevisiae* transformants were grown on plates containing synthetic complete medium (SC: 2% agar w/v, 0.17% yeast nitrogen base w/v, 0.078%-Ura drop-out supplement w/v, 2% glucose w/v, 2% casamino acids w/v, 0.5% ammonium sulfate w/v, pH 5.5) for 4-5 days at 30° C. Each growth plate was replicated by transferring a portion of each colonies, using sterilized velvet, to a screen-out plate containing SC medium plus 0.1% esculin hydrate and 0.03% FeCl$_3$. Colonies which turned black after incubation for 3-4 days at 30° C. were identified as expressing active enzyme. Colonies were correlated back to their original growth plate and selected for liquid media expression cultures by toothpick inoculation of 1 mL SC media in 96-deepwell plates containing one glass bead (1.5-2.0 mm). Expression cultures were grown for 3 days at 30° C. and 250 rpm with humidity control. Glycerol stocks were prepared by transferring 0.050 mL of liquid culture to the corresponding wells of a microplate containing 0.050 mL of 40% glycerol and stored at −80° C. Expression culture plates were centrifuged at 1600×g for 5 minutes to pellet cells and supernatant was aspirated for screening assays.

Example 6

Screening of Gene Libraries for Modified TrCel3A Beta-glucosidases with Improved Stability at Low pH This example describes the screening of modified *Trichoderma reesei* TrCel3As for improved stability at low pH by comparison to parent TrCel3A that had been cloned into *Saccharomyces cerevisiae*.

Figure 4:
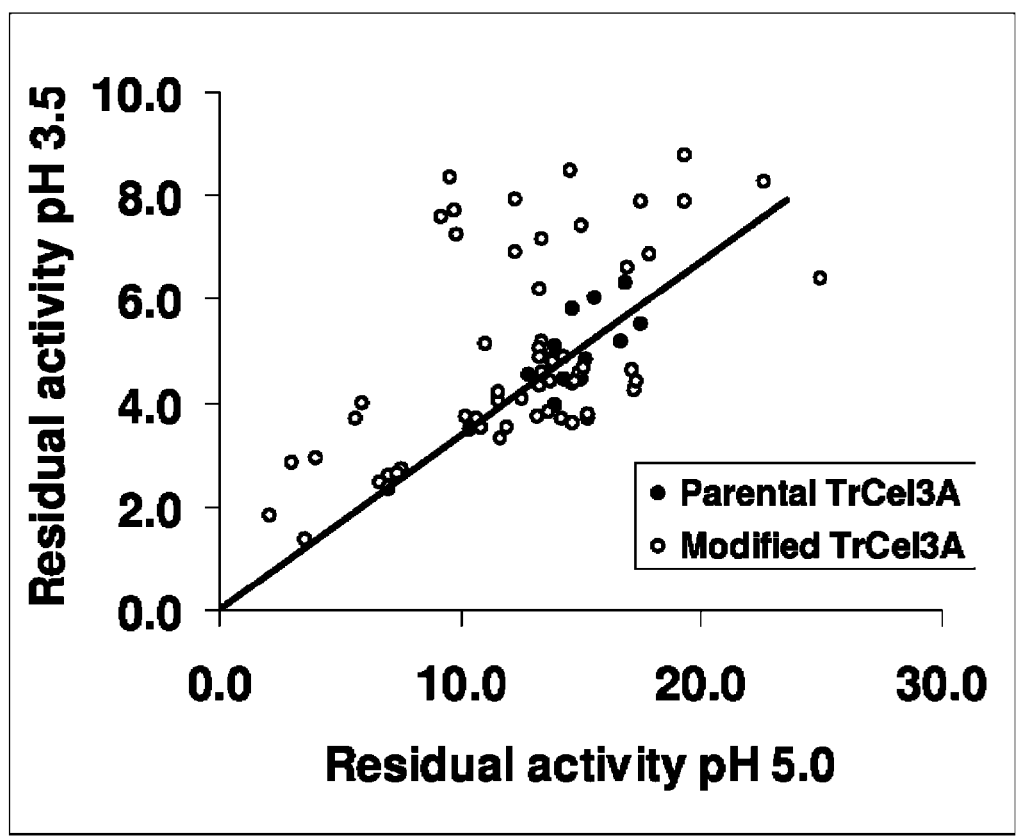
FIG. 4 is a scatter plot of residual enzyme activity following pre-incubation at pH 3.5 versus pH 5.0. The data relate to the screening of one 96-well culture plate containing parental and modified TrCel3A beta-glucosidases. The parental TrCel3A data was fit by linear regression in which the y-intercept was fixed to zero.

Modified TrCel3As from yeast microcultures, as described in Example 5, were pre-incubated using two distinct 0.1 mL citrate buffered conditions in a 96-well PCR plate format. An aliquot of supernatant from each microculture was pre-incubated at both pH 5.0 and pH 3.5 (200 mM citrate buffer) for 30 minutes at 46° C. Residual beta-glucosidase activity of each modified TrCel3A was assessed by adding an aliquot of the pre-incubated mixture to 0.5 mM 4-nitrophenyl-β-D-glucopyranoside (pNPG) in 200 mM pH 5.0 citrate buffer and incubating at 50° C. for 20 minutes. The reaction was stopped by the addition of 400 mM $Na_2CO_3$ buffer. Absorbance was measured at 420 nm. Contained in each 96-well PCR plate were six parental TrCel3A controls used for comparison. A 3.5 pH/5.0 pH stability ratio was calculated for all modified TrCel3As and parental TrCel3A by dividing the activity after pre-incubation at pH 3.5 by the activity after pre-incubation at pH 5.0. The pH 3.5/pH 5.0 stability ratio for each modified TrCel3A was compared to the average ratio of the six parental TrCel3A controls on each plate and positives were selected at the 95% confidence level using a t-test. A sample of the data from one screening plate can be found in FIG. 4. All positive modified TrCel3A beta-glucosidases were produced again in microculture and re-screened to reduce the number of false positives.

Example 7

Expression of Parental and Modified TrCel3As from Large Scale Cultures 500 mL of sterile YPD media (10 g/L yeast extract, 20 g/L peptone, 20 g/L glucose) was inoculated with 10 mL of overnight cultures of transformed *Saccharomyces cerevisiae* in the same media which had been inoculated with cells freshly picked from an agar plate. The culture was then incubated for 96 hours at 30° C. with shaking at 250 rpm.

After incubation, the 500 mL yeast culture was centrifuged for 10 minutes at 16,000×g and the yeast cell pellet was discarded. A standard antibody capture ELISA was followed (Harlow and Lane, 1988, p. 564-565). Yeast filtrates were diluted with carbonate buffer (pH 9.6) and boiled for 5 min prior to microplate (Costar #9018) coating. Primary His-tag antibody (Sigma #H1029) and peroxidase labeled secondary antibody (Sigma #A4416) were used at a dilution of 1:2000.

Example 8

Characterization of Modified TrCel3A Beta-glucosidases at Low pH and High Agitation Yeast culture supernatants containing the parental and modified TrCel3As were collected as described in Example 7 and adjusted to pH 3.0 or pH 5.0 with 10 mL of 250 mM citrate and 500 mM phosphate buffers in the proportions 4:1 or 1:1, respectively. The samples were then incubated in baffled flasks at 30° C. with agitation at 400 rpm. The concentration of TrCel3A for the different samples in each assay was normalized to the sample with the lowest concentration. The difference in volume was made up with cell-free spent medium from fermentation of *Saccharomyces* containing the empty vector to a total volume of 50 mL. The range of TrCel3A concentration in the different assays was 4.8-10.8 μg/mL.

Aliquots were sampled over a period of 96 hours and measured for activity on 0.4 mM para-nitrophenyl β-D-glucopyranoside (pNPG) in 167 mM citrate pH 5.0 at 50° C. The concentration of enzyme was 1.9-4.3 μg/mL. The slope of the change in absorbance at 340 nm (A340) was used as a measure of enzyme activity. Data were plotted as a function of time and fit with a first-order decay model using the Solver function in Microsoft Excel. 95% confidence intervals of the fit for the $k_i$ values obtained were calculated using standard methods (Motulsky and Christopolous, 2003). For each modified TrCel3A the tau (in hours), which is the inverse of the inactivation constant $k_i$, was compared to that of the parental TrCel3A using a type 2, two-tailed t-test.

The results in FIG. 5 and Table 2 show that the following amino acid substitutions increase the tau value, and hence improve the stability, of TrCel3A at low pH: V66I, S72N, V101M, T235S, N248K, N369K, A386T.

Example 9

Determining the Enzymatic Activity of Modified TrCel3A Beta-glucosidases

The concentration of parental or modified TrCel3A in yeast filtrates was determined by ELISA as described in Example 7.

The enzymatic activity of yeast culture filtrates containing parental and modified TrCel3A beta-glucosidases was measured in a pNPG assay (0.4 mM pNPG, 50 mM citrate pH 5.0, 50° C.) as described in Example 1. For each activity assay, sufficient yeast culture filtrate was added to the pNPG substrate solution to bring the concentration of parental or modified TrCel3A to a final concentration of 5 μg/mL (based on the concentrations determined by ELISA) and the change in absorbance at 340 nm was monitored. The initial slope of the pNP production curve was determined using Microsoft Excel and taken as a measure of the activity of the variant. Activities were measured in triplicate and the mean activity of each variant was compared to the mean activity of the parental TrCel3A using a t-test (type 2, two-tailed).

Figure 6:
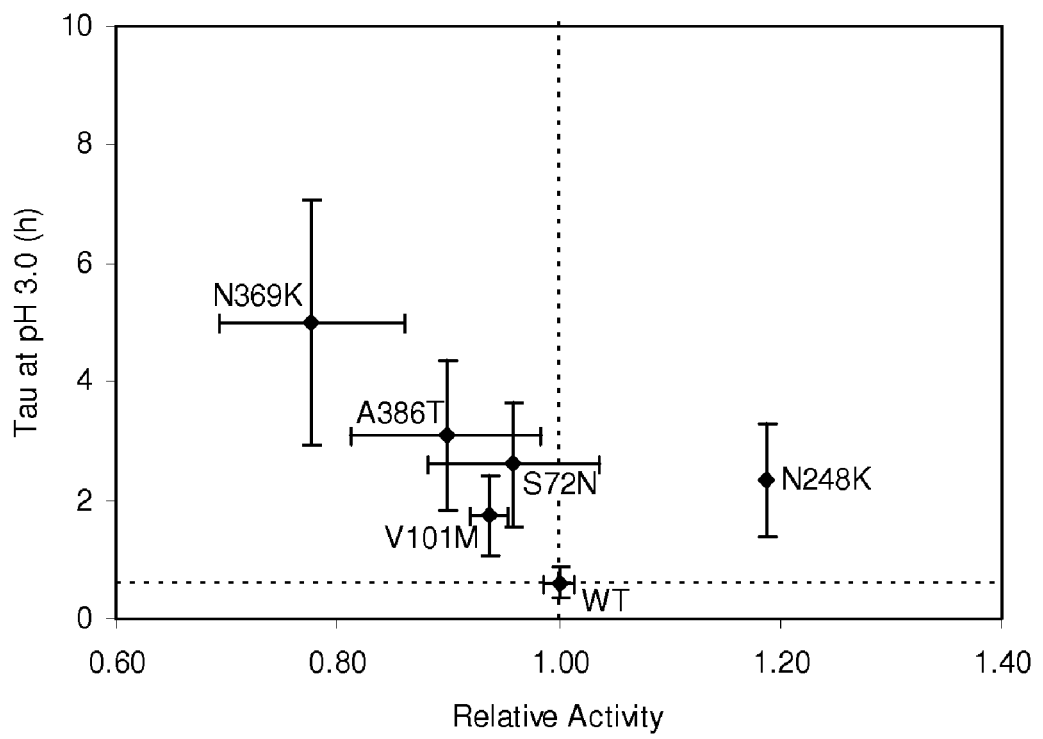
FIG. 6 is a plot of the inactivation constants, tau (in h), versus the relative activity of parental and modified TrCel3A beta-glucosidases. The activity of the wildtype is set to 1.0 and all variants are compared to this value. Data represent the mean of triplicates, except for N248K which was assayed as a singleton, and the error bars represent +/- one standard deviation.

The activities of the modified and parental TrCel3A beta-glucosidases are plotted versus the tau value for each in FIG. 6. The activity of the modified TrCel3A beta-glucosidases are within 20% of the activity of the parental TrCel3A demonstrating that the amino acid substitutions that lead to improved stability are not detrimental to the activity of the enzyme.

Example 10

Construction of Aggregate Modified TrCel3A Beta-glucosidases with Multiple Amino Acid Substitutions Using YEp352/PGK91-1/$\alpha_{ss}$ 6H-Cel3A-S72N as a template, additional mutations were introduced using a two-step PCR method involving megaprimer synthesis followed by megaprimer PCR using the High Fidelity iProof Taq Polymerase (BioRad). The internal primers were modified to introduce the desired amino acid substitutions into the TrCel3A construct. The external plasmid primers (YalphaN21 and 3'PGK-term) were used to amplify the final product. The megaprimers and final products were purified using the Wizard® SV Gel and PCR Clean-Up System.

TABLE 3

Generation of aggregate modified TrCel3A enzymes by PCR.

| PCR | Step | Template | Primer 1 | Primer 2 | Amplicon | Modified TrCel3A |
|---|---|---|---|---|---|---|
| 1 | 1 | YEp352/PGK91-1-α$_{ss}$-6H-TrCel3A-S72N | YalphaN21 | DK006 | PCR 1 Step 1 | TrCel3A-S72N-F96L-V101M |
|  | 1 | YEp352/PGK91-1-α$_{ss}$-6H-TrCel3A-S72N | DK005 | 3'PGK-term | PCR 1 Step 1 |  |
|  | 2 | Both PCR 1 Step 1 megaprimers | YalphaN21 | 3'PGK-term | YEp352/PGK91-1-α$_{ss}$-6H-TrCel3A-S72N-F96L-V101M |  |
| 2 | 1 | YEp352/PGK91-1-α$_{ss}$-6H-TrCel3A-S72N-F96L-V101M | YalphaN21 | DK010 | PCR 2 Step 1 | TrCel3A-S72N-F96L-V101M-N369K-A386T |
|  | 1 | YEp352/PGK91-1-α$_{ss}$-6H-TrCel3A-S72N-F96L-V101M | DK009 | 3'PGK-term | PCR 2 Step 1 |  |
|  | 2 | Both PCR 2 Step 1 megaprimers | YalphaN21 | 3'PGK-term | YEp352/PGK91-1-α$_{ss}$-6H-TrCel3A-S72N-F96L-V101M-N369K-A386T |  |
| 3 | 1 | YEp352/PGK91-1-α$_{ss}$-6H-TrCel3A-S72N-F96L-V101M-N369K-A386T | YalphaN21 | DK186 | PCR 3 Step 1 | TrCel3A-S72N-F96L-V101M-N369K |
|  | 1 | YEp352/PGK91-1-α$_{ss}$-6H-TrCel3A-S72N-F96L-V101M-N369K-A386T | DK185 | 3'PGK-term | PCR 3 Step 1 |  |
|  | 2 | Both PCR 3 Step 1 megaprimers | YalphaN21 | 3'PGK-term | YEp352/PGK91-1-α$_{ss}$-6H-TrCel3A-S72N-F96L-V101M-N369K |  |
| 4 | 1 | YEp352/PGK91-1-α$_{ss}$-6H-TrCel3A-S72N-F96L-V101M-N369K-A386T | YalphaN21 | DK068 | PCR 4 Step 1 | TrCel3A-S72N-V101M-N369K-A386T |
|  | 1 | YEp352/PGK91-1-α$_{ss}$-6H-TrCel3A-S72N-F96L-V101M-N369K-A386T | DK067 | 3'PGK-term | PCR 4 Step 1 |  |
|  | 2 | Both PCR 4 Step 1 megaprimers | YalphaN21 | 3'PGK-term | YEp352/PGK91-1-α$_{ss}$-6H-TrCel3A-S72N-V101M-N369K-A386T |  |
| 5 | 1 | YEp352/PGK91-1-α$_{ss}$-6H-TrCel3A-S72N-V101M-N369K-A386T | YalphaN21 | DK066 | PCR 5 Step 1 | TrCel3A-V66I-S72N-V101M-N369K-A386T |
|  | 1 | YEp352/PGK91-1-α$_{ss}$-6H-TrCel3A-S72N-V101M-N369K-A386T | DK065 | 3'PGK-term | PCR 5 Step 1 |  |
|  | 2 | Both PCR 5 Step 1 megaprimers | YalphaN21 | 3'PGK-term | YEp352/PGK91-1-α$_{ss}$-6H-TrCel3A-V66I-S72N-V101M-N369K-A386T |  |
| 6 | 1 | YEp352/PGK91-1-α$_{ss}$-6H-TrCel3A-S72N-F96L-V101M-N369K-A386T | YalphaN21 | DK066 | PCR 6 Step 1 | TrCel3A-V66I-S72N-F96L-V101M-N369K-A386T |
|  | 1 | YEp352/PGK91-1-α$_{ss}$-6H-TrCel3A-S72N-F96L-V101M-N369K-A386T | DK065 | 3'PGK-term | PCR 6 Step 1 |  |
|  | 2 | Both PCR 6 Step 1 megaprimers | YalphaN21 | 3'PGK-term | YEp352/PGK91-1-α$_{ss}$-6H-TrCel3A-V66I-S72N-F96L-V101M-N369K-A386T |  |

To facilitate cloning, the final product was digested with NheI+BamHI and ligated into vector YEp352/PGK91-1/α$_{ss}$ 6H-Cel3A linearized with NheI+BamHI. The ligation mix was transformed into DH5α chemically-competent *E. coli* cells, plasmid extracted, and sequenced. Plasmids encoding the modified beta-glucosidases were transformed into yeast strain BJ3505.

```
5'YalphaN21
                                          (SEQ ID NO: 27)
5'-AGCACAAATAACGGGTTATTG-3'

3'PGK-term
                                          (SEQ ID NO: 28)
5'-GCAACACCTGGCCCTTACC-3'

5'DK005
                                          (SEQ ID NO: 37)
5'-CGCGAACGTGGACAGCTGATCGGTGAGGAGATGAAGGCCTC-3'

3'DK006
                                          (SEQ ID NO: 38)
5'-GAGGCCTTCATCTCCTCACCGATCAGCTGTCCACGTTCGCG-3'

5'DK009
                                          (SEQ ID NO: 39)
5'-CGACGGGGCCTTGGGCATGGGTTGGGGTTCCGGCACCGTCAACT
A-3'

3'DK010
                                          (SEQ ID NO: 40)
5'-CCATGCCCAAGGCCCCGTCGTCGCAGCCTTTGTCCTTGCACGAG
G-3'

5'DK065
                                          (SEQ ID NO: 41)
5'-GACGGACCCCTCGGTATCCGATACTCGACAGGC-3'

3'DK066
                                          (SEQ ID NO: 42)
5'-GCCTGTCGAGTATCGGATACCGAGGGGTCCGTC-3'

5'DK067
                                          (SEQ ID NO: 43)
5'-CGCGAACGTGGACAGTTCATCGGTGAGGAGATG-3'

3'DK068
                                          (SEQ ID NO: 44)
5'-CATCTCCTCACCGATGAACTGTCCACGTTCGCG-3'

5'DK185
                                          (SEQ ID NO: 45)
5'-GGGTTCCGGCGCCGTCAACTATC-3'

3'DK186
                                          (SEQ ID NO: 46)
5'-GATAGTTGACGGCGCCGGAACCC-3'
```

The aggregate modified TrCel3A beta-glucosidases produced by the PCR reactions in Table 3 were expressed from the yeast transformants using the methods described in Example 7. The stability of the aggregate modified TrCel3A beta-glucosidases were characterized using the methods described in Examples 8. As shown in Table 2 and FIG. 7, aggregates comprising a combination of two, three, four or five of the amino acid substitutions selected from V66I, S72N, V101M, N369K, A386T, exhibit tau values that are from 19-fold to over 200-fold higher than the tau value for the parental TrCel3A.

The vector encoding the aggregate modified TrCel3A comprising amino acid substituions S72N, F96L, V101M, N369K, and A386T (YEp352/PGK91-1/α$_{ss}$6H-Cel3A-AT003) was used as a template for site-saturation mutagenesis in Example 11. The aggregate modified TrCel3A encoded by this vector (TrCel3A-AT003) was expressed in *Trichoderma reesei* as described in Example 12 and the yeast vector encoding this aggregate modified TrCel3A.

Example 11

Construction of Site-Saturation Mutagenesis Libraries

Four amino acid positions in TrCel3A (S72, V101, N369 and A386) were chosen for site-saturation mutagenesis in order to find an amino acid which further improves stability at low pH. Site-saturation mutagenesis was performed by PCR (one-step PCR reaction and ligation of both fragments) using NNS primers (listed below). The YEp352/PGK91-1/α$_{ss}$6H-Cel3A-AT003 (S72N, F96L, V101M, N369K and A386T) vector was used as template, PCR was performed with iProof High-Fidelity DNA Polymerase (Biorad) and PCR fragments were ligated with T4 DNA ligase (Fermentas). One SSM library was generated for each position, keeping the other positions unchanged in the template. The PCR for fragment 1 was done using the NNS primer and the complementary external primer 3'PGK-term. The PCR for the second fragment was done with the second primer which did not contain NNS and the complementary external primer YalphaN21. No purification step was performed and both amplified PCR fragments were ligated since primers were phosphorylated. The ligated amplicons were cloned in YEp352/PGK91-1/α$_{ss}$ 6HNKE using the gap repair method in yeast.

```
5'N72X-F:
                                          (SEQ ID NO: 29)
5'-P-GA TAC TCG ACA GGC NNS ACA GCC TTT ACG

5' N72X-R:
                                          (SEQ ID NO: 30)
5'-P-GAA CAC CGA GGG GTC CGT CTT G

5'M101X-F:
                                          (SEQ ID NO: 31)
5'-P-C GGT GAG GAG NNS AAG GCC TCG G

5'M101-R:
                                          (SEQ ID NO: 32)
5'-P-ATG AAC TGT CCA CGT TCG CGG

5'K369X-F:
                                          (SEQ ID NO: 33)
5'-P-G CCC TCG TGC NNS GAC AAA GGC TG

5'K369X-R:
                                          (SEQ ID NO: 34)
5'-P-GAG TTT CTG GCG TGG TTA CC

5'T386X-F:
                                          (SEQ ID NO: 35)
5'-P-G GGT TCC GGC NNS GTC AAC TAT CC

5'T386X-R:
                                          (SEQ ID NO: 36)
5' P-CAA CCC ATG CCC AAG GCC
```

To perform a gap repair the vector YEp352/PGK91-1/α$_{ss}$6HNKE was digested with Nhe I and Kpn I and purified on gel. *Saccharomyces cerevisiae* strain BJ3505 was used as the host. The digested YEp352/PGK91-1/α$_{ss}$6HNKE vector and the ligated amplicons were transformed in the yeast strain BJ3505 using the procedure described by Gietz, R. D. and Woods, R. A. (Gietz, R. D. and Woods, R. A. 2002). The resulting site-saturation libraries were screened for modified TrCel3A beta-glucosidases with improved stability at low pH using the methods described in Examples 5 and 6. As shown in FIG. 3 and Table 2, two modified TrCel3A beta-glucosidases (TrCel3A-S72E-F96L-V101M-N369K-A386T and TrCel3A-S72N-F96L-V101M-N369P-A386T) were identified with significantly improved stability at low pH over the parental TrCel3A-S72N-F96L-V101M-N369K-A386T), indicating that the S72E and N369P substitutions are superior to the S72N and N369K substitutions for improving the stability of TrCel3A at low pH.

Example 12

Expression of an Aggregate Modified TrCel3A Beta-glucosidase in *Trichoderma reesei*

12.1. Construction of *T. reesei* Transformation Vector

Figure 2:
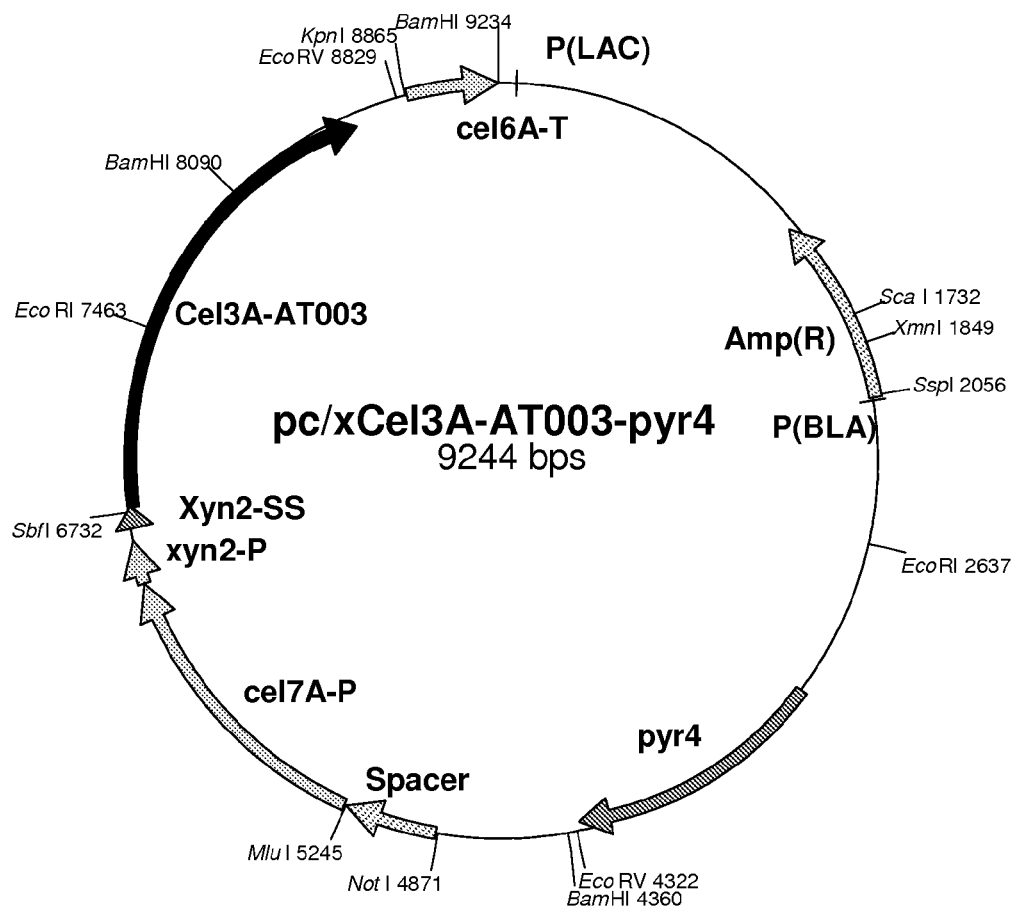
FIG. 2 depicts plasmid vector pc/xCel3A-AT003-pyr4 directing the expression and secretion modified TrCel3A from recombinant *Trichoderma reesei*.

The backbone for the *T. reesei* vector expressing the aggregate modified TrCel3A containing amino acid substitutions S72N, F96L, V101M, N369K, and A386T (TrCel3A-AT003) was constructed as described bellow. The Spacer DNA required to introduce additional unique restriction sites, MluI and NotI, was amplified from pCAMBIA1301 (see URL: cambia.org/daisy/cambia/materials/vectors/585.html#dsy585_Description and GenBank Accession No. AF234297) using primers AC168 and AC169 and cloned into the SacI/BamHI sites of pUC19 to form pUC19-SP. The expression cassette, c/x-Cel6A-cbh2, containing cel7a promoter, cel6a coding gene and cel6a terminator was isolated from vector pC/X-S413P-TV (U.S. Publication No. US2008-0076152A1). The vector was digested with NdeI restriction enzyme, blunt-ended and digested with XbaI. This fragment was then cloned into the EcoRI/XbaI sites for pUC19-SP to form the vector pUC19-SP-c/xCel6A. To construct the TrCel3A-AT003 expression cassette, the cel7-xyn2 promoter and xyn2 secretion signal were amplified using primers AC230 and AC231 and the pC/X-S413P-TV vector (U.S. Publication No. 2008-0076152A1) as a template. The TrCel3A-AT003 coding sequence was amplified using AC232 and AC233 and YEp352/PGK91-1/α$_{ss}$6H-Cel3A-AT003 vector (Example 10) as a template. The generated fragments had short overlapping identical sequences at the 3' and 5' ends, respectively. Thus, both fragments were used as primers and templates in a ten-cycle PCR reaction, annealed to each other and filled ends to generate the c/x-Cel3A-AT003 fragment. The generated fragment was amplified using outside primers, AC231 and AC232. The amplified fragment was cloned into pJET (see URL: fermentas.com/catalog/kits/clonejetperclon.htm) to generate pJET-c/xCel3A-AT003, which was verified by sequencing. The c/x-Cel3A-AT003 fragment was then isolated from pJET-c/xCel3A-AT003 vector as a MluI/KpnI fragment and ligated into the same sites of pUC19-SP-c/xCel6A to generate pUC19-SP-c/xCel3A-AT003. A selectable marker cassette containing the *Neurospora crassa* pyr4 gene was amplified from pNCBgl-NSNB(r) (U.S. Publication No. 2008-0076152A1) using primers AC323 and AC343 digested with PacI/NotI restriction enzymes and cloned into PvuI/NotI sites of pUC19-SP-c/xCel3A-AT003 vector generating final *T. reesei* transformation vector, pc/xCel3A-AT003-pyr4 (FIG. 2).

AC168
(SEQ ID NO: 47)
5'-GCAGAGCTCGCGGCCGCGAACCGACGACTCGTCCGTC-3'

AC169
(SEQ ID NO: 48)
5'-CTGGGATCCGATATCACGCGTGTGACATCGGCTTCAAATGGC-3'

AC230
(SEQ ID NO: 49)
5'-TTTACGCGTGATTATGGCGTACTAGAGAGCGG-3'

AC231
(SEQ ID NO: 50)
5'-CTGCAGGAGGTACAACCTGGCGCTTCTCCACAGCCACGG-3'

AC232
(SEQ ID NO: 51)
5'-GTGGAGAAGCGCCAGGTTGTACCTCCTGCAGGGACTCCATG-3'

AC233
(SEQ ID NO: 52)
5'-TTTGGTACCCTACGCTACCGACAGAGTGCTCG-3'

AC323
(SEQ ID NO: 53)
5'-TTTGCGGCCGCCATCATTCGTCGCTTTCGG-3'

AC343
(SEQ ID NO: 54)
5'-TTCGATCGACTATACCACCACCCACCG-3'

12.2. Transformation of *Trichoderma reesei*

*Trichoderma* strains BTR213aux and P107Baux (Example 2) were transformed with the pc/xCel3A-AT003-pyr4 vector by biolistic gold particle bombardment using PDS-1000/He system (BioRad; E.I. DuPont de Nemours and Company). Gold particles (median diameter of 0.6 um, BioRad Cat. No. 1652262) were used as microcarriers. The following parameters were used in the optimization of the transformation: a rupture pressure of 1100 psi, a helium pressure of 29 mm Hg, a gap distance of 0.95 cm, a macrocarrier travel distance of 16 mm, and a target distance of 9 cm. The spore suspension was prepared by washing *T. reesei* spores from the PDA plates incubated for 4-5 days at 30° C. with sterile water. Approximately $1 \times 10^6$ spores was plated on 60 mm diameter plates containing minimal medium agar (MM). After particle delivery, all transformation plates were incubated at 30° C. for 5-10 days. Transformants arising on the transformation plates were transferred to MM media and incubated at 30° C. Isolated stable transformants were used for subsequent analysis.

Minimal medium (MM) agar:

| Component | Amount for 1 L of medium |
|---|---|
| KH$_2$PO$_4$ | 10 g |
| (NH$_4$)$_2$SO$_4$ | 6 g |
| Na$_3$Citrate-2H$_2$O | 3 g |
| FeSO$_4$—7H$_2$O | 5 mg |
| MnSO$_4$—H$_2$O | 1.6 mg |
| ZnSO$_4$—7H$_2$O | 1.4 mg |
| CaCl$_2$—2H$_2$O | 2 mg |
| Agar | 20 g |
| 20% Glucose f.s. | 50 ml |
| 1 M MgSO4—7H$_2$O f.s. | 4 mL |
| | pH 5.5 |

12.3. Production of Modified TrCel36A-AT003 in Microcultures

To identify the transformants expressing the aggregate modified TrCel3A protein, all isolated stable transformants were grown in microculture. Approximately 5000 *T. reesei* spores were inoculated in each well of 24-well culture dish (COSTAR) containing 1 mL of *Trichoderma* microculture media. Plates were incubated for 5-7 days at 30° C. with shaking at 250 rpm.

*Trichoderma* Microculture Media

| Component | Concentration g/L |
|---|---|
| Cellulase-inducing cocktail | 35 |
| Ammonium sulphate | 12.7 |
| $KH_2PO_4$ | 8.0 |
| $MgSO_4$—7H2O | 4.0 |
| $CaCl_2$—$2H_2O$ | 1.0 |
| $FeSO_4$—7H2O | 0.1 |
| $MnSO_4$—7H2O | 0.032 |
| $ZnSO_4 7H_2O$ | 0.028 |
| $CaCO_3$ | 20 |
| Corn Steep Liquor (powder) | 5 |
| | pH 4.24 |

**cellulase-inducing cocktail comprising, as a function of total carbohydrate, 56% gentiobiose, 14% sophorose, 6% cellobiose, 10% trehalose, 6% maltotriose, 4% glucose and 14% other carbohydrates Cultures were transferred to microfuge tubes, cells were pelleted by microcentrifugation at 12,000 rpm, and the culture supernatants transferred to clean microfuge tubes. The total protein concentration of each supernatant was measured by Bradford protein assay as described in Example 1. The relative concentration of the aggregate modified TrCel3A produced by transformants was determined by ELISA as follows. Culture supernatents and purified component standards were diluted 0.01-10 μg/mL (based on total protein) in phosphate-buffered saline, pH 7.2 (PBS) and incubated overnight at 4° C. in microtitre plates (Costar EIA #9018). These plates were washed with PBS containing 0.1% Tween-20 (PBS/Tween) and then incubated in PBS containing 1% bovine serum albumin (PBS/BSA) for 1 h at room temperature. Blocked microtitre wells were washed with PBS/Tween. Rabbit polyclonal antisera specific for TrCel3A was diluted (1:16,000) in PBS/BSA, added to separate microtitre plates and incubated for 2 h at room temperature. Plates were washed and incubated with a goat anti-rabbit antibody coupled to horseradish peroxidase (Sigma #A6154), diluted $\frac{1}{2000}$ in PBS/BSA, for 1 hr at room temperature. After washing, tetramethylbenzidine was added to each plate and incubated for 30 min at room temperature. The absorbance at 360 nm was measured in each well and converted into protein concentration using the TrCel3A standard curve. The relative concentration of TrCel3A protein was calculated by dividing TrCel3A concentration by the total amount of protein produced and the transformants possessing a relative TrCel3A abundance at about 20-30% of total protein were selected for analysis in 14 L fermentation (Table 3).

TABLE 3

Relative Cel3A expression levels produced by *T. reesei* transformants grown in microcultures with cellulase inducible carbohydrates and selected for further analysis in 14L fermentation

| Strain name | Relative amount of Cel3A, % of total protein |
|---|---|
| P59G (control) | 42.7 |
| BTR213aux (host) | 6.0 |
| BTRc/x-penta 54 | 29.1 |
| BTRc/x-penta 46 | 54.3 |
| BTRc/x-penta 69S | 51.8 |
| P107Baux (host) | 6.4 |
| P107Bc/x-penta 15S | 36.1 |
| P107Bc/x-penta 22 | 42.9 |

Example 13

Production of a Cellulase Mixture Comprising Modified TrCel3A

Spores of the selected *T. reesei* transformants were inoculated onto standard 85 mm Petri plates containing potato dextrose agar (PDA). These plates were incubated at 30° C. for 5 days to achieve a confluent growth of fresh green spores. To prepare the inoculum for fermentation testing, spores from a single PDA plate were transferred to 2 L, baffled Erlenmeyer flask containing 750 mL of liquid Berkley media (pH 5.5). Flasks were incubated at 28° C. for 3 days using an orbital agitator (Model G-52 New Brunswick Scientific Co.) running at 100 rpm.

Berkley Media for Flasks

| Component | Concentration, g/L |
|---|---|
| $(NH_4)_2SO_4$ | 1.4 |
| $KH_2PO_4$ | 2.0 |
| $MgSO_4 \cdot 7H_2O$ | 0.31 |
| $CaCl_2 \cdot 2H_2O$ | 0.53 |
| Dry Corn Steep Liquor | 5.1 |
| Glucose | 10 |
| Trace elements* | 1 mL/L |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.

The contents of each inoculum flask were transferred to a 14 L pilot scale fermentation vessel (Model MF114 New Brunswick Scientific Co.) set up with 10 L of Initial Media for Feb-Batch fermentation (pH 5.5). The vessel was run in batch mode until the glucose in the media was depleted. At this point, a cellulase-inducing cocktail comprising, as a function of total carbohydrate, 56% gentiobiose, 14% sophorose, 6% cellobiose, 10% trehalose, 6% maltotriose, 4% glucose and 14% other carbohydrates, was feed on a continuous basis from a stock that was 35% w/v of solids dissolved in water. Peristaltic pumps were used to deliver the carbon source at a feed at a rate of 0.4 grams of carbon per liter culture per hour. Operational parameters during both the batch and fed-batch portions of the run were: mixing by impeller agitation at 500 rpm, air sparging at 8 standard liters per minute, and a temperature of 28° C. Culture pH was maintained at 4.0-4.5 during batch growth and pH 3.0 or 5.0 during cellulase production using an automated controller connected to an online pH probe and a pump enabling the addition of a 10% ammonium hydroxide solution. Periodically, 100 mL samples of broth were drawn for biomass and protein analysis. After 165 hours of fermentation time 1 L of fermentation media was collected and filtered for further protein analysis.

Initial Media for Fed-Batch Fermentations

| Component | Concentration, g/L |
|---|---|
| $(NH_4)_2SO4$ | 2.20 |
| $KH_2PO_4$ | 1.39 |
| $MgSO_4 \cdot 7H_2O$ | 0.70 |
| $CaCl_2 \cdot 2H_2O$ | 0.185 |
| Dry Corn Steep Liquor | 6.00 |
| Glucose | 13.00 |
| Trace elements* | 0.38 mL/L |

*Trace elements solution contains 5 g/L $FeSO4 \cdot 7H2O$; 1.6 g/L $MnSO4 \cdot H2O$; 1.4 g/L $ZnSO4 \cdot 7H2O$.

The total protein concentration of the final fermentation filtrates was measured by Bradford assay as described in Example 1. The concentration of TrCel3A-type enzymes in the final fermentation filtrates was measured by ELISA as described in Example 12.3.

Example 14

Assay of Specific Cellobiase Activity of Parental and Modified TrCel3A Beta-glucosidases Produced in pH 3.0 and pH 5.0 Fermentations This example demonstrates that the relative specific activity, in this instance the specific activity of the beta-glucosidase produced in *Trichoderma reesei* fermentations conducted at pH 3.0 divided by the specific activity of the beta-glucosidase produced in *Trichoderma reesei* fermentations conducted at pH 5.0, is higher for the aggregate modified TrCel3A-AT003 (TrCel3A with amino acid substitutions S72N, F96L, V101M, N369K, and A386T) than for the parental TrCel3A.

Initial rate assays were used to measure the specific activity of the parental TrCel3A and the aggregate modified TrCel3A-AT003 beta-glucosidase in cellulase mixtures produced from *Trichoderma reesei* fermentations conducted at pH 5.0 or 3.0, on cellobiose. The cellulase enzyme mixtures comprising the beta-glucosidases were incubated with 30 mM cellobiose in 50 mM citrate buffer at pH 5.0. Six dilutions of the cellulase mixture, ranging from 1000- to 6000-fold were used. Samples were incubated at 50° C. for 30 min in deep well plates and then placed in a boiling water bath for 10 min to stop the reaction. The concentration of glucose produced at each dilution of cellulase mixture was measured using a glucose oxidase/horseradish peroxidise coupled system (Trinder P., 1969). The specific activity, in IU/mg, was determined by dividing the number of μmoles of glucose produced by the length of the assay, 30 min, and then by the number of milligrams of TrCel3A-type enzyme present in the reaction. The concentration of TrCel3A-type enzyme (parental or aggregate modified) in each experiment was determined using the protein concentration of the crude enzyme, as determined by the Bradford method as described in Example 1, and the fractional TrCel3A-type enzyme content of each culture filtrate, as determined by the ELISA as described in Example 13. Specific activity determinations were performed in triplicate.

Figure 9:
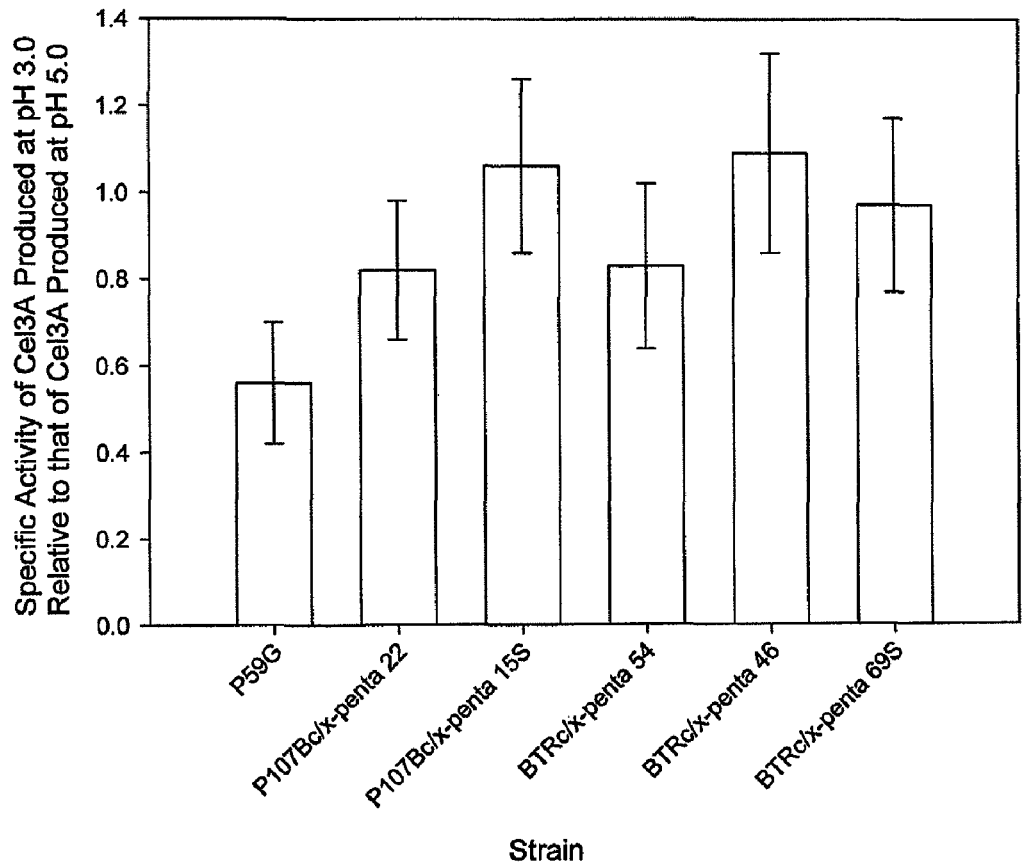
FIG. 9 depicts the relative stability of parental and modified beta-glucosidase. The specific cellobiase activity (measured at pH 5.0) of the parental TrCel3A and aggregate modified TrCel3A-AT003 beta-glucosidases in cellulase mixtures produced in pilot *Trichoderma reesei* fermentations conducted for 165 hours at 28° C. and at either pH 3.0 and pH 5.0 expressed as a ratio. A ratio of 1.0 indicates that a beta-glucosidase is equally stable at pH 3.0 and pH 5.0; lower values indicate reduced stability at pH 3.0 vs. pH 5.0. Error bars represent one standard deviation.

As shown in FIG. 9, the specific cellobiase activity of the TrCel3A-type beta-glucosidase enzyme produced at pH 3.0 divided by the specific cellobioase activity of the TrCel3A-type beta-glucosidase enzyme produced at pH 5.0 is significantly higher for the aggregate TrCel3A-AT003 produced by the transformants of the BTR213aux or P107Baux host strains than for the parental TrCel3A produced by the P59G control strain. Therefore, the TrCel3A-AT003 beta-glucosidase is more stable under the low pH, highly aerated and highly agitated conditions of the *Trichoderma reesei* fermentations than is the parental TrCel3A.

Example 15

Stability of Modified and Parental TrCel3A under Conditions Mimicking Those of a Cellulose Hydrolysis Reaction This example demonstrates that the stability of the aggregate modified TrCel3A is improved at reduced pH at a standard hydrolysis temperature, improved at a higher temperature at a standard pH, and improved under conditions of both increased temperature and reduced pH.

*Trichoderma* strains expressing cellulase mixtures comprising the parental and aggregate modified TrCel3A variants were fermented at pH 5.0 as described in Example 13. 10 mL samples of pH-adjusted cellulase mixtures were prepared in 35 mL screw-top glass centrifuge tubes through the addition of 9 mL cellulase mixture to 1 mL of 1.0 M citrate buffer, pH 5.0, 4.0, 3.5 and 3.0. These samples were incubated at 50° C. or 60° C. in air-heated incubators with 250 rpm orbital shaking. Samples were taken at 0, 0.5, 1, 2, 4, 6, 11.5, 24.5, 74 and 98 h and assayed for beta-glucosidase activity using the pNPG method described in Example 1.

Figure 10:
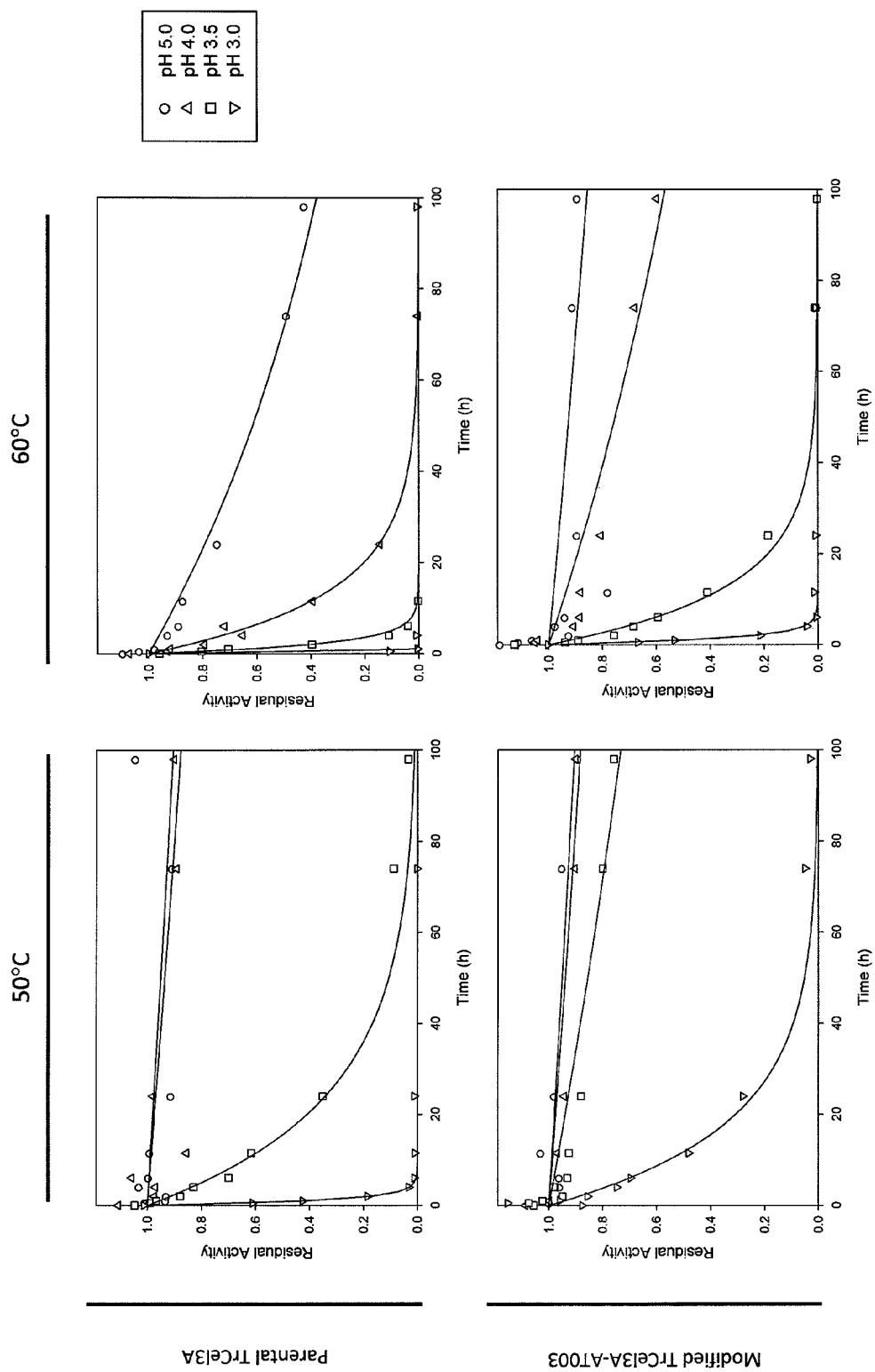
FIG. 10 depicts the stability of parental and modified beta-glucosidase under conditions which could be used for cellulose hydrolysis. Parental and modified beta-glucosidase, within a cellulase mixture, was incubated at 50 or 60° C. at pH 3.0, 3.5, 4.0 or 5.0. Samples were taken from the enzyme at the times indicated and tested in a pNPGase assay. A model of first-order exponential decay was fit to the data to determine the mean life-time of each enzyme under each set of conditions. All data were normalized to the best fit value of initial activity as determined by the model and inactivation curves are displayed with respect to this initial activity.

As shown in FIG. 10 and in Table 4, the aggregate modified TrCel3A-AT003 beta-glucosidase is significantly more stable than the parental TrCel3A at 50° C. and pH 3.5 or 3.0 and at 60° C. at all pH's tested. These results suggest that the amino acid substitutions in TrCel3A-AT003 (S72N, F96L, V101M, N369K, and A386T) confer improved stability at low pH and at elevated temperature.

TABLE 4

Stability of parental TrCel3A and aggregate modified TrCel3A-AT003 at low pH and elevated temperature.

| | | Tau (h) | |
|---|---|---|---|
| | pH | TrCel3A | TrCel3A-AT003 |
| 50° C. | 5.0 | 1000 | 1000 |
| | 4.0 | 761 | 800 |
| | 3.5 | 22.4 | 322 |
| | 3.0 | 1.13 | 17.0 |
| 60° C. | 5.0 | 130 | 639 |
| | 4.0 | 12.6 | 176 |
| | 3.5 | 2.20 | 11.9 |
| | 3.0 | 0.224 | 1.38 |

The present invention has been described with regard to one or more embodiments. However, it will be apparent to persons skilled in the art that a number of variations and modifications can be made without departing from the scope of the invention as defined in the claims.

REFERENCES

Bhatia, Y., Mishra, S., and Bisaria, V. S. (2002) Microbial beta-Glucosidases: Cloning, Properties and Applications. *Crit. Rev. Biotech.* 22:375-407.

Bommarius, A. S, and Karau, A. (2005) Deactivation of Formate Dehydrogenase (FDH) in Solution and at Gas-Liquid Interfaces. *Biotechnol. Prog.* 21:1663-72.

Butler, T. and Alcalde, M. 2003. In Methods in Molecular Biology, vol. 231: (F. H. Arnold and G. Georgiou, editors), Humana Press Inc. Totowa (New Jersey), pages 17-22

Cummings, C. and Fowler, T. (1996) Secretion of *Trichoderma reesei* beta-glucosidase by *Saccharomyces cerevisiae*. *Curr. Genet.* 29:227-33.

Eijsink V G, Gaseidnes C., Borchert T V, van den Burg B. 2005. Directed Evolution of Enzyme Stability. *Biomol. Eng.* 22:21-30

Elias, C. B. and Joshi, J. B. (1998) Role of Hydrodynamic Shear on Activity and Structure of Proteins. *Adv. Biochem. Eng.* 59:47-71.

Fersht, A. (1998) Structure and Mechanism in Protein Science. W.H. Freeman and Co. USA Gietz, R. D. and Woods, R. A. 2002. Meth. Enzym. 350: 87-96

Gunjikar, T. P., Sudhir S. B., and Joshi, J. B. (2001) Shear Deactivation of Cellulase, Exoglucanase, Endoglucanase and beta-Glucosidase in a Mechanically Agitated Reactor. *Biotechnol. Prog.* 17:1166-8.

Harlow E. and Lane D. (1988) Antibodies: A Laboratory Manual., Cold Spring Harbor Laboratory press (Cold Spring Harbor, N.Y.), pages 564-565.

Henrissat, B. (1991) A classification of glycosyl-dydrolases based on amino acid sequence similarities. *Biochemical Journal*, 293:781-788;

Henrissat, B. and Bairoch, A. (1996) Updating the sequence-based classification of glycosyl hydrolases. *Biochemical Journal*, 316:695-696

Jones, E. O., and Lee, J. M. (1988) Kinetic analysis of bioconversion of cellulose in attrition bioreactor. *Biotechnol. Bioeng.* 31:35-40.

Montenecourt, B. and Eveleigh, D. 1979. Adv. Chem. Ser. 181: 289-301

Motulsky, H. J. and Christopolous, A. (2003) Fitting models to biological data using linear and nonlinear regression. A pratical guide to curve fitting. GraphPad Software Inc., San Diego, Calif.

Reese, E. T. (1980) Inactivation of Cellulase by Shaking and its Prevention by Surfactants. *J. Appl. Biochem.* 2:36-9.

Sachse, H., Kude, J., Kerns, G., and Berger, R. (1990) Production of cellulase in a rotating disc fermenter using immobilized *Trichoderma reesei* cells. *Acta Biotechnol.* 10:523-29.

Sinnott, M. L. (1990) Catalytic mechanisms of enzymic glycosyl transfer. *Chem. Rev.* 90:1171-202.

Trinder, P. (1969) Determination of glucose in blood using glucose oxidase with an alternative oxygen accepter. *Annals of Clinical Biochemistry*, 6:24-27.

Varghese, J. N., Hrmova, M., Fincher, G. B. (1999) Three-dimensional structure of a barley beta-D-glucan exohydrolase, a family 3 glycosyl hydrolase. *Structure Fold. Des.* 7: 179-190

Weijers, S. R. and Van't Riet, K. (1992) Enzyme Stability in Downstream Processing 2: Quantification of Inactivation. *Biotech. Adv.* 10:251-73.

Woodward, J. and Arnold, S. L. (1981) The Inhibition of beta-Glucosidase Activity in *Trichoderma reesei* C30 Cellulase by Derivatives and Isomers of Glucose. *Biotech. Bioeng.* 23:1553-62.

---

The embodiments of the invention in which an exclusive property or privilege is claimed are defined as follows:

1. An isolated *Trichoderma reesei* TrCel3A beta-glucosidase comprising one or more amino acid substitutions selected from the group consisting of V66I, S72E, S72N, F96L, V101M, T235S, N248K, N369K, N369P and A386T, wherein the amino acid sequence of the isolated TrCel3A beta-glucosidase comprises a sequence which is from about 90% to about 99.9% identical to wild-type *Trichoderma reesei* TrCel3A beta-glucosidase encoded by SEQ ID NO:100 and exhibits at least a 2-fold improvement in stability, relative to said wild-type *Trichoderma reesei* TrCel3A beta-glucosidase when incubated in an aqueous solution at a pH from about 2.0 to about pH 4.5.

2. The isolated *Trichoderma reesei* TrCel3A beta-glucosidase of claim 1, comprising an amino acid sequence which from about 95% to about 99.9% identical to SEQ ID NO: 100.

3. The isolated *Trichoderma reesei* TrCel3A beta-glucosidase of claim 1, wherein the isolated *Trichoderma reesei* TrCel3A beta-glucosidase exhibits from about a 2-fold to about a 500-fold improvement in stability, relative to said wild-type *Trichoderma reesei* TrCel3A beta-glucosidase when incubated in an aqueous solution at a pH from about 2.0 to about pH 4.5.

4. The isolated *Trichoderma reesei* TrCel3A beta-glucosidase of claim 1, further comprising one or more amino acid substitutions selected from the group consisting of V43X, F96X, F260X, and I543X.

5. The isolated *Trichoderma reesei* TrCel3A beta-glucosidase of claim 4, further comprising one or more amino acid substitutions selected from the group consisting of V43I, V43C, F96L, V101A, V101G, F260I, F260V, F260Q, F260D, I543N, I543W, I543A, I543S, I543G, and I543L.

6. The isolated *Trichoderma reesei* TrCel3A beta-glucosidase of claim 1, wherein the aqueous solution is subject to aeration at a superficial gas velocity of from about 0.1 to about 100 cm/s, to agitation by shaking at from about 300 to about 1000 rpm, or to agitation by stirring with impeller at a tip speed of from about 0.5 to about 10 m/s.

7. The isolated *Trichoderma reesei* TrCel3A beta-glucosidase of claim 1, wherein the aqueous solution is subject to aeration at a superficial gas velocity of from about 0.5 to about 5 vvm, or to agitation in a bioreactor at from about 0.2 to about 15 hp/100 gallons.

8. The isolated *Trichoderma reesei* TrCel3A beta-glucosidase of claim 1, which exhibits at least a 2-fold improvement in stability, relative to said wild-type *Trichoderma reesei* TrCel3A beta-glucosidase when incubated in an aqueous solution at a pH from about 2.0 to about pH 4.5 and a temperature between about 30° C. and 60° C.

9. An isolated genetic construct comprising a nucleic acid sequence encoding the *Trichoderma reesei* TrCel3A beta-glucosidase according to claim 1.

10. The isolated genetic construct of claim 9, further comprising regulatory nucleic acid sequences that direct the expression and secretion of the *Trichoderma reesei* TrCel3A beta-glucosidase.

11. An isolated genetically modified microbe comprising the genetic construct of claim 9.

12. The isolated genetically modified microbe of claim 11, wherein said microbe is a species of yeast or filamentous fungus.

13. The isolated genetically modified microbe of claim 12, wherein said microbe is *Saccharomyces cerevisiae* or *Trichoderma reesei*.

14. A process for producing a *Trichoderma reesei* TrCel3A beta-glucosidase, comprising the steps of culturing the isolated genetically modified microbe of claim 11 under conditions that induce the expression and secretion of the *Trichoderma reesei* Tr Cel3A beta-glucosidase and recovering the *Trichoderma reesei* TrCel3A beta-glucosidase from the culture medium.

15. The process of claim 14, wherein the step of culturing is conducted at a pH from about 2.0 to about 4.5, a superficial gas velocity of about 0.1 to about 100 cm/s and an impeller tip speed of from about 0.5 to 10 m/s.

16. The process of claim 14, wherein the step of culturing is conducted at a pH from about 3.0 to about 4.5, a superficial gas velocity of about 0.5 to 5 vvm and is agitated at from about 0.2 to about 15 hp/100 gallons.

17. A process for the hydrolyzing a cellulose substrate comprising contacting said substrate with a cellulase mixture comprising the *Trichoderma reesei* TrCel3A beta-glucosidase of claim 1.

18. The process of claim 17, wherein the cellulose substrate is a pretreated lignocellulosic feedstock.

19. The process of claim 18, wherein the pretreated lignocellulosic feedstock is contacted with the cellulase mixture for about 12 hours to 200 hours at a pH from about 3.0 to 7.5 and a temperature from about 45° C. and 75° C.

20. A process for producing a *Trichoderma reesei* TrCel3A beta-glucosidase, comprising the steps of (i) transforming fungal host cells with the isolated genetic construct as defined in claim 9 to produce recombinant fungal strains; (ii) selecting the recombinant fungal strains expressing the *Trichoderma reesei* TrCel3A beta-glucosidase; and (iii) culturing selected recombinant strains in submerged liquid fermentations under conditions that induce the expression of the *Trichoderma reesei* TrCel3A beta-glucosidase.

21. An isolated *Trichoderma reesei* TrCel3A beta-glucosidase comprising the amino acid sequence of:
SEQ ID NO: 111 (TrCel3A-S72N-F96L-V101M-N369K full).

* * * * *

UNITED STATES PATENT AND TRADEMARK OFFICE
CERTIFICATE OF CORRECTION

PATENT NO. : 8,143,049 B2
APPLICATION NO. : 12/550615
DATED : March 27, 2012
INVENTOR(S) : Christopher Hill et al.

It is certified that error appears in the above-identified patent and that said Letters Patent is hereby corrected as shown below:

ON COVER PAGE AT: (56) OTHER PUBLICATIONS:

Under "Sauna et al.", "polymorhisms" should read --polymorphisms--.

COLUMN 2:

Line 7, "MIST" should read --M15T--.

COLUMN 3:

Line 19, "low pH with high agitation," (first occurrence) should read --low pH with high aeration,--; and
Line 66, "stifling" should read --stirring--.

COLUMN 4:

Line 25, "comprise" should read --comprises--.

COLUMN 5:

Line 60, "wildtype" should read --wild-type--.

COLUMN 6:

Line 67, "aryl," should read --aryl-,--.

COLUMN 7:

Line 54, "ild-type" should read --wild-type--.

Signed and Sealed this
Fifth Day of June, 2012

David J. Kappos
*Director of the United States Patent and Trademark Office*

CERTIFICATE OF CORRECTION (continued)
U.S. Pat. No. 8,143,049 B2

COLUMN 8:

Line 18, "96 260" should read --96, 260--.

COLUMN 10:

Line 41, "stifling" should read --stirring--;
Line 56, "stabilityrelative" should read --stability relative--.

COLUMN 12:

Line 24, "Ascomycota." should be italicized.

COLUMN 13:

Line 14, "of" should read --to--.

COLUMN 17:

Line 15, "perature" should read --perature.--;
Line 24, "stiffing" should read --stirring--; and
Line 54, "stifling" should read --stirring--.

COLUMN 20:

Line 7, "were" should read --was--; and
Line 40, "nies," should read --ny,--.

COLUMN 27:
Line 18, "bellow." should read --below.--;
Line 46, "(see URL: fermentas.com/catalog/kits/" should be deleted; and
Line 47, "clonejetperclon.htm)" should be deleted.

COLUMN 28:

Line 37, "was" should read --were--.

COLUMN 29:

Line 10, "MgSO$_4$–7H2O" should read --MgSO$_4$–7H$_2$O--;
Line 12, "FeSO$_4$–7H2O" should read --FeSO$_4$–7H$_2$O--; and
Line 13, "MnSO$_4$–7H2O" should read --MnSO$_4$–7H$_2$O--.

CERTIFICATE OF CORRECTION (continued)
U.S. Pat. No. 8,143,049 B2

COLUMN 30:

Line 59, "$(NH_4)_2SO4$" should read --$(NH_4)_2SO_4$--;
Line 66, "$FeSO4•7H2O$;" should read --$FeSO_4•H_2O$;-- and "$MnSO4•H2O$;" should read --$MnSO_4•H_2O$;--; and
Line 67, "$ZnSO4•7H2O$." should read --$ZnSO_4•7H_2O$.--.

COLUMN 32:

Line 54, "17-22" should read --17-22.--;
Line 60, "22:21-30" should read --22:21-30.--;
Line 65, "USA" should read --USA.--; and
Line 67, "87-96" should read --87:96.--.

COLUMN 33:

Line 10, "293:781-788;" should read --293:781-788.--;
Line 13, "316:695-696" should read --316:695-696.--; and
Line 18, "181: 289-301" should read --181:289-301.--.

COLUMN 34:

Line 15, "179-190" should read --179-190.--.

COLUMN 295:

Line 55, "which" should read --which is--.

COLUMN 298:

Line 10, "and" (second occurrence) should read --to--.